United States Patent
Zhang et al.

(10) Patent No.: US 11,548,868 B2
(45) Date of Patent: Jan. 10, 2023

(54) HETEROCYCLIC COMPOUNDS, COMPOSITIONS COMPRISING HETEROCYCLIC COMPOUND, AND METHODS OF USE THEREOF

(71) Applicant: JS INNOPHARM (SHANGHAI) LTD, Shanghai (CN)

(72) Inventors: Jintao Zhang, Shanghai (CN); Wen Xu, Shanghai (CN); Shanzhong Jian, Shanghai (CN); Ao Li, Shanghai (CN); Qun Li, Shanghai (CN)

(73) Assignee: JS Innopharm (Shanghai) Ltd., Shanghai (CN)

( * ) Notice: Subject to any disclaimer, the term of this patent is extended or adjusted under 35 U.S.C. 154(b) by 0 days.

(21) Appl. No.: 16/757,146

(22) PCT Filed: Oct. 19, 2018

(86) PCT No.: PCT/CN2018/110950
§ 371 (c)(1),
(2) Date: Apr. 17, 2020

(87) PCT Pub. No.: WO2019/076358
PCT Pub. Date: Apr. 25, 2019

(65) Prior Publication Data
US 2020/0339533 A1    Oct. 29, 2020

(30) Foreign Application Priority Data

Oct. 19, 2017  (CN) .......................... 201710978720.9
Mar. 9, 2018   (CN) .......................... 201810195244.8

(51) Int. Cl.
| | | |
|---|---|---|
| C07D 401/12 | (2006.01) |
| C07D 231/56 | (2006.01) |
| C07D 403/04 | (2006.01) |
| C07D 405/12 | (2006.01) |
| C07D 405/14 | (2006.01) |
| C07D 413/12 | (2006.01) |
| C07D 471/04 | (2006.01) |
| C07D 487/04 | (2006.01) |
| C07D 519/00 | (2006.01) |
| C07K 16/28 | (2006.01) |
| A61K 45/06 | (2006.01) |

(52) U.S. Cl.
CPC ......... *C07D 401/12* (2013.01); *C07D 231/56* (2013.01); *C07D 403/04* (2013.01); *C07D 405/12* (2013.01); *C07D 405/14* (2013.01); *C07D 413/12* (2013.01); *C07D 471/04* (2013.01); *C07D 487/04* (2013.01); *C07D 519/00* (2013.01); *C07K 16/2818* (2013.01); *C07K 16/2827* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 10,590,086 B2 * | 3/2020 | Cowley | A61K 31/445 |
| 10,603,331 B2 * | 3/2020 | Ito | A61K 31/5513 |
| 2015/0225367 A1 | 8/2015 | Crosignani et al. | |

FOREIGN PATENT DOCUMENTS

| | | |
|---|---|---|
| CN | 106794176 A | 5/2017 |
| CN | 107108556 A | 8/2017 |
| JP | 2013-53785 A | 10/2013 |
| WO | WO 2012/036253 A1 | 3/2012 |
| WO | WO 2014048865 A1 | 4/2014 |
| WO | WO 2016024233 A1 | 2/2016 |
| WO | WO 2016071293 A2 | 8/2016 |
| WO | WO 2016161960 A1 | 10/2016 |
| WO | WO 2017/007700 A1 | 1/2017 |
| WO | WO 2018057973 A1 | 3/2018 |

OTHER PUBLICATIONS

International Patent Application No. PCT/CN2018/110950: International Search Report and Written Opinion, dated Jan. 23, 2019 (9 pages).
Badawy, A. (2013). Tryptophan: The key to boosting brain serotonin synthesis in depressive illness. *J. Psychopharmacol.* 27(10):878-893.
Dounay. A.B. et al. (2015). Challenges and Opportunities in the Discovery of New Therapeutics Targeting the Kynurenine Pathway. *J. Med. Chem.* 58:8762-8782.
Guillemin, G.J. et al. (2007). Characterization of the Kynurenine Pathway in Human Neurons. *J. Neurosci.* 27(47):12884-12892.
Optiz, C.A. et al. (2011). An endogenous tumour-promoting ligand of the human aryl hydrocarbon receptor. *Nature*. 478:197-203.

(Continued)

*Primary Examiner* — Samantha L Shterengarts
(74) *Attorney, Agent, or Firm* — Finnegan, Henderson, Farabow, Garrett & Dunner LLP

(57) ABSTRACT

Disclosed herein are compounds of formula I and/or a stereoisomer, stable isotopologue, and/or pharmaceutically acceptable salts thereof; and therapeutic uses of these compounds, which are inhibitors of tryptophan 2, 3-dioxygenase 2 (TDO2) and/or indoleamine 2, 3-dioxygenase 1 (IDO1), potentially useful in the treatment of diseases treatable, such as cancers.

(I)

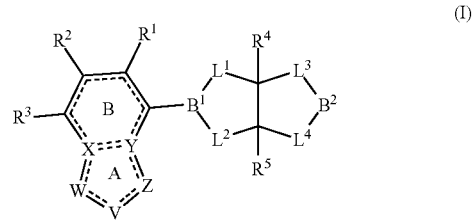

40 Claims, No Drawings

(56) References Cited

OTHER PUBLICATIONS

Pilotte, L. et al. (2012). Reversal of tumoral immune resistance by inhibition of tryptophan 2,3-dioxygenase. *Proc. Natl. Acad. Sci. U.S.A.* 109(7):2497-2502.
Stone, T.W. and Darlington, L.G. (2013). The kynurenine pathway as a therapeutic target in cognitive and neurodegenerative disorders. *Br. J. Pharmacol.* 169:1211-1227.
CAS Registry Database, RN 1945871-43-1, Jul. 5, 2016.

* cited by examiner

HETEROCYCLIC COMPOUNDS, COMPOSITIONS COMPRISING HETEROCYCLIC COMPOUND, AND METHODS OF USE THEREOF

CROSS REFERENCE TO RELATED APPLICATION

The present application is a national stage filing under 35 U.S.C. § 371 of International Application No. PCT/CN2018/110950, filed on Oct. 19, 2018, which claims the benefit of priority to Chinese Application No. 201710978720.9, filed on Oct. 19, 2017, the content of which is incorporated herein by reference.

TECHNICAL BACKGROUND

The tryptophan catabolism plays a central role in maintaining the immunosuppressive microenvironment in various types of cancers. Depletion of tryptophan levels and formation of the metabolites in the kynurenine pathway are thought to cause suppression of T cell proliferation. Additionally, the production of metabolites in the kynurenine pathway provides a source of nicotinamide dinucleotide ($NAD^+$) and modulates other biological effects, particularly in the immune, reproductive, and central nervous systems. Tryptophan 2,3-dioxygenase (TDO2) and indoleamine 2,3-dioxygenase (IDO1 and IDO2) are related immune regulatory enzymes that oxidize tryptophan in the first step of the kynurenine pathway leading to the formation of kynurenine. Tryptophan is an essential amino acid obtained through diet required for the biosynthesis of proteins, neurotransmitters such as serotonin, melatonin and Vitamin B3 (niacin). Although these enzymes catalyze the same reaction, differential expression and compartamentalization of TDO2 and IDO in different tissues is thought to mediate their different biological roles. IDO1 is a monomer distributed ubiquitously in extrahepatic tissues particularly in lung, small intestine and placenta. Compared to IDO1, IDO2 possesses a lower affinity for L-tryptophan and is expressed mainly in brain and placenta, also present in many other tissues, such as liver, small intestine, spleen, placenta, thymus lung, brain, kidney and colon. TDO2 is a tetramer expressed predominanity in liver and placenta.

High level of IDO1 in tumors and tumor-draining lymph nodes induces T-cell apoptosis and increases regulatory T cells, which create an environment in which tumor-specific cytotoxic T lymphocytes are no longer able to attack a patient's cancer cells, and therefore is associated with a poor prognosis in various malignancies. Inhibition of IDO1 suppresses tumour formation in animal models and several IDO1 inhibitors are currently tested in various stages of clinical development (A. B. Dounay, et al. *J. Med. Chem.* 2015, 58, 8762-8782).

Recent studies have showed that TDO2 is equally capable of inhibiting antitumour immune responses. TDO2 is expressed in a significant proportion of human tumors. A survey of 104 cancer cell lines indicated that 16% of the cell lines expressed IDO1 positive, 19% of the cell lines expressed TDO2 positive, and 15% of the cell lines expressed both TDO2 and IDO1 positive (L. Pilotte, et al. *Proc Natl Acad Sci USA*. 2012, 109, 2497-2502). In a preclinical model, TDO2 expression by tumors prevented their rejection by immunized mice, while systemic treatment of a TDO2 inhibitor restored the ability of mice to reject TDO2-expressing tumors. TDO2-derived kynurenine was found to suppress antitumour immune responses and promote tumour-cell survival and motility through activating the aryl hydrocarbon receptor (AHR) (C. A. Opitz, et al. *Nature* 2011, 478, 197-203). Emerging evidence indicates a tumour-promoting role of the AHR. TDO2-AHR pathway is active in human brain tumours and is associated with malignant progression and poor survival. These observations suggest that TDO2 is a promising target for cancer immunotherapy. Inhibition of TDO2 can reverse the immune suppression at the tumor site and allow the generation of an effective anticancer immune response.

Kynurenine pathway is also implicated in a variety of other diseases and disorders, including autoimmune diseases or disorders, such as rheumatoid arthritis, and immunologic tolerance and prevention of fetal rejection in utero, acquired immune deficiency syndrome (AIDS), chronic infections, dementia complex, alzheimer's disease (AD), huntington's disease, amyotrophic lateral sclerosis (ALS), schizophrenia, psychiatric disorders and depressive disorders (*J. Neurosci.* 2007, 27, 12884-12892; *Br. J. Pharmacol.* 2013, 169, 1211-27; *J. Psychopharmacology* 2013, 27, 878-893).

Thus IDO1 and/or TDO2 have been shown to play an important role in immunosuppression, tumor resistance and other diseases such as chronic infections, HIV-infection, AIDS, autoimmune diseases or disorders, and immunologic tolerance and prevention of fetal rejection in utero. Inhibitors of IDO1 and TDO2 that suppress tryptophan degradation are desirable. Specific or dual inhibitors of IDO1 and TDO2 can be used to activate T cells and therefore enhance T cell activation when the T cells are suppressed by pregnancy, malignancy or a virus such as HIV. Inhibition of TDO2 and/or IDO1 may also be important to treat patients with neurological or neuropsychiatric diseases or disorders.

SUMMARY OF THE DISCLOSURE

Disclosed herein are a novel series of heterocyclic compounds that can serve as inhibitors of TDO2. They may also be inhibitors of IDO1, or duo inhibitors of both TDO2 and IDO1. Further disclosed herein are methods for preparing the novel compounds, pharmaceutical compositions comprising at least one of such novel compounds, as well as methods of using at least one of such compounds in the treatment of diseases and disorders mediated by tryptophan deficiency such as cancer, acquired immune deficiency syndrome (AIDS), dementia, Alzheimer's disease (AD), schizophrenia, Huntington's disease, amyotrophic lateral sclerosis (ALS), autoimmune disorders such as rheumatoid arthritis etc.

Disclosed herein are compounds of formula I:

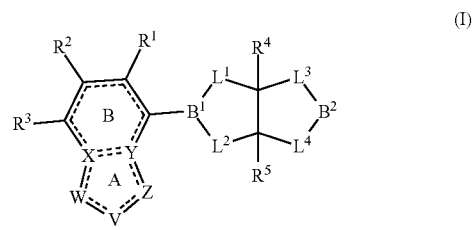

(I)

and/or a stereoisomer, stable isotope, or pharmaceutically acceptable salt thereof, wherein $R^1$, $R^2$, $R^3$, $R^4$, $R^5$, $B^1$, $B^2$, $L^1$, $L^2$, $L^3$, $L^4$, X, Y, Z, V, and W are defined as follows:

$R^1$, $R^2$ and $R^3$ are independently selected from H, D, CN, halo, $NH_2$, and an optionally substituted group selected from C1-C6 alkyl, C1-C6 alkenyl, C1-C6 alkynyl, C3-C8 cycloalkyl, C4-C8 cycloalkenyl, saturated or unsaturated 4-8 membered heterocyclyl containing 1-2 heteroatoms independently selected from N, O, and S as ring members, aryl, heteroaryl containing 1-3 heteroatoms independently selected from N, O, and S as ring members, C1-C6-alkyloxyl, C3-C8 cycloalkyloxyl, C1-C6-alkylamino, and C3-C8 cycloalkylamino, wherein the optional substituents are 1-3 substituents independently selected from $R^6$, wherein $R^6$ is independently selected from H, D, halo, —OH, Oxo, CN, $N_3$, ethynyl, and an optionally substituted group selected from C1-C4 alkyl, C1-C4 alkoxy, C1-C4 haloalkyl, C1-C4 hydroxyalkyl, C1-C4 haloalkoxy, C3-C6 cycloalkyl, C3-C6 cycloalkoxy, 4-6 membered heterocyclyl containing 1-2 heteroatoms independently selected from N, O, and S as ring members, aryl, heteroaryl containing 1-3 heteroatoms independently selected from N, O, and S as ring members, —$CO_2R^A$, —$C(O)N(R^BR^C)$, —$C(=NR^D)N(R^BR^C)$, —$C(O)R^A$, —$SO_{0-2}R^E$, —$SO(=NR^D)R^E$, —$SO_{1-2}N(R^BR^C)$, —$N(R^BR^C)$, —$N(R^A)C(O)R^E$, —$N(R^A)C(=NR^D)R^E$, —$N(R^A)SO_{1-2}R^E$, —$N(R^A)C(O)N(R^BR^C)$, —$N(R^A)C(=NR^D)N(R^BR^C)$, —$N(R^A)SO_{1-2}N(R^BR^C)$, and —$N(R^A)CO_2R^E$, wherein the optional substituents are 1-3 groups independently selected from H, halo, —OH, Oxo, $NH_2$, CN, $N_3$, C1-C4 alkyl, C1-C4 alkoxy, C1-C5 alkylamino, C3-C6 cycloalkyl, C3-C6 cycloalkoxy, 4-6 membered heterocyclyl containing 1-2 heteroatoms independently selected from N, O, and S as ring members, aryl, and heteroaryl containing 1-3 heteroatoms independently selected from N, O, and S as ring members; wherein $R^A$, $R^B$, $R^C$ and $R^E$ are independently selected from H and an optionally substituted group selected from C1-C4 alkyl, C3-C6 cycloalkyl, 4-6 membered heterocyclyl containing 1-2 heteroatoms independently selected from N, O, and S as ring members, aryl, and heteroaryl containing 1-3 heteroatoms independently selected from N, O, and S as ring members; $R^D$ is independently selected from H, CN, OH, and an optionally substituted group selected from C1-C4 alkyl and C1-C4 alkoxy, wherein the optional substituents for $R^A$, $R^B$, $R^C$, $R^D$ and $R^E$ are 1-3 substituents independently selected from $R^6$;

$R^4$ and $R^5$ are independently selected from H, D, halo, —OH, CN, $N_3$, and an optionally substituted group selected from C1-C4 alkyl, C1-C4 alkoxy, C1-C4 haloalkyl, C1-C4 hydroxyalkyl, C1-C4 haloalkoxy, C3-C6 cycloalkyl, C3-C6 cycloalkoxy, 4-6 membered heterocyclyl containing 1-2 heteroatoms independently selected from N, O, and S as ring members, aryl, heteroaryl containing 1-3 heteroatoms independently selected from N, O, and S as ring members, —$CO_2R^A$, —$C(O)N(R^BR^C)$, —$C(=NR^D)N(R^BR^C)$, —$C(O)R^A$, —$SO_{0-2}R^E$, —$SO(=NR^D)R^E$, —$SO_{1-2}N(R^BR^C)$, —$N(R^BR^C)$, —$N(R^A)C(O)R^E$, —$N(R^A)C(=NR^D)R^E$, —$N(R^A)SO_{1-2}R^E$, —$N(R^A)C(O)N(R^BR^C)$, —$N(R^A)C(=NR^D)N(R^BR^C)$, —$N(R^A)SO_{1-2}N(R^BR^C)$, and —$N(R^A)CO_2R^E$, wherein $R^A$, $R^B$, $R^C$, $R^D$ and $R^E$ are defined above;

wherein the optional substituents for $R^4$ and $R^5$ are 1-3 groups independently selected from H, halo, —OH, Oxo, $NH_2$, CN, $N_3$, C1-C4 alkyl, C1-C4 alkoxy, C1-C5 alkylamino, C3-C6 cycloalkyl, C3-C6 cycloalkoxy, 4-6 membered heterocyclyl containing 1-2 heteroatoms independently selected from N, O, and S as ring members, aryl, and heteroaryl containing 1-3 heteroatoms independently selected from N, O, and S as ring members;

Alternatively, $R^4$ and $R^5$ can optionally be taken together to form a C3-C7 cycloalkyl ring, or a 4-7 membered heterocyclic ring containing 1-2 heteroatoms independently selected from N, O, and S, wherein the ring formed can be optionally substituted with 1-2 groups independently selected from $R^6$, wherein $R^6$ is defined above;

A ring and B ring together form a bicyclic aromatic ring wherein:
i). W is NH and V is N, and X and Y are C, and Z is $CR^F$; or
ii). Z is NH, and V is N, X and Y are C, and W is $CR^F$; or
iii). V and Y are N, and X is C, and W and Z are $CR^F$; or
iv). V and X are N, and Y is C, and W and Z are $CR^F$; or
v). V, X and Z are N, and Y is C, W is $CR^F$; or
vi). V, Y and W are N, and X is C, Z is $CR^F$; or
vii). V, Y and Z are N, and X is C, W is $CR^F$; or
viii). V, X and W are N, and Y is C, Z is $CR^F$; or
ix). W is NH, and V and Z are N, and X and Y are C;
wherein $R^F$ is independently selected from H, D, OH, CN, halo, and an optionally substituted group selected from C1-C4 alkyl, and C1-C4 alkylamino, and wherein the optional substituents are 1-3 groups independently selected from $R^6$, wherein $R^6$ is defined above;

$B^1$ is N,

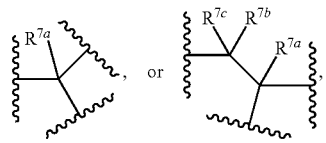

wherein $R^{7a}R^{7b}$ and $R^{7c}$ are independently selected from H, D, OH, CN, halo, and an optionally substituted group selected from C1-C6 alkyl, and C1-C6 alkoxyl, and wherein the optional substituents are 1-3 groups independently selected from $R^6$, wherein $R^6$ is defined above;

$B^2$ is

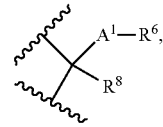

or $N(R^9)$—, wherein $A^1$ is a bond or C1-C4 alkylene; $R^8$ is selected from H, D, halo, and an optionally substituted group selected from C1-C4 alkyl; $R^9$ is selected from H and an optionally substituted group selected from C1-C4 alkyl, C1-C4 haloalkyl, C1-C4 hydroxyalkyl, C1-C4 haloalkoxy, C3-C6 cycloalkyl, 4-6 membered heterocyclyl containing 1-2 heteroatoms independently selected from N, O, and S as ring members, aryl, heteroaryl containing 1-3 heteroatoms independently selected from N, O, and S as ring members, —$CO_2R^A$, —$C(O)N(R^BR^C)$, —$C(=NR^D)N(R^BR^C)$, —$C(O)R^A$, —$SO_{0-2}R^E$, —SO and —$SO_{1-2}N(R^BR^C)$, wherein $R^A$, $R^D$, $R^C$, $R^D$ and $R^E$ are defined above, wherein the optional substituents are 1-3 groups independently selected from $R^6$, wherein $R^6$ is defined above;

$L^1$, $L^2$, $L^3$ and $L^4$ are independently selected from a bond, —O—, —$NR^B$—, —CO—, —$SO_{1-2}$—$C(R^{10}R^{11})_n$—, —$C(R^{10}R^{11})_nSO_{1-2}$—, —$C(R^{10}R^{11})_nCO$—, and —$C(R^{10}R^{11})_nNR^B$—, wherein n is 1, 2, or 3; $R^{10}$ and $R^{11}$ are each independently selected from H, D, OH, CN, halo, and an optionally substituted group selected from C1-C4 alkyl and C1-C4 alkoxyl, and wherein the optional substituents are 1-3 groups independently selected from $R^6$, wherein $R^6$ is defined above; or $R^{10}$ and $R^{11}$ can optionally together form a C3-C7 cycloalkyl ring or a 4-7 membered heterocyclic ring containing 1-2 heteroatoms independently selected from N, O, and S, wherein the ring is optionally substituted with 1-2 groups independently selected from $R^6$, wherein $R^6$ is defined above.

Also disclosed herein is a pharmaceutical composition, comprising a compound of formula I and/or a stereoisomer, a stable isotope, or a pharmaceutically acceptable salt thereof disclosed herein and a pharmaceutically acceptable carrier.

Further disclosed herein is a method of inhibiting the activity of TDO2 and/or IDO1 with an effective amount of a compound of formula I and/or a stereoisomer, a stable isotope, or a pharmaceutically acceptable salt thereof disclosed herein.

Further disclosed herein is a method of treating a disease treatable by inhibition of TDO2 and/or IDO1 in a patient, comprising administering to the patient in recognized need of such treatment, an effective amount of a compound of formula I and/or a stereoisomer, a stable isotope, or a pharmaceutically acceptable salt thereof disclosed herein.

Further disclosed herein is a method of treating a disease treatable by inhibition of TDO2 and/or IDO1 in a patient, comprising administering to the patient in recognized need of such treatment, an effective amount of a pharmaceutical composition comprising a compound of formula I and/or a stereoisomer, a stable isotope, or a pharmaceutically acceptable salt thereof disclosed herein and a pharmaceutically acceptable carrier.

Further disclosed herein is a method of treating a cancer in a patient, comprising administering to the patient in recognized need of such treatment, an effective amount of a pharmaceutical composition comprising a compound of formula I and/or a stereoisomer, a stable isotope, or a pharmaceutically acceptable salt thereof disclosed herein and a pharmaceutically acceptable carrier. In some embodiments, the cancer is colon, pancreas, breast, prostate, lung, brain, ovary, cervix, testes, renal, head, or neck cancer, or lymphoma, leukemia, or melanoma.

Further disclosed herein is a method of enhancing the effectiveness of an anti-cancer treatment comprising administering an anti-cancer agent and a compound of formula I, or a pharmaceutical composition comprising a compound of formula I, and/or a stereoisomer, a stable isotope, or a pharmaceutically acceptable salt thereof disclosed herein. In some embodiments, the cancer is colon, pancreas, breast, prostate, lung, brain, ovary, cervix, testes, renal, head, or neck cancer, or lymphoma, leukemia, or melanoma.

Further disclosed herein is a method of treating immunosuppression associated with cancer by inhibition of TDO2 and/or IDO1 in a patient, comprising administering to the patient in recognized need of such treatment, an effective amount of a compound of formula I and/or a stereoisomer, a stable isotope, or a pharmaceutically acceptable salt thereof disclosed herein.

Further disclosed herein is a use of a compound of formula I and/or a stereoisomer, a stable isotope, or a pharmaceutically acceptable salt thereof in preparation of a medication for treating a disease responsive to inhibition of TDO2 and/or IDO1, such as cancer or immune disorder. In some embodiments, the cancer is colon cancer, gastric cancer, leukemia, lymphoma, melanoma, or pancreatic cancer. In some embodiments, the immune disorders are acquired immune deficiency syndrome (AIDS), dementia, Alzheimer's disease (AD), schizophrenia, Huntington's disease, amyotrophic lateral sclerosis (ALS), autoimmune disorders like rheumatoid arthritis etc.

Further disclosed herein is a method of a use of a compound of formula I and/or a pharmaceutically acceptable salt thereof in treating other diseases in a patient, comprising administering to the patient in recognized need of such treatment, an effective amount of a pharmaceutical composition comprising a compound of formula I and/or a pharmaceutically acceptable salt thereof disclosed herein and a pharmaceutically acceptable carrier. In some embodiments, the other diseases are acquired immune deficiency syndrome (AIDS), dementia, Alzheimer's disease (AD), schizophrenia, Huntington's disease, amyotrophic lateral sclerosis (ALS), autoimmune disorders like rheumatoid arthritis etc.

Further disclosed herein are compounds of formula I and the subgenera of formula I described herein, as well as pharmaceutically acceptable salts of these compounds, and all stereoisomers (including diastereoisomers and enantiomers), and isotopically enriched versions thereof (including deuterium substitutions). These compounds can be used to treat conditions responsive to inhibition of TDO2 and/or IDO1, such as those disclosed herein, and for use in the preparation of a medicament for treating these disorders. The pharmaceutical compositions and methods disclosed herein can also be used with or formulated with a co-therapeutic agent; for example, compounds of formula I and sub-formula thereof can be used with or formulated with inhibitors of immune checkpoint (such as inhibitors of PD-1 and PD-L1) and other therapeutic agents as further disclosed herein.

Further disclosed are methods of making the compounds of formula I as well as key intermediate compounds useful for making the compounds disclosed herein.

Further disclosed herein is the use of any compounds of formula I disclosed herein for making a medicament for treatment of medical conditions that benefit from the inhibition of IDO1 and/or TDO2.

As used herein, the following words, phrases and symbols are generally intended to have the meanings as set forth below, except to the extent that the context in which they are used indicates otherwise. The following abbreviations and terms have the indicated meanings throughout.

DETAILED DESCRIPTION

The following definitions apply unless otherwise provided or apparent from context:

A dash ("-") that is not between two letters or symbols is used to indicate a point of attachment for a substituent. For example, —$CONR_aR_b$ is attached through the carbon atom.

Unless clearly indicated otherwise, use of the terms "a", "an" and the like refers to one or more.

The term "halogen" or "halo" herein refers to fluorine (F), chlorine (Cl), bromine (Br) or iodine (I). Halogen-substituted groups and moieties, such as alkyl substituted by halogen (haloalkyl) can be mono-, poly-, or per-halogenated. In some embodiments, chloro and fluoro are halo substituents on alkyl or cycloalkyl groups, unless otherwise specified; fluoro, chloro, and bromo are, for example, on aryl or heteroaryl groups, unless otherwise specified.

The term "heteroatoms" or "hetero atoms" as used herein refers to nitrogen (N) or oxygen (O) or sulfur (S) atoms, such as nitrogen or oxygen, unless otherwise specified.

The term "optional" or "optionally" used herein means that the subsequently described event or circumstance may or may not occur, and that the description includes instances where the event or circumstance occurs and instances in which it does not. For example, "alkyl optionally substituted with X" encompasses both "alkyl without substitution of X" and "alkyl substituted with X." It will be understood by those skilled in the art, with respect to any group containing one or more substituents, that such groups are not intended to introduce any substitution or substitution patterns that are sterically impractical, synthetically non-feasible and/or inherently unstable in water at room temperature for at least long enough to be administered as a pharmaceutical agent. When multiple substituents are present, the substituents are selected independently unless otherwise indicated, so where 2 or 3 substituents are present, for example, those substituents may be the same or different.

In some embodiments, "substituted with at least one group" refers to one hydrogen on the designated atom or group being replaced with one selection from the indicated group of substituents. In some embodiments, "substituted with at least one group" refers to two hydrogens on the designated atom or group being independently replaced with two selections from the indicated group of substituents. In some embodiments, "substituted with at least one group" refers to three hydrogens on the designated atom or group being independently replaced with three selections from the indicated group of substituents. In some embodiments, "substituted with at least one group" refers to four hydrogens on the designated atom or group being independently replaced with four selections from the indicated group of substituents.

The term "alkyl" herein refers to a hydrocarbon group chosen from linear and branched saturated hydrocarbon groups having up to 18 carbon atoms, such as from 1 to 12, further such as from 1 to 8, even further such as from 1 to 6, carbon atoms. Representative examples of alkyl include, but not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like.

Unless indicated specifically, alkyl group can be optionally substituted by one or more substituents in place of hydrogen atoms of the unsubstituted alkyl, such as one, two or three substituents, or 1-4 substituents, up to the number of hydrogens present on the unsubstituted alkyl group. Suitable substituents for alkyl groups, if not otherwise specified, may be selected from halogen, D, CN, oxo, hydroxyl, substituted or unsubstituted C1-C4 alkoxy, substituted or unsubstituted C3-C6 cycloalkyl, substituted or unsubstituted 3-7 membered heterocycloalkyl containing 1 or 2 heteroatoms selected from N, O and S as ring members, substituted or unsubstituted aryl, substituted or unsubstituted heteroaryl containing 1 to 4 heteroatoms selected from N, O and S as ring members, amino, —NH(C1-C4 alkyl), —N(C1-C4 alkyl)$_2$, —S(=O)$_{0\text{-}2}$(C1-C4 alkyl), —S(=NR)(=O) (C1-C4 alkyl), —C(=O)(C1-C4 alkyl), —C(=NOH)(C1-C4 alkyl), —CO$_2$H, —CO$_2$(C1-C4 alkyl), —S(=O)$_{1\text{-}2}$NH$_2$, —S(=O)$_{1\text{-}2}$NH(C1-C4 alkyl), —S(=O)$_{1\text{-}2}$N(C1-C4 alkyl)$_2$, —CONH$_2$, —C(=O)NH(C1-C4 alkyl), —C(=O)N(C1-C4 alkyl)$_2$, —C(=NOH)NH(C1-C4 alkyl), —OC(=O)(C1-C4 alkyl), —NHC(=O)(C1-C4 alkyl), —NHC(=NOH)(C1-C4 alkyl), —NH(C=O)NH$_2$, —NHC(=O)O (C1-C4 alkyl), —NHC(=O)NH(C1-C4 alkyl), NHC(=NOH)NH(C1-C4 alkyl), —NHS(=O)$_{1\text{-}2}$(C1-C4 alkyl), —NHS(=O)$_{1\text{-}2}$NH$_2$, and —NHS(=O)$_{1\text{-}2}$NH(C1-C4 alkyl); wherein the substituents for substituted C1-C4 alkoxy, substituted C3-C6 cycloalkyl, substituted 3-7 membered heterocycloalkyl, substituted aryl, and substituted heteroaryl are up to three groups independently selected from halogen, D, —CN, C1-C4 alkyl, C1-C4 haloalkyl, oxo, hydroxy, C1-C4 alkoxy, amino, —NH(C1-C4 alkyl), and —N(C1-C4 alkyl)$_2$. In some embodiments, the substituents for alkyl groups, unless otherwise specified, are selected from halogen, CN, oxo, hydroxy, C1-C4 alkoxy, C3-C6 cycloalkyl, phenyl, amino, —NH(C1-C4 alkyl), —N(C1-C4 alkyl)$_2$, C1-C4 alkylthio, C1-C4 alkylsulfonyl, —C(=O)(C1-C4 alkyl), —CO$_2$H, —CO$_2$(C1-C4 alkyl), —OC(=O)(C1-C4 alkyl), —NHC(=O)(C1-C4 alkyl) and —NHC(=O)O(C1-C4 alkyl).

The term "alkoxy" herein refers to a straight or branched alkyl group comprising from 1 to 18 carbon atoms attached through an oxygen bridge such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Typically, alkoxy groups comprise from 1 to 6 carbon atoms, such as from 1 to 4 carbon atoms, attached through the oxygen bridge.

Unless indicated specifically, alkoxyl group can be optionally substituted by one or more substituents in place of hydrogen atoms of the unsubstituted alkyl portion of the alkoxyl, such as one, two or three substituents, or 1-4 substituents, up to the number of hydrogens present on the unsubstituted alkoxyl group. Unless otherwise specified, suitable substituents are selected, for example, from the substituents listed above for alkyl groups, except that hydroxyl and amino are not normally present on the carbon that is directly attached to the oxygen of the substituted alkyl-O group.

The term "alkenyl" herein refers to a hydrocarbon group selected from linear and branched hydrocarbon groups, comprising at least one C=C double bond and from 2 to 18, such as from 2 to 6, carbon atoms. Examples of the alkenyl group may be selected from ethenyl or vinyl (—CH=CH$_2$), prop-1-enyl (—CH=CHCH$_3$), prop-2-enyl (—CH$_2$CH=CH$_2$), 2-methylprop-1-enyl, buta-1-enyl, buta-2-enyl, buta-3-enyl, buta-1,3-dienyl, 2-methylbuta-1,3-diene, hex-1-enyl, hex-2-enyl, hex-3-enyl, hex-4-enyl, and hexa-1,3-dienyl groups. The point of attachment can be on the unsaturated carbon or saturated carbon.

Unless indicated specifically, alkenyl group can be optionally substituted by one or more substituents in place of hydrogen atoms of the unsubstituted alkenyl, such as one, two or three substituents, or 1-4 substituents, up to the number of hydrogens present on the unsubstituted alkenyl group. Unless otherwise specified, suitable substituents are selected, for example, from the substituents listed above for alkyl groups.

The term "alkynyl" herein refers to a hydrocarbon group selected from linear and branched hydrocarbon groups, comprising at least one —C≡C— triple bond and from 2 to 18, such as from 2 to 6, carbon atoms. Examples of the alkynyl group include ethynyl (—C≡CH), 1-propynyl (—C≡CCH$_3$), 2-propynyl (propargyl, —CH$_2$C≡CH), 1-butynyl, 2-butynyl, and 3-butynyl groups. The point of attachment can be on the unsaturated carbon or saturated carbon.

Unless indicated specifically, alkynyl group can be optionally substituted by one or more substituents in place of hydrogen atoms of the unsubstituted alkynyl, such as one, two or three substituents, or 1-4 substituents, up to the number of hydrogens present on the unsubstituted alkynyl group. Unless otherwise specified, suitable substituents are selected, for example, from the substituents listed above for alkyl groups.

The term "alkylene" refers to a divalent alkyl group comprising from 1 to 10 carbon atoms, and two open valences to attach to other molecular components. The two molecular components attached to an alkylene can be on the same carbon atom or on different carbon atoms; thus, for example, propylene is a 3-carbon alkylene that can be 1,1-disubstituted, 1,2-disubstituted or 1,3-disubstituted. Unless otherwise specified, alkylene refers to moieties comprising from 1 to 6 carbon atoms, such as from 1 to 4 carbon atoms. Examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like. A substituted alkylene is an alkylene group containing one or more, such as one, two or three substituents; unless otherwise specified, suitable substituents are selected, for example, from the substituents listed above for alkyl groups.

Unless indicated specifically, alkylenyl group can be optionally substituted by one or more substituents in place of hydrogen atoms of the unsubstituted alkylenyl, such as one, two or three substituents, or 1-4 substituents, up to the number of hydrogens present on the unsubstituted alkylenyl group. Unless otherwise specified, suitable substituents are selected, for example, from the substituents listed above for alkyl groups.

Similarly, "alkenylene" and "alkynylene" refer to alkylene groups comprising a double bond or a triple bond, respectively; they are, for example, 2-6, such as 2-4, carbon atoms in length, and can be substituted as discussed above for alkylene groups.

The term "haloalkyl" refers to an alkyl as defined herein, which is substituted by one or more halo groups as defined herein. Unless otherwise specified, the alkyl portion of the haloalkyl comprises 1-4 carbon atoms. The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. The polyhaloalkyl comprises, for example, up to 6, or 4, or 3, or 2 halo groups. Examples of haloalkyl include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo-alkyl refers to an alkyl having all hydrogen atoms replaced with halo atoms, e.g., trifluoromethyl. In some embodiments, the haloalkyl groups, unless specified otherwise, include monofluoro-, difluoro- and trifluoro-substituted methyl and ethyl groups, e.g. —$CF_3$, —$CF_2H$, —$CFH_2$ and —$CH_2CF_3$.

Unless indicated specifically, haloalkyl group can be optionally substituted by one or more substituents in place of hydrogen atoms of the unsubstituted haloalkyl, such as one, two or three substituents, or 1-4 substituents, up to the number of hydrogens present on the unsubstituted haloalkyl group. Unless otherwise specified, suitable substituents are selected, for example, from the substituents listed above for alkyl groups.

As used herein, the term "haloalkoxy" refers to haloalkyl-O—, wherein haloalkyl is defined above. Examples of haloalkoxy include, but are not limited to, fluoromethoxy, difluoromethoxy, trifluoromethoxy, trichloromethoxy, 2-chloroethoxy, 2,2,2-trifluoroethoxy, 1,1,1,3,3,3-hexafluoro-2-propoxy, and the like. In some embodiments, haloalkyloxy groups comprise 1-4 carbon atoms, and up to three halogens, e.g., monofluoro, difluoro and trifluoro substituted methoxy groups and ethoxy groups.

Unless indicated specifically, haloalkoxyl group can be optionally substituted by one or more substituents in place of hydrogen atoms of the unsubstituted alkyl portion of the haloalkoxyl, such as one, two or three substituents, or 1-4 substituents, up to the number of hydrogens present on the unsubstituted haloalkoxyl group. Unless otherwise specified, suitable substituents are selected, for example, from the substituents listed above for alkyl groups, except that hydroxyl and amino are not normally present on the carbon that is directly attached to the oxygen of the substituted haloalkyl-O group.

The term "cycloalkyl" herein refers to a hydrocarbon group selected from saturated and partially unsaturated cyclic hydrocarbon groups comprising from 3 to 20 carbon atoms, such as monocyclic and polycyclic (e.g., bicyclic and tricyclic, admantanyl and spirocycloalkly) groups. Monocycloalkyl groups are cyclic hydrocarbon groups comprising from 3 to 20 carbon atoms, such as from 3 to 8 carbon atoms. Examples of monocyclic cycloalkyl include, but are not limited to, cyclopropyl, cyclobutyl, cyclopentyl, cyclohexyl, cycloheptyl, cyclooctyl, cyclodecanyl, cyclododecanyl, and cyclohexenyl. Bicycloalkyl groups include, for example, bridged bicycloalkyl, fused bicycloalkyl, and spirocycloalkyls. Bridged bicycloalkyl contains a monocyclic cycloalkyl ring where two non-adjacent carbon atoms of the monocyclic ring are linked by an alkylene bridge of one to three additional carbon atoms (i.e. a bridging group of the form —(CH2)n-, wherein n is 1, 2, or 3). Examples of bridged bicycloalkyl include, but are not limited to, bicyclo[2.2.1]heptenes, bicyclo[3.1.1]heptanes, bicyclo[2.2.1]heptanes, bicyclo[2.2.2]octane, bicyclo[3.2.2]nonane, bicyclo[3.3.1]nonane, and bicycle[4.2.1]nonane. Fused bicycloalkyl contains a monocyclic cycloalkyl ring fused to either a phenyl, a monocyclic cycloalkyl, or a monocyclic heteroaryl. Examples of fused bicycloalkyl include, but are not limited to, bicyclo[4.2.0]octa-1,3,5-triene, 2,3-dihydro-1H-indene, 6,7-dihydro-5H-cyclopenta[b]pyridine, 5,6-dihydro-4H-cyclopenta[b]thiophene, and decahydronaphthalene. Spirocycloalkyl contains two monocyclic ring systems that share a carbon atom forming a biclyclic ring system. Examples of spirocycloalkyls include, but are not limited to,

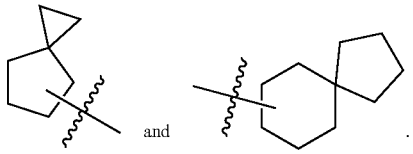

and

Bicyclic cycloalkyl groups comprise, for example, from 7 to 12 carbon atoms. Monocycloalkyl or bicycloalkyl is attached to the parent molecular moiety through any carbon atom contained within the cycloalkyl ring. Tricycloalkyl groups include bridged tricycloalkyl as used herein referring to 1) a bridged bicycloalkyl ring where two non-adjacent carbon atoms of the bridged bicycloalkyl ring are linked by an alkylene bridge of one to three additional carbon atoms (i.e. a bridging group of the form —($CH_2$)n-, wherein n is 1, 2, or 3), or 2) a fused bicycloalkyl ring where two unshared ring atoms on each ring are linked by an alkylene bridge of one to three additional carbon atoms (i.e. a bridging group of the form —($CH_2$)n-, wherein n is 1, 2, or 3), wherein "a fused bicycloalkyl ring" refers to a monocycloalkyl ring fused to a monocycloalkyl ring. Examples of bridged tricycloalkyl groups include, but are not limited to, admantanyl

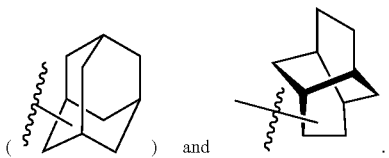

Bridged tricycloalkyl, as used herein, is appended to the parent molecular moiety through any ring atom. The ring atom disclosed herein refers to the carbon atom on the ring skeleton. The cycloalkyl may be saturated or comprise at least one double bond (i.e. partially unsaturated), but is not fully conjugated, and is not aromatic, as aromatic is defined herein. The cycloalkyl may be substituted with at least one hetero atom selected, for example, from O, S, and N.

Unless indicated specifically, cycloalkyl group can be optionally substituted by one or more substituents in place of hydrogen atoms of the unsubstituted cycloalkyl, such as one, two or three substituents, or 1-4 substituents, up to the number of hydrogens present on the unsubstituted cycloalkyl group. In some embodiments, a substituted cycloalkyl comprises 1-4, such as 1-2, substituents. Unless otherwise specified, suitable substituents are selected, for example, from the substituents listed above for alkyl groups.

The term "heterocycloalkyl," "heterocyclyl," or "heterocyclic" disclosed herein refers to "cycloalkyl" as defined above with at least one ring carbon atom being replaced by a heteroatom independently selected from O, N, and S. Heterocyclyl comprises, for example, 1, 2, 3, or 4 heteroatoms, and the N, C or S can independently be oxidized in the cyclic ring system. The N atom can further be substituted to form tertiary amine or ammonium salts. The point of attachment of heterocyclyl can be on the heteroatom or carbon. "Heterocyclyl" herein also refers to a 5- to 7-membered saturated or partially unsaturated carbocyclic ring comprising at least one heteroatom selected, for example, from N, O, and S (heterocyclic ring) fused with 5-, 6-, and/or 7-membered cycloalkyl, heterocyclic or carbocyclic aromatic ring, provided that the point of attachment is at the heterocyclic ring when the heterocyclic ring is fused with a carbocyclic aromatic ring, and that the point of attachment can be at the cycloalkyl or heterocyclic ring when the heterocylic ring is fused with cycloalkyl. "Heterocyclyl" herein also refers to an aliphatic spirocyclic ring comprising at least one heteroatom selected, for example, from N, O, and S. The rings may be saturated or have at least one double bond (i.e. partially unsaturated). The heterocyclyl may be substituted with, for example, oxo. The point of the attachment may be carbon or heteroatom. A heterocyclyl is not a heteroaryl as defined herein.

Examples of the heterocycle include, but are not limited to, pyrrolidinyl, imidazolidinyl, pyrazolidinyl, piperidinyl, piperidinyl, piperazinyl, pyranyl, morpholinyl, oxiranyl, aziridinyl, thiiranyl, azetidinyl, oxetanyl, thietanyl, dithietanyl, dihydropyridinyl, tetrahydropyridinyl, thiomorpholinyl, thioxanyl, homopiperazinyl, homopiperidinyl, azepanyl, oxepanyl, thiepanyl, oxathianyl, dioxepanyl, oxathiepanyl, oxaazepanyldithiepanyl, thiazepanyl and diazepane, dithianyl, azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, indolinyl, dioxanyl, pyrazolinyl, dithianyl, dithiolanyl, pyrazolidinylimidazolinyl, pyrimidinonyl, 1,1-dioxo-thiomorpholinyl, 3-azabicyclo[3.1.0]hexanyl, 3-azabicyclo[4.1.0]heptanyl and azabicyclo[2.2.2]hexanyl. Substituted heterocycles also include ring systems substituted with one or more oxo moieties, such as piperidinyl N-oxide, morpholinyl-N-oxide, 1-oxo-1-thiomorpholinyl, 1,1-dioxo-1-thiomorpholinyl,

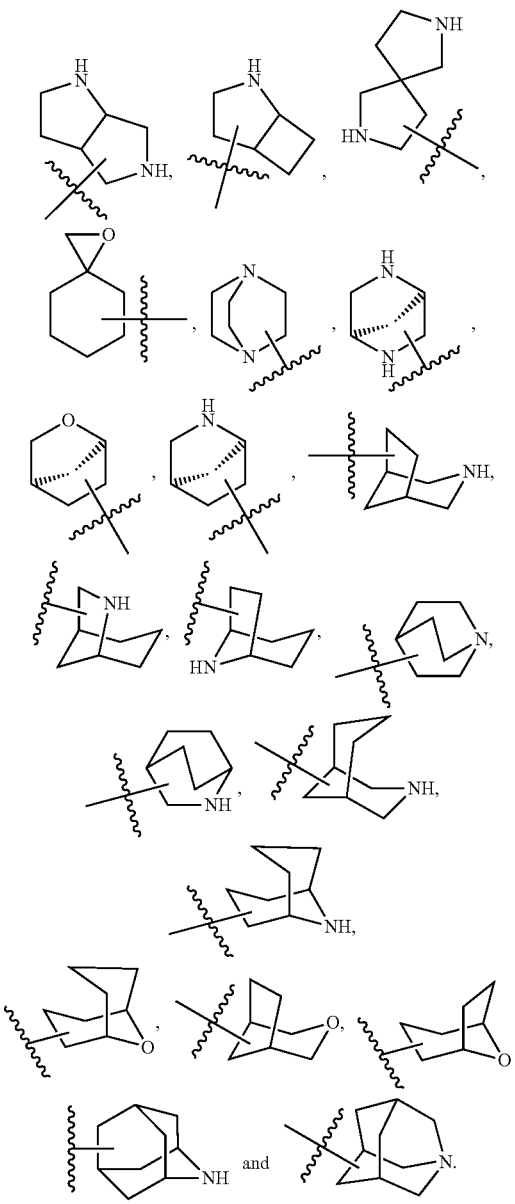

Unless indicated specifically, heterocyclyl group can be optionally substituted by one or more substituents in place of hydrogen atoms of the unsubstituted heterocyclyl, such as one, two or three substituents, or 1-4 substituents, up to the number of hydrogens present on the unsubstituted heterocyclyl group. In some embodiments, a substituted heterocycloalkyl comprises 1-4 such as 1-2 substituents. Unless otherwise specified, suitable substituents are selected, for example, from the substituents listed above for alkyl groups.

The term "aryl" refers to an aromatic hydrocarbon group comprising 5-15 carbon atoms in the ring portion. In some embodiments, aryl refers to a group selected from 5- and 6-membered carbocyclic aromatic rings, for example, phenyl; bicyclic ring systems such as 7 to 12 membered bicyclic ring systems wherein at least one ring is carbocyclic and aromatic, selected, for example, from naphthalene, indane, and 1,2,3,4-tetrahydroquinoline; and tricyclic ring systems such as 10 to 15 membered tricyclic ring systems, wherein at least one ring is carbocyclic and aromatic, for example, fluorene.

In some embodiments, the aryl group is selected from 5 and 6-membered carbocyclic aromatic rings fused to a 5- to 7-membered cycloalkyl or heterocyclic ring (as defined in "heterocyclyl" or "heterocyclic" below) optionally comprising at least one heteroatom selected, for example, from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring (e.g., a heteroaryl as defined below), the resulting ring system is heteroaryl, not aryl, as defined herein.

Unless indicated specifically, aryl group can be optionally substituted by one or more substituents in place of hydrogen atoms of the unsubstituted aryl, such as one, two or three substituents, or 1-4 substituents, up to the number of hydrogens present on the unsubstituted aryl group. In some embodiments, a substituted aryl group comprises 1-5 substituents. Unless otherwise specified, suitable substituents are selected, for example, from the substituents listed above for alkyl groups.

The term "heteroaryl" herein refers to a group selected from 5- to 7-membered aromatic, monocyclic rings comprising at least one heteroatom, for example, from 1 to 4, or, in some embodiments, from 1 to 3, heteroatoms, selected, for example, from N, O, and S, with the remaining ring atoms being carbon; 8- to 12-membered bicyclic rings comprising at least one heteroatom, for example, from 1 to 4, or, in some embodiments, from 1 to 3, or, in other embodiments, 1 or 2, heteroatoms, selected, for example, from N, O, and S, with the remaining ring atoms being carbon and wherein at least one ring is aromatic and at least one heteroatom is present in the aromatic ring, and with the point of attachment being on any ring and being on either carbon or the heteroatom; and 11- to 14-membered tricyclic rings comprising at least one heteroatom, for example, from 1 to 4, or in some embodiments, from 1 to 3, or, in other embodiments, 1 or 2, heteroatoms, selected, for example, from N, O, and S, with the remaining ring atoms being carbon and wherein at least one ring is aromatic and at least one heteroatom is present in an aromatic ring, and with the point of attachment being on any ring.

In some embodiments, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

In some embodiments, the heteroaryl group includes a 5- to 7-membered heterocyclic aromatic ring fused to a 5- to 7-membered aryl ring. For such fused, bicyclic heteroaryl ring systems wherein only one of the rings comprises at least one heteroatom, the point of attachment may be at the heteroaromatic ring or at the aryl ring. Non-limiting examples include quinolinyl and quinazolinyl.

In some embodiments, the heteroaryl group includes a 5- to 7-membered heterocyclic aromatic ring fused to another 5- to 7-membered heterocyclic aromatic ring. Non-limiting examples include 1H-pyrazolo[3,4-b]pyridinyl and 1H-pyrrolo[2,3-b]pyridinyl.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, pyridyl, cinnolinyl, pyrazinyl, pyrimidinyl, imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrimidinyl, pyrrolyl, triazolyl, quinolinyl, isoquinolinyl, pyrazolyl, pyrrolopyridinyl (such as 1H-pyrrolo[2,3-b]pyridin-3-yl), pyrazolopyridinyl (such as 1H-pyrazolo[3,4-b]pyridin-3-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

Unless indicated specifically, heteroaryl group can be optionally substituted by one or more substituents in place of hydrogen atoms of the unsubstituted heteroaryl, such as one, two or three substituents, or 1-4 substituents, up to the number of hydrogens present on the unsubstituted heteroaryl group. In some embodiments, a substituted heteroaryl group comprises 1, 2 or 3 substituents. Unless otherwise specified, suitable substituents are selected, for example, from the substituents listed above for alkyl groups.

Compounds disclosed herein may contain an asymmetric center and may thus exist as enantiomers. Where the compounds disclosed herein possess two or more asymmetric centers, they may additionally exist as diastereomers. Enantiomers and diastereomers fall within the broader class of stereoisomers. It is well-known in the art how to prepare optically active forms, such as by resolution of materials or by asymmetric synthesis. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

When the compounds disclosed herein contain olefinic double bonds, unless specified otherwise, such double bonds are meant to include both E and Z geometric isomers.

"A pharmaceutically acceptable salt" includes, but is not limited to, salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—$(CH_2)$n-COOH, wherein n is selected from 0 to 4. Similarly, examples of pharmaceutically acceptable cations include, but are not limited to, sodium, potassium, calcium, aluminum, lithium, and ammonium.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" or "alleviation" refers to administering at least one compound and/or at least one stereoisomer thereof, if any, at least one stable isotope thereof, or at least one pharmaceutically acceptable salt thereof disclosed herein to a subject in recognized need thereof that has, for example, cancer.

The term "effective amount" refers to an amount of at least one compound and/or at least one stereoisomer thereof, if any, at least one stable isotope thereof, or at least one pharmaceutically acceptable salt thereof disclosed herein effective to "treat," as defined above, a disease or disorder in a subject.

Various embodiments are described herein. It will be recognized that features specified in each embodiment may be combined with other specified features to provide further embodiments of the present disclosure. The following enumerated embodiments are representative of the present disclosure.

Embodiment 1

Disclosed herein are compounds of formula I:

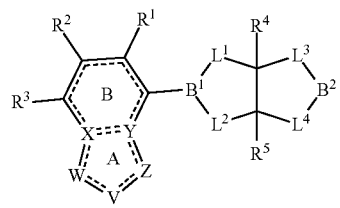

(I)

and/or a stereoisomer, stable isotope, or pharmaceutically acceptable salt thereof, wherein $R^1$, $R^2$, $R^3$, $R^4$, $R^5$, $B^1$, $B^2$, $L^1$, $L^2$, $L^3$, $L^4$, X, Y, Z, V, and W are defined as follows:

$R^1$, $R^2$ and $R^3$ are independently selected from H, D, CN, halo, $NH_2$, and an optionally substituted group selected from C1-C6 alkyl, C1-C6 alkenyl, C1-C6 alkynyl, C3-C8 cycloalkyl, C4-C8 cycloalkenyl, saturated or unsaturated 4-8 membered heterocyclyl containing 1-2 heteroatoms independently selected from N, O, and S as ring members, aryl, heteroaryl containing 1-3 heteroatoms independently selected from N, O, and S as ring members, C1-C6-alkyloxyl, C3-C8 cycloalkyloxyl, C1-C6-alkylamino, and C3-C8 cycloalkylamino, wherein the optional substituents are 1-3 substituents independently selected from $R^6$, wherein $R^6$ is independently selected from H, D, halo, —OH, Oxo, CN, $N_3$, ethynyl, and an optionally substituted group selected from C1-C4 alkyl, C1-C4 alkoxy, C1-C4 haloalkyl, C1-C4 hydroxyalkyl, C1-C4 haloalkoxy, C3-C6 cycloalkyl, C3-C6 cycloalkoxy, 4-6 membered heterocyclyl containing 1-2 heteroatoms independently selected from N, O, and S as ring members, aryl, heteroaryl containing 1-3 heteroatoms independently selected from N, O, and S as ring members, —$CO_2R^A$, —$C(O)N(R^BR^C)$, —$C(=NR^D)N(R^BR^C)$, —$C(O)R^A$, —$SO_{0-2}R^E$, —$SO(=NR^D)R^E$, —$SO_{1-2}N(R^BR^C)$, —$N(R^BR^C)$, —$N(R^A)C(O)R^E$, —$N(R^A)C(=NR^D)R^E$, —$N(R^A)SO_{1-2}R^E$, —$N(R^A)C(O)N(R^BR^C)$, —$N(R^A)C(=NR^D)N(R^BR^C)$, —$N(R^A)SO_{1-2}N(R^BR^C)$, and —$N(R^A)CO_2R^E$, wherein the optional substituents are 1-3 groups independently selected from H, halo, —OH, Oxo, $NH_2$, CN, $N_3$, C1-C4 alkyl, C1-C4 alkoxy, C1-C5 alkylamino, C3-C6 cycloalkyl, C3-C6 cycloalkoxy, 4-6 membered heterocyclyl containing 1-2 heteroatoms independently selected from N, O, and S as ring members, aryl, and heteroaryl containing 1-3 heteroatoms independently selected from N, O, and S as ring members; wherein $R^A$, $R^B$, $R^C$ and $R^E$ are independently selected from H and an optionally substituted group selected from C1-C4 alkyl, C3-C6 cycloalkyl, 4-6 membered heterocyclyl containing 1-2 heteroatoms independently selected from N, O, and S as ring members, aryl, and heteroaryl containing 1-3 heteroatoms independently selected from N, O, and S as ring members; $R^D$ is independently selected from H, CN, OH, and an optionally substituted group selected from C1-C4 alkyl and C1-C4 alkoxy, wherein the optional substituents for $R^A$, $R^B$, $R^C$, $R^D$ and $R^E$ are 1-3 substituents independently selected from $R^6$;

$R^4$ and $R^5$ are independently selected from H, D, halo, —OH, CN, $N_3$, and an optionally substituted group selected from C1-C4 alkyl, C1-C4 alkoxy, C1-C4 haloalkyl, C1-C4 hydroxyalkyl, C1-C4 haloalkoxy, C3-C6 cycloalkyl, C3-C6 cycloalkoxy, 4-6 membered heterocyclyl containing 1-2 heteroatoms independently selected from N, O, and S as ring members, aryl, heteroaryl containing 1-3 heteroatoms independently selected from N, O, and S as ring members, —$CO_2R^A$, —$C(O)N(R^BR^C)$, —$C(=NR^D)N(R^BR^C)$, —$C(O)R^A$, —$SO_{0-2}R^E$, —$S(=NR^D)R^E$, —$SO_{1-2}N(R^BR^C)$, —$N(R^BR^C)$, —$N(R^A)C(O)R^E$, —$N(R^A)C(=NR^D)R^E$, —$N(R^A)SO_{1-2}R^E$, —$N(R^A)C(O)N(R^BR^C)$, —$N(R^A)C(=NR^D)N(R^BR^C)$, —$N(R^A)SO_{1-2}N(R^BR^C)$, and —$N(R^A)CO_2R^E$, wherein $R^A$, $R^B$, $R^C$, $R^D$ and $R^E$ are defined above;

wherein the optional substituents for $R^4$ and $R^5$ are 1-3 groups independently selected from H, halo, —OH, Oxo, $NH_2$, CN, $N_3$, C1-C4 alkyl, C1-C4 alkoxy, C1-C5 alkylamino, C3-C6 cycloalkyl, C3-C6 cycloalkoxy, 4-6 membered heterocyclyl containing 1-2 heteroatoms independently selected from N, O, and S as ring members, aryl, and heteroaryl containing 1-3 heteroatoms independently selected from N, O, and S as ring members;

Alternatively, $R^4$ and $R^5$ can optionally be taken together to form a C3-C7 cycloalkyl ring, or a 4-7 membered heterocyclic ring containing 1-2 heteroatoms independently selected from N, O, and S, wherein the ring formed can be optionally substituted with 1-2 groups independently selected from $R^6$, wherein $R^6$ is defined above;

A ring and B ring together form a bicyclic aromatic ring wherein:
i). W is NH, and V is N, and X and Y are C, and Z is $CR^F$; or
ii). Z is NH, and V is N, X and Y are C, and W is $CR^F$; or
iii). V and Y are N, and X is C, and W and Z are $CR^F$; or
iv). V and X are N, and Y is C, and W and Z are $CR^F$; or
v). V, X and Z are N, and Y is C, W is $CR^F$; or
vi). V, Y and W are N, and X is C, Z is $CR^F$; or
vii). V, Y and Z are N, and X is C, W is $CR^F$; or
viii). V, X and W are N, and Y is C, Z is $CR^F$; or
ix). W is NH, and V and Z are N, and X and Y are C;
wherein $R^F$ is independently selected from H, D, OH, CN, halo, and an optionally substituted group selected from C1-C4 alkyl and C1-C4 alkylamino, and wherein the optional substituents are 1-3 groups independently selected from $R^6$, wherein $R^6$ is defined above;

$B^1$ is N,

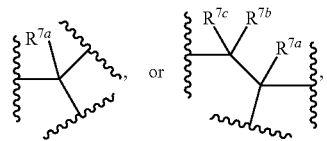

wherein $R^{7a}$, $R^{7b}$ and $R^{7c}$ are independently selected from H, D, OH, CN, halo, and an optionally substituted group selected from C1-C6 alkyl and C1-C6 alkoxyl, and wherein the optional substituents are 1-3 groups independently selected from $R^6$, wherein $R^6$ is defined above;

$B^2$ is

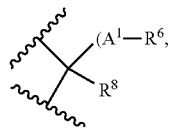

or $N(R^9)$—, wherein $A^1$ is a bond or C1-C4 alkylene; $R^8$ is selected from H, D, halo, and an optionally substituted group selected from C1-C4 alkyl; $R^9$ is selected from H and an optionally substituted group selected from C1-C4 alkyl, C1-C4 haloalkyl, C1-C4 hydroxyalkyl, C1-C4 haloalkoxy, C3-C6 cycloalkyl, 4-6 membered heterocyclyl containing 1-2 heteroatoms independently selected from N, O, and S as ring members, aryl, heteroaryl containing 1-3 heteroatoms independently selected from N, O, and S as ring members, —$CO_2R^A$, —$C(O)N(R^BR^C)$, —$C(=NR^D)N(R^BR^C)$, —$C(O)R^A$, —$SO_{0-2}R^E$, —$SO(=NR^D)R^E$, and —$SO_{1-2}N(R^BR^C)$, wherein $R^A$, $R^B$, $R^C$, $R^D$ and $R^E$ are defined above, wherein the optional substituents are 1-3 groups independently selected from $R^6$, wherein $R^6$ is defined above;

$L^1$, $L^2$, $L^3$ and $L^4$ are independently selected from a bond, —O—, —$NR^B$—, —CO—, —$SO_{1-2}$—, —$C(R^{10}R^{11})_n$—, —$C(R^{10}R^{11})_nSO_{1-2}$—, —$C(R^{10}R^{11})_nCO$—, and —$C(R^{10}R^{11})_nNR^B$—, wherein n is 1, 2, or 3; $R^{10}$ and $R^{11}$ are each independently selected from H, D, OH, CN, halo, and an optionally substituted group selected from C1-C4 alkyl, and C1-C4 alkoxyl, and wherein the optional substituents are 1-3 groups independently selected from $R^6$, wherein $R^6$ is defined above; or
$R^{10}$ and $R^{11}$ can optionally together form a C3-C7 cycloalkyl ring or a 4-7 membered heterocyclic ring containing 1-2 heteroatoms independently selected from N, O, and S, wherein the ring can be optionally substituted with 1-2 groups independently selected from $R^6$, wherein $R^6$ is defined above.

Embodiment 2

The compound according to embodiment 1 and/or a stereoisomer, a stable isotope, or a pharmaceutically acceptable salt thereof, wherein W is NH, V is N, X and Y are C, and Z is $CR^F$.

Embodiment 3

The compound according to embodiment 1 and/or a stereoisomer, a stable isotope, or a pharmaceutically acceptable salt thereof, wherein Z is NH, V is N, X and Y are C, and W is $CR^F$.

Embodiment 4

The compound according to embodiment 1 and/or a stereoisomer, a stable isotope, or a pharmaceutically acceptable salt thereof, wherein V and Y are N, X is C, and W and Z are $CR^F$.

Embodiment 5

The compound according to embodiment 1 and/or a stereoisomer, a stable isotope, or a pharmaceutically acceptable salt thereof, wherein V and X are N, Y is C, and W and Z are $CR^F$.

Embodiment 6

The compound according to embodiment 1 and/or a stereoisomer, a stable isotope, or a pharmaceutically acceptable salt thereof, wherein V, X and Z are N, Y is C and W is $CR^F$.

Embodiment 7

The compound according to embodiment 1 and/or a stereoisomer, a stable isotope, or a pharmaceutically acceptable salt thereof, wherein V, Y and W are N, X is C, and Z is $CR^F$.

Embodiment 8

The compound according to embodiment 1 and/or a stereoisomer, a stable isotope, or a pharmaceutically acceptable salt thereof, wherein V, Y and Z are N, X is C, and W is $CR^F$.

Embodiment 9

The compound according to embodiment 1 and/or a stereoisomer, a stable isotope, or a pharmaceutically acceptable salt thereof, wherein V, X and W are N, Y is C, and Z is $CR^F$.

Embodiment 10

The compound according to embodiment 1 and/or a stereoisomer, a stable isotope, or a pharmaceutically acceptable salt thereof, wherein W is NH, V and Z are N, and X and Y are C.

Embodiment 11

The compound according to embodiments 1-10 and/or a stereoisomer, a stable isotope, or a pharmaceutically acceptable salt thereof, wherein $B^1$ is N.

Embodiment 12

The compound according to embodiments 1-10 and/or a stereoisomer, a stable isotope, or a pharmaceutically acceptable salt thereof, wherein $B^1$ is

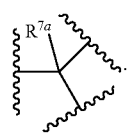

Embodiment 13

The compound according to embodiments 1-11 and/or a stereoisomer, a stable isotope, or a pharmaceutically acceptable salt thereof, wherein $L^1, L^2, L^3, L^4, B^1, B^2, R^4$, and $R^5$ together form an optionally substituted structure

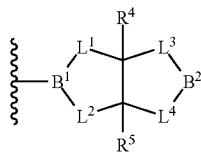

selected from:

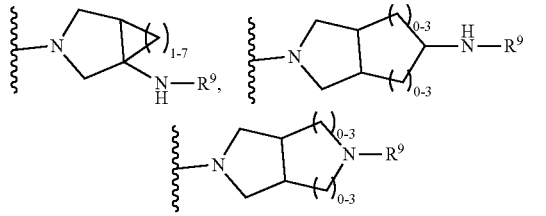

wherein the optional substituents on the rings of the above structural motifs are 1-4 groups independently selected from OH, CN, halo, and an optionally substituted group selected from C1-C4 alkyl and C1-C4 alkoxyl, wherein the optional substituents are 1-3 groups independently selected from $R^6$; or wherein two optional substituents on

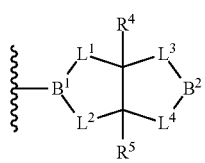

can be taken together to form a C3-C7 cycloalkyl ring or a 4-7 membered heterocyclic ring containing 1-2 heteroatoms independently selected from N, O, and S, wherein the ring formed can be optionally substituted with 1-2 groups independently selected from $R^6$;

Embodiment 14

The compound according to embodiments 1-10 and 12 and/or a stereoisomer, a stable isotope, or a pharmaceutically acceptable salt thereof, wherein $L^1, L^2, L^3, L^4, B^1, B^2, R^4$, and $R^5$ together form an optionally substituted structure

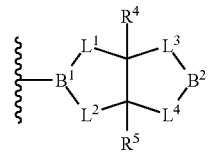

selected from:

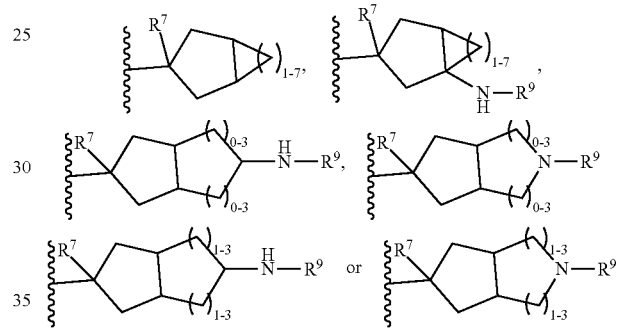

wherein the optional substituents on the rings of the above structural motifs are 1-4 groups independently selected from OH, CN, halo, and an optionally substituted group selected from C1-C4 alkyl and C1-C4 alkoxyl, wherein the optional substituents are 1-3 groups independently selected from $R^6$; or wherein two optional substituents on

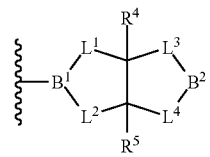

can be taken together to form a C3-C7 cycloalkyl ring or a 4-7 membered heterocyclic ring containing 1-2 heteroatoms independently selected from N, O, and S, wherein the ring formed can be optionally substituted with 1-2 groups independently selected from $R^6$.

Embodiment 15

The compound according to embodiments 1-11 and/or a stereoisomer, a stable isotope, or a pharmaceutically acceptable salt thereof, wherein $L^1, L^2, L^3, L^4, B^1, B^2, R^4$, and $R^5$ together form an optionally substituted structure selected from:

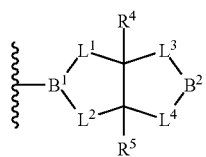

wherein the optional substituents on the ring of above structural motif are 1-4 groups independently selected from OH, CN, halo, and an optionally substituted group selected from C1-C4 alkyl and C1-C4 alkoxyl, wherein the optional substituents are 1-3 groups independently selected from $R^6$; or wherein two optional substituents on

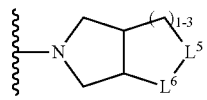

can be taken together to form a C3-C7 cycloalkyl ring or a 4-7 membered heterocyclic ring containing 1-2 heteroatoms independently selected from N, O, and S, wherein the ring formed can be optionally substituted with 1-2 groups independently selected from $R^6$;

$L^5$ is selected from —$NR^{12}CO$—, —$NR^{12}SO_2$—, —$CONR^{12}$—, and —$SO_2NR^{12}$—; and $L^6$ is a bond or —$(CH_2)_{1-3}$, wherein $R^{12}$ is an optionally substituted group selected from C1-C6 alkyl, C3-C8 cycloalkyl, C4-C8 cycloalkenyl, saturated or unsaturated 4-8 membered heterocyclyl containing 1-2 heteroatoms independently selected from N, O, and S as ring members, aryl, and heteroaryl containing 1-3 heteroatoms independently selected from N, O, and S as ring members, wherein the optional substituents are 1-3 substituents independently selected from $R^6$.

Embodiment 16

The compound according to embodiments 1-10 and 12 and/or a stereoisomer, a stable isotope, or a pharmaceutically acceptable salt thereof, wherein $L^1$, $L^2$, $L^3$, $L^4$, $B^1$, $B^2$, $R^4$, and $R^5$ together form an optionally substituted structure

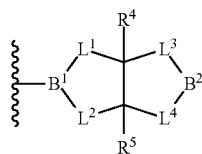

selected from:

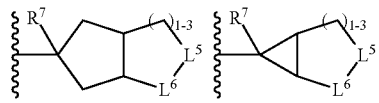

wherein the optional substituents on the ring of the above structural motifs are 1-4 groups independently selected from OH, CN, halo, C1-C6 alkyl, and C1-C6 alkoxyl, wherein the optional substituents are 1-3 groups independently selected from $R^6$; or wherein two optional substituents on the rings of above structural motifs can be taken together to form a C3-C7 cycloalkyl ring or a 4-7 membered heterocyclic ring containing 1-2 heteroatoms independently selected from N, O, and S, wherein the ring formed can be optionally substituted with 1-2 groups independently selected from $R^6$;

$L^5$ is selected from —$NR^{12}CO$—, —$NR^{12}SO_2$—, —$CONR^{12}$—, and —$SO_2NR^{12}$—; and $L^6$ is a bond or —$(CH_2)_{1-3}$, wherein $R^{12}$ is an optionally substituted group selected from C1-C6 alkyl, C3-C8 cycloalkyl, C4-C8 cycloalkenyl, saturated or unsaturated 4-8 membered heterocyclyl containing 1-2 heteroatoms independently selected from N, O, and S as ring members, aryl, and heteroaryl containing 1-3 heteroatoms independently selected from N, O, and S as ring members, wherein the optional substituents are 1-3 groups independently selected from $R^6$.

Embodiment 17

The compound of embodiments 1, 2, 3, 11 and 13 having structure of formula I-A, I-B, I-C, or I-D:

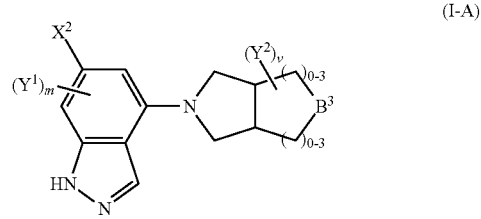

(I-A)

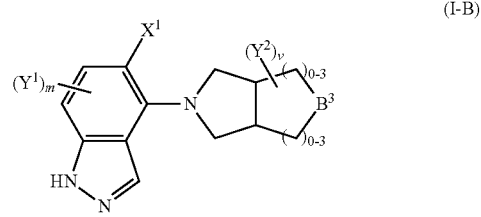

(I-B)

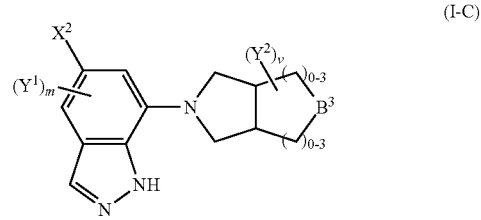

(I-C)

-continued (I-D)

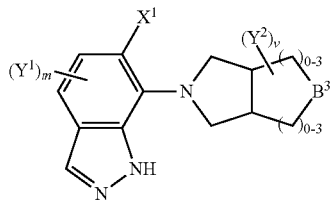

and/or a stereoisomer, a stable isotope, or a pharmaceutically acceptable salt thereof, wherein $X^1$ and $X^2$ are independently selected from CN, halo, $CF_3$, and an optionally substituted group selected from C1-C6 alkyl, C3-C6 cycloalkyl, and C1-C6 alkoxy, wherein the optional substituents are 1-3 groups independently selected from $R^6$;

$Y^1$ is independently selected from H, D, CN, halo, $NH_2$, and an optionally substituted group selected from C1-C6 alkyl, C1-C6 alkoxy, and C1-C6 alkylamino, wherein the optional substituents are 1-3 groups independently selected from $R^6$;

$Y^2$ is independently selected from H, OH, CN, halo, and an optionally substituted group selected from C1-C4 alkyl and C1-C4 alkoxyl, wherein the optional substituents are 1-3 substituents independently selected from $R^6$; or the two adjacent $Y^2$ substituents can optionally be taken together to form a C3-C7 cycloalkyl ring or a 4-7 membered heterocyclic ring containing 1-2 heteroatoms independently selected from N, O, and S, wherein the ring formed can be optionally substituted with 1-2 groups independently selected from $R^6$;

$B^3$ is

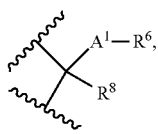

—$C(R^8)(NHR^{13})$— or $N(R^{13})$—, wherein $R^{13}$ is selected from —$COR^{14}$, —$SO_2R^{14}$, —$CONR^{15}R^{16}$, and —$SO_2NR^{15}R^{16}$, wherein $R^{14}$ is an optionally substituted group selected from C1-C6 alkyl, C3-C8 cycloalkyl, saturated or unsaturated 4-8 membered heterocyclyl containing 1-2 heteroatoms independently selected from N, O, and S as ring members, aryl, and heteroaryl containing 1-3 heteroatoms independently selected from N, O, and S as ring members, wherein the optional substituents are 1-3 groups independently selected from $R^6$; wherein $R^{15}$ and $R^{16}$ are independently H or $R^{14}$.

m is 1-2; and v is 1-4.

Embodiment 18

The compound of embodiments 1, 4, 5, 11 and 13 having structure of formula I-E, I-F, I-G or I-H:

(I-E)

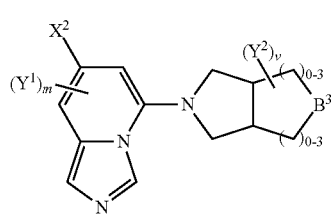

(I-F)

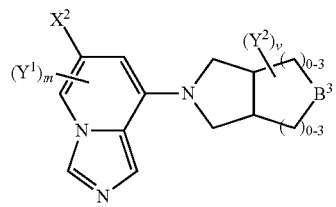

(I-G)

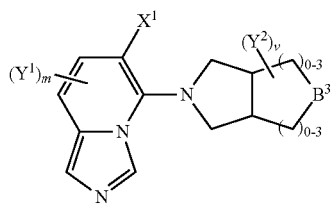

(I-H)

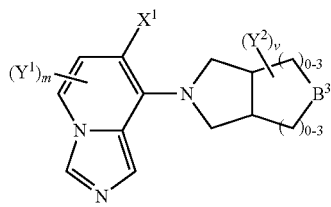

and/or a stereoisomer, a stable isotope, or a pharmaceutically acceptable salt thereof, wherein $X^1$ and $X^2$ are independently selected from CN, halo, and an optionally substituted group selected from C1-C6 alkyl, C1-C6 haloalkyl, C3-C6 cycloalkyl, and C1-C6 alkoxy, wherein the optional substituents are 1-3 groups independently selected from $R^6$;

$Y^1$ is independently selected from H, D, CN, halo, $NH_2$, and an optionally substituted group selected from C1-C6 alkyl, C1-C6 alkoxy, and C1-C6 alkylamino, wherein the optional substituents are 1-3 groups independently selected from $R^6$;

$Y^2$ is independently selected from H, OH, CN, halo, and an optionally substituted group selected from C1-C4 alkyl and C1-C4 alkoxyl, wherein the optional substituents are 1-3 groups independently selected from $R^6$; or two adjacent $Y^2$ substituents can be taken together to form a C3-C7 cycloalkyl ring or a 4-7 membered heterocyclic ring containing 1-2 heteroatoms independently selected from N, O, and S, wherein the ring formed can be optionally substituted with 1-2 groups independently selected from $R^6$;

$B^3$ is

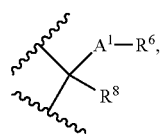

—$C(R^8)(NHR^{13})$— or —$N(R^{13})$—, wherein $R^{13}$ is selected from —$COR^{14}$, —$SO_2R^{14}$, —$CONR^{15}R^{16}$, and —SO$_2$NR$^{15}$R$^{16}$, wherein R$^{14}$ is an optionally substituted group selected from C1-C6 alkyl, C3-C8 cycloalkyl, saturated or unsaturated 4-8 membered heterocyclyl containing 1-2 heteroatoms independently selected from N, O, and S as ring members, aryl, and heteroaryl containing 1-3 heteroatoms independently selected from N, O, and S as ring members, wherein the optional substituents are 1-3 groups independently selected from R$^6$; wherein R$^{15}$ and R$^{16}$ are independently H or R$^{14}$;

m is 1-2; and v is 1-4.

Embodiment 19

The compound of embodiments 1, 2, 3, 12, and 14 having structure of formula I-I, I-J, I-K, I-L, I-M, I-N, I-O, or I-P:

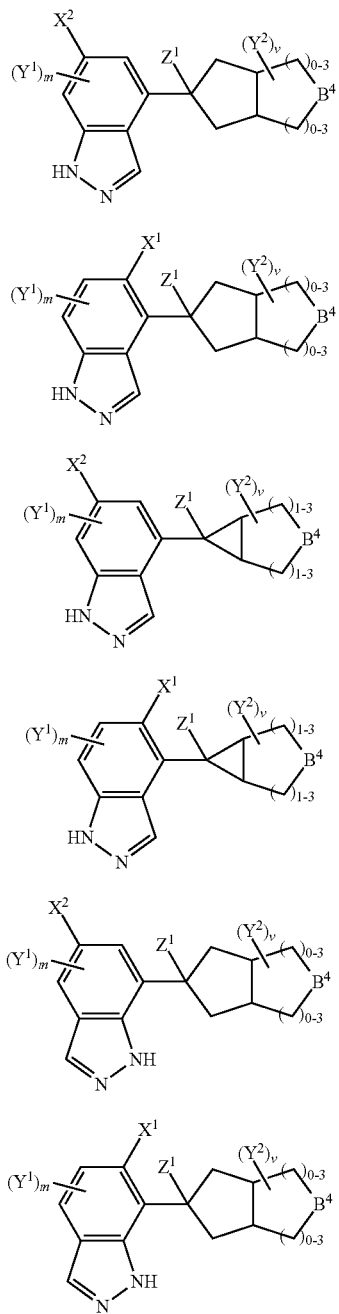

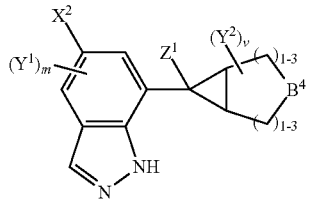

(I-O)

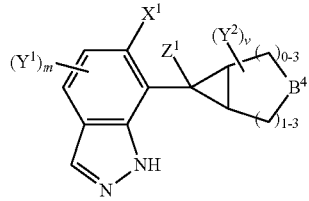

(I-P)

and/or a stereoisomer, a stable isotope, or a pharmaceutically acceptable salt thereof, wherein Z$^1$ is selected from H, OH, CN, halo, and an optionally substituted group selected from C1-C6 alkyl and C1-C6 alkoxy, wherein the optional substituents are 1-3 groups independently selected from R$^6$;

X$^1$ and X$^2$ are independently selected from CN, halo, and an optionally substituted group selected from C1-C6 alkyl, C1-C6 haloalkyl, C3-C6 cycloalkyl, and C1-C6 alkoxy, wherein the optional substituents are 1-3 groups independently selected from R$^6$;

Y$^1$ is independently selected from H, D, CN, halo, NH$_2$, and an optionally substituted group selected from C1-C6 alkyl, C1-C6 alkoxy, and C1-C6 alkylamino, wherein the optional substituents are 1-3 groups independently selected from R$^6$;

Y$^2$ is independently selected from H, OH, CN, halo, and an optionally substituted group selected from C1-C4 alkyl and C1-C4 alkoxyl, wherein the optional substituents are 1-3 groups independently selected from R$^6$; or two adjacent Y$^2$ substituents can be taken together to form a C3-C7 cycloalkyl ring or a 4-7 membered heterocyclic ring containing 1-2 heteroatoms independently selected from N, O, and S, wherein the ring formed can be optionally substituted with 1-2 groups independently selected from R$^6$;

B$^4$ is

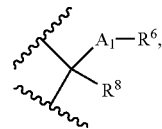

—C(R$^8$)(NHR$^{13}$)—, or N(R$^{13}$)—, wherein R is selected from —COR$^{14}$, —SO$_2$R$^{14}$, —CONR$^{15}$R$^{16}$, and —SO$_2$NR$^{15}$R$^{16}$, wherein R$^{14}$ is an optionally substituted group selected from C1-C6 alkyl, C3-C8 cycloalkyl, saturated or unsaturated 4-8 membered heterocyclyl containing 1-2 heteroatoms independently selected from N, O, and S as ring members, aryl, and heteroaryl containing 1-3 heteroatoms independently selected from N, O, and S as ring members, wherein the optional substituents are 1-3 groups independently selected from R$^6$; wherein R$^{15}$ and R$^{16}$ are independently H or R$^{14}$;

m is 1-2; and v is 1-4.

Embodiment 20

The compound of embodiments 1, 4, 5, 12, and 14 having structure of formula I-Q, I-R, I-S, I-T, I-U, I-V, I-W, or I-X:

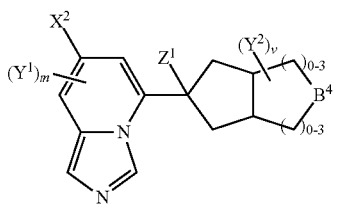
(I-Q)

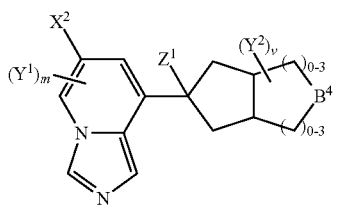
(I-R)

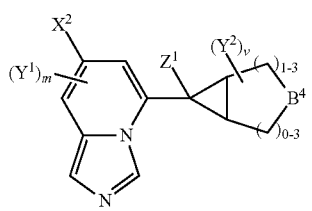
(I-S)

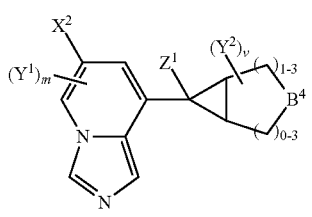
(I-T)

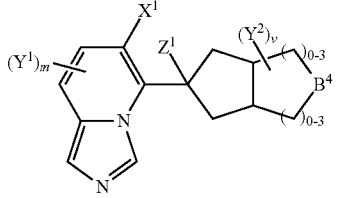
(I-U)

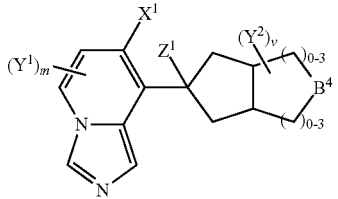
(I-V)

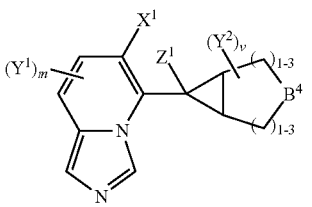
(I-W)

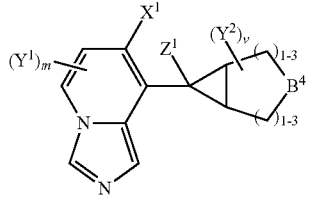
(I-X)

and/or a stereoisomer, a stable isotope, or a pharmaceutically acceptable salt thereof, wherein $Z^1$ is selected from H, OH, CN, halo, and an optionally substituted group selected from C1-C6 alkyl and C1-C6 alkoxy, wherein the optional substituents are 1-3 groups independently selected from $R^6$, $X^1$ and $X^2$ are independently selected from CN, halo, and an optionally substituted group selected from C1-C6 alkyl, C1-C6 haloalkyl, C3-C6 cycloalkyl, and C1-C6 alkoxy, wherein the optional substituents are 1-3 groups independently selected from $R^6$;

$Y^1$ is independently selected from H, D, CN, halo, $NH_2$, and an optionally substituted group selected from C1-C6 alkyl, C1-C6 alkoxy, and C1-C6 alkylamino, wherein the optional substituents are 1-3 groups independently selected from $R^6$;

$Y^2$ is independently selected from H, OH, CN, halo, and an optionally substituted group selected from C1-C4 alkyl and C1-C4 alkoxyl, wherein the optional substituents are 1-3 groups independently selected from $R^6$; or two adjacent $Y^2$ substituents can be taken together to form a C3-C7 cycloalkyl ring or a 4-7 membered heterocyclic ring containing 1-2 heteroatoms independently selected from N, O, and S, wherein the ring formed can be optionally substituted with 1-2 groups independently selected from $R^6$;

$B^4$ is

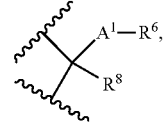

—$C(R^8)(NHR^{13})$—, or $N(R^{13})$—, wherein $R^{13}$ is selected from —$COR^{14}$, —$SO_2R^{14}$, —$CONR^{15}R^{16}$, and —$SO_2NR^{15}R^{16}$, wherein $R^{14}$ is an optionally substituted group selected from C1-C6 alkyl, C3-C8 cycloalkyl, saturated or unsaturated 4-8 membered heterocyclyl containing 1-2 heteroatoms independently selected from N, O, and S as ring members, aryl, and heteroaryl containing 1-3 heteroatoms independently selected from N, O, and S as ring members, wherein the optional substituents are 1-3 groups independently selected from $R^6$; wherein $R^{15}$ and $R^{16}$ are independently H or $R^{14}$;

m is 1-2; and v is 1-4.

Embodiment 21

The compound of embodiments 1, 2, 4, 5, 12, 14, 19, and 20 having structure of formula I-Y. I-Z, I-AA, I-BB, I-CC, I-DD, I-EE, I-FF, or I-GG:

(I-Y)
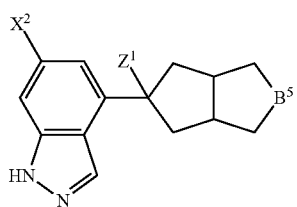

(I-Z)
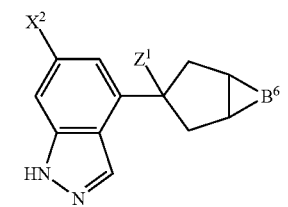

(I-AA)
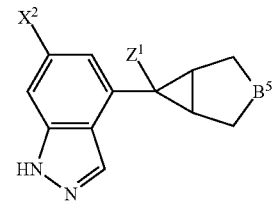

(I-BB)
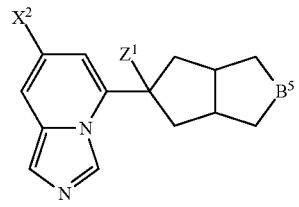

(I-CC)
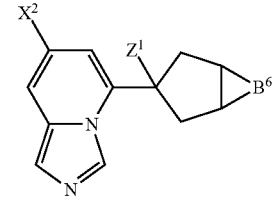

(I-DD)
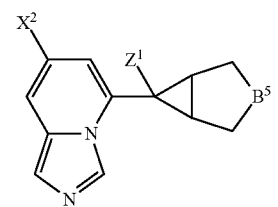

(I-EE)
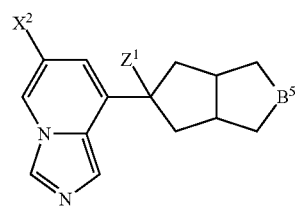

(I-FF)
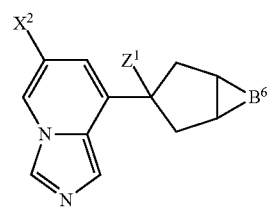

(I-GG)
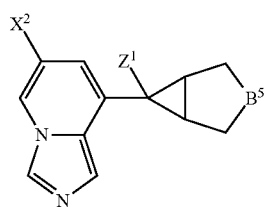

and/or a stereoisomer, a stable isotope, or a pharmaceutically acceptable salt thereof, wherein $Z^1$ is selected from H, OH, CN, halo, and an optionally substituted group selected from C1-C6 alkyl and C1-C6 alkoxy, wherein the optional substituents are 1-3 groups independently selected from $R^6$;

$X^2$ are independently selected from CN, halo, and an optionally substituted group selected from C1-C6 alkyl, C1-C6 haloalkyl, C3-C6 cycloalkyl, and C1-C6 alkoxy, wherein the optional substituents are 1-3 groups independently selected from $R^6$;

$B^5$ is

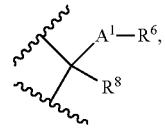

—C($R^8$)(NH$R^{13}$)—, or N($R^{13}$)—, wherein $R^{13}$ is selected from —CO$R^{14}$, —SO$_2$R$^{14}$, —CONR$^{15}$R$^{16}$, and —SO$_2$NR$^{15}$R$^{16}$, wherein $R^{14}$ is an optionally substituted group selected from C1-C6 alkyl, C3-C8 cycloalkyl, saturated or unsaturated 4-8 membered heterocyclyl containing 1-2 heteroatoms independently selected from N, O, and S as ring members, aryl, and heteroaryl containing 1-3 heteroatoms independently selected from N, O, and S as ring members, wherein the optional substituents are 1-3 groups independently selected from $R^6$; wherein $R^{15}$ and $R^{16}$ are independently H or $R^{14}$;

$B^6$ is

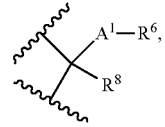

or —C($R^8$)(NH$R^{13}$)—, wherein $R^{13}$ is selected from —COR$^{14}$, —SO$_2$R$^{14}$, —CONR$^{15}$R$^{16}$, and —SO$_2$NR$^{15}$R$^{16}$, wherein $R^{14}$ is an optionally substituted group selected from C1-C6 alkyl, C3-C8 cycloalkyl, saturated or unsaturated 4-8 membered heterocyclyl containing 1-2 heteroatoms independently selected from N, O, and S as ring members, aryl, and heteroaryl containing 1-3 heteroatoms independently selected from N, O, and S as ring members, wherein the optional substituents are 1-3 groups independently selected from $R^6$; wherein $R^{15}$ and $R^{16}$ are independently H or $R^{14}$;

Embodiment 22

The compound of embodiments 17-21 and/or a stereoisomer, a stable isotope, or a pharmaceutically acceptable salt thereof, wherein $X^1$ and $X^2$ are independently selected from halogen, C1-C6 alkyl, C1-C6 haloalkyl, and C3-C6 cycloalkyl.

Embodiment 23

The compound of embodiments 17-22 and/or a stereoisomer, a stable isotope, or a pharmaceutically acceptable salt thereof, wherein $X^1$ and $X^2$ are independently selected from Cl, $CF_3$, and cyclopropyl.

Embodiment 24

The compound of embodiment 1, selected from the following compounds:
6-chloro-4-(4,4-dimethyl-5-(methylsulfonyl)hexahydropyrrolo[3,4-c]pyrrol-2(1H)-yl)-1H-indazole;
6-chloro-4-((3aS,6aR)-4,4-dimethyl-5-(methylsulfonyl)hexahydropyrrolo[3,4-c]pyrrol-2(1H)-yl)-1H-indazole;
6-chloro-4-((3aR,6aS)-4,4-dimethyl-5-(methylsulfonyl)hexahydropyrrolo[3,4-c]pyrrol-2(1H)-yl)-1H-indazole;
(3aR,5r,6aS)-5-(6-chloro-1H-indazol-4-yl)-2-(methylsulfonyl)octahydrocyclopenta[c]pyrrol-5-ol;
N-((2r,3aR,5r,6aS)-5-(6-chloro-1H-indazol-4-yl)-5-hydroxyoctahydropentalen-2-yl)methanesulfonamide;
1-((3aR,5r,6aS)-5-(6-(trifluoromethyl)imidazo[1,5-a]pyridin-8-yl)hexahydrocyclopenta[c]pyrrol-2(1H)-yl)ethanone;
Racemic-6-chloro-4-((3aR,6aS)-2-(methylsulfonyl)-1,2,3,3a,4,6a-hexahydrocyclopenta[c]pyrrol-5-yl)-1H-indazole;
1-((3aR,5r,6aS)-5-(6-chloroimidazo[1,5-a]pyridin-8-yl)-5-hydroxyhexahydrocyclopenta[c]pyrrol-2(1H)-yl)ethanone;
1-((3aR,5r,6aS)-5-(6-chloroimidazo[1,5-a]pyridin-5-yl)-5-hydroxyhexahydrocyclopenta[c]pyrrol-2(1H)-yl)ethanone;
1-((3aR,5r,6aS)-5-(5-chloro-1H-indazol-7-yl)-5-hydroxyhexahydrocyclopenta[c]pyrrol-2(1H)-yl)ethanone;
N'-methyl-N-((1R,3r,5S,6r)-3-(6-chloro-1H-indazol-4-yl)-3-hydroxybicyclo[3.1.0]hexan-6-yl)sulfuric diamide;
N-((1R,3r,5S,6r)-3-hydroxy-3-(6-(trifluoromethyl)-1H-indazol-4-yl)bicyclo[3.1.0]hexan-6-yl)methanesulfonamide;
1-(6-chloro-1H-indazol-4-yl)cyclopropanol;
6-chloro-4-((3aR,6aS)-5-(methylsulfonyl)hexahydropyrrolo[3,4-c]pyrrol-2(1H)-yl)-1H-indazole;
6-chloro-4-(1-(methylsulfonyl)hexahydro-1H-pyrrolo[3,4-b]pyridin-6(2H)-yl)-1H-indazole;
1-((3aR,6aS)-5-(6-chloro-1H-indazol-4-yl)hexahydropyrrolo[3,4-c]pyrrol-2(1H)-yl)ethanone;
1-(6-(6-chloro-1H-indazol-4-yl)octahydro-1H-pyrrolo[3,4-b]pyridin-1-yl)ethanone;
N-((1R,5S)-3-(6-chloro-1H-indazol-4-yl)-3-azabicyclo[3.1.0]hexan-6-yl)methanesulfonamide;
N-((1R,5S)-3-(6-chloro-1H-indazol-4-yl)-3-azabicyclo[3.1.0]hexan-6-yl)acetamide;
1-(5-(6-chloro-1H-indazol-4-yl)-1,1-dimethylhexahydropyrrolo[3,4-c]pyrrol-2(1H)-yl)ethanone;
1-(5-(6-chloro-1H-indazol-4-yl)hexahydropyrrolo[3,4-b]pyrrol-1(2H)-yl)ethanone;
6-chloro-1-methyl-4-(1-(methylsulfonyl)hexahydropyrrolo[3,4-b]pyrrol-5(1H)-yl)-1H-indazole;
N-((1R,5S,6r)-3-(6-chloro-1H-indazol-4-yl)-3-azabicyclo[3.1.0]hexan-6-yl)acetamide;
1-((3aR,5r,6aS)-5-(6-chloro-1H-indazol-4-yl)-5-hydroxyhexahydrocyclopenta[c]pyrrol-2(1H)-yl)ethanone;
6-chloro-4-(1-(methylsulfonyl)hexahydropyrrolo[3,4-b]pyrrol-5(1H)-yl)-1H-indazole;
N-((1R,5S,6r)-3-(6-chloro-1H-indazol-4-yl)-3-azabicyclo[3.1.0]hexan-6-yl)methanesulfonamide;
(1R,3r,5S)-3-(6-chloro-1H-indazol-4-yl)bicyclo[3.1.0]hexan-3-ol;
4-(5-(6-chloro-1H-indazol-4-yl)-1,1-dimethylhexahydropyrrolo[3,4-c]pyrrol-2(1H)-ylsulfonyl)benzonitrile;
4-(5-(6-chloro-1H-indazol-4-yl)-1,1-dimethyloctahydropyrrolo[3,4-c]pyrrole-2-carbonyl)benzonitrile;
6-chloro-4-(5-(cyclopropylsulfonyl)-4,4-dimethylhexahydropyrrolo[3,4-c]pyrrol-2(1H)-yl)-1H-indazole;
(5-(6-chloro-1H-indazol-4-yl)-1,1-dimethylhexahydropyrrolo[3,4-c]pyrrol-2(1H)-yl)(cyclopropyl)methanone;
(2r,3aR,6aS)-2-(6-chloro-1H-indazol-4-yl)octahydropentalen-2-ol;
Racemic-(3 aS,6aR)-5-(6-chloro-1H-indazol-4-yl)-1,1-dimethylhexahydropyrrolo[3,4-c]pyrrole-2(1H)-carboxamide;
(2r,3aR,5s,6aS)-2-(6-chloro-1H-indazol-4-yl)octahydropentalene-2,5-diol;
4-(((3aR,6aS)-5-(6-chloro-1H-indazol-4-yl)hexahydropyrrolo[3,4-c]pyrrol-2(1H)-yl)sulfonyl)benzonitrile;
4-((3aR,6aS)-5-(6-chloro-1H-indazol-4-yl)octahydropyrrolo[3,4-c]pyrrole-2-carbonyl)benzonitrile;
(3aR,5r,6aS)-5-(6-chloro-1H-indazol-4-yl)-2-(phenylsulfonyl)octahydrocyclopenta[c]pyrrol-5-ol;
((3aR,5r,6aS)-5-(6-chloro-1H-indazol-4-yl)-5-hydroxyhexahydrocyclopenta[c]pyrrol-2(1H)-yl)(phenyl)methanone;
(3aR,5r,6aS)-5-(6-chloro-1H-indazol-4-yl)-2-(cyclopropylsulfonyl)octahydrocyclopenta[c]pyrrol-5-ol;
(3aR,5r,6aS)-5-(6-chloro-1H-indazol-4-yl)-5-hydroxyhexahydrocyclopenta[c]pyrrol-2(1H)-yl)(cyclopropyl)methanone;
4-(((3aR,5r,6aS)-5-(6-chloro-1H-indazol-4-yl)-5-hydroxyhexahydrocyclopenta[c]pyrrol-2(1H)-yl)sulfonyl)benzonitrile;
((3aR,5r,6aS)-5-(6-chloro-1H-indazol-4-yl)-5-hydroxyhexahydrocyclopenta[c]pyrrol-2(1H)-yl)(pyridin-4-yl)methanone;
Racemic-1-((3aS,6aR)-5-(6-chloroimidazo[1,5-a]pyridin-8-yl)-1,1-dimethylhexahydropyrrolo[3,4-c]pyrrol-2(1H)-yl)ethanone;
4-((3aR,5r,6aS)-5-(6-chloro-1H-indazol-4-yl)-5-hydroxyoctahydrocyclopenta[c]pyrrole-2-carbonyl)benzonitrile;
Racemic-1-((3aS,6aR)-5-(7-chloroimidazo[1,5-a]pyridin-5-yl)-1,1-dimethylhexahydropyrrolo[3,4-c]pyrrol-2(1H)-yl)ethanone;
Racemic-7-chloro-5-((3aR,6aS)-4,4-dimethyl-5-(methylsulfonyl)hexahydropyrrolo[3,4-c]pyrrol-2(1H)-yl)imidazo[1,5-a]pyridine;
Racemic-1-((3aS,6aR)-1,1-dimethyl-5-(6-(trifluoromethyl)imidazo[1,5-a]pyridin-8-yl)hexahydropyrrolo[3,4-c]pyrrol-2(1H)-yl)ethanone;
Racemic-8-((3aR,6aS)-4,4-dimethyl-5-(methylsulfonyl)hexahydropyrrolo[3,4-c]pyrrol-2(1H)-yl)-6-(trifluoromethyl)imidazo[1,5-a]pyridine;

Racemic-1-((3aS,6aR)-1,1-dimethyl-5-(6-(trifluoromethyl)imidazo[1,5-a]pyridin-5-yl)hexahydropyrrolo[3,4-c]pyrrol-2(1H)-yl)ethanone;

Racemic-5-((3aR,6aS)-4,4-dimethyl-5-(methylsulfonyl)hexahydropyrrolo[3,4-c]pyrrol-2(1H)-yl)-6-(trifluoromethyl)imidazo[1,5-a]pyridine;

Racemic-6-chloro-8-((3aR,6aS)-4,4-dimethyl-5-(methylsulfonyl)hexahydropyrrolo[3,4-c]pyrrol-2(1H)-yl)imidazo[1,5-a]pyridine;

Racemic-5-((3aR,6aS)-4,4-dimethyl-5-(methylsulfonyl)hexahydropyrrolo[3,4-c]pyrrol-2(1H)-yl)-7-(trifluoromethyl)imidazo[1,5-a]pyridine;

Racemic-1-((3aS,6aR)-1,1-dimethyl-5-(7-(trifluoromethyl)imidazo[1,5-a]pyridin-5-yl)hexahydropyrrolo[3,4-c]pyrrol-2(1H)-yl)ethanone;

(3aR,5r,6aS)-5-(6-chloroimidazo[1,5-a]pyridin-8-yl)-2-(methylsulfonyl)octahydrocyclopenta[c]pyrrol-5-ol;

(3aR,5r,6aS)-5-(6-chloroimidazo[1,5-a]pyridin-5-yl)-2-(methylsulfonyl)octahydrocyclopenta[c]pyrrol-5-ol;

(3aR,5r,6aS)-tert-butyl 5-(6-chloro-1H-indazol-4-yl)-5-hydroxyhexahydrocyclopenta[c]pyrrole-2(1H)-carboxylate;

Racemic-6-cyclopropyl-5-((3aR,6aS)-4,4-dimethyl-5-(methylsulfonyl)hexahydropyrrolo[3,4-c]pyrrol-2(1H)-yl)imidazo[1,5-a]pyridine;

Racemic-1-((3aS,6aR)-5-(6-cyclopropylimidazo[1,5-a]pyridin-5-yl)-1,1-dimethylhexahydropyrrolo[3,4-c]pyrrol-2(1H)-yl)ethanone;

Racemic-8-((3aR,6aS)-4,4-dimethyl-5-(methylsulfonyl)hexahydropyrrolo[3,4-c]pyrrol-2(1H)-yl)-7-(trifluoromethyl)imidazo[1,5-a]pyridine;

Racemic-1-((3aS,6aR)-1,1-dimethyl-5-(7-(trifluoromethyl)imidazo[1,5-a]pyridin-8-yl)hexahydropyrrolo[3,4-c]pyrrol-2(1H)-yl)ethanone;

((3aR,5r,6aS)-5-(6-chloro-1H-indazol-4-yl)-5-hydroxyhexahydrocyclopenta[c]pyrrol-2(1H)-yl)(cyclopentyl)methanone;

((3aR,5r,6aS)-5-(6-chloro-1H-indazol-4-yl)-5-hydroxyhexahydrocyclopenta[c]pyrrol-2(1H)-yl)(cyclobutyl)methanone;

(3aR,5r,6aS)-isopropyl 5-(6-chloro-1H-indazol-4-yl)-5-hydroxyhexahydrocyclopenta[c]pyrrole-2(1H)-carboxylate;

((3aR,5r,6aS)-5-(6-chloro-1H-indazol-4-yl)-5-hydroxyhexahydrocyclopenta[c]pyrrol-2(1H)-yl)(cyclohexyl)methanone;

N-((1R,3r,5S,6r)-3-(6-chloro-1H-indazol-4-yl)-3-hydroxybicyclo[3.1.0]hexan-6-yl)methanesulfonamide;

N-((1R,3r,5S,6r)-3-(6-chloro-1H-indazol-4-yl)-3-hydroxybicyclo[3.1.0]hexan-6-yl)acetamide;

1-((3aR,5r,6aS)-5-(6-chloro-1H-indazol-4-yl)-5-hydroxyhexahydrocyclopenta[c]pyrrol-2(1H)-yl)-2-methylpropan-1-one;

((3aR,5R,6aS)-5-(6-chloro-1H-indazol-4-yl)-5-hydroxyhexahydrocyclopenta[c]pyrrol-2(1H)-yl)((1r,4R)-4-hydroxycyclohexyl)methanone;

(3aR,5r,6aS)-methyl 5-(6-chloro-1H-indazol-4-yl)-5-hydroxyhexahydrocyclopenta[c]pyrrole-2(1H)-carboxylate;

((3aR,5r,6aS)-5-(6-chloro-1H-indazol-4-yl)-5-hydroxyhexahydrocyclopenta[c]pyrrol-2(1H)-yl)(tetrahydrofuran-3-yl)methanone;

1-((3aR,5r,6aS)-5-(6-chloro-1H-indazol-4-yl)-5-hydroxyhexahydrocyclopenta[c]pyrrol-2(1H)-yl)-2-cyclopropylethanone;

1-((3aR,5r,6aS)-5-(6-chloro-1H-indazol-4-yl)-5-hydroxyhexahydrocyclopenta[c]pyrrol-2(1H)-yl)propan-1-one;

N-((1R,3r,5S,6r)-3-(6-chloro-1H-indazol-4-yl)-3-hydroxybicyclo[3.1.0]hexan-6-yl)ethanesulfonamide;

N-((1R,3r,5S,6r)-3-(6-chloro-1H-indazol-4-yl)-3-hydroxybicyclo[3.1.0]hexan-6-yl)tetrahydrofuran-3-carboxamide;

N-((1R,3r,5S,6r)-3-(6-chloro-1H-indazol-4-yl)-3-hydroxybicyclo[3.1.0]hexan-6-yl)cyclopropanesulfonamide;

N-((1R,3r,5S,6r)-3-(6-chloro-1H-indazol-4-yl)-3-hydroxybicyclo[3.1.0]hexan-6-yl)cyclopentanesulfonamide;

N-((1R,3r,5S,6r)-3-(6-chloro-1H-indazol-4-yl)-3-hydroxybicyclo[3.1.0]hexan-6-yl)tetrahydrofuran-2-carboxamide;

N-((1R,3r,5S,6r)-3-(6-chloro-1H-indazol-4-yl)-3-hydroxybicyclo[3.1.0]hexan-6-yl)cyclopropanecarboxamide;

N-((1R,3r,5S,6r)-3-(6-chloro-1H-indazol-4-yl)-3-hydroxybicyclo[3.1.0]hexan-6-yl)propane-2-sulfonamide;

N-((1R,3r,5S,6r)-3-(6-chloro-1H-indazol-4-yl)-3-hydroxybicyclo[3.1.0]hexan-6-yl)cyclohexanesulfonamide;

N-((1R,3r,5S,6r)-3-(6-chloro-1H-indazol-4-yl)-3-hydroxybicyclo[3.1.0]hexan-6-yl)cyclopentanecarboxamide;

Methyl ((1R,3r,5S,6r)-3-(6-chloro-1H-indazol-4-yl)-3-hydroxybicyclo[3.1.0]hexan-6-yl)carbamate;

Ethyl ((1R,3r,5S,6r)-3-(6-chloro-1H-indazol-4-yl)-3-hydroxybicyclo[3.1.0]hexan-6-yl)carbamate;

N-((1R,3r,5S,6r)-3-(6-chloro-1H-indazol-4-yl)-3-hydroxybicyclo[3.1.0]hexan-6-yl)propionamide;

N-((1R,3r,5S,6r)-3-(6-chloro-1H-indazol-4-yl)-3-hydroxybicyclo[3.1.0]hexan-6-yl)isonicotinamide;

N-((1R,3r,5S,6r)-3-(6-chloro-1H-indazol-4-yl)-3-hydroxybicyclo[3.1.0]hexan-6-yl)cyclobutanecarboxamide;

N-((1R,3r,5S,6r)-3-(6-chloro-1H-indazol-4-yl)-3-hydroxybicyclo[3.1.0]hexan-6-yl)cyclohexanecarboxamide;

Isopropyl ((1R,3r,5S,6r)-3-(6-chloro-1H-indazol-4-yl)-3-hydroxybicyclo[3.1.0]hexan-6-yl)carbamate;

(3aR,5r,6aS)-5-(6-chloro-1H-indazol-4-yl)-5-hydroxy-N-methylhexahydrocyclopenta[c]pyrrole-2(1H)-sulfonamide;

((3aR,5r,6aS)-5-(6-chloro-1H-indazol-4-yl)-5-hydroxyhexahydrocyclopenta[c]pyrrol-2(1H)-yl)(tetrahydro-2H-pyran-4-yl)methanone;

1-((3aR,5r,6aS)-5-(5-chloro-1H-indazol-7-yl)-5-hydroxyhexahydrocyclopenta[c]pyrrol-2(1H)-yl)ethanone;

N-((1R,3r,5S,6r)-3-(6-chloro-1H-indazol-4-yl)-3-hydroxybicyclo[3.1.0]hexan-6-yl)pivalamide;

N-((1R,3r,5S,6r)-3-(6-chloro-1H-indazol-4-yl)-3-hydroxybicyclo[3.1.0]hexan-6-yl)tetrahydro-2H-pyran-4-carboxamide;

N-((1R,3r,5S,6r)-3-(6-chloro-1H-indazol-4-yl)-3-hydroxybicyclo[3.1.0]hexan-6-yl)isobutyramide;

N-((1R,3r,5S,6r)-3-(6-chloro-1H-indazol-4-yl)-3-hydroxybicyclo[3.1.0]hexan-6-yl)benzamide;

N-((1R,3r,5S,6r)-3-(6-chloro-1H-indazol-4-yl)-3-hydroxybicyclo[3.1.0]hexan-6-yl)tetrahydro-2H-pyran-4-sulfonamide;

N-((1R,3r,5S,6r)-3-(6-chloro-1H-indazol-4-yl)-3-hydroxybicyclo[3.1.0]hexan-6-yl)benzenesulfonamide;

(3aR,5r,6aS)-5-(5-chloro-1H-indazol-7-yl)-2-(methylsulfonyl)octahydrocyclopenta[c]pyrrol-5-ol;

((3aR,5r,6aS)-5-(5-chloro-1H-indazol-7-yl)-5-hydroxyhexahydrocyclopenta[c]pyrrol-2(1H)-yl)(tetrahydro-2H-pyran-4-yl)methanone;

((3aR,5r,6aS)-5-(5-chloro-1H-indazol-7-yl)-5-hydroxyhexahydrocyclopenta[c]pyrrol-2(1H)-yl)(phenyl)methanone;

((3aR,5r,6aS)-5-(5-chloro-1H-indazol-7-yl)-5-hydroxyhexahydrocyclopenta[c]pyrrol-2(1H)-yl)(cyclopropyl)methanone;

(3aR,5r,6aS)-5-(5-chloro-1H-indazol-7-yl)-2-(cyclopropylsulfonyl)octahydrocyclopenta[c]pyrrol-5-ol;

(3aR,5r,6aS)-5-(5-chloro-1H-indazol-7-yl)-2-((tetrahydro-2H-pyran-4-yl)sulfonyl)octahydrocyclopenta[c]pyrrol-5-ol;

(3aR,5r,6aS)-5-(5-chloro-1H-indazol-7-yl)-2-(phenylsulfonyl)octahydrocyclopenta[c]pyrrol-5-ol;

2-amino-N-((1R,3r,5S,6r)-3-(6-chloro-1H-indazol-4-yl)-3-hydroxybicyclo[3.1.0]hexan-6-yl)acetamide hydrochloride;

1-((3aR,6aS)-5-((6-chloro-1H-indazol-4-yl)(hydroxy)methyl)hexahydrocyclopenta[c]pyrrol-2(1H)-yl)ethanone;

(6-chloro-1H-indazol-4-yl)((3aR,6aS)-2-(methylsulfonyl)octahydrocyclopenta[c]pyrrol-5-yl)methanol;

(2r,3aR,5s,6aS)-2-(5-chloro-1H-indazol-7-yl)octahydropentalene-2,5-diol;

N-((1R,3r,5S,6r)-3-(5-chloro-1H-indazol-7-yl)-3-hydroxybicyclo[3.1.0]hexan-6-yl)cyclopropanecarboxamide;

N-((1R,3r,5S,6r)-3-(5-chloro-1H-indazol-7-yl)-3-hydroxybicyclo[3.1.0]hexan-6-yl)acetamide;

N-((1R,3r,5S,6r)-3-(5-chloro-1H-indazol-7-yl)-3-hydroxybicyclo[3.1.0]hexan-6-yl)methanesulfonamide;

N-((1R,3r,5S,6r)-3-(5-chloro-1H-indazol-7-yl)-3-hydroxybicyclo[3.1.0]hexan-6-yl)cyclopropanesulfonamide;

1R,3r,5S)-3-(6-chloro-1H-indazol-4-yl)-6-(hydroxymethyl)bicyclo[3.1.0]hexan-3-ol;

1-((3aR,6aS)-5-((5-chloro-1H-indazol-7-yl)(hydroxy)methyl)hexahydrocyclopenta[c]pyrrol-2(1H)-yl)ethanone;

(5-chloro-1H-indazol-7-yl)((3aR,6aS)-2-(methylsulfonyl)octahydrocyclopenta[c]pyrrol-5-yl)methanol;

1-((1R,3r,5S,6r)-3-(6-chloro-1H-indazol-4-yl)-3-hydroxybicyclo[3.1.0]hexan-6-yl)-3-methylurea;

1-((1R,3r,5S,6r)-3-(6-chloro-1H-indazol-4-yl)-3-hydroxybicyclo[3.1.0]hexan-6-yl)-3-phenylurea;

(3aR,5r,6aS)-5-(6-chloro-1H-indazol-4-yl)-2-(pyridin-4-yl)octahydrocyclopenta[c]pyrrol-5-ol;

(3aR,5r,6aS)-5-(5-chloro-1H-indazol-7-yl)-2-(pyridin-4-yl)octahydrocyclopenta[c]pyrrol-5-ol;

(1R,3r,5S)-3-(5-chloro-1H-indazol-7-yl)bicyclo[3.1.0]hexan-3-ol;

4-chloro-N-((1R,3r,5S,6r)-3-(6-chloro-1H-indazol-4-yl)-3-hydroxybicyclo[3.1.0]hexan-6-yl)benzamide;

1-((1R,3r,5S,6r)-3-(6-chloro-1H-indazol-4-yl)-3-hydroxybicyclo[3.1.0]hexan-6-yl)-3-cyclopropylurea;

1-((1R,3r,5S,6r)-3-(6-chloro-1H-indazol-4-yl)-3-hydroxybicyclo[3.1.0]hexan-6-yl)-3-(4-chlorophenyl)urea;

1-((1R,3r,5S,6r)-3-(6-chloro-1H-indazol-4-yl)-3-hydroxybicyclo[3.1.0]hexan-6-yl)-3-(3-chlorophenyl)urea;

N'-cyclohexyl-N-((1R,3r,5S,6r)-3-(6-chloro-1H-indazol-4-yl)-3-hydroxybicyclo[3.1.0]hexan-6-yl)sulfuric diamide;

3-chloro-N-((1R,3r,5S,6r)-3-(6-chloro-1H-indazol-4-yl)-3-hydroxybicyclo[3.1.0]hexan-6-yl)benzamide;

1-((1R,3r,5S,6r)-3-(6-chloro-1H-indazol-4-yl)-3-hydroxybicyclo[3.1.0]hexan-6-yl)-3-ethylurea;

1-((1R,3r,5S,6r)-3-(6-chloro-1H-indazol-4-yl)-3-hydroxybicyclo[3.1.0]hexan-6-yl)-3-cyclohexylurea;

N-((1R,3r,5S,6r)-3-(6-chloro-1H-indazol-4-yl)-3-hydroxybicyclo[3.1.0]hexan-6-yl)-4-(2-methoxyphenyl)-1H-pyrrole-3-carboxamide;

N'-ethyl-N-((1R,3r,5S,6r)-3-(6-chloro-1H-indazol-4-yl)-3-hydroxybicyclo[3.1.0]hexan-6-yl)sulfuric diamide;

N-((1R,3r,5S,6r)-3-(5-chloro-1H-indazol-7-yl)-3-hydroxybicyclo[3.1.0]hexan-6-yl)benzamide;

N-((1R,3r,5S,6r)-3-(5-chloro-1H-indazol-7-yl)-3-hydroxybicyclo[3.1.0]hexan-6-yl)isonicotinamide;

N-((1R,3r,5S,6r)-3-(5-chloro-1H-indazol-7-yl)-3-hydroxybicyclo[3.1.0]hexan-6-yl)benzenesulfonamide;

1-((1R,3r,5S,6r)-3-(5-chloro-1H-indazol-7-yl)-3-hydroxybicyclo[3.1.0]hexan-6-yl)-3-phenylurea;

1-((1R,3r,5S,6r)-3-(5-chloro-1H-indazol-7-yl)-3-hydroxybicyclo[3.1.0]hexan-6-yl)-3-methylurea;

(5-chloro-1H-benzo[d]imidazol-2-yl)((3aR,5r,6aS)-5-(6-chloro-1H-indazol-4-yl)-5-hydroxyhexahydrocyclopenta[c]pyrrol-2(1H)-yl)methanone;

1-((1R,3r,5S,6r)-3-(6-chloro-1H-indazol-4-yl)-3-hydroxybicyclo[3.1.0]hexan-6-yl)urea;

5-chloro-N-((1R,3r,5S,6r)-3-(6-chloro-1H-indazol-4-yl)-3-hydroxybicyclo[3.1.0]hexan-6-yl)-1H-benzo[d]imidazole-2-carboxamide;

N-((1R,3r,5S,6r)-3-(6-chloro-1H-indazol-4-yl)-3-hydroxybicyclo[3.1.0]hexan-6-yl)-2-cyanoacetamide;

N-((1R,3r,5S,6r)-3-(6-chloro-1H-indazol-4-yl)-3-hydroxybicyclo[3.1.0]hexan-6-yl)-3,3,3-trifluoropropanamide;

N-((1R,3r,5S,6r)-3-(6-chloro-1H-indazol-4-yl)-3-hydroxybicyclo[3.1.0]hexan-6-yl)-2,2,2-trifluoroethanesulfonamide;

N-((1R,3r,5S,6r)-3-(6-chloro-1H-indazol-4-yl)-3-hydroxybicyclo[3.1.0]hexan-6-yl)sulfuric diamide;

N-((1R,3r,5S,6r)-3-(6-chloro-1H-indazol-4-yl)-3-hydroxybicyclo[3.1.0]hexan-6-yl)-3-(methylsulfonamido)benzamide;

N-((1R,3r,5S,6r)-3-(6-chloro-1H-indazol-4-yl)-3-hydroxybicyclo[3.1.0]hexan-6-yl)-3-(trifluoromethyl)benzamide;

N-((1R,3r,5S,6r)-3-(6-chloro-1H-indazol-4-yl)-3-hydroxybicyclo[3.1.0]hexan-6-yl)-3-fluorobenzamide;

N-((1R,3r,5S,6r)-3-(6-chloro-1H-indazol-4-yl)-3-hydroxybicyclo[3.1.0]hexan-6-yl)-3-cyanobenzamide;

N-((1R,3r,5S,6r)-3-(6-chloro-1H-indazol-4-yl)-3-hydroxybicyclo[3.1.0]hexan-6-yl)-3-(trifluoromethoxy)benzamide;

3-bromo-N-((1R,3r,5S,6r)-3-(6-chloro-1H-indazol-4-yl)-3-hydroxybicyclo[3.1.0]hexan-6-yl)benzamide;

1-((1R,3r,5S,6r)-3-(6-chloro-1H-indazol-4-yl)-3-hydroxybicyclo[3.1.0]hexan-6-yl)-3-(4-fluorophenyl)urea;

N-((1R,3r,5S,6r)-3-(6-chloro-1H-indazol-4-yl)-3-hydroxybicyclo[3.1.0]hexan-6-yl)nicotinamide;

N-((1R,3r,5S,6r)-3-(6-chloro-1H-indazol-4-yl)-3-hydroxybicyclo[3.1.0]hexan-6-yl)-2-(4-chlorophenyl)acetamide;

3-chloro-N-((1R,3r,5S,6r)-3-(6-chloro-1H-indazol-4-yl)-3-hydroxybicyclo[3.1.0]hexan-6-yl)-4-fluorobenzamide;

3-acetamido-N-((1R,3r,5S,6r)-3-(6-chloro-1H-indazol-4-yl)-3-hydroxybicyclo[3.1.0]hexan-6-yl)benzamide;

3-chloro-N-((1R,3r,5S,6r)-3-(6-chloro-1H-indazol-4-yl)-3-hydroxybicyclo[3.1.0]hexan-6-yl)-5-fluorobenzamide;

N-((1R,3r,5S,6r)-3-(6-chloro-1H-indazol-4-yl)-3-hydroxybicyclo[3.1.0]hexan-6-yl)-3-(methylsulfonyl)benzamide;

N-((1R,3r,5S,6r)-3-(6-chloro-1H-indazol-4-yl)-3-hydroxybicyclo[3.1.0]hexan-6-yl)-5-methylisoxazole-3-carboxamide;

N-((1R,3r,5S,6r)-3-(6-chloro-1H-indazol-4-yl)-3-hydroxybicyclo[3.1.0]hexan-6-yl)-1-methyl-1H-pyrazole-4-carboxamide;

N-((1R,3r,5S,6r)-3-(6-chloro-1H-indazol-4-yl)-3-hydroxybicyclo[3.1.0]hexan-6-yl)-2-(trifluoromethyl)isonicotinamide;

N1-((1R,3r,5S,6r)-3-(6-chloro-1H-indazol-4-yl)-3-hydroxybicyclo[3.1.0]hexan-6-yl)isophthalamide;

N-((1R,3r,5S,6r)-3-(6-chloro-1H-indazol-4-yl)-3-hydroxybicyclo[3.1.0]hexan-6-yl)isoxazole-4-carboxamide;

N-((1R,3r,5S,6r)-3-(6-chloro-1H-indazol-4-yl)-3-hydroxybicyclo[3.1.0]hexan-6-yl)-1,2,5-oxadiazole-3-carboxamide;

N'-propyl-N-((1R,3r,5S,6r)-3-(6-chloro-1H-indazol-4-yl)-3-hydroxybicyclo[3.1.0]hexan-6-yl)sulfuric diamide;

N-((1R,3r,5S,6r)-3-(6-chloro-1H-indazol-4-yl)-3-hydroxybicyclo[3.1.0]hexan-6-yl)-2-(trifluoromethoxy)isonicotinamide;

N'-methyl-N-((1R,3r,5S,6r)-3-hydroxy-3-(6-(trifluoromethyl)-1H-indazol-4-yl)bicyclo[3.1.0]hexan-6-yl)sulfuric diamide;

3-chloro-N-((1R,3r,5S,6r)-3-hydroxy-3-(6-(trifluoromethyl)-1H-indazol-4-yl)bicyclo[3.1.0]hexan-6-yl)benzamide;

N-((1R,3r,5S,6r)-3-hydroxy-3-(6-(trifluoromethyl)-1H-indazol-4-yl)bicyclo[3.1.0]hexan-6-yl)acetamide;

(3aR,5r,6aS)-5-(6-chloro-1H-indazol-4-yl)-N-(4-chlorophenyl)-5-hydroxyhexahydrocyclopenta[c]pyrrole-2(1H)-carboxamide;

3-chloro-N-((2r,3aR,5r,6aS)-5-(6-chloro-1H-indazol-4-yl)-5-hydroxyoctahydropentalen-2-yl)benzamide;

N-((2r,3aR,5r,6aS)-5-(6-chloro-1H-indazol-4-yl)-5-hydroxyoctahydropentalen-2-yl)acetamide;

N-((1R,3r,5S,6r)-3-(6-chloro-1H-indazol-4-yl)-3-hydroxybicyclo[3.1.0]hexan-6-yl)-3,4-difluorobenzamide;

N-((1R,3r,5S,6r)-3-(6-chloro-1H-indazol-4-yl)-3-hydroxybicyclo[3.1.0]hexan-6-yl)quinoline-4-carboxamide;

5-Bromo-N-((1R,3r,5S,6r)-3-(6-chloro-1H-indazol-4-yl)-3-hydroxybicyclo[3.1.0]hexan-6-yl)nicotinamide;

N-((1R,3r,5S,6r)-3-(6-chloro-1H-indazol-4-yl)-3-hydroxybicyclo[3.1.0]hexan-6-yl)-[1,1'-biphenyl]-3-carboxamide;

N-((1R,3r,5S,6r)-3-(6-chloro-1H-indazol-4-yl)-3-hydroxybicyclo[3.1.0]hexan-6-yl)-4-fluoro-3-(trifluoromethyl)benzamide;

N-((1R,3r,5S,6r)-3-(6-chloro-1H-indazol-4-yl)-3-hydroxybicyclo[3.1.0]hexan-6-yl)-5-fluoronicotinamide;

N-((1R,3r,5S,6r)-3-(6-chloro-1H-indazol-4-yl)-3-hydroxybicyclo[3.1.0]hexan-6-yl)-3-ethynylbenzamide;

1-((3aR,5r,6aS)-5-(6-chloro-1H-indazol-4-yl)-5-hydroxyhexahydrocyclopenta[c]pyrrol-2(1H)-yl)-2-(4-chlorophenyl)ethanone;

3-bromo-N-((1R,3r,5S,6r)-3-(6-chloro-1H-indazol-4-yl)-3-hydroxybicyclo[3.1.0]hexan-6-yl)-4-fluorobenzamide;

N-((1R,3r,5S,6r)-3-(6-chloro-1H-indazol-4-yl)-3-hydroxybicyclo[3.1.0]hexan-6-yl)-6-fluoroquinoline-4-carboxamide;

N-((1R,3r,5S,6r)-3-(6-chloro-1H-indazol-4-yl)-3-hydroxybicyclo[3.1.0]hexan-6-yl)-3-cyclopropylbenzamide;

5-chloro-N-((1R,3r,5S,6r)-3-(6-chloro-1H-indazol-4-yl)-3-hydroxybicyclo[3.1.0]hexan-6-yl)nicotinamide;

N-((1R,3r,5S,6r)-3-(6-chloro-1H-indazol-4-yl)-3-hydroxybicyclo[3.1.0]hexan-6-yl)-4-fluoro-3-(trifluoromethoxy)benzamide;

N-((1R,3r,5S,6r)-3-(6-chloro-1H-indazol-4-yl)-3-hydroxybicyclo[3.1.0]hexan-6-yl)-5-cyanonicotinamide;

N-((1R,3r,5S,6r)-3-(6-chloro-1H-indazol-4-yl)-3-hydroxybicyclo[3.1.0]hexan-6-yl)-5-(trifluoromethyl)nicotinamide;

Racemic-N-((1S,5R,6S)-3-(6-chloro-1H-indazol-4-yl)bicyclo[3.1.0]hex-2-en-6-yl)cyclopropanecarboxamide;

(1R,5S,6r)-6-(6-chloro-1H-indazol-4-yl)-3-(methylsulfonyl)-3-azabicyclo[3.1.0]hexan-6-ol;

N-(((1R,3r,5S,6s)-3-(6-chloro-1H-indazol-4-yl)-3-hydroxybicyclo[3.1.0]hexan-6-yl)methyl)acetamide;

N-(((1R,3r,5S,6s)-3-(6-chloro-1H-indazol-4-yl)-3-hydroxybicyclo[3.1.0]hexan-6-yl)methyl)methanesulfonamide;

N-((1R,3r,5S,6r)-3-(6-chloro-1H-indazol-4-yl)-3-hydroxybicyclo[3.1.0]hexan-6-yl)-5-(trifluoromethoxy)nicotinamide;

N-((1R,3r,5S,6r)-3-(6-chloro-1H-indazol-4-yl)-3-hydroxybicyclo[3.1.0]hexan-6-yl)-5-(trifluoromethyl)isoxazole-3-carboxamide;

N-((1R,3r,5S,6r)-3-(6-chloro-1H-indazol-4-yl)-3-hydroxybicyclo[3.1.0]hexan-6-yl)-3-(trifluoromethyl)isoxazole-5-carboxamide;

1-((1R,5S,6r)-6-(6-chloro-1H-indazol-4-yl)-6-hydroxy-3-azabicyclo[3.1.0]hexan-3-yl)ethanone;

((1R,5S,6r)-6-(6-chloro-1H-indazol-4-yl)-6-hydroxy-3-azabicyclo[3.1.0]hexan-3-yl)(cyclopropyl)methanone;

(1R,5S,6r)-6-(6-chloro-1H-indazol-4-yl)-3-(cyclopropylsulfonyl)-3-azabicyclo[3.1.0]hexan-6-ol;

(1R,5S,6r)-6-(6-chloro-1H-indazol-4-yl)-6-hydroxy-N-methyl-3-azabicyclo[3.1.0]hexane-3-sulfonamide;

((1R,5S,6r)-6-(6-chloro-1H-indazol-4-yl)-6-hydroxy-3-azabicyclo[3.1.0]hexan-3-yl)(5-chloropyridin-3-yl)methanone;

N-((1R,3s,5S,6s)-6-(6-chloro-1H-indazol-4-yl)-6-hydroxybicyclo[3.1.0]hexan-3-yl)acetamide;

N-((1R,3s,5S,6s)-6-(6-chloro-1H-indazol-4-yl)-6-hydroxybicyclo[3.1.0]hexan-3-yl)methanesulfonamide;

N'-methyl-N-((1R,3s,5S,6s)-6-(6-chloro-1H-indazol-4-yl)-6-hydroxybicyclo[3.1.0]hexan-3-yl)sulfuric diamide;

N'-methyl-N-((2r,3aR,5r,6aS)-5-(6-chloro-1H-indazol-4-yl)-5-hydroxyoctahydropentalen-2-yl)sulfuric diamide;

N'-phenyl-N-((1R,3r,5S,6r)-3-(6-chloro-1H-indazol-4-yl)-3-hydroxybicyclo[3.1.0]hexan-6-yl)sulfuric diamide;

N'-(4-chlorophenyl)-N-((1R,3r,5S,6r)-3-(6-chloro-1H-indazol-4-yl)-3-hydroxybicyclo[3.1.0]hexan-6-yl)sulfuric diamide;

N'-(3-chlorophenyl)-N-((1R,3r,5S,6r)-3-(6-chloro-1H-indazol-4-yl)-3-hydroxybicyclo[3.1.0]hexan-6-yl)sulfuric diamide;

N-((1R,3r,5S,6r)-3-(6-chloro-1H-indazol-4-yl)-3-hydroxybicyclo[3.1.0]hexan-6-yl)-1-phenylmethanesulfonamide;

N-(((1R,3r,5S,6r)-3-(6-chloro-1H-indazol-4-yl)-3-hydroxybicyclo[3.1.0]hexan-6-yl)methyl)methanesulfonamide;

N-(((1R,3r,5S,6r)-3-(6-chloro-1H-indazol-4-yl)-3-hydroxybicyclo[3.1.0]hexan-6-yl)methyl)acetamide;

(1R,3r,5S,6r)-3-(6-chloro-1H-indazol-4-yl)-3-hydroxybicyclo[3.1.0]hexane-6-carboxamide;

(1R,3r,5S,6r)-3-(6-chloro-1H-indazol-4-yl)-3-hydroxy-N-methylbicyclo[3.1.0]hexane-6-carboxamide;

N-((1R,3r,5S,6r)-3-(6-chloroimidazo[1,5-a]pyridin-8-yl)-3-hydroxybicyclo[3.1.0]hexan-6-yl)methanesulfonamide;

N'-methyl-N-((1R,3r,5S,6r)-3-(6-chloroimidazo[1,5-a]pyridin-8-yl)-3-hydroxybicyclo[3.1.0]hexan-6-yl)sulfuric diamide;

N-((1R,3r,5S,6r)-3-(6-chloroimidazo[1,5-a]pyridin-8-yl)-3-hydroxybicyclo[3.1.0]hexan-6-yl)acetamide;

3-chloro-N-((1R,3r,5S,6r)-3-(6-chloroimidazo[1,5-a]pyridin-8-yl)-3-hydroxybicyclo[3.1.0]hexan-6-yl)benzamide;

N-((1R,3r,5S,6r)-3-(6-chloroimidazo[1,5-a]pyridin-8-yl)-3-hydroxybicyclo[3.1.0]hexan-6-yl)-3-fluorobenzamide;
3-bromo-N-((1R,3r,5S,6r)-3-(6-chloroimidazo[1,5-a]pyridin-8-yl)-3-hydroxybicyclo[3.1.0]hexan-6-yl)benzamide;
N-((1R,3r,5S,6r)-3-(6-chloroimidazo[1,5-a]pyridin-8-yl)-3-hydroxybicyclo[3.1.0]hexan-6-yl)-3-cyanobenzamide;
N-((1R,3r,5S,6r)-3-(6-chloroimidazo[1,5-a]pyridin-8-yl)-3-hydroxybicyclo[3.1.0]hexan-6-yl)-3-(trifluoromethyl)benzamide;
N-((1R,3r,5S,6r)-3-(6-chloroimidazo[1,5-a]pyridin-8-yl)-3-hydroxybicyclo[3.1.0]hexan-6-yl)-3-(trifluoromethoxy)benzamide;
N-((1R,3r,5S,6r)-3-(6-chloroimidazo[1,5-a]pyridin-8-yl)-3-hydroxybicyclo[3.1.0]hexan-6-yl)nicotinamide;
5-chloro-N-((1R,3r,5S,6r)-3-(6-chloroimidazo[1,5-a]pyridin-8-yl)-3-hydroxybicyclo[3.1.0]hexan-6-yl)nicotinamide;
N-((1R,3r,5S,6r)-3-(6-chloroimidazo[1,5-a]pyridin-8-yl)-3-hydroxybicyclo[3.1.0]hexan-6-yl)-5-fluoronicotinamide;
5-chloro-N-((1R,3r,5S,6r)-3-(6-chloroimidazo[1,5-a]pyridin-8-yl)-3-hydroxybicyclo[3.1.0]hexan-6-yl)nicotinamide;
N-((1R,3r,5S,6r)-3-(6-chloroimidazo[1,5-a]pyridin-8-yl)-3-hydroxybicyclo[3.1.0]hexan-6-yl)-5-cyanonicotinamide;
N-((1R,3r,5S,6r)-3-(6-chloroimidazo[1,5-a]pyridin-8-yl)-3-hydroxybicyclo[3.1.0]hexan-6-yl)-5-(trifluoromethyl)nicotinamide;
N-((1R,3r,5S,6r)-3-(6-chloroimidazo[1,5-a]pyridin-8-yl)-3-hydroxybicyclo[3.1.0]hexan-6-yl)-5-(trifluoromethoxy)nicotinamide;
3-chloro-N-((1R,3r,5S,6r)-3-(6-chloroimidazo[1,5-a]pyridin-8-yl)-3-hydroxybicyclo[3.1.0]hexan-6-yl)-4-fluorobenzamide;
3-chloro-N-((1R,3r,5S,6r)-3-(6-chloroimidazo[1,5-a]pyridin-8-yl)-3-hydroxybicyclo[3.1.0]hexan-6-yl)-5-fluorobenzamide; and
N-((1R,3r,5S,6r)-3-(6-chloroimidazo[1,5-a]pyridin-8-yl)-3-hydroxybicyclo[3.1.0]hexan-6-yl)-5-methylisoxazole-3-carboxamide;
N-((1R,3r,5S,6r)-3-(6-chloro-1H-indazol-4-yl)-3-hydroxybicyclo[3.1.0]hexan-6-yl)-2-hydroxyacetamide;
N-((1R,3r,5S,6r)-3-(6-chloro-1H-indazol-4-yl)-3-hydroxybicyclo[3.1.0]hexan-6-yl)-2-hydroxy-2-phenylacetamide;
N-((1R,3r,5S,6r)-3-(6-chloro-1H-indazol-4-yl)-3-hydroxybicyclo[3.1.0]hexan-6-yl)-6-methoxynicotinamide;
(1R,3r,5S)-3-(6-chloro-1H-indazol-4-yl)bicyclo[3.1.0]hexane-3,6-diol;
(1R,5S,6s)-6-(6-chloro-1H-indazol-4-yl)bicyclo[3.1.0]hexane-3,6-diol;
(3aR,5r,6aS)-5-(6-chloro-1H-indazol-4-yl)hexahydro-1H-cyclopenta[c]furan-5-ol;
and pharmaceutically acceptable salt thereof.

Embodiment 25

A pharmaceutical composition comprising a compound according to any one of embodiments 1-24 admixed with at least one pharmaceutically acceptable excipient.

Embodiment 26

The pharmaceutical composition of embodiment 25, further comprising at least one therapeutic co-agent or co-treatment selected from anti-viral agents, chemotherapeutics or other anti-cancer agents, immune enhancers, immunosuppressants, radiation, anti-tumor and anti-viral vaccines, agents for cytokine therapy, another indoleamine 2,3-dioxygenase 1 (IDO1) inhibitor, and kinase inhibitors.

Embodiment 27

The pharmaceutical composition of embodiment 26, wherein the at least one therapeutic co-agent or co-treatment is combined with the compound in a single dosage form, or the at least one therapeutic co-agent is administered simultaneously or sequentially as separate dosage forms.

Embodiment 28

The pharmaceutical composition of embodiments 26-27, wherein the therapeutic co-agent is anticancer compound selected from chemotherapeutic or other anti-cancer agent, immune enhancer, immune checkpoint inhibitor, radiation, anti-tumor vaccine, agent for cytokine therapy, and kinase inhibitor.

Embodiment 29

A method to treat cancer, comprising administering to a subject in need of such treatment a therapeutically effective amount of a compound according to any of embodiments 1-24 or a pharmaceutical composition of any of embodiments 25-28.

Embodiment 30

The method of embodiment 29, wherein the cancer is selected from adenoma, bladder cancer, brain cancer, breast cancer, cervical cancer, colorectal cancer, colon cancer, epidermal carcinoma, follicular carcinoma, genitourinary cancers, glioblastoma, head and neck cancers, Hodgkin's disease, non-Hodgkin's lymphoma, hepatoma, head and neck cancers, kidney cancer, lung cancers such as small cell or non-small cell lung cancer, leukemias such as AML or CML, multiple myeloma, lymphoid disorders, skin cancers including melanoma, neuroblastoma, ovarian cancer, pancreatic cancer, prostate cancer, rectal cancer, sarcoma, testicular cancer, thyroid cancer.

Embodiment 31

A method for treating a disease associated with TDO2 and/or IDO1 mediated immunosuppression in a subject in need thereof, comprising administering an effective TDO2 and/or IDO1 inhibiting amount of a compound according to any one of embodiments 1-24 or a pharmaceutical composition according to any of embodiments 25-28.

Embodiment 32

A method of embodiment 31, wherein the treatment comprises co-administering a therapeutic co-agent or co-treatment selected from an anti-viral agent, chemotherapeutic or other anti-cancer agent, immune enhancer, immunosuppressant, radiation, anti-tumor or anti-viral vaccine, agent for cytokine therapy, and kinase inhibitor.

Embodiment 33

The method of embodiment 32, wherein the administering the compound is conducted simultaneously or serially with the administering the therapeutic co-agent.

Embodiment 34

The method of embodiment 32, wherein administering the therapeutic co-agent comprises an IDO1 inhibitor.

Embodiment 35

The method of embodiment 32, wherein the administering the therapeutic co-agent comprises inhibitors of PD-1 or PD-L1.

Embodiment 36

The method of embodiment 35, wherein the therapeutic co-agent is pembrolizumab, nivolumab, pidilizumab, BMS 936559, atezolizumab, or avelumab.

Embodiment 37

A kit comprising a compound according to any of embodiments 1-24 or a pharmaceutically acceptable salt thereof, or a pharmaceutical composition according to any of embodiments 25-28, and a therapeutic co-agent.

Embodiment 38

The kit of embodiment 37, wherein the therapeutic co-agent is pembrolizumab, nivolumab, pidilizumab, BMS 936559, atezolizumab, or avelumab.

Embodiment 39

A compound according to any one of embodiments 1-24 or a pharmaceutically acceptable salt thereof, or a pharmaceutical composition according to any of embodiments 25-28 for use as a medicament.

Embodiment 40

Use of a compound according to any one of embodiments 1 to 24 or a pharmaceutically acceptable salt thereof in the manufacture of a medicament for the treatment of cancer; or use of a compound according to any one of embodiments 1-24 or a pharmaceutically acceptable salt thereof in medicine for treatment of a cancer.

Embodiment 41

A method for treating a disease associated with TDO2 and/or IDO1 in kynurenine pathway in a patient comprising administering to a subject in need of such treatment a therapeutically effective amount of a compound according to any of embodiments 1-24 or a pharmaceutically acceptable salt thereof, or a pharmaceutical composition of any of embodiments 25-28, and a pharmaceutically acceptable carrier, wherein the disease is selected from cancer, viral infection, depression, neurodegenerative disorder, trauma, age-related cataracts, organ transplantation, and autoimmune.

Embodiment 42

The method according to embodiment 41, wherein the viral infection is HIV infection.

Embodiment 43

The method according to embodiment 41, wherein the neurodegenerative disorder is Alzheimer's disease or Huntington's disease.

Embodiment 44

The method according to embodiment 41, wherein the autoimmune disease is asthma, rheumatoid arthritis, multiple sclerosis, inflammatory bowel disease, psoriasis or systemic lupus erythematosusor.

In some embodiments of the compounds of formula I and other embodiments disclosed above, $R^1$ and $R^2$ are halogen, alkyl, haloalkyl, or C1-C6 cycloalkyl, such Cl, $CF_3$ or cyclopropyl.

Also disclosed herein is a pharmaceutical composition, comprising a compound of formula I (such as formula I-A to I-Z and I-AA to I-GG) and/or a stereoisomer, a stable isotope, or a pharmaceutically acceptable salt thereof disclosed herein and a pharmaceutically acceptable carrier.

Further disclosed herein is a method of inhibiting the activity of TDO2 and/or IDO1 with an effective amount of a compound of formula I (such as formula I-A to I-Z and I-AA to I-GG) and/or a stereoisomer, a stable isotope, or a pharmaceutically acceptable salt thereof disclosed herein.

Further disclosed herein is a method of treating a disease treatable by inhibition of TDO2 and/or IDO1 in a patient, comprising administering to the patient in recognized need of such treatment, an effective amount of a compound of formula I (such as formula I-A to I-Z and I-AA to I-GG) and/or a stereoisomer, a stable isotope, or a pharmaceutically acceptable salt thereof disclosed herein.

Further disclosed herein is a method of treating a disease treatable by inhibition of TDO2 and/or IDO1 in a patient, comprising administering to the patient in recognized need of such treatment, an effective amount of a pharmaceutical composition comprising a compound of formula I (such as formula I-A to I-Z and I-AA to I-GG) and/or a stereoisomer, a stable isotope, or a pharmaceutically acceptable salt thereof disclosed herein and a pharmaceutically acceptable carrier.

Further disclosed herein is a method of treating a cancer in a patient, comprising administering to the patient in recognized need of such treatment, an effective amount of a pharmaceutical composition comprising a compound of formula I (such as formula I-A to I-Z and I-AA to I-GG) and/or a stereoisomer, a stable isotope, or a pharmaceutically acceptable salt thereof disclosed herein and a pharmaceutically acceptable carrier. In some embodiments, the cancer is colon, pancreas, breast, prostate, lung, brain, ovary, cervix, testes, renal, head, or neck cancer, or lymphoma, leukemia, or melanoma.

Further disclosed herein is a method of enhancing the effectiveness of an anti-cancer treatment comprising administering an anti-cancer agent and a compound of formula I (such as formula I-A to I-Z and I-AA to I-GG) or a pharmaceutical composition comprising a compound of formula I (such as formula I-A to I-Z and I-AA to I-GG) and/or a stereoisomer, a stable isotope, or a pharmaceutically acceptable salt thereof disclosed herein. In some embodiments, the cancer is colon, pancreas, breast, prostate, lung, brain, ovary, cervix, testes, renal, head, or neck cancer, or lymphoma, leukemia, or melanoma.

Further disclosed herein is a method of treating immunosuppression associated with cancer by inhibition of TDO2 and/or IDO1 in a patient, comprising administering to the patient in recognized need of such treatment, an effective amount of a compound of formula I (such as formula I-A to I-Z and I-AA to I-GG) and/or a stereoisomer, a stable isotope, or a pharmaceutically acceptable salt thereof disclosed herein.

Further disclosed herein is a use of a compound of formula I (such as formula I-A to I-Z and I-AA to I-GG) and/or a stereoisomer, a stable isotope, or a pharmaceutically acceptable salt thereof in preparation of a medication for treating a disease responsive to inhibition of TDO2 and/or IDO1, such as cancer or immune disorder. In some embodiments, the cancer is colon cancer, gastric cancer, leukemia, lymphoma, melanoma, or pancreatic cancer. In some embodiments, the immune disorders are acquired immune deficiency syndrome (AIDS), dementia, Alzheimer's disease (AD), schizophrenia, Huntington's disease, amyotrophic lateral sclerosis (ALS), autoimmune disorders like rheumatoid arthritis etc.

Further disclosed herein is a method of a use of a compound of formula I (such as formula I-A to I-Z and I-AA to I-GG) and/or a stereoisomer, a stable isotope, or a pharmaceutically acceptable salt thereof in treating other diseases in a patient, comprising administering to the patient in recognized need of such treatment, an effective amount of a pharmaceutical composition comprising a compound of formula I and/or a stereoisomer, a stable isotope, or a pharmaceutically acceptable salt thereof disclosed herein and a pharmaceutically acceptable carrier. In some embodiments, the other diseases are acquired immune deficiency syndrome (AIDS), dementia, Alzheimer's disease (AD), schizophrenia, Huntington's disease, amyotrophic lateral sclerosis (ALS), autoimmune disorders like rheumatoid arthritis etc.

Further disclosed herein are compounds of formula I (such as formula I-A to I-Z and I-AA to I-GG) described herein, as well as pharmaceutically acceptable salts of these compounds, and all stereoisomers (including diastereoisomers and enantiomers), and isotopically enriched versions thereof (including deuteroium substitutions). These compounds can be used to treat conditions responsive to inhibition of TDO2, and/or IDO1, such as those described herein, and for use in the preparation of a medicament for treating these disorders. The pharmaceutical compositions and methods described herein can also be used with or formulated with a co-therapeutic agent; for example, compounds of formula I (such as formula I-A to I-Z and I-AA to I-GG) can be used with or formulated with inhibitors of immune checkpoint (such as inhibitors of PD-1 and PD-L1) or other therapeutic agents as further disclosed herein.

Further disclosed are methods of making the compounds of formula I such as formula I-A to I-Z and I-AA to I-GG) as well as key intermediate compounds useful for making the compounds disclosed herein.

Further disclosed herein is a use of a compound of formula I (such as formula I-A to I-Z and I-AA to I-GG) disclosed herein for making a medicament for the treatment of medical conditions that benefit from the inhibition of IDOI and/or TDO2.

Further disclosed herein is a use of a compound of formula I (such as formula I-A to I-Z and I-AA to I-GG) and/or a stereoisomer, a stable isotope, or a pharmaceutically acceptable salt thereof in combination therapy medication for treating a disease responsive to inhibition of TDO2 and/or IDO1 such as a cancer. One or more additional pharmaceutical agents for treatment methods such as, for example, anti-viral agents, chemotherapeutics or other anti-cancer agents, immune enhancers, immunosuppressants, radiation, anti-tumor and anti-viral vaccines, agents for cytokine therapy (e.g., IL2, GM-CSF, etc.), and/or indoleamine 2,3-dioxygenase (IDO) inhibitors can be used in combination with the compounds and pharmaceutical compositions described herein for treatment of TDO2-associated diseases, disorders or conditions (as noted above) or for enhancing the effectiveness of the treatment of a disease state or condition, such as cancer. The agents can be combined with the compound disclosed herein in a single dosage form, or the agents can be administered simultaneously or sequentially as separate dosage forms.

Therapeutic agents that constitute the standard of care for a particular cancer type or infectious disease are expected to benefit when combined with the TDO2 and/or IDO1 inhibitors disclosed herein. For example, in the case of tumors, the tumor is sensitive to the cytotoxic effects of the chemotherapeutic agent to stimulate the release of antigens that will eventually mediate an immune response that will be enhanced by addition of TDO2 inhibitors to the combination treatment. A person of skill in the art would know how to select such chemotherapeutic agent based on the clinical characteristics and known sensitivity of each tumor to different antineoplastic agents.

Suitable antiviral agents contemplated for use in combination with the compounds disclosed herein can include, for example, nucleoside and nucleotide reverse transcriptase inhibitors (NRTIs), non-nucleoside reverse transcriptase inhibitors (NNRTIs), protease inhibitors and other antiviral drugs. Suitable NRTIs include, for example, zidovudine (AZT), didanosine (ddl), zalcitabine (ddC), stavudine (d4T), amivudine (3TC), abacavir (1592U89), adefovir dipivoxil (bis(POM)-PMEA), lobucavir (BMS-180194), BCH-10652, emitricitabine ((−)-FTC), beta-L-FD4 (also called beta-L-D4C and named beta-L-2', 3'-dicleoxy-5-fluoro-cytidine), DAPD, ((−)-beta-D-2,6-diamino-purine dioxolane), and lodenosine (FddA). Suitable NNRTIs include, for example, nevirapine (BI-RG-587), delaviradine (BHAP, U-90152), efavirenz (DMP-266), PNU-142721, AG-1549, MKC-442 (1-(ethoxy-methyl)-5-(1-methylethyl)-6-(phenylmethyl)- (2,4 (1H, 3H)-pyrimidinedione), and (+)-calanolide A (NSC-675451) and B. Suitable protease inhibitors include, for example, saquinavir (Ro 31-8959), ritonavir (ABT-538), indinavir (MK-639), nelfnavir (AG-1343), amprenavir (141W94), lasinavir (BMS-234475), DMP-450, BMS-2322623, ABT-378, and AG-1549. Other antiviral agents include, for example, hydroxyurea, ribavirin, IL-2, IL-12, pentafuside and Yissum Project No. 11607.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, *vinca* alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol™), docetaxel, mithramycin, deoxycoformycin, mitomycin-C, L-asparaginase, interferons (especially IFN-a), etoposide, and teniposide.

Other cytotoxic agents include, for example, navelbene, CPT-11, anastrazole, letrazole, capecitabine, reloxafme, cyclophosphamide, ifosamide, and droloxafme.

Also suitable cytotoxic agents include, for example, epidophyllotoxin, an antineoplastic enzyme, a topoisomerase inhibitor, procarbazine, mitoxantrone, platinum coordination complexes such as cis-platin and carboplatin, biological response modifiers, growth inhibitors, antihormonal therapeutic agents, leucovorin, tegafur, and haematopoietic growth factors.

Other anti-cancer agents include, for example, antibody therapeutics such as trastuzumab (Herceptin), antibodies to costimulatory molecules such as CTLA-4, 4-1BB, or antibodies to cytokines (IL-10, TGF-β, etc.).

Other anti-cancer agents also include, for example, those that block immune cell migration such as antagonists to chemokine receptors, including CCR2, CCR4 and CCR6.

Other anti-cancer agents also include, for example, those that augment the immune system such as adoptive T cell transfer.

Anti-cancer vaccines include, for example, dendritic cells, synthetic peptides, DNA vaccines and recombinant viruses.

The compounds disclosed herein can also be used in combination therapy with immune checkpoint inhibitors, such as PD-1 (programmed cell death protein 1) or its ligand PD-L1. Such therapeutic treatments include those that suppress or inhibit the expression of PD-1 or PD-L1 as well as those that suppress or inhibit the activity of the PD-1 or PD-L1 proteins themselves. Examples of anti-PD-1 compounds include, for example, pembrolizumab, nivolumab, pidilizumab, and BMS 936559. Examples of anti-PD-L1 include atezolizumab and avelumab.

The pharmaceutical composition comprising a compound of formula I (such as formula I-A to I-Z and I-AA to I-GG) and/or a stereoisomer, a stable isotope, or a pharmaceutically acceptable salt thereof, and a pharmaceutically acceptable carrier, can be administered in various known manners, such as orally, topically, rectally, parenterally, by inhalation spray, or via an implanted reservoir, although the most suitable route in any given case depends on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The compound of formula I (such as formula I-A to I-Z and I-AA to I-GG) and/or a stereoisomer, a stable isotope, or a pharmaceutically acceptable salt thereof can be administered orally in solid dosage forms, such as capsules, tablets, troches, dragées, granules and powders, or in liquid dosage forms, such as elixirs, syrups, emulsions, dispersions, and suspensions. The compound of formula I (such as formula I-A to I-Z and I-AA to I-GG) and/or a stereoisomer, a stable isotope, or a pharmaceutically acceptable salt thereof can also be administered parenterally, in sterile liquid dosage forms, such as dispersions, suspensions or solutions. Other dosages forms that can also be used to administer the compound of formula I (such as formula I-A to I-Z and I-AA to I-GG) and/or a stereoisomer, a stable isotope, or a pharmaceutically acceptable salt thereof include, for example, ointment, cream, drops, transdermal patch or powder for topical administration, an ophthalmic solution or suspension formation, i.e., eye drops, for ocular administration, an aerosol spray or powder composition for inhalation or intranasal administration, or a cream, ointment, spray or suppository for rectal or vaginal administration.

Gelatin capsules containing the compound of formula I (such as formula I-A to I-Z and I-AA to I-GG) and/or a stereoisomer, a stable isotope, or a pharmaceutically acceptable salt thereof and powder carriers, such as lactose, starch, cellulose derivatives, magnesium stearate, stearic acid, and the like, can also be used. Similar diluents can be used to make compressed tablets. Both tablets and capsules can be manufactured as sustained release products, for example, to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected, for example, from coloring and flavoring agents to increase patient acceptance.

In general, water, suitable oil, saline, aqueous dextrose (glucose), and related sugar solutions and glycols such as propylene glycol or polyethylene glycols can be examples of suitable carriers for parenteral solutions. Solutions for parenteral administration may comprise a water soluble salt of the at least one compound disclosed herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is selected, for example, from the carriers that are compatible with active ingredients of the pharmaceutical composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are disclosed in *Remington's Pharmaceutical Sciences*, A. Osol, a standard reference text in the art.

The compound of formula I (such as formula I-A to I-Z and I-AA to I-GG) and/or a stereoisomer, a stable isotope, or a pharmaceutically acceptable salt thereof can be examined for efficacy in treating cancer by in vivo assays. For example, the compound of formula I (such as formula I-A to I-Z and I-AA to I-GG) and/or a stereoisomer, a stable isotope, or a pharmaceutically acceptable salt thereof can be administered to an animal (e.g., a mouse model) having cancer and its therapeutic effects can be accessed. Positive results in one or more of such tests are sufficient to increase the scientific storehouse of knowledge and hence sufficient to demonstrate practical utility of the compounds and/or salts tested. Based on the results, an appropriate dosage range and administration route for animals, such as humans, can also be determined.

For administration by inhalation, the compound of formula I (such as formula I-A to I-Z and I-AA to I-GG) and/or a stereoisomer, a stable isotope, or a pharmaceutically acceptable salt thereof may be conveniently delivered in the form of an aerosol spray presentation from pressurized packs or nebulisers. The compound of formula I (such as formula I-A to I-Z and I-AA to I-GG) and/or a stereoisomer, a stable isotope, or a pharmaceutically acceptable salt thereof may also be delivered as powders, which may be formulated and the powder composition may be inhaled with the aid of an insufflation powder inhaler device. One exemplary delivery system for inhalation can be a metered dose inhalation (MDI) aerosol, which may be formulated as a suspension or solution of a compound of formula I (such as formula I-A to I-Z and I-AA to I-GG) and/or a stereoisomer, a stable isotope, or a pharmaceutically acceptable salt thereof in at least one suitable propellant, selected, for example, from fluorocarbons and hydrocarbons.

For ocular administration, an ophthalmic preparation may be formulated with an appropriate weight percentage of a solution or suspension of the compound of formula I (such as formula I-A to I-Z and I-AA to I-GG) and/or a stereoisomer, a stable isotope, or a pharmaceutically acceptable salt thereof in an appropriate ophthalmic vehicle, such that the compound of formula I (such as formula I-A to I-Z and I-AA to I-GG) and/or a stereoisomer, a stable isotope, or a pharmaceutically acceptable salt thereof is maintained in contact with the ocular surface for a sufficient time period to allow the compound to penetrate the corneal and internal regions of the eye.

Useful pharmaceutical dosage-forms for administration of the compound of formula I (such as formula I-A to I-Z and I-AA to I-GG) and/or a stereoisomer, a stable isotope, or a pharmaceutically acceptable salt thereof include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, the compound of formula I (such as formula I-A to I-Z and I-AA to I-GG) and/or a stereoisomer, a stable isotope, or a pharmaceutically acceptable salt thereof can be present in an amount of 1, 5, 10, 15, 20, 25, 50, 75, 80, 85, 90, 95, 100, 125, 150, 200, 250, 300, 400, 500, or 1000 mg in a capsule.

In some embodiments, a large number of unit capsules can be prepared by filling standard two-piece hard gelatin capsules each with, for example, 100 milligrams of the compound of formula I (such as formula I-A to I-Z and I-AA to I-GG) and/or a stereoisomer, a stable isotope, or a pharmaceutically acceptable salt thereof in powder, 150 milligrams of lactose, 50 milligrams of cellulose, and 6 milligrams magnesium stearate.

In some embodiments, a mixture of the compound of formula I (such as formula I-A to I-Z and I-AA to I-GG) and/or a stereoisomer, a stable isotope, or a pharmaceutically acceptable salt thereof and a digestible oil such as soybean oil, cottonseed oil or olive oil can be prepared and injected by means of a positive displacement pump into gelatin to form soft gelatin capsules containing 75 or 100 milligrams of the active ingredient. The capsules are washed and dried.

In some embodiments, the compound of formula I (such as formula I-A to I-Z and I-AA to I-GG) and/or a stereoisomer, a stable isotope, or a pharmaceutically acceptable salt thereof can be present in an amount of 1, 5, 10, 15, 20, 25, 50, 75, 80, 85, 90, 95, 100, 125, 150, 200, 250, 300, 400, 500, or 1000 mg in a tablet.

In some embodiments, a large number of tablets can be prepared by conventional procedures so that the dosage unit comprises, for example, 100 milligrams of the compound of formula I (such as formula I-A to I-Z and I-AA to I-GG) and/or a stereoisomer, a stable isotope, or a pharmaceutically acceptable salt thereof, 0.2 milligrams of colloidal silicon dioxide, 5 milligrams of magnesium stearate, 275 milligrams of microcrystalline cellulose, 11 milligrams of starch, and 98.8 milligrams of lactose. Appropriate coatings may, for example, be applied to increase palatability or delay absorption.

In some embodiments, a parenteral composition suitable for administration by injection can be prepared by stirring 1.5% by weight of a compound of formula I (such as formula I-A to I-Z and I-AA to I-GG) and/or a stereoisomer, a stable isotope, or a pharmaceutically acceptable salt thereof in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided compound of formula I (such as formula I-A to I-Z and I-AA to I-GG) and/or a stereoisomer, a stable isotope, or a pharmaceutically acceptable salt thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound of formula I (such as formula I-A to I-Z and I-AA to I-GG) and/or a stereoisomer, a stable isotope, or a pharmaceutically acceptable salt thereof are administered stepwise or in conjunction with at least one other therapeutic agent. When drugs are administered in physical combination, the dosage form and administration route should be selected depending on the compatibility of the combined drugs. Thus, the term "co-administration" is understood to include the administration of at least two agents concomitantly or sequentially, or alternatively as a fixed dose combination of the at least two active components.

The compound of formula I (such as formula I-A to I-Z and I-AA to I-GG) and/or a stereoisomer, a stable isotope, or a pharmaceutically acceptable salt thereof can be administered as the sole active ingredient or in combination with at least one second active ingredient, selected, for example, from other active ingredients known to be useful for treating the target disease, such as cancers including, for example, colon cancer, gastric cancer, leukemia, lymphoma, melanoma, and pancreate cancer in a patient.

As used herein, the term "optical isomer" or "stereoisomer" refers to any of the various stereo isomeric configurations which may exist for a given compound of the present disclosure and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. The present disclosure includes enantiomers, diastereomers or racemates of the compounds. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog 1R-SJ system. When a compound is a pure enantiomer, the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and synthesis procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. Disclosed here are compounds that include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration unless specified. If the compound contains a di-substituted cycloalkyl, the cycloalkyl substituent may have a cis- or trans-configuration, unless otherwise specified. All tautomeric forms are also intended to be included.

In some cases, the compounds disclosed herein are capable of forming acid and/or base salts by virtue of the presence of amino and/or carboxyl groups or groups similar thereto. As used herein, the terms "salt" or "salts" refers to an acid addition or base addition salt of the compound disclosed herein. "Salts" include, for example, "pharmaceutical acceptable salts." The term "pharmaceutically acceptable salts" refers to salts that retain the biological effectiveness and properties of the compounds disclosed herein and, which typically are not biologically or otherwise undesirable.

Pharmaceutically acceptable acid addition salts can be formed with inorganic acids and organic acids, e.g., acetate, adipate, aluminum, ascorbate, aspartate, benzoate, besylate, bromide/hydrobromide, bicarbonate/carbonate, bisulfate/sulfate, camphorsulfonate, caproate, chloride/hydrochloride, chloroprocaine, chlortheophyllonate, citrate, edetate, calcium edetate, ethandisulfonate, ethylsulfonate, ethylene diamine, fumarate, galactarate (mucate), gluceptate, gluconate, glucuronate, glutamate, glycolate, hexyl resorcinate, hippurate, hydroiodide/iodide, hydroxynapthoate (xinafoate), isethionate, lactate, lactobionate, laurylsulfate, lithium, malate, maleate, malonate, mandelate, mesylate, methylsulphate, naphthoate, napsylate, nicotinate, nitrate, octadecanoate, oleate, oxalate, palmitate, pamoate, pantothenate, phosphate/hydrogen phosphate/dihydrogen phosphate, polygalacturonate procaine, propionate, salicylate, sebacate, stearate, subacetate, succinate, sulfate, sulfosalicylate, tannate, tartrate, bitartrate, tosylate, triphenylacetate, and trifluoroacetate salts. Lists of additional suitable salts can be found, e.g., in REMINGTON'S PHARMACEUTICAL SCIENCES, 20th ed., Mack Publishing Company, Easton, Pa., (1985); and in HANDBOOK OF PHARMACEUTICAL SALTS: PROPERTIES, SELECTION, AND USE, by Stahl and Wermuth (Wiley-VCH, Weinheim, Germany, 2002). Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, trifluoroacetic, sulfosalicylic acid, and the like.

Pharmaceutically acceptable base addition salts can be formed with inorganic or organic bases and can have inorganic or organic counterions.

Inorganic counterions for such base salts include, for example, ammonium salts and metals from columns I to XII of the periodic table. In certain embodiments, the counterion is selected from sodium, potassium, ammonium, alkylammonium having one to four C1-C4 alkyl groups, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Suitable organic amines include isopropylamine, benzathine, cholinate, diethanolamine, diethylamine, lysine, meglumine, piperazine and tromethamine.

The pharmaceutically acceptable salts disclosed herein can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, tetrahydrofuran, toluene, chloroform, dichloromethane, methanol, ethanol, isopropanol, or acetonitrile is desirable, where practicable.

Any formula given herein is intended to represent unlabeled forms (i.e., compounds wherein all atoms are present at natural isotopic abundances and not isotopically enriched) as well as isotopically enriched or labeled forms of the compounds. Isotopically enriched or labeled compounds have structures depicted by the formulas given herein except that at least one atom of the compound is replaced by an atom of the same element but having an atomic mass or mass number different from the atomic mass or the atomic mass distribution that occurs naturally. Examples of isotopes that can be incorporated into enriched or labeled compounds disclosed herein include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{125}I$ respectively. Disclosed herein are the compounds including various isotopically labeled compounds as defined herein, for example, those in which radioactive isotopes, such as $^{3}H$ and $^{14}C$, or those in which non-radioactive isotopes, such as $^2H$ and $^{13}C$, are present at levels significantly above the natural abundance for these isotopes. These isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. For example, an $^{18}F$ or labeled compound may be desirable for PET or SPECT studies. Isotopically-labeled compounds of formula I can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of formula I if it is incorporated at substantially above the level of natural isotopic abundance. Disclosed are the compounds that include isotopically enriched versions of the compounds, e.g., deuterated versions as well as non-deuterated versions. Deuterated versions may be deuterated at a single site or at multiple sites.

The degree of incorporation of such an isotope in an isotopically-enriched compound, such as deuterium, may be defined by the isotopic enrichment factor. The term "isotopic enrichment factor" as used herein means the ratio between the isotopic abundance of a specified isotope in a sample, and the natural abundance of the isotope in a non-enriched sample. If a substituent in a compound disclosed herein is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, REMINGTON'S PHARMACEUTICAL SCIENCES, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of the compound disclosed herein refers to an amount of the compound disclosed herein that can elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "therapeutically effective amount" refers to the amount of the compound disclosed herein that, when administered to a subject, is effective to (1) at least partially alleviate, inhibit, prevent and/or ameliorate a condition, or a disorder or a disease (i) mediated by kynurenine pathway, or (ii) associated with activity of TDO2 and/or IDO1, or (iii) characterized by activity (normal or abnormal) of TDO2 and/or IDO1; or (2) reduce or inhibit the activity of TDO2 and/or IDO1, or (3) reduce or inhibit the expression of TDO2 and/or IDO1.

In another non-limiting embodiment, the term "a therapeutically effective amount" refers to the amount of the compound disclosed herein that, when administered to a cell, or a tissue, or a non-cellular biological material, or a medium, is effective to at least partially reduce or inhibit the activity of TDO2, or at least partially reduce or inhibit the expression of TDO2.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In one embodiment, the subject is a human.

As used herein, the term "inhibit", "inhibition" or "inhibiting" refers to the reduction or suppression of a given condition, activity, effect, symptom, or disorder, or disease, or a significant decrease in the baseline activity of a biological activity or process.

As used herein, the term "treat," "treating" or "treatment" of any disease or disorder refers in one embodiment, to ameliorating the disease or disorder (i.e., slowing or arresting or reducing the development of the disease or at least one of the clinical symptoms thereof). In another embodiment, "treat," "treating" or "treatment" refers to alleviating or ameliorating at least one physical parameter including those which may not be discernible by the patient. In yet another embodiment, "treat," "treating" or "treatment" refers to modulating the disease or disorder, either physically, (e.g., stabilization of a discernible symptom), physiologically, (e.g., stabilization of a physical parameter), or both. In yet another embodiment, "treat," "treating" or "treatment" refers to delaying the development or progression of the disease or disorder.

As used herein, a subject is "in need of" a treatment if such subject would be expected to benefit biologically, medically or in quality of life from such treatment.

As used herein, the term "a," "an," "the," and similar terms used in the context of the present disclosure (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the present disclosure and does not pose a limitation on the scope of the invention otherwise claimed.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)-configuration; i.e., for optically active compounds, it is often exemplary to use one enantiomer to the substantial exclusion of the other enantiomer. Substituents at atoms with carbon-carbon double bonds may, where possible, be present in cis- (Z)- or trans- (E)-form, and both are included in the invention unless otherwise indicated.

Accordingly, as used herein the compound disclosed herein can be in the form of one of the possible isomers, rotamers, atropisomers, or tautomers or as a mixture thereof, for example, as substantially pure geometric (cis- or trans-) isomers, diastereomers, optical isomers (antipodes), racemates or mixtures thereof. 'Substantially pure' or 'substantially free of other isomers" as used herein means the product contains less than 5%, and exemplary less than 2%, of other isomers relative to the amount of the exemplary isomer, by weight.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds disclosed herein into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

The compounds of formula I (such as formula I-A to I-Z and I-AA to I-GG) can be made by the general synthetic method as illustrated in Scheme 1.

Scheme 1

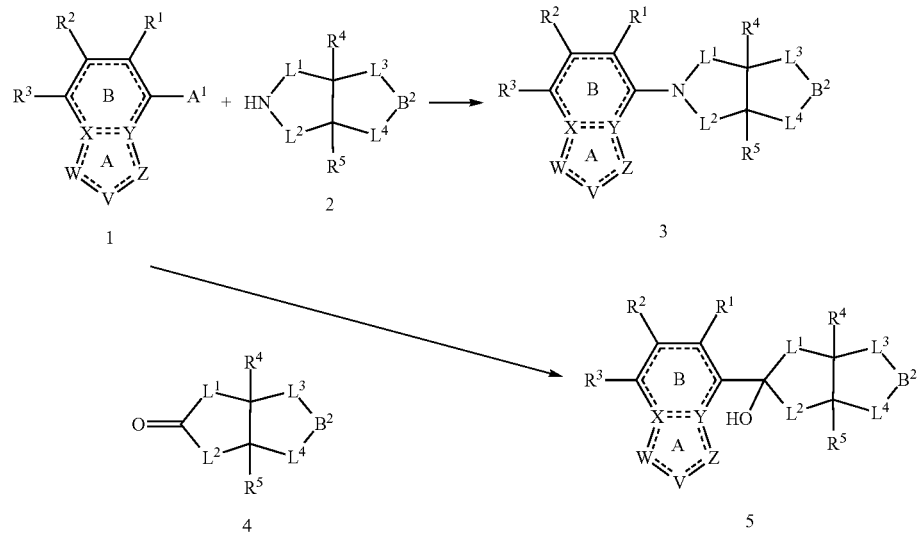

Bicyclic compounds 1, wherein $A^1$ group is chlorine, bromine, iodine, or triflate, which can be made by many methods known to the skilled person, can be coupled with appropriate bicyclic amines 2 via Buckward reaction or related palladium-catalyzed cross coupling reactions to give compounds of formula 3. Reaction of the appropriate bicyclic compounds 1, wherein $A^1$ is bromine or iodinine, with alkylthoium such as n-butyllithium or t-butyllithium to form lithium salts, which react with the appropriate ketones 4 to form compounds of formula 5. Compounds 2 and 4 can be made by many methods known to the skilled person. $B^2$ groups of compounds of Formula 3 and 5 may require further modifications such as deprotection, hydrogenation, acylation or sulfonylation reactions by conventional methods leading to the desired substituents. The desired formula 3 and 5 are compounds of formula I (such as formula I-A to I-Z and I-AA to I-GG).

The Schemes 2-4 in some instances illustrate preparation of compounds 13, 14, 15, 24, 25, 26, 27, 33, 34, 35, 36, 38, 39, 40 and 41, but methods for preparing suitable compounds encompassed by Formula I are readily apparent to the skilled person in view of the many methods known for making the requisite bicyclic aromatic AB rings and

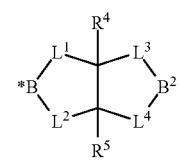

intermediates, so these methods are equally applicable to preparation of compounds with other embodiments.

Scheme 2

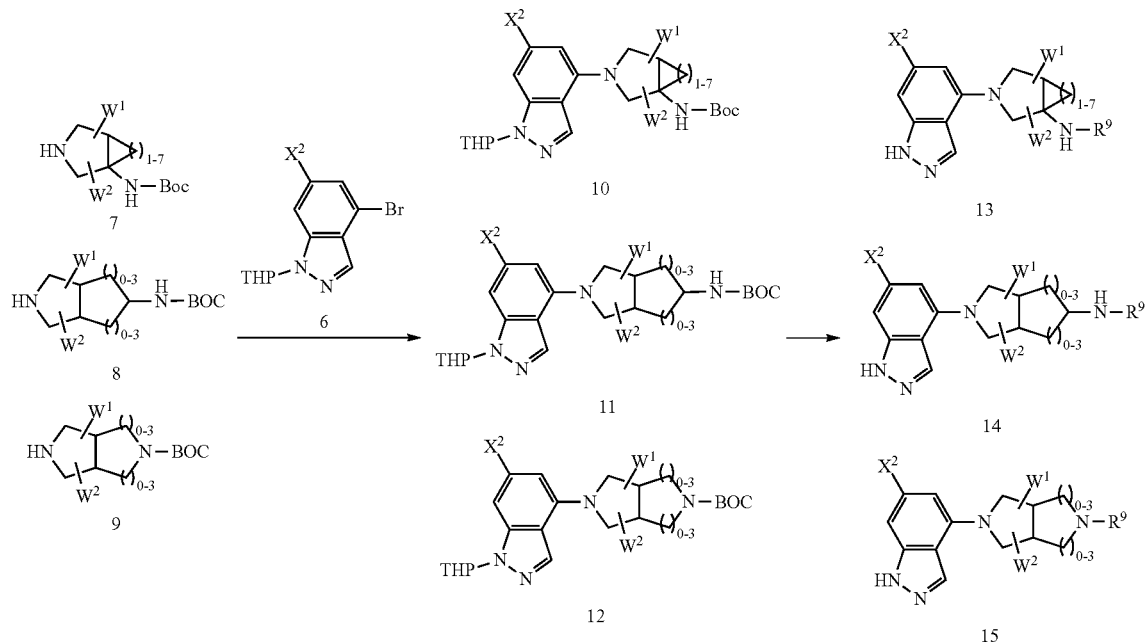

Scheme 2 illustrates the synthetic methods to compounds of formula 13, 14 and 15. Bicyclic amines 7, 8, and 9 can be made by many methods known to the skilled person. They can coupled with THP protected 4-bromo-indazole 6, wherein $X^2$ is exemplary chlorine, $CF_3$ or cyclopropyl, via Buckward reaction or other related palladium-catalyzed chemistry to provide compounds 10, 11 and 12. The THP protective groups on compounds 10, 11 and 12 are removed under acidic conditions, which may require further modifications such as hydrogenation, acylation or sulfonylation reactions by conventional methods leading to the desired substituents.

In Scheme 3, bicyclic ketones 16, 17, 18 and 19 can be made by many methods known to the skilled person. The THP protected 4-bromo-indazole 6, wherein $X^2$ is exemplary chlorine, $CF_3$ or cyclopropyl, is converted to the lithium salt by reacting with butyllithium at low temperature at −78° C., which reacts with above protected ketones to provide intermediate compounds 20, 21, 22 and 23. The protective groups on compounds 20-23 are removed under acidic conditions, which may require further modifications such as hydrogenation, acylation or sulfonylation reactions by conventional methods leading to the desired substituents of compounds of formula 24, 25, 26 and 27.

Scheme 3

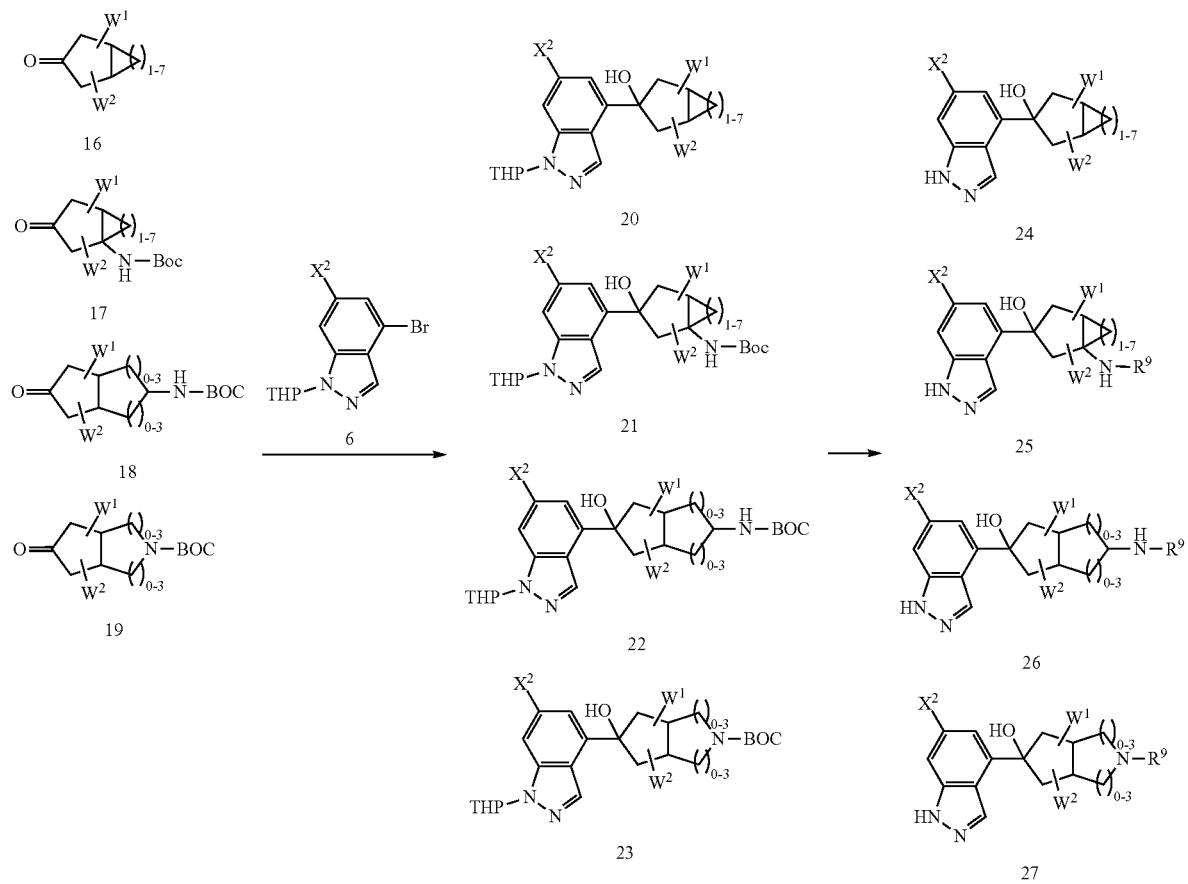

Scheme 4 illustrates the synthetic methods to compounds of formula 33, 34, 35, 36, 38, 39, 40 and 41. Starting materials 28, 29, 30, 31, 32, and 37 can be made by many methods known to the skilled person. Compounds 28, 29, 30 and 31, wherein $A^2$ group is chlorine, bromine, iodine, or triflate; $X^1$ and $X^2$ are exemplary chlorine, $CF_3$ or cyclopropyl, can form compounds of 33, 34, 35 and 36 by coupled with bicyclic amines 32 via Buckward reaction or other related palladium-catalyzed chemistry. Compounds 28, 29, 30 and 31, wherein $A^1$ group is exemplary bromine or iodine, can converted to the lithium salts by reacting with alkyllithium such n-butyllithium and t-butyllithium at low temperature at −78° C., which then react with ketones 37 to provide compounds of 38, 39, 40 and 41. $B^4$ in compounds 32 and 37 are exemplary selected from —CH(R)—, —CH(NHR$^9$)—, or —N(R$^9$)—. The coupling products may require further modifications at $B^3$ such as deprotection, hydrogenation, acylation, sulfonylation or other reactions by conventional methods leading to the desired substituents of compounds of formula 33, 34, 35, 36, 38, 39, 40 and 41.

Scheme 4

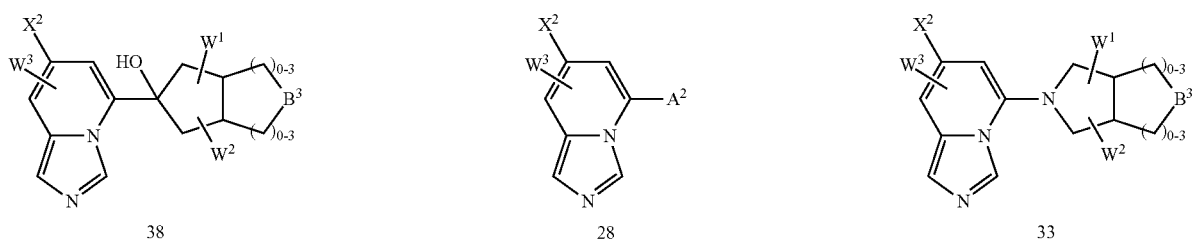

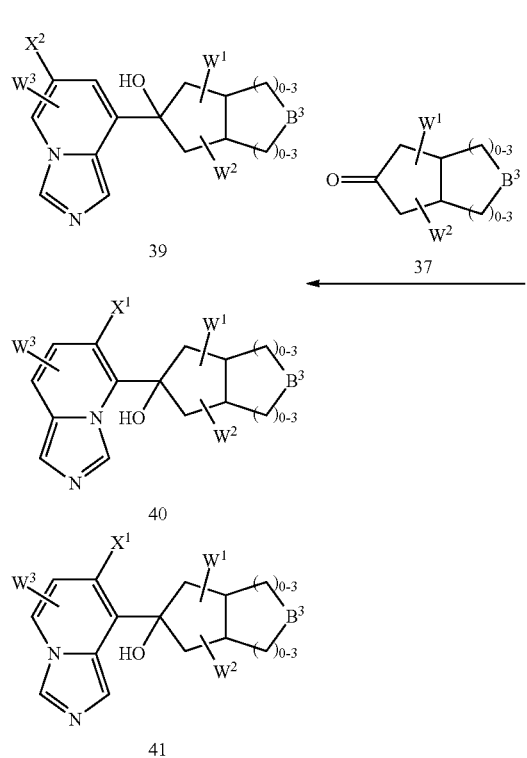
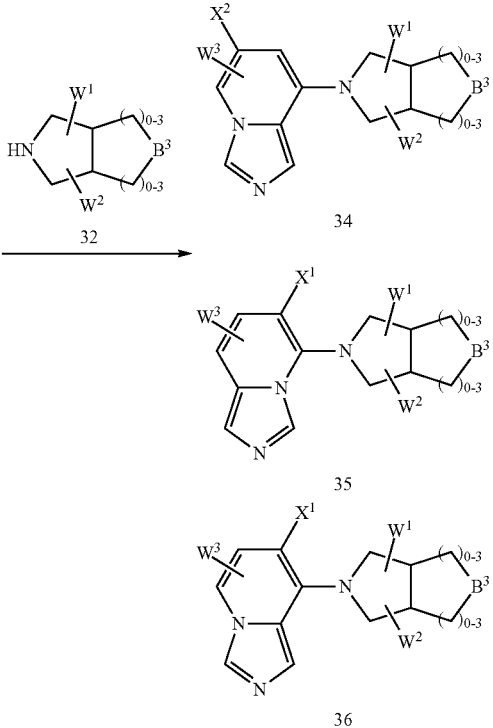

EXAMPLES

The following examples illustrate certain embodiments of the present disclosure and how to make and use them. They are not intended to limit the scope of the invention. Those of skill in the art will readily recognize a variety of noncritical parameters and conditions which can be changed or modified to yield essentially the same results. The example compounds below were found to be inhibitors of TDO2 and/or IDO1 according to one or more of the assays described herein.

In the following examples, the abbreviations below are used:

BINAP (±)-2,2'-Bis(diphenylphosphino)-1,1'-binaphthalene
$B_2Pin_2$ Bis(pinacolato)diboron
BTEAC Benzyl triethyl ammonium chloride
DCM Dichloromethane
DIAD Diisopropyl azodicarboxylate
DIPEA Di-isopropylethylamine
DMSO Diemthylsulfoxide
EtOAc Ethyl acetate
LiTMP Lithium tetramethylpiperidide
MeOH Methanol
Ms Methanesulfonyl
MSCl Methanesulfonyl chloride
$Pd_2(dba)_3$ Tris(dibenzylideneacetone)dipalladium
$Pd(dppf)Cl_2$ [1,1'Bis(diphenylphosphino)ferrocene]dichloropalladium(II)
PE Petroleum ether
PPTS Pyridinium p-toluenesulfonic acid
TLC Thin layer chromatography
TEA Triethylamine
THF Tetrahydrofuran

Example 1 (Method 1)

Preparation of 6-chloro-4-(4,4-dimethyl-5-(methylsulfonyl)hexahydropyrrolo[3,4-c]pyrrol-2(1H)-yl)-1H-indazole

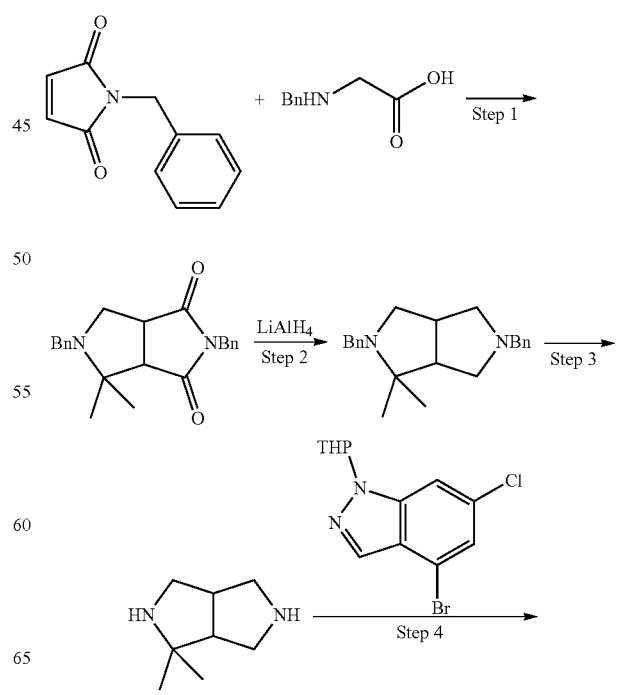

-continued

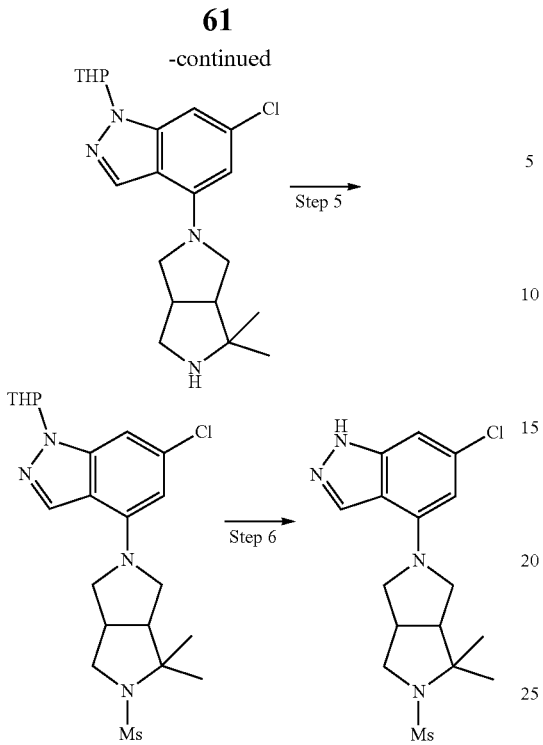

Step 1. 2,5-dibenzyl-4,4-dimethyltetrahydropyrrolo[3,4-c]pyrrole-1,3(2H,3aH)-dione The solution of 1-benzyl-1H-pyrrole-2,5-dione (23.4 g, 0.125 mol), 2-(benzylamino)acetic acid (31 g, 0.188 mol) and acetone (22 g, 0.375 mol) in toluene was stirred at 130° C. for 18 h. The precipitate after cooling to room temperature was filtered off and the filter cake was washed with EtOAc (50 mL) The filtrate was concentrated in vacuo and the crude product was purified by silica gel flash column chromatography (PE/EtOAc=5/1-3/2) to give the title compound (32.2 g, 74% yield).

Step 2. 2,5-dibenzyl-1,1-dimethyloctahydropyrrolo[3,4-c]pyrrole

To the solution of LiAlH$_4$ (10.5 g, 0.277 mol) in dry THF (400 mL) under cooling of an ice-bath, the solution of the product of Step 1 above (32.2 g, 0.092 mol) in THF (100 mL) was added dropwisely. The resulting mixture was heated to reflux for 18 h and then cooled to room temperature. The cold EtOAc (1.2 L), anhydrous Na$_2$SO$_4$ (200 g) and H$_2$O (250 mL) were added sequentially to the reaction mixture with stirring. The solid was filtered off. The filtrate was concentrated in vacuo and the crude product was purified by silica gel flash column chromatography (PE/EtOAc=5/1) to give the title compound (5.2 g, 19% yield).

Step 3. 1,1-dimethyloctahydropyrrolo[3,4-c]pyrrole

The mixture of the product of Step 2 above (6.4 g, 0.02 mol) and Pd/C (1.0 g) in MeOH (80 mL) was stirred at 80° C. under 8 atm of H$_2$ in an autoclave for 18 h. After cooled to room temperature, the solid was filtered off. The filtrate was concentrated in vacuo to give the title compound (2.9 g, 100% yield).

Step 4. 6-chloro-4-(4,4-dimethylhexahydropyrrolo[3,4-c]pyrrol-2(1H)-yl)-1-(tetrahydro-2H-pyran-2-yl)-1H-indazole The mixture of the product of Step 3 above (2.4 g, 0.017 mol), Pd$_2$(dba)$_3$ (120 mg, 0.13 mmol), BINAP (162 mg, 0.26 mmol) and Cs$_2$CO$_3$ (8.5 g, 0.026 mol) in dioxane (60 mL) was stirred at 100° C. overnight. After cooled to room temperature, the solid was filtered off. The filtrate was concentrated in vacuo and the crude product was purified by silica gel flash column chromatography (DCM/MeOH=40/1-DCM/MeOH=10/1, containing 5% NH$_4$OH) to give the title compound (3.2 g, 67% yield).

Step 5. 6-chloro-4-(4,4-dimethyl-5-(methylsulfonyl)hexahydropyrrolo[3,4-c]pyrrol-2(1H)-yl)-1-(tetrahydro-2H-pyran-2-yl)-1H-indazole To the solution of the product of Step 4 above (1.5 g, 0.004 mol) and TEA (0.8 g, 0.008 mol) in DCM (40 mL) pre-cooled in ice-water bath, MsCl (0.7 g, 0.006 mol) was added. The resulting mixture was stirred at room temperature for 1 h and then diluted with DCM (100 mL), washed with aqueous Na$_2$CO$_3$ (50 mL), H$_2$O (50 mL) and brine (50 mL). The organic phase was dried over anhydrous Na$_2$SO$_4$, filtered off, and concentrated in vacuo. The crude product was purified by silica gel flash column chromatography (DCM/MeOH=40/1) to give the title compound (1.78 g, 98% yield).

Step 6. 6-chloro-4-(4,4-dimethyl-5-(methylsulfonyl)hexahydropyrrolo[3,4-c]pyrrol-2(1H)-yl)-1H-indazole The mixture of the product of Step 5 above (1.78 g, 0.004 mol) in HCl/MeOH (4 N, 40 mL) was stirred at room temperature overnight. The precipitate formed in the mixture was collected by filtration. The solid was dissolved in MeOH (50 mL) and aqueous NaOH (5 N) was added to adjust the PH value of the mixture to 8-9 under ice-water bath cooling. The mixture was concentrated in vacuo. The residue was diluted with DCM/MeOH (10/1, 200 mL), which was washed by brine (50 mL), dried over anhydrous Na$_2$SO$_4$, filtered off and concentrated in vacuo. The crude product was purified by silica gel flash column chromatography (DCM/MeOH=30/1) to give the title compound (1.3 g, 90% yield). MS (ESI) m/z: 368.9 [M+1]$^+$; $^1$H NMR (400 MHz, CDCl$_3$) δ 8.10 (s, 1H), 6.80 (s, 1H), 6.05 (s, 1H), 3.91 (dd, J=18.6, 9.5 Hz, 2H), 3.76 (dd, J=19.3, 10.6 Hz, 1H), 3.61 (dd, J=17.8, 9.2 Hz, 2H), 3.26 (dd, J=19.6, 10.0 Hz, 1H), 3.18 (dd, J=14.4, 6.9 Hz, 1H), 2.89 (s, 3H), 2.78 (dd, J=15.2, 7.8 Hz, 1H), 1.58 (s, 3H), 1.55 (s, 3H).

Example 1a and 1b (Method 2)

Preparation of Optical 2 Pure Isomers: 6-chloro-4-((3aS,6aR)-4,4-dimethyl-5-(methylsulfonyl)hexahydropyrrolo[3,4-c]pyrrol-2(1H)-yl)-1H-indazole and 6-chloro-4-((3aR,6aS)-4,4-dimethyl-5-(methylsulfonyl)hexahydropyrrolo[3,4-c]pyrrol-2(1H)-yl)-1H-indazole The racemic product of Example 1 was separated by chiral SFC (EnantioPak 5 μm AD 5 column, 4.6×100 mm, MeOH (0.2% Methanol Ammonia), 1.6 mL/min).

Example 1a: One of the two pure optical isomers of racemic 6-chloro-4-(4,4-dimethyl-5-(methylsulfonyl)hexahydropyrrolo[3,4-c]pyrrol-2(1H)-yl)-1H-indazole that came out from the column first with Rt=3.28 min. MS (ESI) m/z: 368.8 [M+1]+, $^1$HNMR (400 MHz, CDCl$_3$) δ 9.98 (s, 1H), 8.10 (s, 1H), 6.80 (s, 1H), 6.05 (d, J=1.1 Hz, 1H), 3.99-3.85 (m, 2H), 3.81-3.70 (m, 1H), 3.66-3.54 (m, 2H), 3.32-3.23 (m, 1H), 3.21-3.12 (m, 1H), 2.82-2.72 (m, 1H), 1.60 (s, 3H), 1.55 (s, 3H).

Example 1b: One of the two pure optical isomers of racemic 6-chloro-4-(4,4-dimethyl-5-(methylsulfonyl)hexahydropyrrolo[3,4-c]pyrrol-2(1H)-yl)-1H-indazole that came our from the column afterward with Rt=4.5 min. MS (ESI) m/z: 368.6 [M+1]$^+$, $^1$H NMR (400 MHz, CDCl$_3$) δ 10.05 (s, 1H), 8.09 (s, 1H), 6.80 (s, 1H), 6.04 (d, J=1.0 Hz, 1H), 3.96-3.83 (m, 2H), 3.81-3.71 (m, 1H), 3.67-3.53 (m, 2H), 3.32-3.25 (m, 1H), 3.23-3.12 (m, 1H), 2.82-2.72 (m, 1H), 1.60 (s, 3H), 1.55 (s, 3H).

Example 2 (Method 3)

Preparation of (3aR,5r,6aS)-5-(6-chloro-1H-indazol-4-yl)-2-(methylsulfonyl)octahydrocyclopenta-[c]pyrrol-5-ol

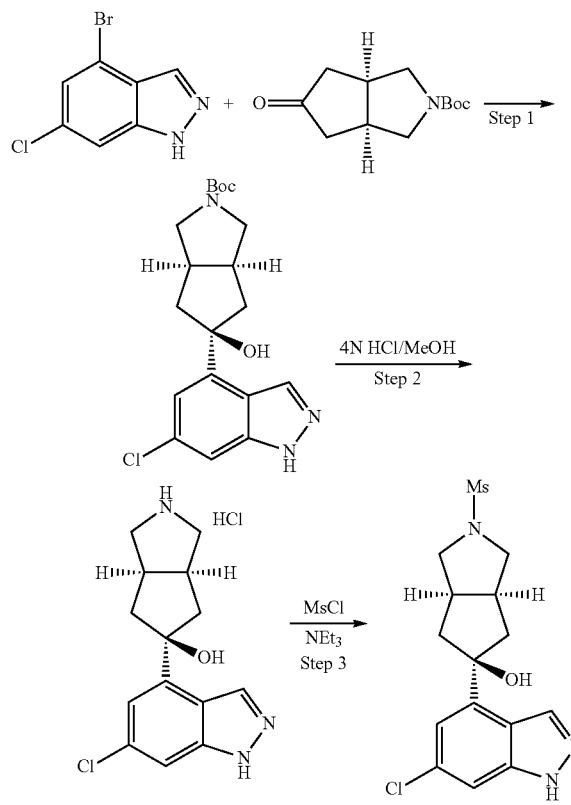

Step 1. (3aR,5r,6aS)-tert-butyl 5-(6-chloro-1H-indazol-4-yl)-5-hydroxyhexahydrocyclopenta-[c]pyrrole-2(1H)-carboxylate To a solution of 4-bromo-6-chloro-1H-indazole (2.31 g, 10 mmol) in THF (60 mL) cooled at 78° C., BuLi in hexane (1.6 M, 12.5 mL, 20 mmol) was added slowly. After the addition, the mixture was stirred at −78° C. for 0.5 h, and a solution of (3aR,6aS)-tert-butyl 5-oxohexahydrocyclopenta-[c]pyrrole-2(1H)-carboxylate (2.5 g, 11.1 mmol) in THF (5 mL) was added dropwise. The reaction mixture was quenched with saturated aqueous NH$_4$Cl (20 mL). The mixture was extracted with EtOAc (100 mL×2). The combined organic layers were washed with brine (50 mL×2), dried over anhydrous Na$_2$SO$_4$, filtered off and concentrated in vacuo. The residue was purified by silica gel flash column chromatography (PE:EA=10:1 to 2:1) to give the title compound (1.055 g, yield: 27%).

Step 2. (3aR,5r,6aS)-5-(6-chloro-1H-indazol-4-yl)octahydrocyclopenta[c]pyrrol-5-ol hydrochloride The product of Step 1 above (1.75 g, 4.6 mmol) was dissolved in HCl/MeOH (4 N, 20 mL) The mixture was stirred at room temperature for 4 h. The reaction solution was concentrated in vacuo to give the crude hydrochloride of the title compound (1.5 g), which was used in the next step without any further purification.

Step 3. (3aR,5r,6aS)-5-(6-chloro-1H-indazol-4-yl)-2-(methylsulfonyl)octahydrocyclopenta[c]-pyrrol-5-ol To the suspension of the crude product of Step 2 above (1.5 g) in DCM (30 mL) was added TEA (4.65 g, 46 mmol). The mixture was cooled in ice-water bath and MsCl (1.05 g, 9.2 mmol) was added slowly. The reaction mixture was allowed to warm to room temperature and stirred overnight. The mixture was diluted with DCM (50 mL) and water (20 mL). The organic layer was separated, washed with brine (20 mL), dried over anhydrous Na$_2$SO$_4$, filtered off and concentrated in vacuo. The residue was purified by silica gel flash column chromatography (DCM:MeOH=100:1 to 20:1) to give the title compound (90 mg, yield: 5.5%). MS (ESI) m/z: 355.8 [M+1]$^+$; $^1$H NMR (400 MHz, DMSO-d6) δ 13.14 (s, 1H), 8.22 (s, 1H), 7.47 (s, 1H), 7.06 (s, 1H), 5.40 (s, 1H), 3.49 (t, J=8.8 Hz, 2H), 3.27 (dd, J=9.4, 5.4 Hz, 7H), 2.94 (d, J=15.1 Hz, 2H), 2.87 (s, 3H), 2.38 (dd, J=13.3, 7.7 Hz, 2H), 1.95 (d, J=13.3 Hz, 2H).

Example 3 (Method 4)

Preparation of N-((2r,3aR,5r,6aS)-5-(6-chloro-1H-indazol-4-yl)-5-hydroxyoctahydropentalen-2-yl)methanesulfonamide

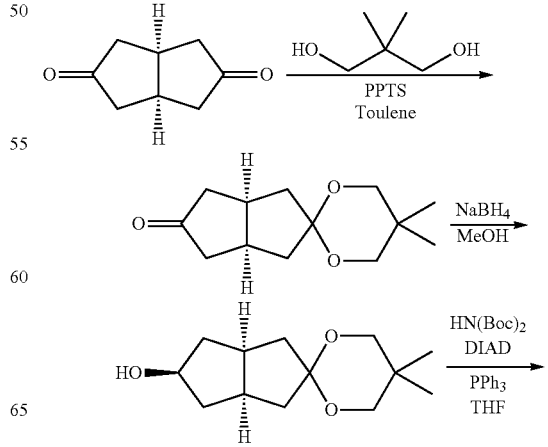

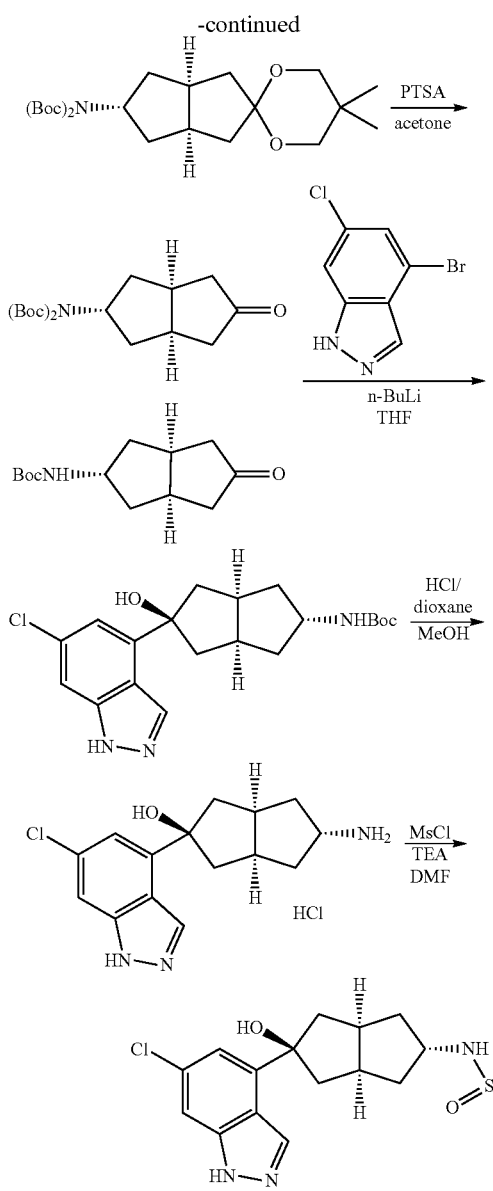

Step 1. (3a'R,6a'S)-5,5-dimethyltetrahydro-1'H-spiro[[1,3]dioxane-2,2'-pentalen]-5'(3'H)-one To a solution of (3as,6as)-tetrahydropentalene-2,5(1H,3H)-dione (15 g, 108.57 mmol) in toluene (150 mL) was added 2,2-dimethylpropane-1,3-diol (11.31 g, 108.57 mmol), followed by the addition of PPTS (250 mg) at rt. The reaction mixture was refluxed overnight with a Dean-Stark trap under $N_2$ atmosphere. After cooled to rt, the reaction mixture was concentrated under vacuum to remove the volatile. The residue was purified by silica gel flash column chromatography (PE:EtOAc=20:1) to give the title compound (16 g, yield: 66%) as a white solid.

Step 2. (3a'R,5's,6a'S)-5,5-dimethylhexahydro-1'H-spiro[[1,3]dioxane-2,2'-pentalen]-5'-ol A solution of the product of Step 1 above (15 g, 66.87 mmol) in MeOH (100 mL) was cooled to 0° C. in an ice-water bath. Then, $NaBH_4$ (3.79 g, 100.31 mmol) was added portionwise to the reaction mixture, maintaining the inner temperature below 30° C. After the addition was complete, the reaction mixture was stirred at 0° C. for 0.5 h before quenching with acetone (~20 mL. The mixture was concentrated under vacuum to remove the volatile. The residue was diluted with DCM/MeOH (10:1, 150 mL), washed with $H_2O$ (100 mL×2) and brine (100 mL), dried over anhydrous sodium sulfate, and concentrated under vacuum to give the title compound (15 g, yield: 99%) as a white solid.

Step 3. di-tert-butyl ((3a'R,5'r,6a'S)-5,5-dimethyl-hexahydro-1'H-spiro[[1,3]dioxane-2,2'-pentalen]-5'-yl)iminodicarboxylate To a solution of the product of Step 2 above (2.37 g, 10.46 mmol) in THF (40 mL) was added di-tert-butyl iminodicarboxylate (2.5 g, 11.51 mmol), followed by the addition of triphenylphosphine (3.02 g, 11.51 mmol) at rt. The reaction mixture was cooled to 0° C. in an ice-water bath under $N_2$ atmosphere and DIAD (2.33 g, 11.51 mmol) was added dropwise while maintaining the inner temperature below 0° C. After the addition was complete, the reaction mixture was stirred at rt overnight. The mixture was concentrated under vacuum to remove the volatile. The residue was diluted with DCM/MeOH (10:1, 100 mL), washed with $NaHCO_3$ (sat. aq, 50 mL), $H_2O$ (50 mL) and brine (50 mL), dried over anhydrous sodium sulfate, and concentrated under vacuum. The residue was purified by silica gel flash column chromatography (PE:EtOAc=30:1-20:1) to give the title compound (1.67 g, yield: 37%) as a white solid.

Step 4. tert-butyl ((2r,3aR,6aS)-5-oxooctahydropentalen-2-yl)carbamate & di-tert-butyl ((2r,3aR,6aS)-5-oxooctahydropentalen-2-yl)iminodicarboxylate To a solution of the product of Step 3 above (1.83 g, 4.3 mmol) in acetone (20 mL) was added PPTS (100 mg, 0.4 mmol) at rt. The mixture was stirred at rt overnight, which was diluted with DCM/MeOH (10:1, 80 mL), transferred to a separatory funnel, washed with $H_2O$ (40 mL×2) and brine (40 mL), dried over anhydrous sodium sulfate, and concentrated under vacuum. The residue was purified by silica gel flash column chromatography (PE:EtOAc=15:1-4:1) to give the mixture of mono- and bis-BOC products (744 mg) as yellow oil.

Step 5. tert-butyl ((2r,3aR,5r,6aS)-5-(6-chloro-1H-indazol-4-yl)-5-hydroxyoctahydropentalen-2-yl)carbamate To a solution of 4-bromo-6-chloro-1H-indazole (552 mg, 2.39 mmol) in THF (20 mL), cooled to −78° C. under $N_2$, was added n-BuLi/THF (2.5M, 3.16 mL, 7.89 mmol) dropwise, maintaining the inner temperature below −78° C. After the addition was complete, the reaction mixture was stirred at −78° C. for 0.5 h and the product of Step 4 above (810 mg) in THF (2 mL) was added dropwise, maintaining the inner temperature below −78° C. After the addition was complete, the reaction mixture was stirred at −78° C. for 1 h before quenching with $NH_4Cl$ (sat. aq, 50 mL). The reaction mixture was extracted with EtOAc (80 mL). The organic phase was washed with $H_2O$ (40 mL) and brine (40 mL), dried over anhydrous sodium sulfate, and concentrated under vacuum. The residue was purified by silica gel flash column chromatography (PE:EtOAc=5:1~1:2) to give the title compound (320 mg) as a yellow solid.

Step 6. (2r,3aR,5r,6aS)-5-amino-2-(6-chloro-1H-indazol-4-yl)octahydropentalen-2-ol hydrochloride To a solution of the product of Step 5 above (320 mg, 0.82 mmol) in MeOH (3 mL) was added HCl/dioxane (4M, 3 mL) at rt. After stirring at rt for 2 h, the mixture was diluted with MeOH (20 mL), and concentrated under vacuum to give the crude title compound (300 mg,) as a yellowish solid.

Step 7. N-((2r,3aR,5r,6aS)-5-(6-chloro-1H-indazol-4-yl)-5-hydroxyoctahydropentalen-2-yl)methanesulfonamide To a solution of the product of Steo 6 above (75 mg, 0.228 mmol) in DMF (1.5 mL) was added TEA (1 mL) at rt. The reaction was cooled to 0° C. in an ice-water bath and methanesulfonyl chloride (62 mg, 0.228 mmol) was added dropwise, maintaining the inner temperature below 0° C. The reaction mixture was allowed to warm up to rt and stirred for 4 h. The mixture was concentrated under vacuum to remove the volatile. The residue was diluted with DCM/isopropyl alcohol (3:1, 40 mL), transferred to a separatory funnel, washed with H$_2$O (20 mL×2) and brine (20 mL), dried over anhydrous sodium sulfate, and concentrated under vacuum. The residue was purified by prep-TLC (DCM:MeOH=10:1) to give the title compound (38.05 mg, yield: 45%) as a white solid. MS (ESI) m/z: 370.1 [M+1]$^+$; $^1$H NMR (400 MHz, DMSO-d6) δ 13.11 (s, 1H), 8.17 (s, 1H), 7.46 (s, 1H), 7.01 (d, J=1.1 Hz, 1H), 6.95 (d, J=7.0 Hz, 1H), 5.29 (s, 1H), 4.07-3.98 (m, 1H), 2.90 (s, 3H), 2.66 (s, 2H), 2.42 (m, 2H), 1.95-1.86 (m, 2H), 1.81 (m, 2H), 1.72 (m, 2H).

Example 4 (Method 5)

Preparation of 1-((3aR,5r,6aS)-5-(6-(trifluoromethyl)imidazo[1,5-a]pyridin-8-yl)hexahydrocyclopenta[c]pyrrol-2(1H)-yl)ethanone

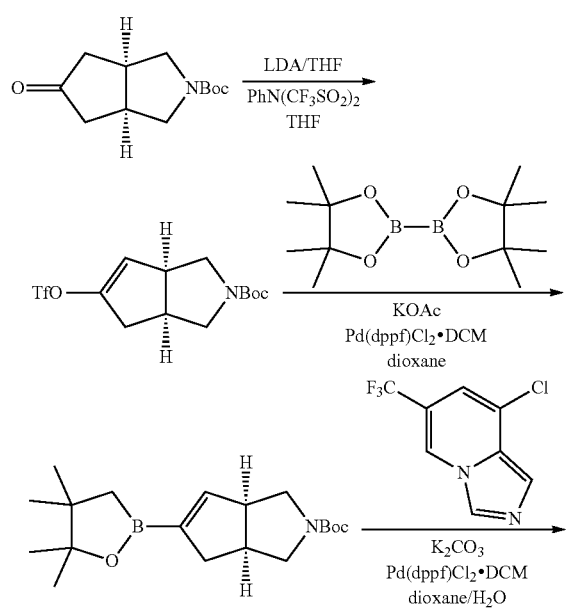

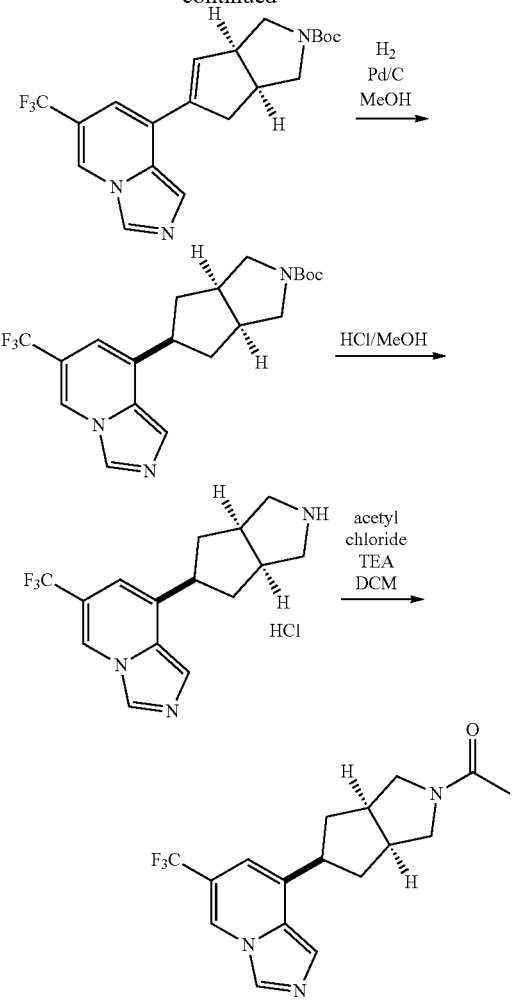

Step 1. (3aS,6aS)-tert-butyl 5-(((trifluoromethyl)sulfonyl)oxy)-3,3a,6,6a-tetrahydrocyclopenta[c]pyrrole-2(1H)-carboxylate The freshly prepared LDA/THF (0.61M, 19.8 mL, 12 mmol) was cooled to −78° C. and (3aR,6aS)-tert-butyl 5-oxohexahydrocyclopenta[c]pyrrole-2(1H)-carboxylate (2.25 g, 10 mmol) in THF (25 mL) was added dropwise, maintaining the inner temperature below −75° C. After stirring at −78° C. for 1 h, PhN(CF$_3$SO$_2$)$_2$ (4.3 g, 12 mmol) in THF (15 mL) was added dropwise, maintaining the inner temperature below −75° C. The reaction mixture was stirred overnight, allowing the temperature to warm up to rt. The reaction mixture was concentrated. The residues was diluted with DCM (100 mL), transferred to a separatory funnel, washed with NaHCO$_3$ (sat. aq, 30 mL) and brine (30 mL), dried over anhydrous sodium sulfate, and concentrated under vacuum. The residue was purified by silica gel flash column chromatography (PE:EtOAc=5:1) to give the title compound (3.5 g, yield: 98%).

Step 2. (3aR,6aS)-tert-butyl 5-(4,4,5,5-tetramethyl-1,3,2-dioxaborolan-2-yl)-3,3a,6,6a-tetrahydrocyclopenta[c]pyrrole-2(1H)-carboxylate To a suspension of the product of Step 1 above (3.5 g, 10 mmol) and B$_2$Pin$_2$ (3.8 g, 15 mmol) in dioxane (100 mL)

was added potassium acetate (1.96 g, 20 mmol) and Pd(dppf)Cl$_2$.DCM (800 mg, 1.0 mmol). The mixture was stirred at 80° C. overnight under N$_2$, cooled to rt before diluting with water (200 mL) and EtOAc (150 mL). The organic layer was separated, washed with H$_2$O (50 mL×2) and brine (50 mL), dried over anhydrous sodium sulfate, and concentrated. The residue obtained was purified by silica gel flash column chromatography (PE:EtOAc=10:1 to 8:1) to give the title compound (2.0 g, yield: 59%).

Step 3. (3aR,6aS)-tert-butyl 5-(6-(trifluoromethyl)imidazo[1,5-a]pyridin-8-yl)-3,3a,6,6a-tetrahydrocyclopenta[c]pyrrole-2(1H)-carboxylate To a suspension of the product of Step 2 above (920 mg, 2.7 mmol) and 8-chloro-6-(trifluoromethyl)imidazo[1,5-a]pyridine (550 mg, 2.5 mmol) in dioxane/H$_2$O (30 mL/5 mL) was added potassium carbonate (690 mg, 4.9 mmol) and Pd(dppf)Cl$_2$.DCM (100 mg, 0.12 mmol). The mixture was stirred at 100° C. for 4 h under N$_2$, cooled to rt and diluted with EtOAc (100 mL). The mixture was washed with water (30 mL×3) and brine (30 mL), dried over anhydrous sodium sulfate, and concentrated. The residue obtained was purified by silica gel flash column chromatography (PE:EtOAc=3:1 to 2:1) to give the title compound (840 mg, yield: 85%).

Step 4. (3aR,5r,6aS)-tert-butyl 5-(6-(trifluoromethyl)imidazo[1,5-a]pyridin-8-yl)hexahydrocyclopenta[c]pyrrole-2(1H)-carboxylate The solution of the product of Step 3 above (100 mg, 0.25 mmol) and Pd/C (10% w/w, 20 mg) in MeOH (5 mL) under hydrogen was stirred at room temperature overnight. The mixture was filtered through celite. The filtrate was concentrated under vacuum to give the crude title compound (100 mg).

Step 5. 8-((3aR,5r,6aS)-octahydrocyclopenta[c]pyrrol-5-yl)-6-(trifluoromethyl)imidazo[1,5-a]pyridine The product of Step 4 above was added to HCl/MeOH (4 N, 5 mL) at rt. The reaction solution was stirred at rt for 2 h and concentrated to give the crude title compound as a HCl salt, which was used directly without further purification.

Step 6. 1-((3aR,5r,6aS)-5-(6-(trifluoromethyl)imidazo[1,5-a]pyridin-8-yl)hexahydrocyclopenta[c]pyrrol-2(1H)-yl)ethanone To a suspension of the crude product of Step 5 above in DCM (10 mL) was added TEA (76 mg, 0.75 mmol) at rt. The mixture was cooled to 0° C. and acetyl chloride (29 mg, 0.375 mmol) was added dropwise. After stirring for 2 h at rt, the mixture was diluted with DCM (50 mL), washed with H$_2$O (15 mL×2) and brine (15 mL), dried over anhydrous sodium sulfate, and concentrated under vacuum. The residue was purified by prep-TLC (silica gel, DCM:MeOH=15:1) to give the title compound (20 mg, yield: 24%). MS (ESI) m/z: 338.1 [M+1]$^+$; $^1$H NMR (400 MHz, CD$_3$OD) δ 8.69 (s, 1H), 8.47 (s, 1H), 7.59 (s, 1H), 6.81 (s, 1H), 3.71 (m, 1H), 3.55 (m, 4H), 3.06-2.78 (m, 2H), 2.49 (m, 2H), 2.05 (s, 3H), 1.75-1.49 (m, 2H).

Example 5 (Method 6)

Preparation of Racemic-6-chloro-4-((3aR,6aS)-2-(methylsulfonyl)-1,2,3,3a,4,6a-hexahydrocyclopenta[c]pyrrol-5-yl)-1H-indazole

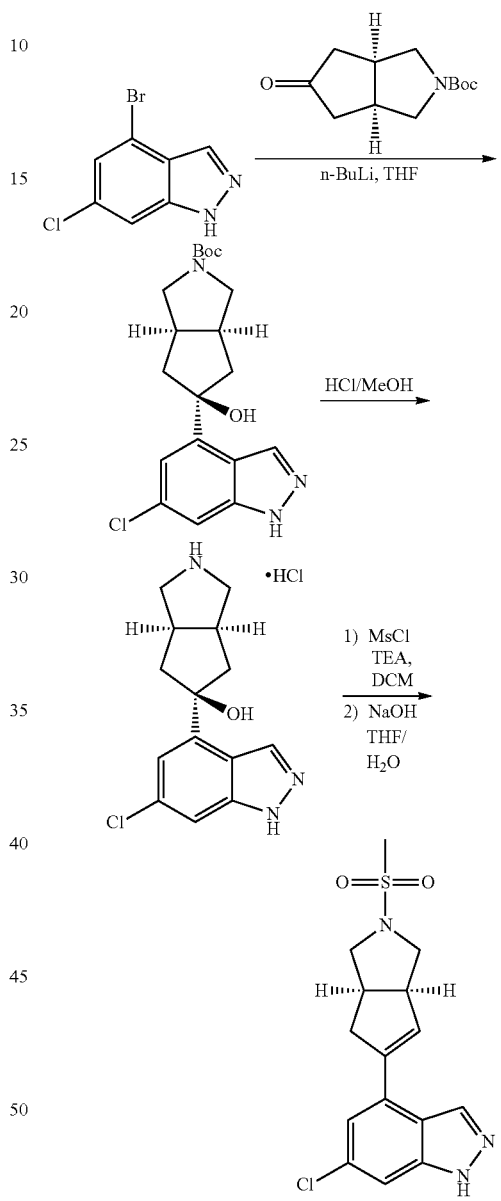

Step 1. (3aR,5r,6aS)-tert-butyl 5-(6-chloro-1H-indazol-4-yl)-5-hydroxyhexahydrocyclopenta-[c]pyrrole-2(1H)-carboxylate To a solution of 4-bromo-6-chloro-1H-indazole (2.31 g, 10 mmol) in THF (60 mL) cooled to −78° C., 1.6 M n-BuLi in hexane (12.5 mL, 20 mmol) was added slowly. The mixture was stirred at −78° C. for 0.5 h and a solution of (3aR,6aS)-tert-butyl 5-oxohexahydrocyclopenta-[c]pyrrole-2(1H)-carboxylate (2.5 g, 11.1 mmol) in THF (5 mL) was added dropwise. After the addition was complete, the reaction mixture was quenched with saturated aqueous NH4Cl (20 mL) and extracted with EtOAc (100 mL×2). The combined organic layers were washed with brine (50 mL×2), dried over anhydrous Na2SO4, and concentrated in vacuo. The residue was purified by silica gel flash column chromatography (PE:EtOAc=10:1 to 2:1) to give the title compound (1.055 g, yield: 27%).

Step 2. (3aR,5r,6aS)-5-(6-chloro-1H-indazol-4-yl)octahydrocyclopenta[c]pyrrol-5-ol hydrochloride A solution of the product of Step 1 above (1.75 g, 4.6 mmol) in 4N HCl/MeOH (20 mL) was stirred at rt for 4 h. The mixture was concentrated in vacuo to give the crude title compound as hydrochloride salt (1.5 g), which was used in the next step without any further purification.

Step 3. Race mic-6-chloro-4-((3aR,6aS)-2-(methylsulfonyl)-1,2,3,3a,4,6a-hexahydrocyclopenta[c]pyrrol-5-yl)-1H-indazole To a suspension of the crude product of Step 2 above (50 mg, 0.18 mmol) in DCM (5 mL) was added TEA (110 mg, 1.08 mmol). The mixture was cooled in an ice-water bath and MsCl (412 mg, 3.6 mmol) was added slowly. After the addition was complete, the mixture was stirred at rt for 2 h. The mixture was diluted with DCM (50 mL) and water (20 mL). The organic layer was separated, washed with brine (20 mL), dried over anhydrous Na2SO4 and concentrated in vacuo. The residue was treated with NaOH (100 mg, 2.5 mmol) in THF/H2O (5 mL/0.5 mL) The mixture was stirred at rt overnight and quenched with saturated NaHCO3 (aq.) to PH of 8-9. The mixture w and diluted with DCM/MeOH (10/1, 20 mL) and water (10 mL). The organic layer was separated, dried over Na2SO4, and concentrated in vacuo. The residue was purified by prep-TLC (silica gel, DCM:MeOH=10:1) to give the title compound (7 mg, yield: 11%). MS (ESI) m/z: 338.3 [M+1]$^+$; $^1$H NMR (400 MHz, DMSO-d6) δ 13.30 (s, 1H), 8.37 (s, 1H), 7.52 (s, 1H), 7.04 (s, 1H), 6.52 (s, 1H), 3.64 (s, 1H), 3.46 (dd, J=8.9, 7.6 Hz, 1H), 3.42-3.36 (m, 1H), 3.34 (d, J=2.7 Hz, 1H), 3.15-2.98 (m, 3H), 2.85 (s, 3H), 2.72 (d, J=14.4 Hz, 1H).

Example 6 and 7 (Method 7)

Preparation of 1-((3aR,5r,6aS)-5-(6-chloroimidazo[1,5-a]pyridin-8-yl)-5-hydroxyhexahydrocyclopenta[c]pyrrol-2(1H)-yl)ethanone and 1-((3aR,5r,6aS)-5-(6-chloroimidazo[1,5-a]pyridin-5-yl)-5-hydroxyhexahydrocyclopenta[c]pyrrol-2(1H)-yl)ethanone

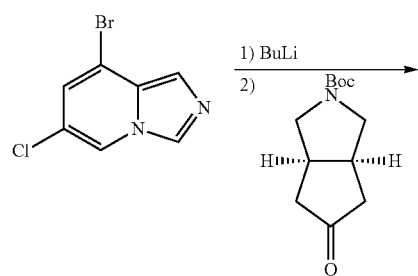

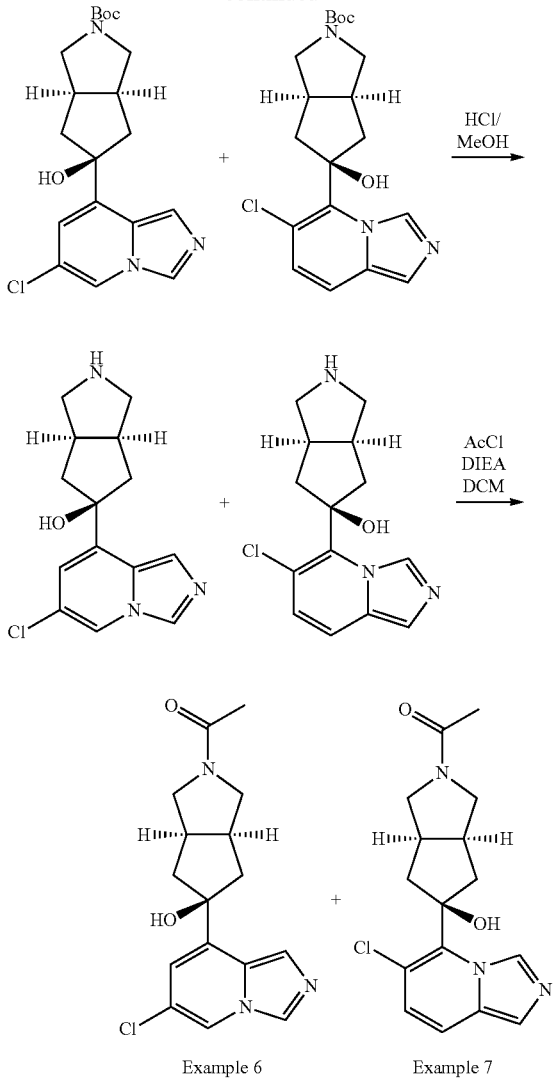

Example 6            Example 7

Step 1. (3aR,5r,6aS)-tert-butyl 5-(6-chloroimidazo[1,5-a]pyridin-8-yl)-5-hydroxyhexahydrocyclopenta[c]pyrrole-2(1H)-carboxylate and (3aR,5r,6aS)-tert-butyl 5-(6-chloroimidazo[1,5-a]pyridin-5-yl)-5-hydroxyhexahydrocyclopenta[c]pyrrole-2(1H)-carboxylate To a solution of 8-bromo-6-chloroimidazo[1,5-a]pyridine (200 mg, 0.87 mmol) cooled to −80° C. in an liquid nitrogen and ethanol bath was added dropwise n-butyl lithium (2.5 N in hexane, 0.5 mL, 1.25 mmol). After the addition is complete, The mixture was stirred at −80° C. for 0.5 h before adding dropwise a solution of (3aR,6aS)-tert-butyl 5-oxo-hexahydrocyclopenta[c]pyrrole-2(1H)-carboxylate (234 mg, 1.04 mmol) in THF (2 mL). After being stirred at −80° C. for 1-2 h, the mixture was stirred for 1 h while the temperature was allowed to warm to rt. The mixture was quenched with water (10 mL), extracted with EtOAc, dried over Na2SO4, and concentrated. The residue was purified by silica gel flash column chromatography (DCM:MeOH=20:1) to give the title mixture (150 mg, yield: 46%).

Step 2. (3aR,5r,6aS)-5-(6-chloroimidazo[1,5-a]pyridin-8-yl)octahydrocyclopenta[c]pyrrol-5-ol hydrochloride and (3aR,5r,6aS)-5-(6-chloroimidazo[1,5-a]pyridin-5-yl)octahydrocyclopenta[c]pyrrol-5-ol hydrochloride To a solution of the mixture of the product of Step 1 above (50 mg, 0.133 mmol) in DCM (1 mL) was added 4N HCl/MeOH (0.5 mL) The mixture was stirred at rt for 2 h and concentrated in vacuo. The crude title mixture (40 mg) obtained was used in the next step without any further purification.

Step 3. 1-((3aR,5r,6aS)-5-(6-chloroimidazo[1,5-a]pyridin-8-yl)-5-hydroxyhexahydrocyclopenta[c]pyrrol-2(1H)-yl)ethanone and 1-((3aR,5r,6aS)-5-(6-chloroimidazo[1,5-a]pyridin-5-yl)-5-hydroxyhexahydrocyclopenta[c]pyrrol-2(1H)-yl)ethanone To a suspension of the mixture of the product of Step 2 above in DCM (1 mL) was added DIPEA (51 mg, 0.398 mmol). The mixture was cooled in an ice-water bath and acetyl chloride (10 mg, 0.133 mmol) was added. After stirring at rt for 2 h, the mixture was diluted with DCM (10 mL) and H$_2$O (5 mL). The organic phase was separated, dried over sodium sulfate, and concentrated. The residue was purified by prep-TLC (silica gel, DCM:MeOH=20:1) to give the two title compounds.

Example 6: 1-((3aR,5r,6aS)-5-(6-chloroimidazo[1,5-a]pyridin-8-yl)-5-hydroxyhexahydrocyclopenta[c]pyrrol-2(1H)-yl)ethanone (12 mg): MS (ESI) m/z: 320.0 [M+1]$^+$; $^1$H NMR (400 MHz, CD$_3$OD) δ 9.01 (s, 1H), 7.46 (d, J=9.5 Hz, 1H), 7.41 (s, 1H), 6.74 (d, J=9.5 Hz, 1H), 3.84 (m, 1H), 3.75-3.65 (m, 3H), 3.05 (m, 2H), 2.87 (m, 2H), 2.50-2.34 (m, 2H), 2.08 (s, 3H).

Example 7

1-((3aR,5r,6aS)-5-(6-chloroimidazo[1,5-a]pyridin-5-yl)-5-hydroxyhexahydrocyclopenta[c]pyrrol-2(1H)-yl)ethanone (10 mg): MS (ESI) m/z: 320.0 [M+1]$^+$; $^1$H NMR (400 MHz, CD$_3$OD) δ 8.34 (s, 1H), 8.31 (s, 1H), 7.57 (s, 1H), 6.83 (d, J=1.4 Hz, 1H), 3.88-3.78 (m, 1H), 3.69 (m, 3H), 3.16-2.98 (m, 2H), 2.61 (m, 2H), 2.07 (s, 3H), 2.00 (m, 2H).

Example 8 (Method 8)

Preparation of 1-((3aR,5r,6aS)-5-(5-chloro-1H-indazol-7-yl)-5-hydroxyhexahydrocyclopenta[c]pyrrol-2(1H)-yl)ethanone

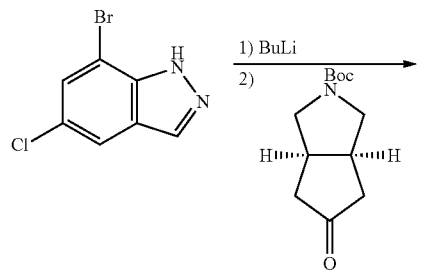

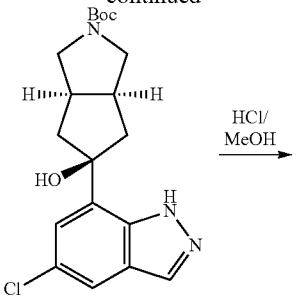
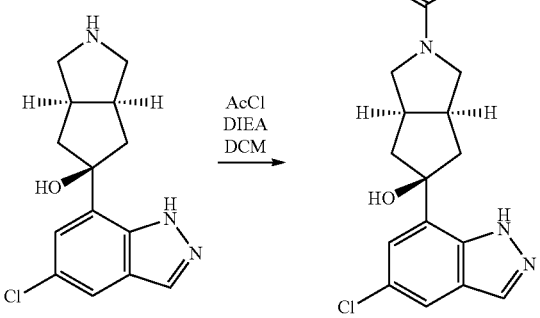

Step 1. (3aR,5r,6aS)-tert-butyl 5-(5-chloro-1H-indazol-7-yl)-5-hydroxyhexahydrocyclopenta[c]pyrrole-2(1H)-carboxylate To a solution of 7-bromo-5-chloro-1H-indazole (231.5 mg, 1.0 mmol) cooled to −78° C. was added n-butyl lithium (2.5 N in hexane, 1.0 mL, 2.5 mmol) dropwise. After the addition is complete, the mixture was stirred at −78° C. for 0.5 h before adding dropwise a solution of (3aR,6aS)-tert-butyl 5-oxohexahydrocyclopenta[c]pyrrole-2(1H)-carboxylate (225.3 mg, 1.0 mmol) in THF (0.5 mL). After stirring at −78° C. for 2 h, the mixture was quenched with saturated NH$_4$Cl (aq., 10 mL) and diluted with EtOAc (20 mL). The organic layer was separated, dried over Na$_2$SO$_4$, and concentrated in vacuo. The residue was purified by silica gel flash column chromatography (PE:EtOAc=10:1 to 2:1) to give the title compound (70 mg, yield: 18%).

Step 2. (3aR,5r,6aS)-5-(5-chloro-1H-indazol-7-yl)octahydrocyclopenta[c]pyrrol-5-ol hydrochloride A solution of the product of Step 1 above (70 mg, 0.185 mmol) in 4N HCl/MeOH (5 mL) was stirred at rt for 2 h. The reaction mixture was concentrated in vacuo to give the crude title compound (50 mg), which was used in the next step without any further purification.

Step 3. 1-((3aR,5r,6aS)-5-(5-chloro-1H-indazol-7-yl)-5-hydroxyhexahydrocyclopenta[c]pyrrol-2(1H)-yl)ethanone To a suspension of the product of Step 2 above (50 mg, ~0.185 mmol) in DCM (5 mL) was added TEA (93 mg, 0.925 mmol). The mixture was cooled in an ice-water bath and acetyl chloride (30 mg, 0.382 mmol) was added. The mixture was stirred at rt for 2 h and diluted with EtOAc (30 mL) and H$_2$O (10 mL) The organic phase was separated, dried over sodium sulfate, and concentrated in vacuo. The residue was dissolved in MeOH (3 mL) and saturated Na$_2$CO$_3$ (aq., 2 mL) was added. The mixture was stirred at rt overnight. The reaction mixture was diluted with DCM (30 mL) and water (20 mL). The organic phase was separated, dried over sodium sulfate, and concentrated. The residue was purified by prep-TLC (silica gel, DCM: MeOH=10:1) to give the title compound (20 mg, yield: 33%). MS (ESI) m/z: 342.2 [M+23]$^+$; $^1$H NMR (400 MHz, CD$_3$OD+CDCl$_3$) δ 7.94 (s, 1H), 7.60 (d, J=1.4 Hz, 1H), 7.15 (d, J=1.4 Hz, 1H), 3.76 m, 1H), 3.72-3.60 (m, 3H), 3.11-2.87 (m, 2H), 2.45 (m, 2H), 2.22-2.08 (m, 2H), 2.06 (s, 3H).

Example 9 (Method 9)

Preparation of N'-methyl-N-((1R,3r,5S,6r)-3-(6-chloro-1H-indazol-4-yl)-3-hydroxybicyclo[3.1.0]hexan-6-yl)sulfuric diamide

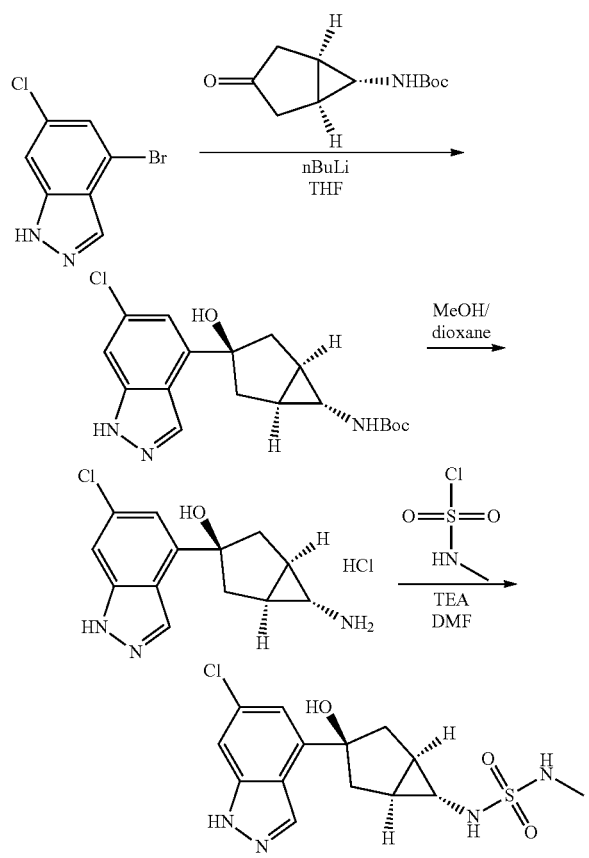

Step 1. tert-butyl ((1R,3r,5S,6r)-3-(6-chloro-1H-indazol-4-yl)-3-hydroxybicyclo[3.1.0]hexan-6-yl)carbamate To a solution of 4-bromo-6-chloro-1H-indazole (25 g, 108 mmol) in THF (250 mL) cooled to −78° C. in a liquid nitrogen/acetone bath was added dropwise n-BuLi (2.5M in THF, 143 mL, 356 mmol), maintaining the inner temperature below −75° C. After stirring at −78° C. for 0.5 h, a solution of tert-butyl ((1R,5S,6r)-3-oxobicyclo[3.1.0]hexan-6-yl)carbamate (23 g, 108 mmol) in THF (150 mL) was added dropwise to the reaction mixture, maintaining the inner temperature below −75° C. After the addition, the reaction mixture was stirred at −78° C. for 2 h before quenching with NH$_4$Cl (sat. aq, 150 mL) at −20° C. and allowed to warm up to rt gradually. EtOAc (400 mL) was added to the reaction mixture, and the organic layer was separated, which was washed with H$_2$O (200 mL) and brine (150 mL), dried over anhydrous sodium sulfate, and concentrated under vacuum. The residue was purified by silica gel flash column chromatography (PE:EtOAc=5:1~DCM: MeOH=20:1) to give the title compound (8.35 g, yield: 21.3%).

Step 2. (1R,3r,5S,6r)-6-amino-3-(6-chloro-1H-indazol-4-yl)bicyclo[3.1.0]hexan-3-ol hydrochloride A mixture of the product of Step 1 above (16.7 g, 46 mmol) in HCl/MeOH (4 N, 180 mL) was stirred at rt for 5 h. The mixture was concentrated under vacuum to give the title compound as a HCl salt (13.8 g, yield: 100%).

Step 3. N'-methyl-N-((1R,3r,5S,6r)-3-(6-chloro-1H-indazol-4-yl)-3-hydroxybicyclo[3.1.0]hexan-6-yl) sulfuric diamide To a solution of the product of Step 2 above (3.0 g, 9.99 mmol) in DMF (40 mL) was added TEA (20 mL) at rt. The reaction solution was cooled to −50° C. and methylsulfamoyl chloride (1.3 g, 9.99 mmol) was added dropwise, maintaining the inner temperature below −50° C. The reaction mixture was stirred at rt overnight and concentrated in vacuo. The residue was diluted with DCM/i-PrOH (3:1, 350 mL), transferred to a separatory funnel, washed with H$_2$O (150 mL×2) and brine (150 mL), dried over anhydrous sodium sulfate, and concentrated under vacuum. The residue was purified by silica gel flash column chromatography (DCM:MeOH=100:1-20:1) to give the title compound (1.81 g, yield: 51%). MS (ESI) m/z: 357.0 [M+1]$^+$; $^1$H NMR (400 MHz, CD$_3$OD) δ 8.09 (s, 1H), 7.42 (s, 1H), 7.17 (d, J=1.4 Hz, 1H), 3.07 (s, 1H), 2.66 (s, 3H), 2.62 (d, J=3.8 Hz, 2H), 2.18 (m, 2H), 1.87-1.76 (m, 2H).

Example 10 (Method 10)

Preparation of N-((1R,3r,5S,6r)-3-hydroxy-3-(6-(trifluoromethyl)-1H-indazol-4-yl)bicyclo[3.1.0]hexan-6-yl)methanesulfonamide

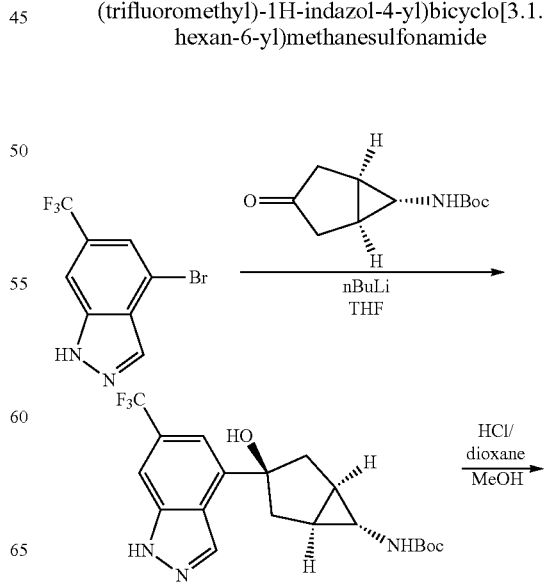

7.78 (s, 1H), 7.36 (s, 1H), 7.26 (d, J=3.1 Hz, 1H), 5.35 (s, 1H), 3.10 (s, 1H), 2.95 (s, 3H), 2.55 (m, 2H), 2.13 (d, J=14.1 Hz, 2H), 1.75 (s, 2H).

Example 11 (Method 11)

Preparation of 1-(6-chloro-1H-indazol-4-yl)cyclopropanol

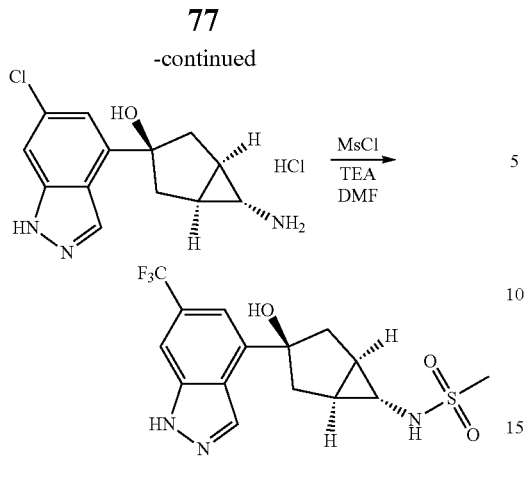

Step 1. tert-butyl ((1R,3r,5S,6r)-3-hydroxy-3-(6-(trifluoromethyl)-1H-indazol-4-yl)bicyclo[3.1.0]hexan-6-yl)carbamate To a solution of 4-bromo-6-(trifluoromethyl)-1H-indazole (3 g, 11.32 mmol) in THF (60 mL) cooled to −78° C. in a liquid nitrogen/acetone bath was added dropwise n-BuLi/THF (2.5M, 15 mL, 37.36 mmol), maintaining the inner temperature below −75° C. After being stirred at −78° C. for 0.5 h, a solution of tert-butyl ((1R,5S,6r)-3-oxobicyclo[3.1.0]hexan-6-yl)carbamate (2.42 g, 11.32 mmol) in THF (10 mL) was added dropwise to the reaction mixture, maintaining the inner temperature below −75° C. After the addition, the reaction was stirred at −78° C. for 1 h before quenching with NH₄Cl (sat. aq, 80 mL) and diluted with EtOAc (150 mL). The organic layer was separated, which was washed with H₂O (80 mL×2) and brine (80 mL), dried over anhydrous sodium sulfate, and concentrated under vacuum. The residue was purified by silica gel flash column chromatography (PE:EtOAc=10:1-3:2) to give the title compound (950 mg, yield: 21%).

Step 2. (1R,3r,5S,6r)-6-amino-3-(6-(trifluoromethyl)-1H-indazol-4-yl)bicyclo[3.1.0]hexan-3-ol hydrochloride To a solution of the product of Step 1 above (950 mg, 2.39 mmol) in MeOH (10 mL) was added HCl/dioxane (4 N, 10 mL) at rt. The reaction mixture was stirred at rt for 2 h and concentrated under vacuum to give the crude title compound as a HCl salt (870 mg).

Step 3. N-((1R,3r,5S,6r)-3-hydroxy-3-(6-(trifluoromethyl)-1H-indazol-4-yl)bicyclo[3.1.0]hexan-6-yl)methanesulfonamide To a solution of the product of Step 2 above (75 mg, 0.225 mmol) in DMF (1 mL) was added TEA (1 mL) at rt. The mixture was cooled to −50° C. and methanesulfonyl chloride (26 mg, 0.225 mmol) was added dropwise. The reaction mixture was stirred at rt for 6 h and concentrated under vacuum. The residue was diluted with DCM/MeOH (10:1, 30 mL), which was transferred to a separatory funnel, washed with H₂O (15 mL×2) and brine (15 mL), dried over anhydrous sodium sulfate, and concentrated under vacuum. The residue was purified by prep-TLC (silica gel, DCM:MeOH=10:1) to give the title compound (32.4 mg, yield: 38%) as a white solid. MS (ESI) m/z: 376.1 [M+1]⁺; ¹H NMR (400 MHz, DMSO-d6) δ 13.54 (s, 1H), 8.17 (s, 1H),

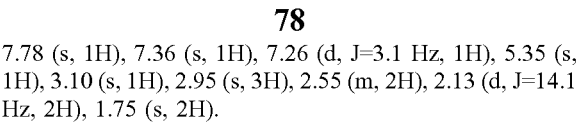

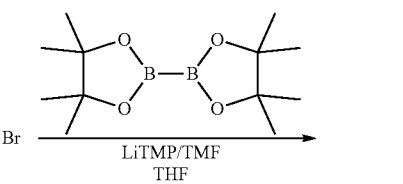

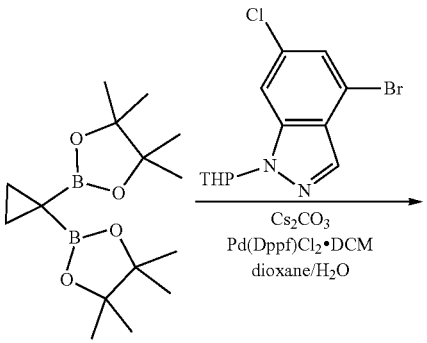

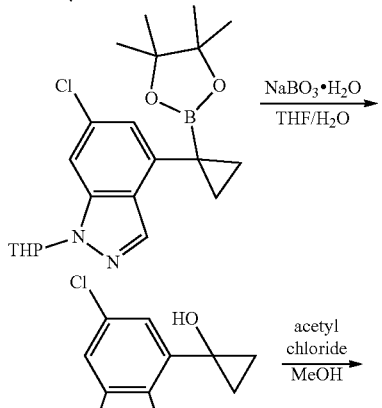

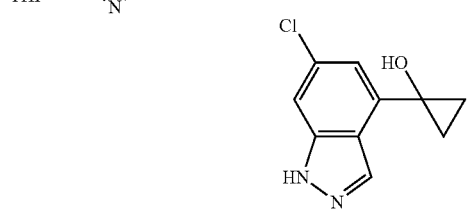

Step 1. 2,2'-(cyclopropane-1,1-diyl)bis(4,4,5,5-tetramethyl-1,3,2-dioxaborolane)

A solution of bromocyclopropane (2 g, 16.53 mmol) and B₂Pin₂ in THF (40 mL) was cooled to −95° C. in a liquid nitrogen/acetone bath. Freshly prepared LiTMP in THF (0.91M, 21.3 mL, 19.4 mmol) was added dropwise to the reaction mixture. After being stirred at −95° C. for 1 h, the reaction mixture was quenched with NaHCO₃ (sat. aq, 50 mL) at −20° C. and allowed to warm up to rt. EtOAc (100 mL) was added and the layers were separated. The organic phase was washed with H₂O (50 mL) and brine (50 mL), dried over anhydrous sodium sulfate, and concentrated under vacuum. The residue was purified by silica gel flash column chromatography (PE:EtOAc=50:1-30:1) to give the title compound (1.15 g, yield: 23%) as a white solid.

Step 2. 6-chloro-1-(tetrahydro-2H-pyran-2-yl)-4-(1-(4,4,5,5-tetramethyl-1,3,2-dioxaborolan-2-yl)cyclopropyl)-1H-indazole To a 20 mL of capped vial was added 4-bromo-6-chloro-1-(tetrahydro-2H-pyran-2-yl)-1H-indazole (320 mg, 1.1013 mmol), the product of Step 1 above (200 mg, 0.675 mmol), Cs₂CO₃ (660 mg, 2.025 mmol), Pd(dppf)Cl₂CH₂Cl₂ (28 mg, 0.03375 mmol), dioxane (5 mL), and H₂O (0.5 mL) sequentially. The vial was flushed with nitrogen and stirred at 100° C. for 12 h. After cooling to rt, the reaction mixture was poured into EtOAc (60 mL). The mixture was transferred to a separatory funnel, washed with H₂O (30 mL×2) and brine (30 mL), dried over anhydrous sodium sulfate, and concentrated in vacuo. The residue obtained was purified by silica gel flash column chromatography (PE:EtOAc=20:1 to 10:1) to give the title compound (154 mg, yield: 57%) as a yellowish solid.

Step 3. 1-(6-chloro-1-(tetrahydro-2H-pyran-2-yl)-1H-indazol-4-yl)cyclopropanol

To a solution of the product of Step 2 above (140 mg, 0.348 mmol) in THF/H₂O (2 mL/2 mL) was added NaBO₃·H₂O (3.02 g, 11.51 mmol) at rt. The reaction mixture was stirred at rt for 2 h. It was diluted with DCM (50 mL), transferred to a separatory funnel, washed with H₂O (20 mL×2) and brine (20 mL), dried over anhydrous sodium sulfate, and concentrated under vacuum. The residue was purified by silica gel flash column chromatography (PE:EtOAc=10:1~4:1) to give the title compound (96 mg, yield: 94%) as a yellow oil.

Step 4. 1-(6-chloro-1H-indazol-4-yl)cyclopropanol

To a solution of the product of Step 3 above (80 mg, 0.273 mmol) in MeOH (5 mL) cooled in an ice-water bath was added dropwise acetyl chloride (393 mg, 5 mmol). The mixture was stirred at rt for 2 h and Na₂CO₃ (sat. aq, 2 mL) was added until pH became 8-9. The resulting solution was diluted with H₂O (30 mL) and extracted with DCM/MeOH (10:1, 60 mL). The organic phase was washed with H₂O (30 mL×2) and brine (30 mL), dried over anhydrous sodium sulfate, and concentrated under vacuum. The residue was purified by prep-TLC (PE:EtOAc=1:1) to give the title compound (38 mg, 66% yield) as a yellowish solid. MS (ESI) m/z: 209.1 [M+1]⁺; ¹H NMR (400 MHz, DMSO-d6) δ 13.13 (s, 1H), 8.10 (s, 1H), 7.41 (s, 1H), 6.96 (d, J=1.5 Hz, 1H), 6.23 (s, 1H), 1.20 (d, J=4.9 Hz, 4H).

Table 1 lists examples that were prepared according to the procedures as described in methods 1-11 as indicated below the structure of each example by using the corresponding intermediates and reagents under appropriate conditions that could be accomplished by the skilled persons.

TABLE 1

| Example | Structure (Synthetic Method) | Chemical Name | LC/MS [M + H]⁺ | ¹H-NMR |
|---|---|---|---|---|
| 12 | 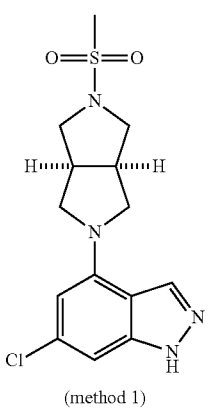 [SMILES: CS(=O)(=O)N1C[C@H]2CN(c3cc(Cl)cc4[nH]ncc34)C[C@H]2C1] (method 1) | 6-chloro-4-((3aR,6aS)-5-(methylsulfonyl)hexahydropyrrolo[3,4-c]pyrrol-2(1H)-yl)-1H-indazole | 341.1 | ¹H NMR (400 MHz, DMSO-d6) δ 12.86 (s, 1H), 8.19 (s, 1H), 6.73 (s, 1H), 5.94 (s, 1H), 3.84-3.72 (m, 2H), 3.55-3.47 (m, 4H), 3.25-3.17 (m, 2H), 3.15-3.08 (m, 2H), 2.94 (s, 3H). |
| 13 | 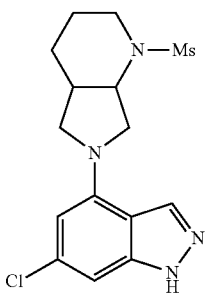 (method 1) | 6-chloro-4-(1-(methylsulfonyl)hexahydro-1H-pyrrolo[3,4-b]pyridin-6(2H)-yl)-1H-indazole | 354.8 | ¹H NMR (400 MHz, DMSO-d6) δ 12.85 (s, 1H), 8.17 (s, 1H), 6.71 (s, 1H), 5.96 (d, J = 1.2 Hz, 1H), 4.51 (dd, J = 15.2, 8.8 Hz, 1H), 3.83 (t, J = 9.6 Hz, 1H), 3.72 (dd, J = 9.5, 5.5 Hz, 1H), 3.65-3.50 (m, 2H), 3.35 (d, J = 8.1 Hz, 1H), 3.09 (d, J = 12.8 Hz, 1H), 3.02 (s, 3H), 2.35 (dt, J = 16.9, 5.3 Hz, 1H), 1.73 (dd, J = 31.5, 11.6 Hz, 2H), 1.49 (dd, J = 25.8, 13.0 Hz, 1H), 1.31 (dt, J = 12.9, 10.0 Hz, 1H). |

TABLE 1-continued

| Example | Structure (Synthetic Method) | Chemical Name | LC/MS [M + H]+ | 1H-NMR |
|---|---|---|---|---|
| 14 | (method 1) | 1-((3aR,6aS)-5-(6-chloro-1H-indazol-4-yl)hexahydropyrrolo[3,4-c]pyrrol-2(1H)-yl)ethanone | 305.3 | 1H NMR (400 MHz, CDCl3) δ 8.07 (s, 1H), 6.79 (s, 1H), 5.99 (s, 1H), 4.02-3.67 (m, 4H), 3.65-3.35 (m, 4H), 3.26-2.96 (m, 2H), 2.09 (s, 3H). |
| 15 | (method 1) | 1-(6-(6-chloro-1H-indazol-4-yl)octahydro-1H-pyrrolo[3,4-b]pyridin-1-yl)ethanone | 319.1 | 1H NMR (400 MHz, CD3OD) δ 8.17 (d, J = 18.4 Hz, 1H), 6.74 (d, J = 4.0 Hz, 1H), 6.01 (d, J = 12.8 Hz, 1H), 5.25 (dd, J = 15.8, 9.0 Hz, 1H), 4.76 (dd, J = 17.2, 10.5 Hz, 1H), 4.53 (d, J = 14.0 Hz, 1H), 3.97-3.59 (m, 4H), 3.45 (t, J = 9.3 Hz, 1H), 2.55-2.28 (m, 1H), 2.19 (d, J = 16.9 Hz, 3H), 1.85 (m, J = 28.6, 17.9, 9.0 Hz, 2H), 1.66-1.40 (m, 2H). |
| 16 | (method 1) | N-((1R,5S)-3-(6-chloro-1H-indazol-4-yl)-3-azabicyclo[3.1.0]hexan-6-yl)methanesulfonamide | 327.2 | 1H NMR (400 MHz, CD3OD) δ 8.17 (s, 1H), 7.25 (d, J = 4.2 Hz, 1H), 6.75 (s, 1H), 6.01 (s, 1H), 3.93 (d, J = 9.6 Hz, 2H), 3.66 (d, J = 9.0 Hz, 2H), 3.02 (s, 4H), 2.42 (s, 1H), 2.13 (s, 2H). |
| 17 | (method 1) | N-((1R,5S)-3-(6-chloro-1H-indazol-4-yl)-3-azabicyclo[3.1.0]hexan-6-yl)acetamide | 291.2 | 1H NMR (400 MHz, DMSO-d6) δ 12.86 (s, 1H), 8.17 (s, 1H), 8.06 (d, J = 3.5 Hz, 1H), 6.71 (s, 1H), 5.92 (s, 1H), 3.82 (d, J = 9.8 Hz, 2H), 3.60 (d, J = 8.9 Hz, 2H), 2.42 (s, 1H), 1.84 (s, 2H), 1.78 (s, 3H). |

TABLE 1-continued

| Example | Structure (Synthetic Method) | Chemical Name | LC/MS [M + H]+ | 1H-NMR |
|---|---|---|---|---|
| 18 | (method 1) | 1-(5-(6-chloro-1H-indazol-4-yl)-1,1-dimethylhexahydropyrrolo[3,4-c]pyrrol-2(1H)-yl)ethanone | 333.1 | 1H NMR (400 MHz, CDCl$_3$) δ 8.14-8.05 (m, 1H), 6.78 (s, 1H), 6.04 (t, J = 4.7 Hz, 1H), 3.92 (dd, J = 9.8, 6.0 Hz, 1H), 3.87-3.73 (m, 2H), 3.68-3.56 (m, 2H), 3.40-3.29 (m, 1H), 3.19-3.09 (m, 1H), 2.73 (dd, J = 15.4, 8.4 Hz, 1H), 2.01 (s, 3H), 1.65 (s, 3H), 1.50 (s, 3H). |
| 19 | (method 1) | 1-(5-(6-chloro-1H-indazol-4-yl)hexahydropyrrolo[3,4-b]pyrrol-1(2H)-yl)ethanone | 304.9 | 1H NMR (400 MHz, CDCl$_3$) δ 8.17-8.06 (s, 1H), 6.76 (s, 1H), 6.14 (s, 1H), 4.65 (td, J = 7.0, 2.7 Hz, 1H), 3.94 (dd, J = 11.0, 6.5 Hz, 1H), 3.88-3.76 (m, 2H), 3.70-3.56 (m, 2H), 3.51 (dd, J = 10.0, 4.9 Hz, 1H), 3.17-3.08 (m, 1H), 2.22 (dd, J = 12.9, 7.3 Hz, 1H), 2.09 (s, 3H), 2.05-1.95 (m, 1H). |
| 20 | (method 1) | 6-chloro-1-methyl-4-(1-(methylsulfonyl)hexahydropyrrolo[3,4-b]pyrrol-5(1H)-yl)-1H-indazole | 354.8 | 1H NMR (400 MHz, CDCl$_3$) δ 7.97 (s, 1H), 7.03 (d, J = 19.9 Hz, 1H), 5.99-5.84 (m, 1H), 4.39-4.32 (m, 1H), 4.14 (s, 3H), 4.01 (dd, J = 10.7, 2.3 Hz, 1H), 3.74 (dd, J = 10.7, 6.2 Hz, 1H), 3.64-3.52 (m, 2H), 3.50-3.44 (m, 1H), 3.39 (dd, J = 9.9, 4.3 Hz, 1H), 3.20-3.06 (m, 1H), 2.89 (s, 3H), 2.20 (td, J = 14.1, 7.1 Hz, 1H), 1.99 (tt, J = 15.7, 7.8 Hz, 1H). |
| 21 | (method 1) | N-((1R,5S,6r)-3-(6-chloro-1H-indazol-4-yl)-3-azabicyclo[3.1.0]hexan-6-yl)acetamide | 290.8 | 1H NMR (400 MHz, DMSO-d6) δ 12.91 (s, 1H), 8.15 (s, 1H), 8.13 (d, J = 3.4 Hz, 1H), 6.71 (s, 1H), 5.90 (s, 1H), 3.87-3.76 (m, 2H), 3.64-3.52 (m, 2H), 2.44-2.36 (m, 1H), 1.85-1.82 (m, 2H), 1.77 (s, 3H). |

TABLE 1-continued

| Example | Structure (Synthetic Method) | Chemical Name | LC/MS [M + H]⁺ | ¹H-NMR |
|---|---|---|---|---|
| 22 | (method 3) | 1-((3aR,5r,6aS)-5-(6-chloro-1H-indazol-4-yl)-5-hydroxyhexahydrocyclopenta[c]pyrrol-2(1H)-yl)ethanone | 319.7 | $^1$H NMR (400 MHz, DMSO-d6) δ 13.14 (s, 1H), 8.19 (s, 1H), 7.46 (s, 1H), 7.07 (s, 1H), 5.34 (s, 1H), 3.78-3.41 (m, 4H), 3.05-2.80 (m, 2H), 2.45-2.32 (m, 2H), 2.06-1.86 (m, 5H). |
| 23 | (method 1) | 6-chloro-4-(1-(methylsulfonyl)hexahydropyrrolo[3,4-b]pyrrol-5(1H)-yl)-1H-indazole | | $^1$H NMR (400 MHz, DMSO-d6) δ 12.88 (s, 1H), 8.11 (s, 1H), 6.74 (s, 1H), 5.93 (s, 1H), 4.34 (dd, J = 8.4, 5.7 Hz, 1H), 3.77-3.66 (m, 3H), 3.53 (dd, J = 10.1, 6.1 Hz, 1H), 3.50-3.41 (m, 2H), 3.15 (d, J = 5.2 Hz, 1H), 2.97 (s, 3H), 2.12-2.02 (m, 1H), 1.92-1.82 (m, 1H). |
| 24 | (method 1) | N-((1R,5S,6r)-3-(6-chloro-1H-indazol-4-yl)-3-azabicyclo[3.1.0]hexan-6-yl)methanesulfonamide | 326.9 | $^1$H NMR (400 MHz, DMSO-d6) δ 12.83 (s, 1H), 8.16 (s, 1H), 7.50 (s, 1H), 6.70 (s, 1H), 5.90 (s, 1H), 3.91-3.75 (m, 2H), 3.68-3.51 (m, 2H), 2.97 (s, 3H), 2.40-2.28 (m, 1H), 2.06-1.90 (m, 2H). |
| 25 | (method 3) | (1R,3r,5S)-3-(6-chloro-1H-indazol-4-yl)bicyclo[3.1.0]hexan-3-ol | 248.8 | $^1$H NMR (400 MHz, DMSO-d6) δ 13.16 (s, 1H), 8.01 (s, 1H), 7.43 (s, 1H), 7.08 (d, J = 1.4 Hz, 1H), 5.11 (s, 1H), 2.47-2.37 (m, 2H), 2.01 (d, J = 13.8 Hz, 2H), 1.57-1.43 (m, 2H), 1.02-0.91 (m, 1H), 0.53-0.42 (m, 1H). |

TABLE 1-continued

| Example | Structure (Synthetic Method) | Chemical Name | LC/MS [M + H]+ | 1H-NMR |
|---|---|---|---|---|
| 26 | 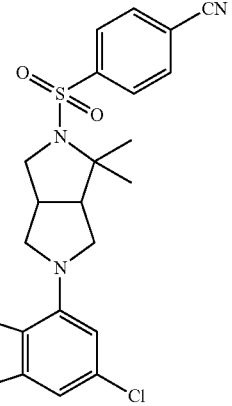 (method 1) | 4-(5-(6-chloro-1H-indazol-4-yl)-1,1-dimethylhexahydro-pyrrolo[3,4-c]pyrrol-2(1H)-ylsulfonyl)benzonitrile | 455.9 | 1H NMR (400 MHz, CD3OD) δ 7.98 (d, J = 7.9 Hz, 3H), 7.82 (d, J = 8.2 Hz, 2H), 6.75 (s, 1H), 5.88 (s, 1H), 3.92 (dd, J = 18.4, 9.2 Hz, 1H), 3.82 (m, 1H), 3.63-3.52 (m, 2H), 3.24-3.09 (m, 3H), 2.76 (m, 1H), 1.50 (s, 3H), 1.48 (s, 3H). |
| 27 | 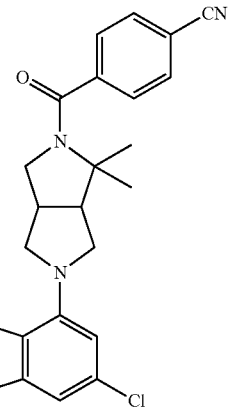 (method 1) | 4-(5-(6-chloro-1H-indazol-4-yl)-1,1-dimethyloctahydro-pyrrolo[3,4-c]pyrrole-2-carbonyl)benzonitrile | 420.0 | 1H NMR (400 MHz, CDCl3) δ 8.09 (s, 1H), 7.67 (d, J = 8.1 Hz, 2H), 7.50 (d, J = 8.1 Hz, 2H), 6.80 (s, 1H), 6.06 (s, 1H), 3.95-3.80 (m, 2H), 3.78-3.69 (m, 1H), 3.52 (dd, J = 22.7, 12.7 Hz, 3H), 3.31 (s, 1H), 3.17-3.03 (m, 1H), 2.83 (dd, J = 15.3, 8.4 Hz, 1H), 1.77 (s, 3H), 1.66 (s, 3H). |
| 28 | 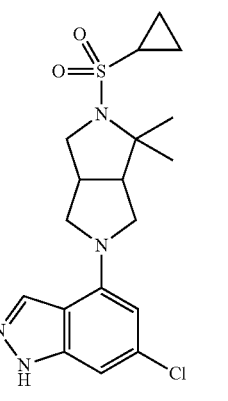 (method 1) | 6-chloro-4-(5-(cyclopropylsulfonyl)-4,4-dimethylhexahydro-pyrrolo[3,4-c]pyrrol-2(1H)-yl)-1H-indazole | 394.8 | 1H NMR (400 MHz, CD3OD) δ 8.09 (s, 1H), 6.76 (s, 1H), 6.00 (s, 1H), 3.95-3.85 (m, 2H), 3.81-3.72 (m, 1H), 3.68-3.56 (m, 2H), 3.28-3.14 (m, 2H), 2.80 (dd, J = 15.0, 7.8 Hz, 1H), 2.48 (ddd, J = 12.8, 8.0, 4.9 Hz, 1H), 1.58 (s, 3H), 1.53 (s, 3H), 1.12-1.07 (m, 2H), 1.01-0.95 (m, 2H). |

TABLE 1-continued

| Example | Structure (Synthetic Method) | Chemical Name | LC/MS [M + H]+ | 1H-NMR |
|---|---|---|---|---|
| 29 | 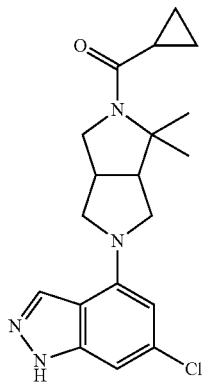 (method 1) | (5-(6-chloro-1H-indazol-4-yl)-1,1-dimethylhexahydro-pyrrolo[3,4-c]pyrrol-2(1H)-yl)(cyclopropyl)methanone | 358.8 | 1H NMR (400 MHz, CD3OD) δ 7.99 (s, 1H), 7.37-7.17 (s, 1H), 6.73 (s, 1H), 4.07 (t, J = 9.8 Hz, 1H), 3.89 (dd, J = 9.7, 5.9 Hz, 1H), 3.72 (d, J = 9.5 Hz, 2H), 3.60 (t, J = 9.9 Hz, 2H), 3.51-3.43 (m, 1H), 3.15-3.08 (m, 1H), 2.70 (dd, J = 15.4, 8.4 Hz, 1H), 1.56 (s, 3H), 1.42 (s, 3H), 0.94 (dt, J = 9.7, 7.7 Hz, 1H), 0.81-0.63 (m, 3H). |
| 30 | 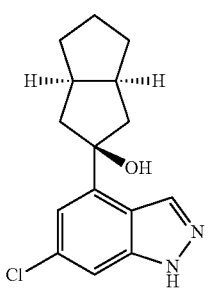 (method 3) | (2r,3aR,6aS)-2-(6-chloro-1H-indazol-4-yl)octahydropentalen-2-ol | 277.0 | 1H NMR (400 MHz, DMSO-d6) δ 13.12 (s, 1H), 8.15 (s, 1H), 7.42 (s, 1H), 6.98 (s, 1H), 5.26 (s, 1H), 2.37 (m, 2H), 1.84-1.44 (m, 10H). |
| 31 | 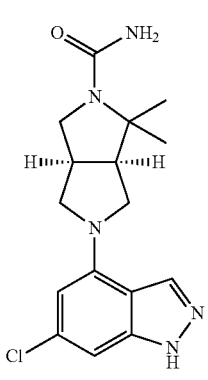 (method 1) | Racemic-(3aS,6aR)-5-(6-chloro-1H-indazol-4-yl)-1,1-dimethylhexahydro-pyrrolo[3,4-c]pyrrole-2(1H)-carboxamide | 334.1 | 1H NMR (400 MHz, DMSO-d6) δ 12.83 (s, 1H), 8.15 (s, 1H), 6.68 (s, 1H), 5.96 (s, 1H), 5.49 (s, 2H), 3.82 (m, 1H), 3.69-3.61 (m, 1H), 3.58 (m, 1H), 3.53-3.40 (m, 2H), 3.12-3.00 (m, 2H), 2.63 (m, 1H), 1.42 (s, 3H), 1.31 (s, 3H). |
| 32 | 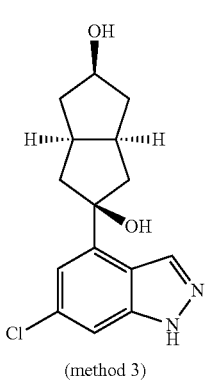 [SMILES: O[C@@H]1C[C@@H]2C[C@@](O)(c3cc(Cl)cc4[nH]ncc34)C[C@@H]2C1] (method 3) | (2r,3aR,5s,6aS)-2-(6-chloro-1H-indazol-4-yl)octahydropentalene-2,5-diol | 293.0 | 1H NMR (400 MHz, DMSO-d6) δ 13.17 (s, 1H), 8.14 (s, 1H), 7.41 (s, 1H), 7.00 (s, 1H), 5.35 (m, 1H), 4.69 (m, 1H), 3.93 (m, 1H), 2.35 (m, 2H), 2.08-1.80 (m, 5H), 1.74-1.59 (m, 2H), 1.43-1.30 (m, 1H). |

TABLE 1-continued

| Example | Structure (Synthetic Method) | Chemical Name | LC/MS [M + H]+ | 1H-NMR |
|---|---|---|---|---|
| 33 | (method 1) | 4-(((3aR,6aS)-5-(6-chloro-1H-indazol-4-yl)hexahydropyrrolo[3,4-c]pyrrol-2(1H)-yl)sulfonyl)benzonitrile | 427.9 | 1H NMR (400 MHz, DMSO-d6) δ 12.94 (s, 1H), 8.06 (m, 2H), 7.99 (m, 3H), 6.71 (s, 1H), 5.77 (s, 1H), 3.62 (m, 2H), 3.46 (m, 2H), 3.20 (m, 4H), 2.96 (m, 2H). |
| 34 | (method 1) | 4-((3aR,6aS)-5-(6-chloro-1H-indazol-4-yl)octahydropyrrolo[3,4-c]pyrrole-2-carbonyl)benzonitrile | 392.1 | 1H NMR (400 MHz, DMSO-d6) δ 12.96 (s, 1H), 8.16 (s, 1H), 7.90 (d, J = 8.2 Hz, 2H), 7.76-7.67 (m, 2H), 6.71 (s, 1H), 5.90 (s, 1H), 3.87-3.78 (m, 2H), 3.72 (m, 7.5 Hz, 1H), 3.62 (m, 2H), 3.48 (m, 2H), 3.41-3.36 (m, 1H), 3.13-2.99 (m, 2H). |
| 35 | (method 3) | (3aR,5r,6aS)-5-(6-chloro-1H-indazol-4-yl)-2-(phenylsulfonyl)octahydrocyclopenta[c]pyrrol-5-ol | 418.0 | 1H NMR (400 MHz, DMSO-d6) δ 13.14 (s, 1H), 8.16 (s, 1H), 7.84-7.77 (m, 2H), 7.76-7.70 (m, 1H), 7.65 (t, J = 7.3 Hz, 2H), 7.45 (s, 1H), 6.97 (s, 1H), 5.21 (s, 1H), 3.44-3.36 (m, 2H), 3.20-3.08 (m, 2H), 2.73 (s, 2H), 2.30 (m, 2H), 1.83 (m, 2H). |

TABLE 1-continued

| Example | Structure (Synthetic Method) | Chemical Name | LC/MS [M + H]+ | 1H-NMR |
|---|---|---|---|---|
| 36 | 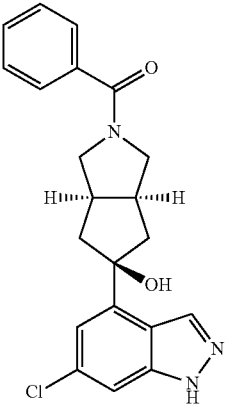 (method 3) | ((3aR,5r,6aS)-5-(6-chloro-1H-indazol-4-yl)-5-hydroxyhexahydrocyclopenta[c]pyrrol-2(1H)-yl)(phenyl)methanone | 382.0 | $^1$H NMR (400 MHz, CD$_3$OD) δ 8.24 (s, 1H), 7.55-7.49 (m, 2H), 7.49-7.41 (m, 4H), 7.15 (d, J = 1.5 Hz, 1H), 3.92 (d, J = 5.8 Hz, 2H), 3.79-3.69 (m, 1H), 3.69-3.61 (m, 1H), 3.03 (m, 2H), 2.68-2.57 (m, 1H), 2.54-2.44 (m, 1H), 2.12 (m, 1H), 1.98 (m, 1H). |
| 37 | 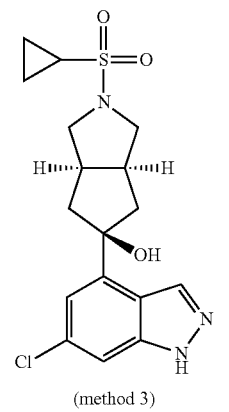 [SMILES: O=S(=O)(C1CC1)N1C[C@@H]2C[C@@](O)(c3cc(Cl)cc4[nH]ncc34)C[C@@H]2C1] (method 3) | (3aR,5r,6aS)-5-(6-chloro-1H-indazol-4-yl)-2-(cyclopropylsulfonyl)octahydrocyclopenta[c]pyrrol-5-ol | 382.0 | $^1$H NMR (400 MHz, DMSO-d6) δ 13.16 (s, 1H), 8.22 (s, 1H), 7.48 (s, 1H), 7.07 (s, 1H), 5.41 (s, 1H), 3.55 (m, 2H), 3.36 (m, 2H), 2.96 (s, 2H), 2.66-2.56 (m, 1H), 2.39 (m, 2H), 1.95 m, 2H), 1.04-0.89 (m, 4H). |
| 38 | 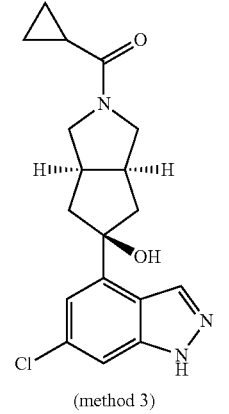 [SMILES: O=C(C1CC1)N1C[C@@H]2C[C@@](O)(c3cc(Cl)cc4[nH]ncc34)C[C@@H]2C1] (method 3) | ((3aR,5r,6aS)-5-(6-chloro-1H-indazol-4-yl)-5-hydroxyhexahydrocyclopenta[c]pyrrol-2(1H)-yl)(cyclopropyl)methanone | 346.0 | $^1$H NMR (400 MHz, DMSO-d6) δ 13.18 (s, 1H), 8.21 (s, 1H), 7.47 (s, 1H), 7.08 (s, 1H), 5.37 (s, 1H), 3.95 (t, J = 9.6 Hz, 1H), 3.74 (dd, J = 10.1, 5.4 Hz, 1H), 3.73-3.59 (m, 1H), 3.46 (m, 1H), 3.04 (d, J = 3.9 Hz, 1H), 2.98-2.81 (m, 1H), 2.42 (m, 2H), 2.09-1.85 (m, 2H), 1.76 (m, 1H), 0.80-0.55 (m, 4H). |

TABLE 1-continued

| Example | Structure (Synthetic Method) | Chemical Name | LC/MS [M + H]+ | 1H-NMR |
|---|---|---|---|---|
| 39 | 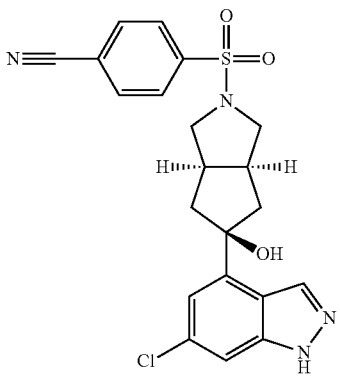 (method 3) | 4-(((3aR,5r,6aS)-5-(6-chloro-1H-indazol-4-yl)-5-hydroxyhexahydrocyclopenta[c]pyrrol-2(1H)-yl)sulfonyl)benzonitrile | 443.1 | 1H NMR (400 MHz, DMSO-d6) δ 13.12 (s, 1H), 8.13 (d, J = 8.6 Hz, 3H), 7.97 (d, J = 8.3 Hz, 2H), 7.44 (s, 1H), 6.97 (s, 1H), 5.12 (s, 1H), 3.51 (t, J = 8.8 Hz, 2H), 3.15 (m, 2H), 2.80 (s, 2H), 2.27 (m, 2H), 1.81 (m, 2H). |
| 40 | 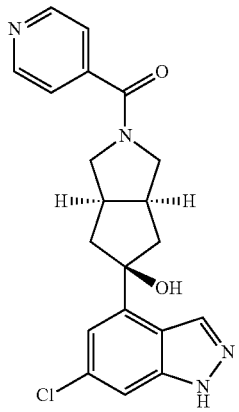 (method 3) | ((3aR,5r,6aS)-5-(6-chloro-1H-indazol-4-yl)-5-hydroxyhexahydrocyclopenta[c]pyrrol-2(1H)-yl)(pyridin-4-yl)methanone | 383.0 | 1H NMR (400 MHz, DMSO-d6) δ 13.16 (s, 1H), 8.66 (dd, J = 4.5, 1.3 Hz, 2H), 8.21 (s, 1H), 7.54-7.37 (m, 3H), 7.09 (d, J = 1.1 Hz, 1H), 5.39 (s, 1H), 3.79 (m, 2H), 3.68-3.57 (m, 1H), 3.49 (m, 1H), 3.06-2.90 (m, 2H), 2.49-2.43 (m, 1H), 2.36 (m, 1H), 2.01 (m, 1H), 1.89 (m, 1H) |
| 41 | 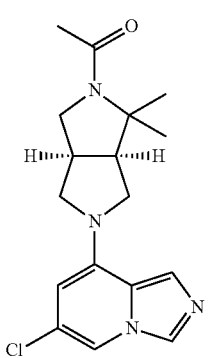 (method 1) | Racemic-1-((3aS,6aR)-5-(6-chloroimidazo[1,5-a]pyridin-8-yl)-1,1-dimethylhexahydropyrrolo[3,4-c]pyrrol-2(1H)-yl)ethanone | 333.2 | 1H NMR (400 MHz, CDCl3) δ 8.19 (s, 1H), 7.34 (s, 1H), 7.08 (s, 1H), 5.89 (d, J = 1.3 Hz, 1H), 3.83 (m, 2H), 3.50 (m, 1H), 3.46-3.33 (m, 2H), 3.23 (m, 1H), 3.18-3.07 (m, 1H), 2.72 (m, 1H), 2.01 (s, 3H), 1.60 (s, 3H), 1.46 (s, 3H). |

TABLE 1-continued

| Example | Structure (Synthetic Method) | Chemical Name | LC/MS [M + H]+ | 1H-NMR |
|---|---|---|---|---|
| 42 | 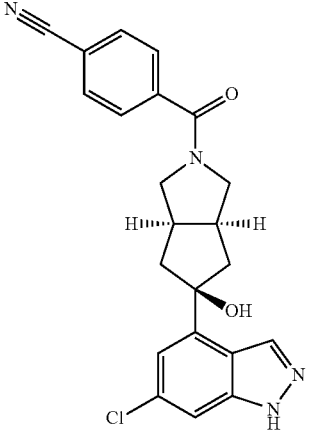<br>(method 3) | 4-((3aR,5r,6aS)-5-(6-chloro-1H-indazol-4-yl)-5-hydroxyoctahydrocyclopenta[c]pyrrole-2-carbonyl)benzonitrile | 407.2 | 1H NMR (400 MHz, DMSO-d6) δ 13.16 (s, 1H), 8.21 (s, 1H), 7.92 (d, J = 8.2 Hz, 2H), 7.66 (d, J = 8.2 Hz, 2H), 7.47 (s, 1H), 7.09 (d, J = 0.9 Hz, 1H), 5.39 (s, 1H), 3.78 (m, 2H), 3.64-3.56 (m, 1H), 3.48 (m, 1H), 2.98 (s, 2H), 2.46 (d, J = 8.7 Hz, 1H), 2.36 (dd, J = 13.4, 8.2 Hz, 1H), 2.01 (m, 1H), 1.88 (m, 1H). |
| 43 | 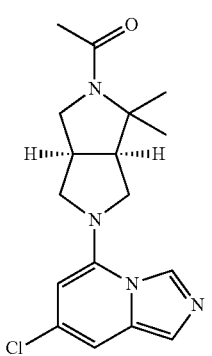<br>(method 1) | Racemic-1-((3aS,6aR)-5-(7-chloroimidazo[1,5-a]pyridin-5-yl)-1,1-dimethylhexahydropyrrolo[3,4-c]pyrrol-2(1H)-yl)ethanone | 333.2 | 1H NMR (400 MHz, CDCl3) δ 8.19 (s, 1H), 7.34 (s, 1H), 7.08 (s, 1H), 5.89 (d, J = 1.3 Hz, 1H), 3.83 (m, 2H), 3.50 m, 1H), 3.46-3.33 (m, 2H), 3.23 (m, 1H), 3.18-3.07 (m, 1H), 2.72 (m, 1H), 2.01 (s, 3H), 1.60 (s, 3H), 1.46 (s, 3H). |
| 44 | 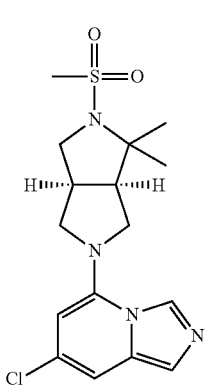<br>(method 1) | Racemic-7-chloro-5-((3aR,6aS)-4,4-dimethyl-5-(methylsulfonyl)hexahydropyrrolo[3,4-c]pyrrol-2(1H)-yl)imidazo[1,5-a]pyridine | 369.0 | 1H NMR (400 MHz, CDCl3) δ 8.14 (s, 1H), 7.37 (s, 1H), 7.16 (s, 1H), 5.94 (s, 1H), 3.92-3.67 (m, 2H), 3.39 (m, 3H), 3.13 (s, 2H), 2.96 (s, 3H), 2.77 (d, J = 6.4 Hz, 1H), 1.58 (s, 3H), 1.50 (s, 3H). |

TABLE 1-continued

| Example | Structure (Synthetic Method) | Chemical Name | LC/MS [M + H]+ | 1H-NMR |
|---|---|---|---|---|
| 45 | 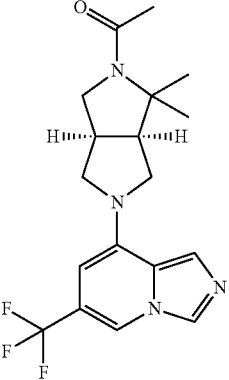<br>(method 1) | Racemic-1-((3aS,6aR)-1,1-dimethyl-5-(6-(trifluoromethyl)imidazo[1,5-a]pyridin-8-yl)hexahydropyrrolo[3,4-c]pyrrol-2(1H)-yl)ethanone | 367.1 | $^1$H NMR (400 MHz, CDCl$_3$) δ 8.12 (s, 1H), 7.74 (s, 1H), 7.65 (s, 1H), 5.51 (s, 1H), 3.97 (dd, J = 9.9, 6.0 Hz, 1H), 3.87-3.73 (m, 2H), 3.66 (m, 2H), 3.34 (m, 1H), 3.13 (m, 1H), 2.71 (m, 1H), 2.01 (s, 3H), 1.63 (s, 3H), 1.49 (s, 3H). |
| 46 | 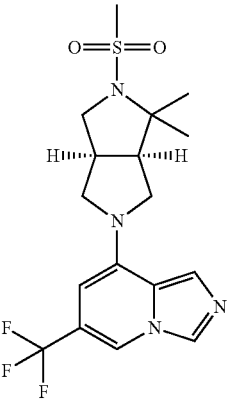<br>(method 1) | Racemic-8-((3aR,6aS)-4,4-dimethyl-5-(methylsulfonyl)hexahydropyrrolo[3,4-c]pyrrol-2(1H)-yl)-6-(trifluoromethyl)imidazo[1,5-a]pyridine | 403.2 | $^1$H NMR (400 MHz, CDCl$_3$) δ 8.12 (s, 1H), 7.76 (s, 1H), 7.64 (s, 1H), 5.52 (s, 1H), 3.97 (m, 1H), 3.88 (m, 1H), 3.81 (m, 1H), 3.66 (m, 2H), 3.33-3.24 (m, 1H), 3.21-3.09 (m, 1H), 2.92 (m, 3H), 2.76 (m, 1H), 1.59 (s, 3H), 1.54 (s, 3H). |
| 47 | 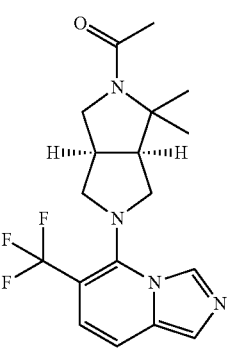<br>(method 1) | Racemic-1-((3aS,6aR)-1,1-dimethyl-5-(6-(trifluoromethyl)imidazo[1,5-a]pyridin-5-yl)hexahydropyrrolo[3,4-c]pyrrol-2(1H)-yl)ethanone | 367.1 | $^1$H NMR (400 MHz, DMSO-d6) δ 8.43 (s, 1H), 7.63-7.56 (m, 2H), 6.93 (d, J = 9.4 Hz, 1H), 3.83 (t, J = 9.8 Hz, 1H), 3.64 (m, 1H), 3.52-3.44 (m, 1H), 3.41-3.36 (m, 2H), 3.15 (m, 2H), 2.85 (m, 1H), 1.93 (s, 3H), 1.42 (s, 3H), 1.35 (s, 3H). |

TABLE 1-continued

| Example | Structure (Synthetic Method) | Chemical Name | LC/MS [M + H]+ | 1H-NMR |
|---|---|---|---|---|
| 48 | 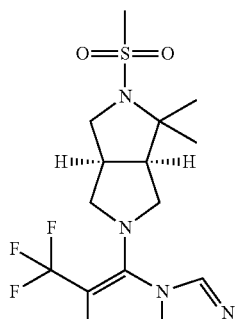 (method 1) | Racemic-5-((3aR,6aS)-4,4-dimethyl-5-(methylsulfonyl)hexahydropyrrolo[3,4-c]pyrrol-2(1H)-yl)-6-(trifluoromethyl)imidazo[1,5-a]pyridine | 403.3 | 1H NMR (400 MHz, DMSO-d6) δ 8.42 (s, 1H), 7.59 (m, 2H), 6.92 (d, J = 10.0 Hz, 1H), 3.74 (m, 1H), 3.65 (m, 1H), 3.39 (m, 2H), 3.31-3.28 (m, 2H), 3.20-3.09 (m, 2H), 2.98 (s, 3H), 2.94-2.88 (m, 1H), 1.39 (s, 3H), 1.36 (s, 3H). |
| 49 | 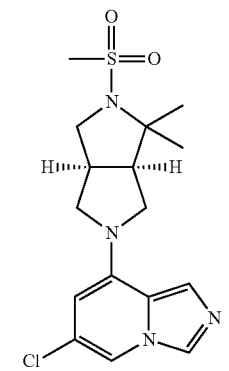 (method 1) | Racemic-6-chloro-8-((3aR,6aS)-4,4-dimethyl-5-(methylsulfonyl)hexahydropyrrolo[3,4-c]pyrrol-2(1H)-yl)imidazo[1,5-a]pyridine | 369.0 | 1H NMR (400 MHz, CDCl3) δ 7.99 (s, 1H), 7.58 (s, 1H), 7.46 (s, 1H), 5.47 (s, 1H), 3.99-3.81 (m, 2H), 3.82-3.71 (m, 1H), 3.62 m, 2H), 3.26 (m, 1H), 3.13 (m, 1H), 2.92 (s, 3H), 2.75 (m, 1H), 1.58 (s, 3H), 1.53 (s, 3H). |
| 50 | 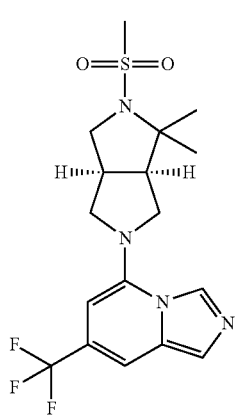 (method 1) | Racemic-5-((3aR,6aS)-4,4-dimethyl-5-(methylsulfonyl)hexahydropyrrolo[3,4-c]pyrrol-2(1H)-yl)-7-(trifluoromethyl)imidazo[1,5-a]pyridine | 403.3 | 1H NMR (400 MHz, DMSO-d6) δ 8.57 (s, 1H), 7.67 (s, 1H), 7.64 (s, 1H), 6.13 (s, 1H), 3.87 (dd, J = 9.6, 7.2 Hz, 1H), 3.68 (t, J = 9.5 Hz, 1H), 3.60-3.52 (m, 1H), 3.42 (t, J = 9.1 Hz, 1H), 3.31-3.22 (m, 2H), 3.08 (m, 1H), 2.99 (s, 3H), 2.80-2.70 (m, 1H), 1.45 (s, 3H), 1.38 (s, 3H). |

TABLE 1-continued

| Example | Structure (Synthetic Method) | Chemical Name | LC/MS [M + H]+ | 1H-NMR |
|---|---|---|---|---|
| 51 | 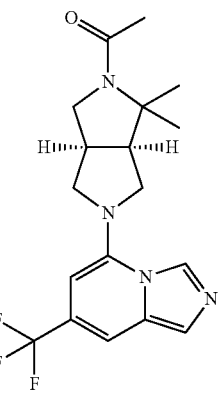<br>(method 1) | Racemic-1-((3aS,6aR)-1,1-dimethyl-5-(7-(trifluoromethyl)imidazo[1,5-a]pyridin-5-yl)hexahydropyrrolo[3,4-c]pyrrol-2(1H)-yl)ethanone | 367.2 | $^1$H NMR (400 MHz, DMSO-d6) δ 8.61 (s, 1H), 7.61 (s, 2H), 6.08 (s, 1H), 3.96 (dd, J = 9.6, 6.6 Hz, 1H), 3.81-3.72 (m, 1H), 3.61 (t, J = 9.4 Hz, 1H), 3.51 (t, J = 8.8 Hz, 1H), 3.43-3.36 (m, 1H), 3.30 (d, J = 1.3 Hz, 1H), 3.11-3.00 (m, 1H), 2.65 (dd, J = 15.7, 7.8 Hz, 1H), 1.90 (s, 3H), 1.52 (s, 3H), 1.34 (s, 3H). |
| 52 | 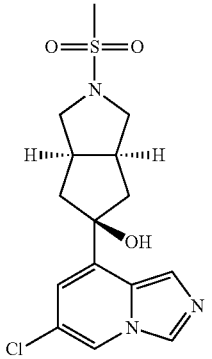<br>(method 7) | (3aR,5r,6aS)-5-(6-chloroimidazo[1,5-a]pyridin-8-yl)-2-(methylsulfonyl)octahydrocyclopenta[c]pyrrol-5-ol | 356.0 | $^1$H NMR (400 MHz, CD$_3$OD) δ 8.35 (s, 1H), 8.33 (s, 1H), 7.61 (s, 1H), 6.81 (d, J = 1.1 Hz, 1H), 3.54 (t, J = 8.8 Hz, 2H), 3.40-3.34 (m, 2H), 3.02 (d, J = 3.4 Hz, 2H), 2.90 (s, 3H), 2.57 (m, 2H), 2.07-1.94 (m, 2H). |
| 53 | 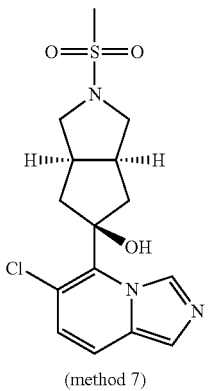 [SMILES: CS(=O)(=O)N1C[C@@H]2C[C@@](O)(c3c(Cl)ccc4cncn34)C[C@@H]2C1]<br>(method 7) | (3aR,5r,6aS)-5-(6-chloroimidazo[1,5-a]pyridin-5-yl)-2-(methylsulfonyl)octahydrocyclopenta[c]pyrrol 5-ol | 355.9 | $^1$H NMR (400 MHz, CD$_3$OD) δ 8.99 (s, 1H), 7.47 (d, J = 9.5 Hz, 1H), 7.43 (s, 1H), 6.74 (d, J = 9.5 Hz, 1H), 3.55 (t, J = 8.8 Hz, 2H), 3.41 (m, 2H), 3.03 (m 2H), 2.90 (s, 3H), 2.89-2.81 (m, 2H), 2.39 (m, 2H). |

TABLE 1-continued

| Example | Structure (Synthetic Method) | Chemical Name | LC/MS [M + H]+ | 1H-NMR |
|---|---|---|---|---|
| 54 | 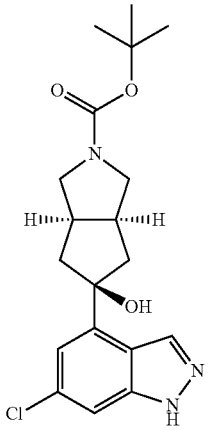<br>(method 3) | (3aR,5r,6aS)-tert-butyl 5-(6-chloro-1H-indazol-4-yl)-5-hydroxyhexahydrocyclopenta[c]pyrrole-2(1H)-carboxylate | 378.2 | 1H NMR (400 MHz, DMSO-d6) δ 13.14 (s, 1H), 8.19 (s, 1H), 7.45 (s, 1H), 7.05 (d, J = 1.3 Hz, 1H), 5.32 (s, 1H), 3.56 (m, 2H), 3.37 (s, 2H), 2.90 (s, 2H), 2.42-2.34 (m, 2H), 1.93 (m, 2H), 1.39 (s, 9H). |
| 55 | 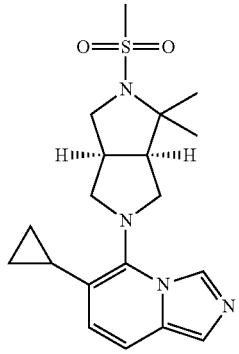<br>(method 1) | Racemic-6-cyclopropyl-5-((3aR,6aS)-4,4-dimethyl-5-(methylsulfonyl)hexahydropyrrolo[3,4-c]pyrrol-2(1H)-yl)imidazo[1,5-a]pyridine | 375.1 | |
| 56 | 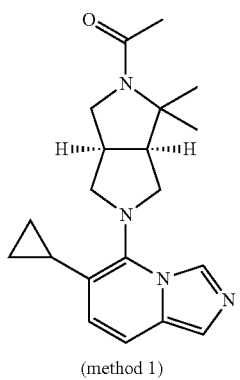 [SMILES: CC(=O)N1C[C@@H]2CN(c3c(C4CC4)ccc4cncn34)C[C@@H]2C1(C)C]<br>(method 1) | Racemic-1-((3aS,6aR)-5-(6-cyclopropylimidazo[1,5-a]pyridin-5-yl)-1,1-dimethylhexahydropyrrolo[3,4-c]pyrrol-2(1H)-yl)ethanone | 339.1 | |

TABLE 1-continued

| Example | Structure (Synthetic Method) | Chemical Name | LC/MS [M + H]+ | 1H-NMR |
|---|---|---|---|---|
| 57 | (method 1) | Racemic-8-((3aR,6aS)-4,4-dimethyl-5-(methylsulfonyl)hexahydropyrrolo[3,4-c]pyrrol-2(1H)-yl)-7-(trifluoromethyl)imidazo[1,5-a]pyridine | 403.1 | 1H NMR (400 MHz, CD3OD) δ 8.43 (s, 1H), 8.06 (d, J = 7.4 Hz, 1H), 7.75 (s, 1H), 6.78 (d, J = 7.4 Hz, 1H), 4.87 (s, 3H), 3.89-3.78 (m, 2H), 3.63-3.53 (m, 2H), 3.40 (dd, J = 9.9, 6.5 Hz, 1H), 3.22-3.13 (m, 1H), 2.96 (s, 1H), 2.84 (q, J = 7.7 Hz, 1H), 1.52 (s, 3H), 1.49 (s, 3H). |
| 58 | (method 1) | Racemic-1-((3aS,6aR)-1,1-dimethyl-5-(7-(trifluoromethyl)imidazo[1,5-a]pyridin-8-yl)hexahydropyrrolo[3,4-c]pyrrol-2(1H)-yl)ethanone | 367.1 | 1H NMR (400 MHz, CD3OD) δ 8.43 (s, 1H), 8.02 (d, J = 7.4 Hz, 1H), 7.74 (d, J = 11.9 Hz, 1H), 6.77 (d, J = 7.4 Hz, 1H), 4.90 (s, 3H), 3.96-3.86 (m, 2H), 3.69-3.53 (m, 3H), 3.34 (m, 1H), 3.18 (m, 1H), 2.81 (m, 1H), 1.56 (s, 3H), 1.47 (s, 3H). |
| 59 | (method 3) | ((3aR,5r,6aS)-5-(6-chloro-1H-indazol-4-yl)-5-hydroxyhexahydrocyclopenta[c]pyrrol-2(1H)-yl)(cyclopentyl)methanone | 374.2 | 1H NMR (400 MHz, Acetone-d6) δ 13.10 (s, 1H), 8.23 (s, 1H), 7.47 (s, 1H), 7.13 (d, J = 1.2 Hz, 1H), 5.31 (s, 1H), 3.84 (s, 1H), 3.70 (m, 2H), 3.56 (m, 1H), 3.05 (m, 1H), 2.94 (m 1H), 2.88 (s, 1H), 2.55-2.45 (m, 2H), 1.88-1.44 (m, 10H). |

TABLE 1-continued

| Example | Structure (Synthetic Method) | Chemical Name | LC/MS [M + H]⁺ | ¹H-NMR |
|---|---|---|---|---|
| 60 | (method 3) | ((3aR,5r,6aS)-5-(6-chloro-1H-indazol-4-yl)-5-hydroxyhexahydrocyclopenta[c]pyrrol-2(1H)-yl)(cyclobutyl)methanone | 360.3 | $^1$H NMR (400 MHz, DMSO-d6) δ 13.14 (s, 1H), 8.18 (s, 1H), 7.46 (s, 1H), 7.06 (d, J = 1.3 Hz, 1H), 5.32 (s, 1H), 3.60 (s, 2H), 3.47 (s, 2H), 3.27-3.19 (m, 1H), 3.02-2.80 (m, 2H), 2.40 (m, 2H), 2.13 (s, 2H), 2.06 (m, 2H), 1.91 (m, 3H), 1.78-1.69 (m, 1H). |
| 61 | (method 3) | (3aR,5r,6aS)-isopropyl 5-(6-chloro-1H-indazol-4-yl)-5-hydroxyhexahydrocyclopenta[c]pyrrole-2(1H)-carboxylate | 364.2 | $^1$H NMR (400 MHz, DMSO-d6) δ 13.14 (s, 1H), 8.19 (s, 1H), 7.46 (s, 1H), 7.06 (d, J = 1.3 Hz, 1H), 5.33 (s, 1H), 4.80-4.68 (m, 1H), 3.59 (m, 2H), 3.40 (m, 2H), 2.92 (s, 2H), 2.37 (s, 2H), 1.96-1.92 (m, 2H), 1.17 (d, J = 6.2 Hz, 6H). |
| 62 | (method 3) | ((3aR,5r,6aS)-5-(6-chloro-1H-indazol-4-yl)-5-hydroxyhexahydrocyclopenta[c]pyrrol-2(1H)-yl)(cyclohexyl)methanone | 388.2 | $^1$H NMR (400 MHz, DMSO-d6) δ 13.15 (s, 1H), 8.19 (s, 1H), 7.46 (s, 1H), 7.07 (d, J = 0.8 Hz, 1H), 5.34 (s, 1H), 3.78 (s, 1H), 3.61 (m, 2H), 3.44 (s, 1H), 3.04-2.82 (m, 2H), 2.40 (m, 3H), 1.94 (s, 2H), 1.79-1.54 (m, 5H), 1.38-1.11 (m, 5H). |

TABLE 1-continued

| Example | Structure (Synthetic Method) | Chemical Name | LC/MS [M + H]+ | 1H-NMR |
|---|---|---|---|---|
| 63 | (method 3) | N-((1R,3r,5S,6r)-3-(6-chloro-1H-indazol-4-yl)-3-hydroxybicyclo[3.1.0]hexan-6-yl)methanesulfonamide | 342.1 | $^1$H NMR (400 MHz, CD$_3$OD) δ 8.09 (s, 1H), 7.42 (s, 1H), 7.17 (d, J = 1.5 Hz, 1H), 3.34 (s, 1H), 3.19 (s, 1H), 3.02 (s, 3H), 2.65 m, 2H), 2.22 (d, J = 6.4 Hz, 1H), 2.18 (s, 1H), 1.87 (m, 2H). |
| 64 | (method 3) | N-((1R,3r,5S,6r)-3-(6-chloro-1H-indazol-4-yl)-3-hydroxybicyclo[3.1.0]hexan-6-yl)acetamide | 306.0 | $^1$H NMR (400 MHz, CD$_3$OD) δ 8.09 (s, 1H), 7.42 (s, 1H), 7.18 (d, J = 1.6 Hz, 1H), 3.49-3.35 (m, 1H), 2.63 (m, 2H), 2.23 (m, 2H), 1.91 (s, 3H), 1.67 (s, 2H). |
| 65 | (method 3) | 1-((3aR,5r,6aS)-5-(6-chloro-1H-indazol-4-yl)-5-hydroxyhexahydrocyclopenta[c]pyrrol-2(1H)-yl)-2-methylpropan-1-one | 370.3 [M + 23]+ | $^1$H NMR (400 MHz, CD$_3$OD) δ 8.25 (s, 1H), 7.45 (s, 1H), 7.15 (d, J = 1.5 Hz, 1H), 3.93-3.84 (m, 1H), 3.84-3.61 (m, 3H), 3.17-2.95 (m, 2H), 2.89-2.74 (m, 1H), 2.60 (m, 2H), 2.09 (m, 2H), 1.14 (d, J = 6.7 Hz, 3H), 1.10 (d, J = 6.7 Hz, 3H). |

TABLE 1-continued

| Example | Structure (Synthetic Method) | Chemical Name | LC/MS [M + H]⁺ | ¹H-NMR |
|---|---|---|---|---|
| 66 | 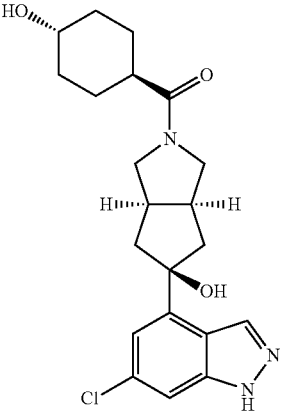 (method 3) | ((3aR,5R,6aS)-5-(6-chloro-1H-indazol-4-yl)-5-hydroxyhexahydrocyclopenta[c]pyrrol-2(1H)-yl)((1r,4R)-4-hydroxycyclohexyl)methanone | 404.2 | $^1$H NMR (400 MHz, CD$_3$OD) δ 8.25 (s, 1H), 7.45 (s, 1H), 7.15 (d, J = 1.4 Hz, 1H), 3.88 (t, J = 9.9 Hz, 1H), 3.82-3.75 (m, 1H), 3.75-3.61 (m, 2H), 3.59-3.44 (m, 1H), 3.16-2.94 (m, 2H), 2.66-2.52 (m, 2H), 2.47 (m, 1H), 2.14-1.94 (m, 4H), 1.85 (m, 2H), 1.62-1.45 (m, 2H), 1.31 (m, 2H). |
| 67 | 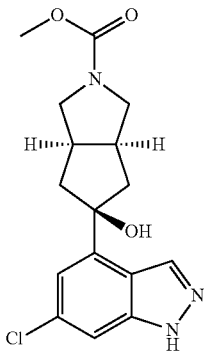 (method 3) | (3aR,5r,6aS)-methyl 5-(6-chloro-1H-indazol-4-yl)-5-hydroxyhexahydrocyclopenta[c]pyrrole-2(1H)-carboxylate | 336.4 | $^1$H NMR (400 MHz, Acetone-d6) δ 12.33 (s, 1H), 8.29 (s, 1H), 7.52 (s, 1H), 7.17 (d, J = 1.4 Hz, 1H), 4.52 (s, 1H), 3.69 (m, 2H), 3.63 (s, 3H), 3.57 (m, 2H), 3.04 (m, 2H), 2.58 (m, 2H), 2.13 (m, 2H). |
| 68 | 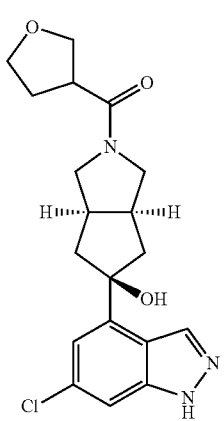 (method 3) | ((3aR,5r,6aS)-5-(6-chloro-1H-indazol-4-yl)-5-hydroxyhexahydrocyclopenta[c]pyrrol-2(1H)-yl)(tetrahydrofuran-3-yl)methanone | 376.2 | $^1$H NMR (400 MHz, DMSO-d6) δ 13.15 (s, 1H), 8.20 (s, 1H), 7.46 (s, 1H), 7.07 (d, J = 1.1 Hz, 1H), 5.34 (d, J = 4.7 Hz, 1H), 3.86 (m, 2H), 3.65 (m, 5H), 3.50 (m, 1H), 3.23-3.13 (m, 1H), 3.05-2.96 (m, 1H), 2.91 (m, 1H), 2.45-2.36 (m, 2H), 1.97 (m, 4H). |

TABLE 1-continued

| Example | Structure (Synthetic Method) | Chemical Name | LC/MS [M + H]+ | 1H-NMR |
|---|---|---|---|---|
| 69 | 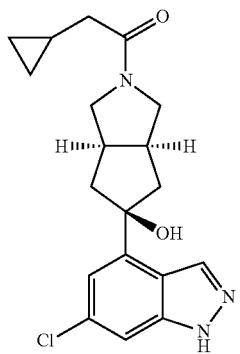 (method 3) | 1-((3aR,5r,6aS)-5-(6-chloro-1H-indazol-4-yl)-5-hydroxyhexahydrocyclopenta[c]pyrrol-2(1H)-yl)-2-cyclopropylethanone | 360.1 | 1H NMR (400 MHz, MSDO-d6) δ 13.15 (s, 1H), 8.19 (s, 1H), 7.46 (s, 1H), 7.07 (s, 1H), 5.34 (s, 1H), 3.75-3.60 (m, 2H), 3.52 (m, 1H), 3.46 (m, 1H), 3.03-2.93 (m, 1H), 2.89 (m, 1H), 2.45-2.35 (m, 2H), 2.17 (d, J = 6.7 Hz, 2H), 2.01-1.89 (m, 2H), 1.02-0.90 (m, 1H), 0.43 (m, 2H), 0.14-0.04 (m, 2H). |
| 70 | 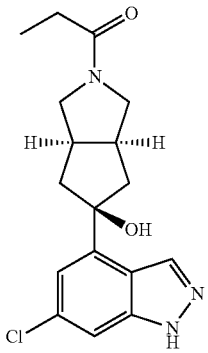 (method 3) | 1-((3aR,5r,6aS)-5-(6-chloro-1H-indazol-4-yl)-5-hydroxyhexahydrocyclopenta[c]pyrrol-2(1H)-yl)propan-1-one | 334.2 | 1H NMR (400 MHz, DMSO-d6) δ 13.15 (s, 1H), 8.19 (s, 1H), 7.46 (s, 1H), 7.07 (s, 1H), 5.34 (s, 1H), 3.71 (t, J = 9.7 Hz, 1H), 3.67-3.58 (m, 1H), 3.53 (dd, J = 10.4, 5.2 Hz, 1H), 3.45 (dd, J = 11.9, 5.1 Hz, 1H), 2.99 (m, 1H), 2.89 (m, 1H), 2.47-2.34 (m, 2H), 2.22 (q, J = 7.3 Hz, 2H), 1.95 (dd, J = 13.9, 11.3 Hz, 2H), 0.97 (t, J = 7.4 Hz, 3H). |
| 71 | 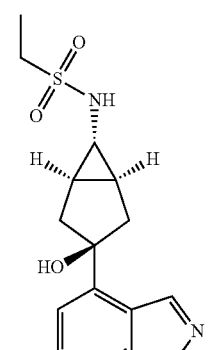 (method 3) | N-((1R,3r,5S,6r)-3-(6-chloro-1H-indazol-4-yl)-3-hydroxybicyclo[3.1.0]hexan-6-yl)ethanesulfonamide | 356.0 | 1H NMR (400 MHz, CD3OD) δ 8.09 (s, 1H), 7.42 (s, 1H), 7.17 (d, J = 1.5 Hz, 1H), 3.15 (m, 3H), 2.65 (m, 2H), 2.20 (s, 1H), 2.16 (s, 1H), 1.88-1.81 (m, 2H), 1.36 (t, J = 7.4 Hz, 3H). |

TABLE 1-continued

| Example | Structure (Synthetic Method) | Chemical Name | LC/MS [M + H]+ | 1H-NMR |
|---|---|---|---|---|
| 72 | 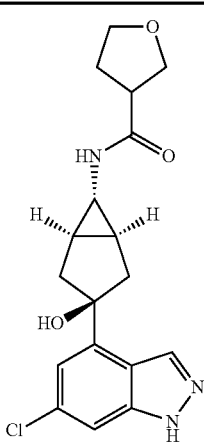 (method 3) | N-((1R,3r,5S,6r)-3-(6-chloro-1H-indazol-4-yl)-3-hydroxybicyclo[3.1.0]hexan-6-yl)tetrahydrofuran-3-carboxamide | 362.3 | 1H NMR (400 MHz, CD$_3$OD) δ 8.09 (s, 1H), 7.42 (s, 1H), 7.18 (d, J = 1.5 Hz, 1H), 3.94 (t, J = 8.3 Hz, 1H), 3.89 (d, J = 8.0 Hz, 1H), 3.33 (d, J = 8.1 Hz, 1H), 2.95 (s, 1H), 2.64 (dd, J = 14.2, 4.3 Hz, 2H), 2.25 (s, 1H), 2.21 (s, 1H), 2.10 (dd, J = 14.5, 7.2 Hz, 2H), 1.68 (d, J = 2.2 Hz, 2H), 1.28 (s, 2H). |
| 73 | 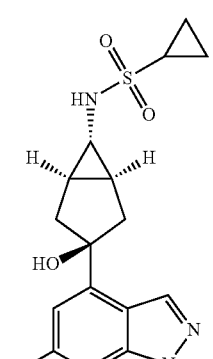 (method 3) | N-((1R,3r,5S,6r)-3-(6-chloro-1H-indazol-4-yl)-3-hydroxybicyclo[3.1.0]hexan-6-yl)cyclopropanesulfonamide | 368.0 | 1H NMR (400 MHz, CD$_3$OD) δ 8.05 (s, 1H), 7.43 (s, 1H), 7.15 (s, 1H), 2.73-2.53 (m, 3H), 2.18 (d, J = 14.4 Hz, 2H), 1.90-1.79 (m, 2H), 1.17-1.01 (m, 5H). |
| 74 | 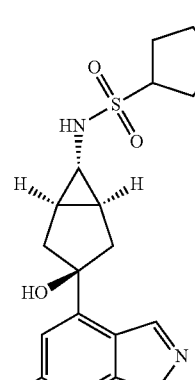 (method 3) | N-((1R,3r,5S,6r)-3-(6-chloro-1H-indazol-4-yl)-3-hydroxybicyclo[3.1.0]hexan-6-yl)cyclopentanesulfonamide | 396.0 | 1H NMR (400 MHz, CD$_3$OD) δ 8.09 (s, 1H), 7.42 (s, 1H), 7.16 (s, 1H), 3.73 (p, J = 8.0 Hz, 1H), 2.69-2.57 (m, 2H), 2.18 (d, J = 14.4 Hz, 2H), 2.05 (d, J = 6.8 Hz, 5H), 1.88-1.79 (m, 4H), 1.73-1.63 (m, 2H). |

TABLE 1-continued

| Example | Structure (Synthetic Method) | Chemical Name | LC/MS [M + H]+ | 1H-NMR |
|---|---|---|---|---|
| 75 | 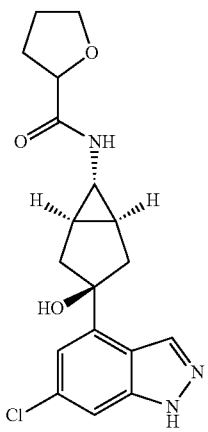 (method 3) | N-((1R,3r,5S,6r)-3-(6-chloro-1H-indazol-4-yl)-3-hydroxybicyclo[3.1.0]hexan-6-yl)tetrahydrofuran-2-carboxamide | 362.2 | 1H NMR (400 MHz, CD$_3$OD) δ 8.09 (s, 1H), 7.42 (s, 1H), 7.18 (s, 1H), 4.26 (dd, J = 8.2, 5.5 Hz, 1H), 3.98 (dd, J = 13.9, 7.0 Hz, 1H), 3.84 (dd, J = 14.6, 6.8 Hz, 1H), 3.33 (m, 1H), 2.65 (m, 2H), 2.25 (d, J = 14.3 Hz, 3H), 2.00-1.84 (m, 3H), 1.73 (m, 2H). |
| 76 | 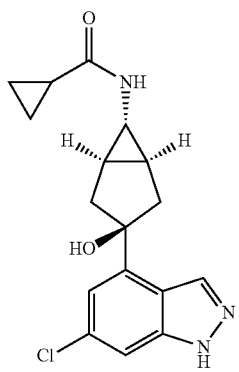 (method 3) | N-((1R,3r,5S,6r)-3-(6-chloro-1H-indazol-4-yl)-3-hydroxybicyclo[3.1.0]hexan-6-yl)cyclopropanecarboxamide | 332.1 | 1H NMR (400 MHz, CD$_3$OD) δ 8.09 (s, 1H), 7.42 (s, 1H), 7.18 (d, J = 1.4 Hz, 1H), 2.64 (dd, J = 14.4, 3.4 Hz, 2H), 2.23 (d, J = 14.4 Hz, 2H), 1.68 (s, 2H), 1.57-1.46 (m, 1H), 0.85 (m, 2H), 0.76-0.66 (m, 2H). |
| 77 | 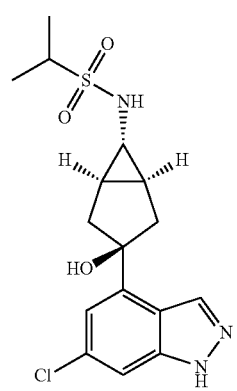 (method 3) | N-((1R,3r,5S,6r)-3-(6-chloro-1H-indazol-4-yl)-3-hydroxybicyclo[3.1.0]hexan-6-yl)propane-2-sulfonamide | 370.1 | 1H NMR (400 MHz, CD$_3$OD) δ 8.09 (s, 1H), 7.42 (s, 1H), 7.17 (d, J = 1.3 Hz, 1H), 3.36 (dd, J = 12.4, 5.5 Hz, 1H), 3.16 (s, 1H), 2.66 (d, J = 3.8 Hz, 1H), 2.62 (d, J = 3.4 Hz, 1H), 2.19 (s, 1H), 2.16 (s, 1H), 1.89-1.81 (m, 2H), 1.38 (d, J = 6.8 Hz, 6H). |

TABLE 1-continued

| Example | Structure (Synthetic Method) | Chemical Name | LC/MS [M + H]⁺ | ¹H-NMR |
|---------|------------------------------|---------------|----------------|--------|
| 78 | (method 3) | N-((1R,3r,5S,6r)-3-(6-chloro-1H-indazol-4-yl)-3-hydroxybicyclo[3.1.0]hexan-6-yl)cyclohexanesulfonamide | 409.9 | 1H NMR (400 MHz, CD$_3$OD) δ 8.09 (s, 1H), 7.42 (s, 1H), 7.17 (d, J = 1.5 Hz, 1H), 3.34 (s, 1H), 3.14 (s, 1H), 2.66 (m, 1H), 2.62 (m, 1H), 2.20 (m, 2H), 2.16 (m, 2H), 1.92 (m, 2H), 1.87-1.82 (m, 2H), 1.74 (m, 1H), 1.54 (m, 2H), 1.45-1.32 (m, 2H), 1.31-1.20 (m, 2H). |
| 79 | (method 3) | N-((1R,3r,5S,6r)-3-(6-chloro-1H-indazol-4-yl)-3-hydroxybicyclo[3.1.0]hexan-6-yl)cyclopentanecarboxamide | 360.2 | 1H NMR (400 MHz, CD$_3$OD) δ 8.09 (s, 1H), 7.43 (s, 1H), 7.18 (s, 1H), 3.66 (s, 1H), 2.67-2.53 (m, 3H), 2.22 (m, 2H), 1.83 (m, 2H), 1.76-1.69 (m, 4H), 1.67 (s, 2H), 1.63-1.53 (m, 2H). |
| 80 | (method 3) | methyl ((1R,3r,5S,6r)-3-(6-chloro-1H-indazol-4-yl)-3-hydroxybicyclo[3.1.0]hexan-6-yl)carbamate | 322.2 | 1H NMR (400 MHz, CD$_3$OD) δ 8.08 (s, 1H), 7.42 (s, 1H), 7.17 (s, 1H), 3.63 (s, 3H), 3.15 (s, 1H), 2.63 (m, 2H), 2.20 (d, J = 14.3 Hz, 2H), 1.74-1.59 (m, 2H). |

TABLE 1-continued

| Example | Structure (Synthetic Method) | Chemical Name | LC/MS [M + H]+ | 1H-NMR |
|---|---|---|---|---|
| 81 | 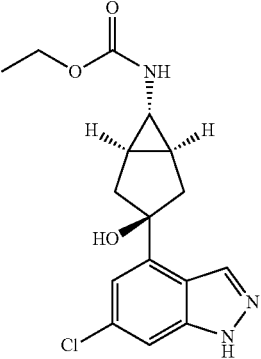<br>(method 3) | ethyl ((1R,3r,5S,6r)-3-(6-chloro-1H-indazol-4-yl)-3-hydroxybicyclo[3.1.0]hexan-6-yl)carbamate | 336.2 | 1H NMR (400 MHz, CD$_3$OD) δ 8.08 (s, 1H), 7.42 (s, 1H), 7.17 (s, 1H), 4.07 (q, J = 6.5 Hz, 2H), 3.15 (s, 1H), 2.63 (m, 2H), 2.20 (d, J = 14.3 Hz, 2H), 1.72-1.64 (m, 2H), 1.22 (t, J = 6.4 Hz, 3H). |
| 82 | 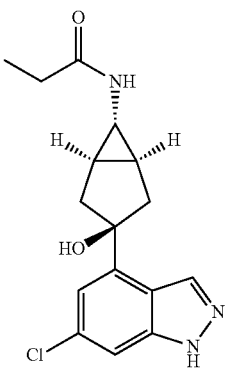<br>(method 3) | N-((1R,3r,5S,6r)-3-(6-chloro-1H-indazol-4-yl)-3-hydroxybicyclo[3.1.0]hexan-6-yl)propionamide | 320.0 | 1H NMR (400 MHz, CD$_3$OD) δ 8.09 (s, 1H), 7.42 (s, 1H), 7.18 (d, J = 1.3 Hz, 1H), 3.30-3.29 (m, 1H), 2.64 (m, 2H), 2.23 (d, J = 14.4 Hz, 2H), 2.16 (q, J = 7.6 Hz, 2H), 1.67 (s, 2H), 1.12 (t, J = 7.6 Hz, 3H). |
| 83 | 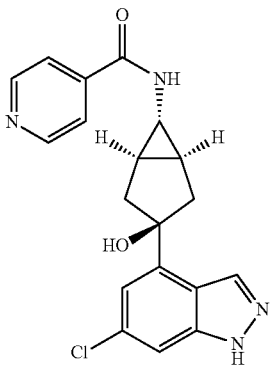<br>(method 3) | N-((1R,3r,5S,6r)-3-(6-chloro-1H-indazol-4-yl)-3-hydroxybicyclo[3.1.0]hexan-6-yl)isonicotinamide | 369.1 | 1H NMR (400 MHz, CD$_3$OD) δ 8.71-8.64 (m, 2H), 8.12 (s, 1H), 7.78 (dd, J = 4.7, 1.4 Hz, 2H), 7.44 (s, 1H), 7.20 (s, 1H), 3.56 (s, 1H), 2.70 (m, 2H), 2.31 (d, J = 14.3 Hz, 2H), 1.87 (s, 2H). |

TABLE 1-continued

| Example | Structure (Synthetic Method) | Chemical Name | LC/MS [M + H]⁺ | ¹H-NMR |
|---|---|---|---|---|
| 84 | (method 3) | N-((1R,3r,5S,6r)-3-(6-chloro-1H-indazol-4-yl)-3-hydroxybicyclo[3.1.0]hexan-6-yl)cyclobutanecarboxamide | 368.1 [M + 23]+ | 1H NMR (400 MHz, CD₃OD) δ 8.08 (s, 1H), 7.42 (s, 1H), 7.18 (d, J = 1.5 Hz, 1H), 3.11-2.99 (m, 1H), 2.63 (dd, J = 14.0, 4.0 Hz, 2H), 2.33-2.18 (m, 5H), 2.15-2.07 (m, 2H), 1.98 (m, 1H), 1.85 (m, 1H), 1.66 (s, 2H). |
| 85 | (method 3) | N-((1R,3r,5S,6r)-3-(6-chloro-1H-indazol-4-yl)-3-hydroxybicyclo[3.1.0]hexan-6-yl)cyclohexanecarboxamide | 396.1 [M + 23]+ | 1H NMR (400 MHz, CD₃OD) δ 8.06 (s, 1H), 7.40 (s, 1H), 7.17 (d, J = 1.4 Hz, 1H), 3.27 (s, 1H), 2.63 (dd, J = 14.3, 3.5 Hz, 2H), 2.23 (d, J = 14.4 Hz, 2H), 2.12 (m, 1H), 1.77 (m, 4H), 1.65 (s, 3H), 1.48-1.38 (m, 2H), 1.35-1.18 (m, 4H). |
| 86 | (method 3) | isopropyl ((1R,3r,5S,6r)-3-(6-chloro-1H-indazol-4-yl)-3-hydroxybicyclo[3.1.0]hexan-6-yl)carbamate | 350.2 | 1H NMR (400 MHz, CD₃OD) δ 8.08 (s, 1H), 7.42 (s, 1H), 7.18 (d, J = 1.2 Hz, 1H), 3.12 (d, J = 12.6 Hz, 1H), 2.63 (dd, J = 14.4, 3.5 Hz, 2H), 2.20 (d, J = 14.3 Hz, 2H), 1.66 (s, 2H), 1.22 (d, J = 5.3 Hz, 6H). |

TABLE 1-continued

| Example | Structure (Synthetic Method) | Chemical Name | LC/MS [M + H]+ | 1H-NMR |
|---|---|---|---|---|
| 87 | 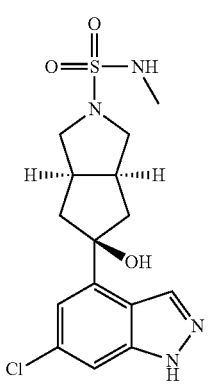<br>(method 3) | (3aR,5r,6aS)-5-(6-chloro-1H-indazol-4-yl)-5-hydroxy-N-methylhexahydrocyclopenta[c]pyrrole-2(1H)-sulfonamide | 371.0 | 1H NMR (400 MHz, CD3OD) δ 8.26 (s, 1H), 7.46 (s, 1H), 7.12 (d, J = 1.2 Hz, 1H), 3.44-3.36 (m, 2H), 3.36-3.32 (m, 2H), 2.94 (m, 2H), 2.73 (s, 3H), 2.58 (m, 2H), 2.05 (m, 2H). |
| 88 | 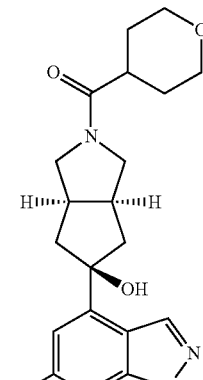<br>(method 3) | ((3aR,5r,6aS)-5-(6-chloro-1H-indazol-4-yl)-5-hydroxyhexahydrocyclopenta[c]pyrrol-2(1H)-yl)(tetrahydro-2H-pyran-4-yl)methanone | 390.2 | 1H NMR (400 MHz, CD3OD) δ 8.21 (s, 1H), 7.43 (s, 1H), 7.12 (s, 1H), 3.99 (m, 2H), 3.89 m, 1H), 3.85-3.61 (m, 3H), 3.49 (m, 2H), 3.16-2.93 (m, 2H), 2.78 (m, 1H), 2.67-2.49 (m, 2H), 2.14-2.00 (m, 2H), 1.90-1.58 (m, 4H). |
| 89 | 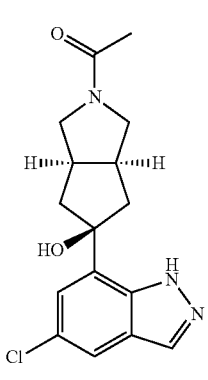<br>(method 8) | 1-((3aR,5r,6aS)-5-(5-chloro-1H-indazol-7-yl)-5-hydroxyhexahydrocyclopenta[c]pyrrol-2(1H)-yl)ethanone | 342.2 [M + 23]+ | 1H NMR (400 MHz, CD3OD + CDCl3) δ 7.94 (s, 1H), 7.60 (d, J = 1.4 Hz, 1H), 7.15 (d, J = 1.4 Hz, 1H), 3.76 m, 1H), 3.72-3.60 (m, 3H), 3.11-2.87 (m, 2H), 2.45 (m, 2H), 2.22-2.08 (m, 2H), 2.06 (s, 3H). |

TABLE 1-continued

| Example | Structure (Synthetic Method) | Chemical Name | LC/MS [M + H]+ | 1H-NMR |
|---|---|---|---|---|
| 90 | 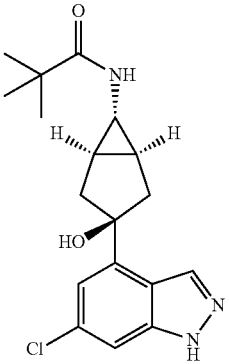<br>(method 3) | N-((1R,3r,5S,6r)-3-(6-chloro-1H-indazol-4-yl)-3-hydroxybicyclo[3.1.0]hexan-6-yl)pivalamide | 348.1 | 1H NMR (400 MHz, CD$_3$OD) δ 8.09 (s, 1H), 7.42 (s, 1H), 7.18 (d, J = 1.5 Hz, 1H), 3.25 (m, 1H), 2.64 (m, 2H), 2.24 (m, 2H), 1.69 (s, 2H), 1.17 (s, 9H). |
| 91 | 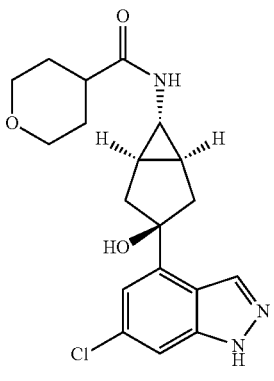<br>(method 3) | N-((1R,3r,5S,6r)-3-(6-chloro-1H-indazol-4-yl)-3-hydroxybicyclo[3.1.0]hexan-6-yl)tetrahydro-2H-pyran-4-carboxamide | 398.0 [M + 23]+ | 1H NMR (400 MHz, CD$_3$OD) δ 8.09 (s, 1H), 7.42 (s, 1H), 7.18 (d, J = 1.5 Hz, 1H), 3.96 (m, 2H), 3.49-3.37 (m, 2H), 3.34 (s, 1H), 2.70-2.57 (m, 2H), 2.45- 2.32 (m, 1H), 2.23 (m, 2H), 2.21-2.15 (m, 1H), 2.02 (d, J = 5.6 Hz, 1H), 1.77 (m, 2H), 1.67 (s, 2H). |
| 92 | 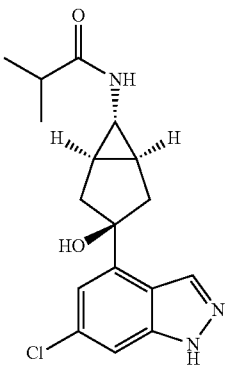<br>(method 3) | N-((1R,3r,5S,6r)-3-(6-chloro-1H-indazol-4-yl)-3-hydroxybicyclo[3.1.0]hexan-6-yl)isobutyramide | 334.3 | 1H NMR (400 MHz, CD$_3$OD) δ 8.09 (s, 1H), 7.42 (s, 1H), 7.18 (d, J = 1.4 Hz, 1H), 3.34 (s, 1H), 2.64 (m, 2H), 2.44-2.33 (m, 1H), 2.25 (m, 1H), 2.22 (m, 1H), 1.66 (m, 2H), 1.10 (d, J = 6.9 Hz, 1H). |

TABLE 1-continued

| Example | Structure (Synthetic Method) | Chemical Name | LC/MS [M + H]+ | 1H-NMR |
|---|---|---|---|---|
| 93 | 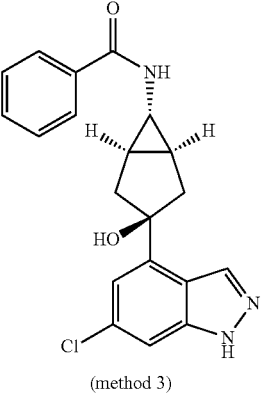 [SMILES: O=C(N[C@H]1[C@@H]2C[C@@](O)(c3cc(Cl)cc4[nH]ncc34)C[C@@H]21)c1ccccc1] (method 3) | N-((1R,3r,5S,6r)-3-(6-chloro-1H-indazol-4-yl)-3-hydroxybicyclo[3.1.0]hexan-6-yl)benzamide | 368.0 | 1H NMR (400 MHz, CD$_3$OD) δ 8.12 (s, 1H), 7.84-7.76 (m, 2H), 7.56-7.49 (m, 1H), 7.47-7.41 (m, 3H), 7.21 (d, J = 1.4 Hz, 1H), 3.51 (t, J = 2.0 Hz, 1H), 2.69 (m, 2H), 2.31 (m, 2H), 1.84 (m, 2H). |
| 94 | 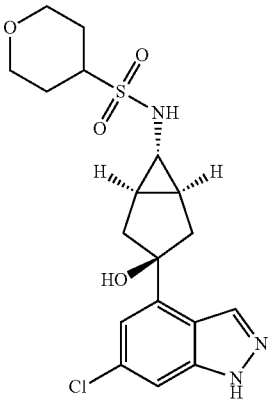 (method 3) | N-((1R,3r,5S,6r)-3-(6-chloro-1H-indazol-4-yl)-3-hydroxybicyclo[3.1.0]hexan-6-yl)tetrahydro-2H-pyran-4-sulfonamide | 412.1 | 1H NMR (400 MHz, CD$_3$OD) δ 8.09 (s, 1H), 7.42 (s, 1H), 7.17 (d, J = 1.3 Hz, 1H), 4.06 (m, 2H), 3.47 (m, 2H), 3.34 (m, 1H), 3.17 (s, 1H), 2.65 (m, 2H), 2.18 (m, 2H), 2.02 (m, 2H), 1.91-1.79 (m, 4H). |
| 95 | 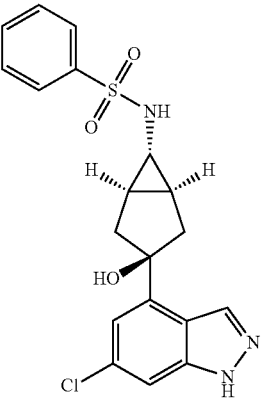 (method 3) | N-((1R,3r,5S,6r)-3-(6-chloro-1H-indazol-4-yl)-3-hydroxybicyclo[3.1.0]hexan-6-yl)benzenesulfonamide | 404.0 | 1H NMR (400 MHz, CD$_3$OD) δ 8.02 (s, 1H), 7.92 (dd, J = 5.2, 3.2 Hz, 2H), 7.62 (m, 3H), 7.40 (s, 1H), 7.11 (d, J = 1.6 Hz, 1H), 2.89 (s, 1H), 2.55 (m, 2H), 2.06 (m, 2H), 1.77-1.63 (m, 2H). |

TABLE 1-continued

| Example | Structure (Synthetic Method) | Chemical Name | LC/MS [M + H]+ | 1H-NMR |
|---|---|---|---|---|
| 96 | 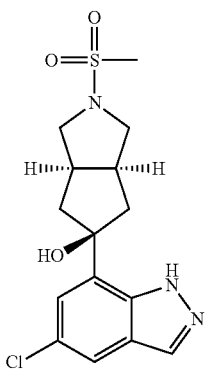<br>(method 8) | (3aR,5r,6aS)-5-(5-chloro-1H-indazol-7-yl)-2-(methylsulfonyl)octa-hydrocyclopenta[c]pyrrol-5-ol | 378.1 [M + 23]+ | 1H NMR (400 MHz, CD$_3$OD) δ 8.17 (s, 1H), 7.83 (d, J = 1.6 Hz, 1H), 7.39 (d, J = 1.6 Hz, 1H), 3.69 (dd, J = 16.5, 8.3 Hz, 2H), 3.61 (dd, J = 9.5, 3.9 Hz, 2H), 3.52 (s, 3H), 3.28-3.17 (m, 2H), 2.68 (dd, J = 13.6, 8.1 Hz, 2H), 2.32 (dd, J = 13.6, 3.4 Hz, 2H). |
| 97 | 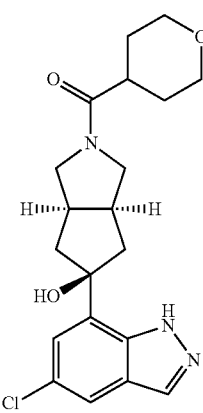<br>(method 8) | ((3aR,5r,6aS)-5-(5-chloro-1H-indazol-7-yl)-5-hydroxyhexahydrocyclo-penta[c]pyrrol-2(1H)-yl)(tetrahydro-2H-pyran-4-yl)methanone | 390.2 | 1H NMR (400 MHz, CD$_3$OD) δ 8.00 (s, 1H), 7.67 (d, J = 1.8 Hz, 1H), 7.27 (d, J = 1.7 Hz, 1H), 3.98 (m, 2H), 3.84 (m, 2H), 3.71 (m, 2H), 3.49 (m, 2H), 3.14-2.91 (m, 2H), 2.82 (m, 1H), 2.49 (m, 2H), 2.12 (m, 2H), 1.84-1.58 (m, 4H). |
| 98 | 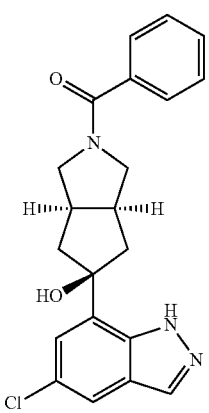<br>(method 8) | ((3aR,5r,6aS)-5-(5-chloro-1H-indazol-7-yl)-5-hydroxyhexahydrocyclo-penta[c]pyrrol-2(1H)-yl)(phenyl)methanone | 404.1 [M + 23]+ | 1H NMR (400 MHz, CD$_3$OD) δ 8.00 (s, 1H), 7.66 (d, J = 1.8 Hz, 1H), 7.52 (m, 2H), 7.49-7.42 (m, 3H), 7.25 (d, J = 1.7 Hz, 1H), 3.95 (m, 2H), 3.71 (m, 2H), 3.01 (m, 2H), 2.46 (m, 2H), 2.19 (m, 1H), 2.01 (m, 1H). |

TABLE 1-continued

| Example | Structure (Synthetic Method) | Chemical Name | LC/MS [M + H]+ | 1H-NMR |
|---|---|---|---|---|
| 99 | 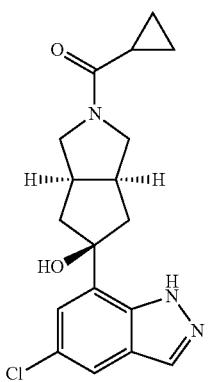 (method 8) | ((3aR,5r,6aS)-5-(5-chloro-1H-indazol-7-yl)-5-hydroxyhexahydrocyclopenta[c]pyrrol-2(1H)-yl)(cyclopropyl)methanone | 368.0 [M + 23]+ | 1H NMR (400 MHz, CD$_3$OD) δ 8.00 (s, 1H), 7.67 (d, J = 1.7 Hz, 1H), 7.27 (d, J = 1.8 Hz, 1H), 4.02 (m, 1H), 3.91 (m, 4.8 Hz, 1H), 3.80-3.64 (m, 2H), 3.15-2.90 (m, 2H), 2.51 (m, 2H), 2.13 (m, 2H), 1.83 (m, 1H), 0.94-0.87 (m, 2H), 0.82 (m, 2H). |
| 100 | 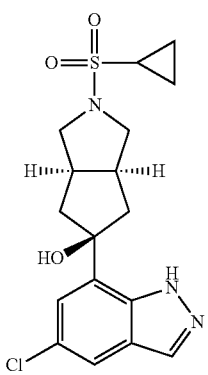 (method 8) | (3aR,5r,6aS)-5-(5-chloro-1H-indazol-7-yl)-2-(cyclopropylsulfonyl)octahydrocyclopenta[c]pyrrol-5-ol | 404.0 [M + 23]+ | 1H NMR (400 MHz, CD$_3$OD) δ 8.01 (s, 1H), 7.68 (d, J = 1.8 Hz, 1H), 7.27 (d, J = 1.8 Hz, 1H), 3.63-3.52 (m, 2H), 3.47 (m, 2H), 3.19 (m, 2H), 3.00-2.92 (m, 2H), 2.64-2.38 (m, 4H), 2.10 (m, 2H), 1.57 (m, 1H), 1.05 (m, 2H), 0.89 (m, 2H). |
| 101 | 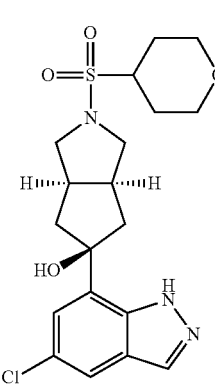 (method 8) | (3aR,5r,6aS)-5-(5-chloro-1H-indazol-7-yl)-2-((tetrahydro-2H-pyran-4-yl)sulfonyl)octahydrocyclopenta[c]pyrrol-5-ol | 448.0 [M + 23]+ | 1H NMR (400 MHz, CD$_3$OD) δ 8.00 (s, 1H), 7.68 (d, J = 1.7 Hz, 1H), 7.26 (d, J = 1.7 Hz, 1H), 4.04 (m, 2H), 3.68-3.60 (m, 2H), 3.51 (m, 2H), 3.44 (m, 3H), 2.99-2.90 (m, 2H), 2.47 (m, 2H), 2.08 (m, 2H), 2.04-1.98 (m, 2H), 1.86 (m, 2H). |

TABLE 1-continued

| Example | Structure (Synthetic Method) | Chemical Name | LC/MS [M + H]+ | 1H-NMR |
|---|---|---|---|---|
| 102 | (method 8) | (3aR,5r,6aS)-5-(5-chloro-1H-indazol-7-yl)-2-(phenylsulfonyl)octa-hydrocyclopenta[c]pyrrol-5-ol | 440.1 [M + 23]+ | 1H NMR (400 MHz, CD$_3$OD) δ 7.98 (s, 1H), 7.86 (s, 1H), 7.84 (s, 1H), 7.69 (m, 1H), 7.66-7.61 (m, 3H), 7.18 (m, 1H), 3.27 (m, 4H), 2.77 (m, 2H), 2.43 (m, 2H), 2.03-1.99 (m, 2H). |
| 103 | (method 3) | 2-amino-N-((1R,3r,5S,6r)-3-(6-chloro-1H-indazol-4-yl)-3-hydroxybicyclo[3.1.0]hexan-6-yl)acetamide hydrochloride | 343.1 [M + 23]+ | 1H NMR (400 MHz, CD$_3$OD) δ 8.60 (s, 1H), 7.41 (s, 1H), 7.25 (s, 1H), 3.62 (m, 2H), 2.70-2.54 (m, 2H), 2.26 (m, 2H), 1.71 (m, 1H), 1.29 (m, 2H). |
| 104 | (method 3) | 1-((3aR,6aS)-5-((6-chloro-1H-indazol-4-yl)(hydroxy)methyl)hexahydrocyclopenta[c]pyrrol-2(1H)-yl)ethanone | 356.0 [M + 23]+ | 1H NMR (400 MHz, CD$_3$OD) δ 8.23 (s, 1H), 7.44 (s, 1H), 7.12 (s, 1H), 4.84-4.76 (m, 1H), 3.75-3.44 (m, 2H), 3.38 (m, 1H), 3.27-3.03 (m, 1H), 2.92-2.70 (m, 1H), 2.70-2.48 (m, 2H), 2.07-1.93 (m, 4H), 1.81-1.53 (m, 2H), 1.53-1.40 (m, 1H). |
| 105 | (method 3) | (6-chloro-1H-indazol-4-yl)((3aR,6aS)-2-(methylsulfonyl)octa-hydrocyclopenta[c]pyrrol-5-yl)methanol | 392.0 [M + 23]+ | 1H NMR (400 MHz, CD$_3$OD) δ 8.22 (s, 1H), 7.43 (s, 1H), 7.08 (s, 1H), 4.83-4.71 (m, 1H), 3.49-3.36 (m, 1H), 3.26-3.07 (m, 3H), 2.84 (s, 3H), 2.76-2.57 (m, 2H), 2.44-2.15 (m, 1H), 1.66-1.37 (m, 2H). |

TABLE 1-continued

| Example | Structure (Synthetic Method) | Chemical Name | LC/MS [M + H]+ | 1H-NMR |
|---|---|---|---|---|
| 106 | 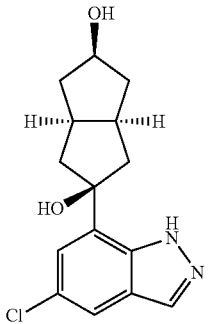<br>(method 8) | (2r,3aR,5s,6aS)-2-(5-chloro-1H-indazol-7-yl)octahydropentalene-2,5-diol | 315.1<br>[M + 23]+ | 1H NMR (400 MHz, DMSO-d6) δ 12.89 (s, 1H), 8.01 (d, J = 0.9 Hz, 1H), 7.68 (d, J = 1.5 Hz, 1H), 7.18 (d, J = 1.7 Hz, 1H), 5.43 (s, 1H), 4.66 (d, J = 4.1 Hz, 1H), 4.01-3.90 (m, 1H), 2.48-2.41 (m, 2H), 2.39-2.28 (m, 2H), 2.00-1.90 (m, 4H), 1.74-1.61 (m, 2H). |
| 107 | 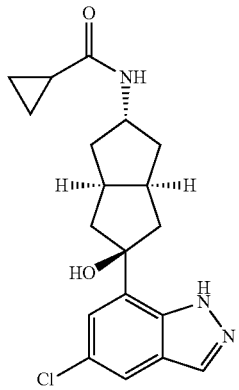<br>(method 8) | N-((1R,3r,5S,6r)-3-(5-chloro-1H-indazol-7-yl)-3-hydroxybicyclo[3.1.0]hexan-6-yl)cyclopropanecarboxamide | 354.2<br>[M + 23]+ | 1H NMR (400 MHz, CD3OD) δ 7.98 (s, 1H), 7.63 (d, J = 1.7 Hz, 1H), 7.27 (d, J = 1.8 Hz, 1H), 3.37 (t, J = 1.9 Hz, 1H), 2.53-2.45 (m, 2H), 2.30 (s, 1H), 2.26 (s, 1H), 1.60 (d, J = 7.4 Hz, 2H), 1.52 (m, 1H), 0.86-0.83 (m, 2H), 0.75-0.70 (m, 2H). |
| 108 | 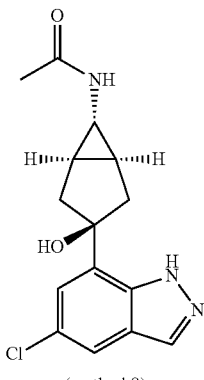<br>(method 8) | N-((1R,3r,5S,6r)-3-(5-chloro-1H-indazol-7-yl)-3-hydroxybicyclo[3.1.0]hexan-6-yl)acetamide | 306.0 | 1H NMR (400 MHz, CD3OD) δ 7.99 (s, 1H), 7.63 (d, J = 1.8 Hz, 1H), 7.27 (d, J = 1.8 Hz, 1H), 3.37 (s, 1H),, 2.49 (m, 2H), 2.30 (s, 1H), 2.27 (s, 1H), 1.91 (s, 3H), 1.63-1.55 (m, 2H). |
| 109 | 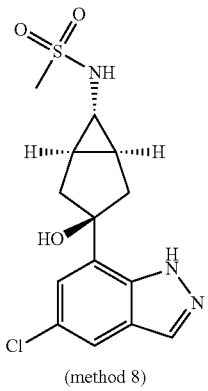 [SMILES: CS(=O)(=O)N[C@H]1[C@@H]2C[C@@](O)(c3cc(Cl)cc4cn[nH]c34)C[C@@H]21]<br>(method 8) | N-((1R,3r,5S,6r)-3-(5-chloro-1H-indazol-7-yl)-3-hydroxybicyclo[3.1.0]hexan-6-yl)methanesulfonamide | 364.1<br>[M + 23]+ | 1H NMR (400 MHz, CD3OD) δ 7.99 (s, 1H), 7.64 (d, J = 1.8 Hz, 1H), 7.29 (d, J = 1.8 Hz, 1H), 3.01 (s, 3H), 2.52 (d, J = 13.7 Hz, 2H), 2.30-2.19 (m, 2H), 2.08-1.95 (m, 1H), 1.81-1.74 (m, 2H). |

TABLE 1-continued

| Example | Structure (Synthetic Method) | Chemical Name | LC/MS [M + H]+ | 1H-NMR |
|---|---|---|---|---|
| 110 | (method 8) | N-((1R,3r,5S,6r)-3-(5-chloro-1H-indazol-7-yl)-3-hydroxybicyclo[3.1.0]hexan-6-yl)cyclopropanesulfonamide | 390.1 [M + 23]+ | 1H NMR (400 MHz, CD3OD) δ 7.99 (s, 1H), 7.64 (d, J = 1.7 Hz, 1H), 7.30 (d, J = 1.7 Hz, 1H), 2.62-2.45 (m, 3H), 2.26 (s, 1H), 2.24-2.18 (m, 1H), 2.02 (d, J = 5.3 Hz, 1H), 1.80 (d, J = 1.5 Hz, 2H), 1.12 (m, 2H), 1.10-1.05 (m, 2H). |
| 111 | (method 3) | (1R,3r,5S)-3-(6-chloro-1H-indazol-4-yl)-6-(hydroxymethyl)bicyclo[3.1.0]hexan-3-ol | 279.1 | 1H NMR (400 MHz, CD3OD) δ 8.29 (s, 1H), 8.08 (s, 0.5H), 7.44 (s, 1H), 7.41 (s, 0.5H), 7.19 (m, 1.5H), 4.01 (d, J = 7.6 Hz, 1.5H), 3.79-3.67 (m, 0.5H), 3.40 (d, J = 7.0 Hz, 1.0H), 2.68-2.45 (m, 4H), 2.14 (m, 1H), 1.96 (m, 2H), 1.82 (m, 1H), 1.74-1.64 (m, 2H), 1.49 (s, 1H), 1.30 (m, 1H) |
| 112 | (method 8) | 1-((3aR,6aS)-5-((5-chloro-1H-indazol-7-yl)(hydroxy)methyl)hexahydrocyclopenta[c]pyrrol-2(1H)-yl)ethanone | 356.0 [M + 23]+ | 1H NMR (400 MHz, CDCl3) δ 8.06-7.89 (m, 1H), 7.65-7.51 (m, 1H), 7.08 (dd, J = 12.4, 1.8 Hz, 1H), 4.91 (d, J = 6.3 Hz, 0.5H), 4.81 (d, J = 7.7 Hz, 0.5H), 3.60-3.45 (m, 2H), 3.43-3.34 (m, 1H), 3.32-3.22 (m, 1H), 2.71-2.46 (m, 3H), 1.98 (s, 1.5H), 1.94 (s, 1.5H), 1.80 (m, 1H), 1.71-1.57 (m, 1H), 1.52-1.31 (m, 2H). |
| 113 | (method 8) | (5-chloro-1H-indazol-7-yl)((3aR,6aS)-2-(methylsulfonyl)octahydrocyclopenta[c]pyrrol-5-yl)methanol | 392.0 [M + 23]+ | 1H NMR (400 MHz, CDCl3) δ 8.01 (s, 0.5H), 8.00 (s, 1H), 7.65 (d, J = 1.7 Hz, 0.5 H), 7.63 (d, J = 1.6 Hz, 1H), 7.10 (d, J = 1.5 Hz, 1H), 7.07 (d, J = 1.5 Hz, 0.5H), 4.85 (d, J = 7.6 Hz, 1H), 4.80 (d, J = 7.3 Hz, 0.5H). 3.47-3.33 (m, 1H), 3.27 (m, 2H), 3.12 (m, 2H), 2.97 (dd, J = 9.9, 4.6 Hz, 0.5H), 2.87 (dd, J = 9.5, 4.8 Hz, 1.5H), 2.82 (s, 3H), 2.77 (s, 1.5 H), 2.66 (m, 3H), 2.40-2.24 (m, 2H), 1.75-1.55 (m, 2H), 1.51-1.32 (m, 3H). |

TABLE 1-continued

| Example | Structure (Synthetic Method) | Chemical Name | LC/MS [M + H]+ | 1H-NMR |
|---|---|---|---|---|
| 114 | (method 3) | 1-((1R,3r,5S,6r)-3-(6-chloro-1H-indazol-4-yl)-3-hydroxybicyclo[3.1.0]hexan-6-yl)-3-methylurea | 321.1 | 1H NMR (400 MHz, CD$_3$OD) δ 8.10 (s, 1H), 7.42 (s, 1H), 7.18 (d, J = 1.5 Hz, 1H), 3.07 (m, 1H), 2.74 (s, 3H), 2.63 (m, 2H), 2.23 (m, 2H), 1.67 (m, 2H). |
| 115 | (method 3) | 1-((1R,3r,5S,6r)-3-(6-chloro-1H-indazol-4-yl)-3-hydroxybicyclo[3.1.0]hexan-6-yl)-3-phenylurea | 383.0 | 1H NMR (400 MHz, CD$_3$OD) δ 8.11 (s, 1H), 7.42 (s, 1H), 7.37 (d, J = 7.6 Hz, 2H), 7.25 (m, 2H), 7.20 (d, J = 1.5 Hz, 1H), 6.98 (t, J = 7.4 Hz, 1H), 3.22 (m, 1H), 2.66 (m, 2H), 2.28 (m, 1H), 2.24 (m, 1H), 1.72 (m, 2H). |
| 116 | (method 3) | (3aR,5r,6aS)-5-(6-chloro-1H-indazol-4-yl)-2-(pyridin-4-yl)octahydrocyclopenta[c]pyrrol-5-ol | 354.9 | 1H NMR (400 MHz, DMSO-d6) δ 13.17 (s, 1H), 8.23 (s, 1H), 8.13 (d, J = 6.5 Hz, 2H), 7.47 (s, 1H), 7.09 (d, J = 1.4 Hz, 1H), 6.61 (t, J = 7.9 Hz, 2H), 5.34 (s, 1H), 3.72 (dd, J = 18.5, 9.1 Hz, 2H), 3.53 (dd, J = 10.4, 3.6 Hz, 2H), 3.15 (d, J = 4.0 Hz, 2H), 2.5 (m, 2H), 2.05 (d, J = 13.4 Hz, 2H). |

TABLE 1-continued

| Example | Structure (Synthetic Method) | Chemical Name | LC/MS [M + H]+ | 1H-NMR |
|---|---|---|---|---|
| 117 | (method 8) | (3aR,5r,6aS)-5-(5-chloro-1H-indazol-7-yl)-2-(pyridin-4-yl)octahydrocyclopenta[c]pyrrol-5-ol | 355.1 | 1H NMR (400 MHz, DMSO-d6) δ 12.99 (s, 1H), 8.12 (d, J = 6.3 Hz, 2H), 8.04 (s, 1H), 7.72 (s, 1H), 7.25 (d, J = 1.6 Hz, 1H), 6.60 (d, J = 6.4 Hz, 2H), 5.41 (s, 1H), 3.73 (t, J = 9.4 Hz, 2H), 3.51 (dd, J = 10.3, 3.4 Hz, 2H), 3.12 (s, 2H), 2.50 (m, 2H), 2.08 (d, J = 12.9 Hz, 2H). |
| 118 | (method 8) | (1R,3r,5S)-3-(5-chloro-1H-indazol-7-yl)bicyclo[3.1.0]hexan-3-ol | 271.1 [M + 23]+ | 1H NMR (400 MHz, CD3OD) δ 7.98 (s, 1H), 7.62 (d, J = 1.5 Hz, 1H), 7.29 (d, J = 1.5 Hz, 1H), 2.52-2.44 (m, 2H), 2.14 (m, 2H), 1.53-1.46 (m, 2H), 1.08 (dd, J = 7.9, 3.9 Hz, 1H), 0.56 (m, 1H). |
| 119 | (method 3) | 4-chloro-N-((1R,3r,5S,6r)-3-(6-chloro-1H-indazol-4-yl)-3-hydroxybicyclo[3.1.0]hexan-6-yl)benzamide | 402.0 | 1H NMR (400 MHz, DMSO-d6) δ 13.24 (s, 1H), 8.46 (d, J = 3.4 Hz, 1H), 8.04 (s, 1H), 7.85 (d, J = 8.5 Hz, 2H), 7.51 (d, J = 8.5 Hz, 2H), 7.46 (s, 1H), 7.11 (s, 1H), 5.30 (s, 1H), 3.15 (d, J = 5.2 Hz, 1H), 2.53 (m, 2H), 2.15 (m,2H), 1.74 (s, 2H). |
| 120 | (method 3) | 1-((1R,3r,5S,6r)-3-(6-chloro-1H-indazol-4-yl)-3-hydroxybicyclo[3.1.0]hexan-6-yl)-3-cyclopropylurea | 347.2 | 1H NMR (400 MHz, DMSO-d6) δ 13.17 (s, 1H), 8.01 (s, 1H), 7.44 (s, 1H), 7.09 (s, 1H), 5.92 (d, J = 5.3 Hz, 2H), 5.18 (s, 1H), 3.03 (s, 1H), 2.44 (m, 2H), 2.39 (m, 1H), 2.07 (d, J = 14.0 Hz, 2H), 1.49 (s, 2H), 0.54 (m, 2H), 0.31 (m, 2H). |

TABLE 1-continued

| Example | Structure (Synthetic Method) | Chemical Name | LC/MS [M + H]+ | 1H-NMR |
|---|---|---|---|---|
| 121 | 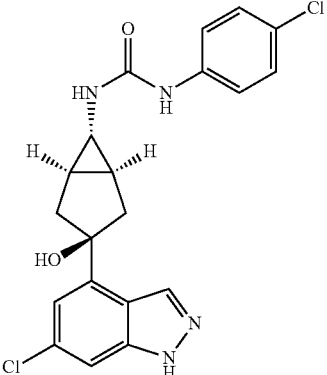<br>(method 3) | 1-((1R,3r,5S,6r)-3-(6-chloro-1H-indazol-4-yl)-3-hydroxybicyclo[3.1.0]hexan-6-yl)-3-(4-chlorophenyl)urea | 417.1 | 1H NMR (400 MHz, DMSO-d6) δ 13.18 (s, 1H), 8.47 (s, 1H), 8.03 (s, 1H), 7.45 (s, 1H), 7.42 (d, J = 8.9 Hz, 2H), 7.24 (d, J = 8.9 Hz, 2H), 7.10 (s, 1H), 6.35 (d, J = 2.7 Hz, 1H), 5.24 (s, 1H), 3.15 (s, 1H), 2.50 (m, 2H), 2.11 (d, J = 14.0 Hz, 2H), 1.56 (s, 2H). |
| 122 | 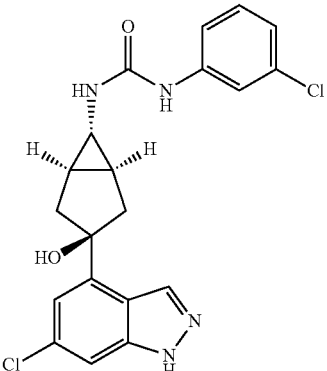<br>(method 3) | 1-((1R,3r,5S,6r)-3-(6-chloro-1H-indazol-4-yl)-3-hydroxybicyclo[3.1.0]hexan-6-yl)-3-(3-chlorophenyl)urea | 417.1 | 1H NMR (400 MHz, DMSO-d6) δ 13.18 (s, 1H), 8.51 (s, 1H), 8.03 (s, 1H), 7.67 (s, 1H), 7.45 (s, 1H), 7.30-7.14 (m, 2H), 7.10 (d, J = 1.5 Hz, 1H), 6.92 (s, 1H), 6.38 (d, J = 2.6 Hz, 1H), 5.24 (s, 1H), 3.16 (s, 1H), 2.51 (m, 2H), 2.12 (m, 2H), 1.57 (s, 2H). |
| 123 | 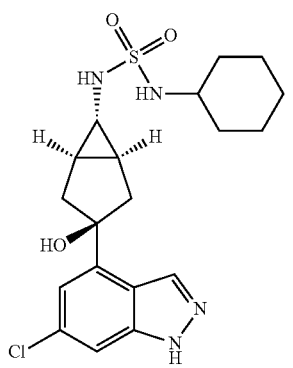<br>(method 9) | N'-cyclohexyl-N-((1R,3r,5S,6r)-3-(6-chloro-1H-indazol-4-yl)-3-hydroxybicyclo[3.1.0]hexan-6-yl)sulfuric diamide | 425.1 | 1H NMR (400 MHz, CD3OD) δ 8.09 (s, 1H), 7.42 (s, 1H), 7.17 (d, J = 1.5 Hz, 1H), 3.19-3.12 (m, 1H), 3.11 (s, 1H), 2.63 (m, 2H), 2.17 (d, J = 14.4 Hz,2H), 2.07 (m, 2H), 1.86-1.82 (m, 2H), 1.78 (m, 2H), 1.60 (m, 1H), 1.34 (m, 3H), 1.31-1.28 (m, 2H). |

TABLE 1-continued

| Example | Structure (Synthetic Method) | Chemical Name | LC/MS [M + H]+ | 1H-NMR |
|---|---|---|---|---|
| 124 | 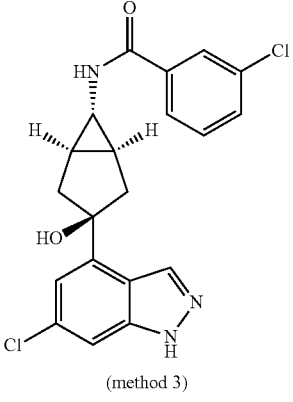 [SMILES: O=C(N[C@H]1[C@@H]2C[C@@](O)(c3cc(Cl)cc4[nH]ncc34)C[C@@H]21)c1cccc(Cl)c1] (method 3) | 3-chloro-N-((1R,3r,5S,6r)-3-(6-chloro-1H-indazol-4-yl)-3-hydroxybicyclo[3.1.0]hexan-6-yl)benzamide | 402.1 | 1H NMR (400 MHz, CD3OD) δ 8.12 (s, 1H), 7.83 (t, J = 1.7 Hz, 1H), 7.74 (d, J = 7.8 Hz, 1H), 7.56-7.51 (m, 1H), 7.44 (dd, J = 10.1, 5.5 Hz, 2H), 7.21 (d, J = 1.6 Hz, 1H), 3.51 (s, 1H), 2.71 (m, 2H), 2.31 (d, J = 14.2 Hz, 2H), 2.29 (s, 1H), 1.84 (s, 2H). |
| 125 | 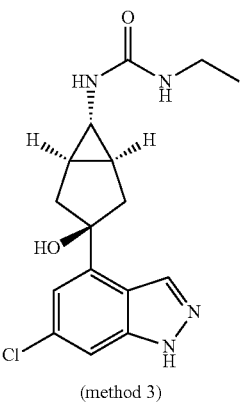 [SMILES: CCNC(=O)N[C@H]1[C@@H]2C[C@@](O)(c3cc(Cl)cc4[nH]ncc34)C[C@@H]21] (method 3) | 1-((1R,3r,5S,6r)-3-(6-chloro-1H-indazol-4-yl)-3-hydroxybicyclo[3.1.0]hexan-6-yl)-3-ethylurea | 357.1 [M + 23]+ | 1H NMR (400 MHz, DMSO-d6) δ 13.17 (s, 1H), 8.03 (s, 1H), 7.45 (s, 1H), 7.10 (d, J = 1.3 Hz, 1H), 5.95 (d, J = 2.5 Hz, 1H), 5.65 (t, J = 5.6 Hz, 1H), 5.17 (s, 1H), 3.04-2.99 (m, 3H), 2.49-2.45 (m, 2H), 2.10 (d, J = 14.0 Hz, 2H), 1.49 (s, 2H), 0.99 (t, J = 7.1 Hz, 3H). |
| 126 | 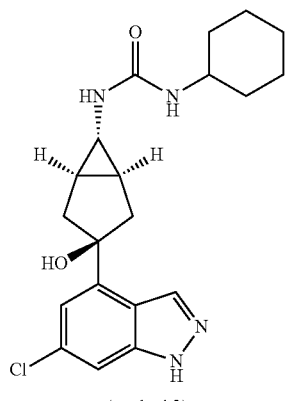 (method 3) | 1-((1R,3r,5S,6r)-3-(6-chloro-1H-indazol-4-yl)-3-hydroxybicyclo[3.1.0]hexan-6-yl)-3-cyclohexylurea | 389.3 | 1H NMR (400 MHz, DMSO-d6) δ 13.17 (s, 1H), 8.03 (s, 1H), 7.44 (d, J = 11.4 Hz, 1H), 7.10 (s, 1H), 5.85 (s, 1H), 5.49 (d, J = 8.0 Hz, 1H), 5.19 (s, 1H), 3.36 (s, 2H), 3.03 (s, 1H), 2.49-2.47 (m, 1H), 2.46 (m, 1H), 2.05 (m, 2H), 1.69 (m, 6H), 1.48 (m, 2H), 1.09 (m, 4H). |

| Example | Structure (Synthetic Method) | Chemical Name | LC/MS [M + H]+ | 1H-NMR |
|---|---|---|---|---|
| 127 | 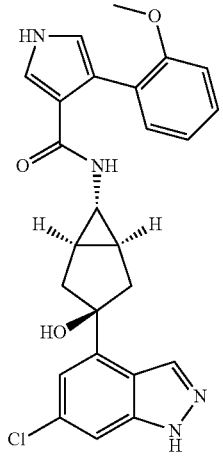 (method 3) | N-((1R,3r,5S,6r)-3-(6-chloro-1H-indazol-4-yl)-3-hydroxybicyclo[3.1.0]hexan-6-yl)-4-(2-methoxyphenyl)-1H-pyrrole-3-carboxamide | 485.3 [M + 23]+ | 1H NMR (400 MHz, CD$_3$OD) δ 8.06 (s, 1H), 7.41 (s, 1H), 7.32 (td, J = 8.2, 1.7 Hz, 1H), 7.28 (d, J = 2.2 Hz, 1H), 7.25 (dd, J = 7.4, 1.7 Hz, 1H), 7.16 (d, J = 1.5 Hz, 1H), 7.04 (d, J = 8.1 Hz, 1H), 6.98 (dd, J = 7.8, 7.1 Hz, 1H), 6.71 (d, J = 2.2 Hz, 1H), 3.79 (s, 3H), 3.13 (s, 1H), 2.58 (dd, J = 14.3, 3.4 Hz, 2H), 2.19 (d, J = 14.4 Hz, 2H), 1.45 (s, 2H). |
| 128 | 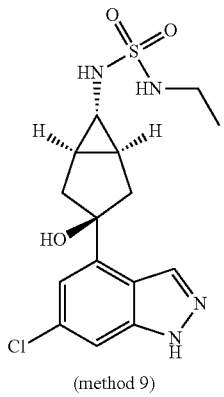 [SMILES: CCNS(=O)(=O)N[C@H]1[C@@H]2C[C@@](O)(c3cc(Cl)cc4[nH]ncc34)C[C@@H]21] (method 9) | N'-ethyl-N-((1R,3r,5S,6r)-3-(6-chloro-1H-indazol-4-yl)-3-hydroxybicyclo[3.1.0]hexan-6-yl)sulfuric diamide | 371.0 | 1H NMR (400 MHz, CD$_3$OD) δ 8.09 (s, 1H), 7.42 (s, 1H), 7.17 (d, J = 1.4 Hz, 1H), 3.06 (m, 3H), 2.64 (dd, J = 14.4, 3.4 Hz, 2H), 2.18 (d, J = 14.4 Hz, 2H), 1.82 (d, J = 1.5 Hz, 2H), 1.21 (t, J = 7.3 Hz, 3H). |
| 129 | 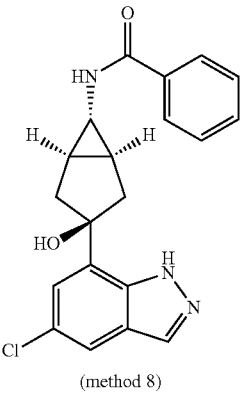 [SMILES: O=C(N[C@H]1[C@@H]2C[C@@](O)(c3cc(Cl)cc4cn[nH]c34)C[C@@H]21)c1ccccc1] (method 8) | N-((1R,3r,5S,6r)-3-(5-chloro-1H-indazol-7-yl)-3-hydroxybicyclo[3.1.0]hexan-6-yl)benzamide | 368.1 | 1H NMR (400 MHz, DMSO-d6) δ 12.93 (s, 1H), 8.31 (d, J = 4.4 Hz, 1H), 8.05 (s, 1H), 7.83 (d, J = 7.1 Hz, 2H), 7.72 (s, 1H), 7.51 (t, J = 7.2 Hz, 1H), 7.45 (t, J = 7.3 Hz, 2H), 7.27 (d, J = 1.7 Hz, 1H), 5.42 (s, 1H), 3.59 (s, 1H), 2.45 (d, J = 11.9 Hz, 2H), 2.27 (d, J = 13.8 Hz, 2H), 1.67 (s, 2H). |

TABLE 1-continued

| Example | Structure (Synthetic Method) | Chemical Name | LC/MS [M + H]+ | 1H-NMR |
|---|---|---|---|---|
| 130 | 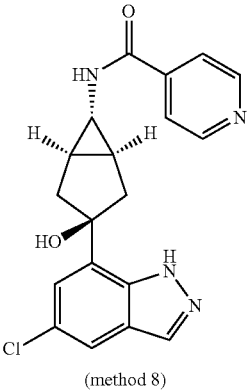 [SMILES: O=C(N[C@H]1[C@@H]2C[C@@](O)(c3cc(Cl)cc4cn[nH]c34)C[C@@H]21)c1ccncc1]<br>(method 8) | N-((1R,3r,5S,6r)-3-(5-chloro-1H-indazol-7-yl)-3-hydroxybicyclo[3.1.0]hexan-6-yl)isonicotinamide | 369.1 | 1H NMR (400 MHz, DMSO-d6) δ 12.94 (s, 1H), 8.71 (d, J = 5.9 Hz, 2H), 8.62 (d, J = 4.6 Hz, 1H), 8.05 (s, 1H), 7.74 (d, J = 6.0 Hz, 2H), 7.72 (d, J = 1.6 Hz, 1H), 7.27 (d, J = 1.7 Hz, 1H), 5.43 (s, 1H), 3.62 (t, 1H), 2.45 (m, 2H), 2.27 (m, 2H), 1.70 (s, 2H). |
| 131 | 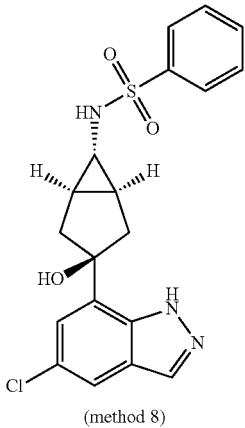 [SMILES: O=S(=O)(N[C@H]1[C@@H]2C[C@@](O)(c3cc(Cl)cc4cn[nH]c34)C[C@@H]21)c1ccccc1]<br>(method 8) | N-((1R,3r,5S,6r)-3-(5-chloro-1H-indazol-7-yl)-3-hydroxybicyclo[3.1.0]hexan-6-yl)benzenesulfonamide | 426.0 [M + 23]+ | 1H NMR (400 MHz, CD3OD) δ 7.98 (s, 1H), 7.93 (d, J = 7.1 Hz, 2H), 7.70-7.57 (m, 4H), 7.24 (d, J = 1.4 Hz, 1H), 2.97 (m, 1H), 2.41 (m, 2H), 2.11 (m, 2H), 1.61 (m, 2H). |
| 132 | 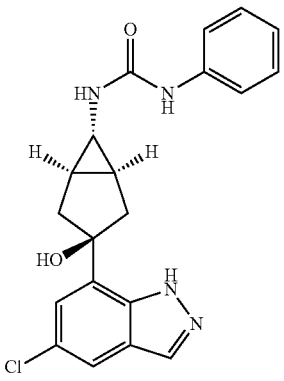<br>(method 8) | 1-((1R,3r,5S,6r)-3-(5-chloro-1H-indazol-7-yl)-3-hydroxybicyclo[3.1.0]hexan-6-yl)-3-phenylurea | 383.1 | 1H NMR (400 MHz, DMSO-d6) δ 12.90 (s, 1H), 8.22 (s, 1H), 8.05 (s, 1H), 7.71 (d, J = 1.3 Hz, 1H), 7.40 (d, J = 7.8 Hz, 2H), 7.28-7.18 (m, 3H), 6.89 (t, J = 7.3 Hz, 1H), 6.25 (d, J = 2.6 Hz, 1H), 5.37 (s, 1H), 3.25 (m, 1H), 2.43 (m, 2H), 2.23 (m, 2H), 1.50 (s, 2H). |

TABLE 1-continued

| Example | Structure (Synthetic Method) | Chemical Name | LC/MS [M + H]+ | 1H-NMR |
|---|---|---|---|---|
| 133 | (method 8) | 1-((1R,3r,5S,6r)-3-(5-chloro-1H-indazol-7-yl)-3-hydroxybicyclo[3.1.0]hexan-6-yl)-3-methylurea | 343.1 [M + 23]+ | 1H NMR (400 MHz, DMSO-d6) δ 12.86 (s, 1H), 8.04 (s, 1H), 7.70 (d, J = 1.6 Hz, 1H), 7.24 (d, J = 1.8 Hz, 1H), 6.01 (d, J = 2.3 Hz, 1H), 5.56 (m, 1H), 5.30 (s, 1H), 3.07 (m, 1H), 2.56 (d, J = 4.6 Hz, 3H), 2.38 (m, 2H), 2.18 (m, 2H), 1.42 (s, 2H). |
| 134 | (method 3) | (5-chloro-1H-benzo[d]imidazol-2-yl)((3aR,5r,6aS)-5-(6-chloro-1H-indazol-4-yl)-5-hydroxyhexahydrocyclopenta[c]pyrrol-2(1H)-yl)methanone | 456.1 | 1H NMR (400 MHz, DMSO-d6) δ 13.28, 13.21 (s + s, 1H), 13.15 (s, 1H), 8.24 (s, 1H), 7.87-7.77 (m, 1H), 7.55 (m, 1H), 7.48 (s, 1H), 7.31 (m, 1H), 7.11 (m, 1H), 5.37 (s, 1H), 4.55 (m, 3H), 4.42-4.32 (m, 1H), 4.05-3.84 (m, 2H), 3.14-3.03 (m, 2H), 2.06 (m, 2H). |
| 135 | (method 3) | 1-((1R,3r,5S,6r)-3-(6-chloro-1H-indazol-4-yl)-3-hydroxybicyclo[3.1.0]hexan-6-yl)urea | 307.1 | 1H NMR (400 MHz, CD3OD) δ 8.10 (s, 1H), 7.43 (s, 1H), 7.18 (d, J = 1.5 Hz, 1H), 3.11 (s, 1H), 2.64 (dd, J = 14.4, 3.8 Hz, 2H), 2.24 (d, J = 14.4 Hz, 1H), 1.70 (s, 2H). |

TABLE 1-continued

| Example | Structure (Synthetic Method) | Chemical Name | LC/MS [M + H]+ | 1H-NMR |
|---|---|---|---|---|
| 136 | (method 3) | 5-chloro-N-((1R,3r,5S,6r)-3-(6-chloro-1H-indazol-4-yl)-3-hydroxybicyclo[3.1.0]hexan-6-yl)-1H-benzo[d]imidazole-2-carboxamide | 464.1 [M + 23]+ | 1H NMR (400 MHz, DMSO-d6) δ 13.40 (m, 1H), 13.20 (s, 1H), 9.00 (s, 1H), 8.07 (s, 1H), 7.74 (m, 1H), 7.54 (s, 1H), 7.48 (s, 1H), 7.37-7.26 (m, 1H), 7.13 (s, 1H), 5.34 (m, 1H), 3.62 (m, 1H), 2.55 (m, 2H), 2.20-2.17 (m, 2H), 1.88 (m, 2H). |
| 137 | (method 3) | N-((1R,3r,5S,6r)-3-(6-chloro-1H-indazol-4-yl)-3-hydroxybicyclo[3.1.0]hexan-6-yl)-2-cyanoacetamide | 331.1 | 1H NMR (400 MHz, CD3OD) δ 8.01 (s, 1H), 7.36 (s, 1H), 7.14 (s, 1H), 3.35 (d, J = 5.6 Hz, 1H), 3.30 (s, 2H), 2.63-2.60 (m, 2H), 2.24-2.20 (m, 2H), 1.66 (s, 2H). |
| 138 | (method 3) | N-((1R,3r,5S,6r)-3-(6-chloro-1H-indazol-4-yl)-3-hydroxybicyclo[3.1.0]hexan-6-yl)-3,3,3-trifluoropropanamide | 374.1 | 1H NMR (400 MHz, CD3OD) δ 8.10 (s, 1H), 7.43 (s, 1H), 7.18 (d, J = 1.3 Hz, 1H), 3.63 (s, 1H), 3.11 (m, 2H), 2.67-2.63 (m, 2H), 2.27-2.23 (m, 2H), 1.70 (s, 2H). |

TABLE 1-continued

| Example | Structure (Synthetic Method) | Chemical Name | LC/MS [M + H]+ | 1H-NMR |
|---|---|---|---|---|
| 139 | (method 3) | N-((1R,3r,5S,6r)-3-(6-chloro-1H-indazol-4-yl)-3-hydroxybicyclo[3.1.0]hexan-6-yl)-2,2,2-trifluoroethanesulfonamide | 410.1 | $^1$H NMR (400 MHz, CD$_3$OD) δ 8.10 (s, 1H), 7.43 (s, 1H), 7.18 (d, J = 1.6 Hz, 1H), 3.23 (m, 1H), 3.20 (m, 2H), 2.68-2.64 (m, 2H), 2.23-2.19 (m, 2H), 1.91-1.87 (m, 2H). |
| 140 | (method 9) | N-((1R,3r,5S,6r)-3-(6-chloro-1H-indazol-4-yl)-3-hydroxybicyclo[3.1.0]hexan-6-yl)sulfuric diamide | 343.1 | $^1$H NMR (400 MHz, CD$_3$OD) δ 8.26 (s, 1H), 7.48 (s, 1H), 7.23 (d, J = 1.4 Hz, 1H), 3.18 (s, 1H), 2.63 (m, 2H), 2.22 (m, 2H), 1.86 (m, 2H). |
| 141 | (method 3) | N-((1R,3r,5S,6r)-3-(6-chloro-1H-indazol-4-yl)-3-hydroxybicyclo[3.1.0]hexan-6-yl)-3-(methylsulfonamido)benzamide | 461.2 | 1H NMR (400 MHz, CD$_3$OD) δ 8.12 (s, 1H), 7.67 (s, 1H), 7.57-7.52 (m, 1H), 7.42 (dd, J = 7.0, 2.8 Hz, 3H), 7.21 (d, J = 1.4 Hz, 1H), 3.51 (s, 1H), 3.00 (s, 3H), 2.69 (m, 2H), 2.32 (d, J = 14.4 Hz, 1H), 1.85 (s, 2H). |

TABLE 1-continued

| Example | Structure (Synthetic Method) | Chemical Name | LC/MS [M + H]+ | 1H-NMR |
|---|---|---|---|---|
| 142 | (method 3) | N-((1R,3r,5S,6r)-3-(6-chloro-1H-indazol-4-yl)-3-hydroxybicyclo[3.1.0]hexan-6-yl)-3-(trifluoromethyl)benzamide | 436.2 | 1H NMR (400 MHz, DMSO-d6) δ 13.19 (s, 1H), 8.62 (d, J = 4.4 Hz, 1H), 8.17 (s, 1H), 8.14 (d, J = 7.9 Hz, 1H), 8.07 (s, 1H), 7.88 (m, 1H), 7.72 (s, 1H), 7.47 (s, 1H), 7.13 (d, J = 1.3 Hz, 1H), 5.32 (s, 1H), 3.54 (s, 1H), 2.55 (m, 2H), 2.18 (d, J = 14.4 Hz, 2H), 1.78 (s, 2H). |
| 143 | (method 3) | N-((1R,3r,5S,6r)-3-(6-chloro-1H-indazol-4-yl)-3-hydroxybicyclo[3.1.0]hexan-6-yl)-3-fluorobenzamide | 408.1 [M + 23]+ | 1H NMR (400 MHz, DMSO-d6) δ 13.19 (s, 1H), 8.44 (d, J = 4.3 Hz, 1H), 8.07 (s, 1H), 7.69 (d, J = 7.8 Hz, 1H), 7.62 (d, J = 9.9 Hz, 1H), 7.51 (dd, J = 7.9, 1.9 Hz, 1H), 7.48 (d, J = 5.4 Hz, 1H), 7.36 (m, 1H), 7.13 (d, J = 1.3 Hz, 1H), 5.30 (s, 1H), 3.56-3.48 (m, 1H), 2.54 (m, 1H), 2.17 (d, J = 14.3 Hz, 1H), 1.75 (s, 2H). |
| 144 | (method 3) | N-((1R,3r,5S,6r)-3-(6-chloro-1H-indazol-4-yl)-3-hydroxybicyclo[3.1.0]hexan-6-yl)-3-cyanobenzamide | 393.1 | 1H NMR (400 MHz, DMSO-d6) δ 13.19 (s, 1H), 8.56 (d, J = 4.4 Hz, 1H), 8.25 (s, 1H), 8.14 (d, J = 8.0 Hz, 1H), 8.07 (s, 1H), 7.99 (d, J = 7.7 Hz, 1H), 7.69 (s, 1H), 7.47 (s, 1H), 7.13 (d, J = 1.3 Hz, 1H), 5.32 (s, 1H), 3.54 (m, 1H), 2.54 (m, 2H), 2.17 (d, J = 14.4 Hz, 1H), 1.77 (s, 2H). |

| Example | Structure (Synthetic Method) | Chemical Name | LC/MS [M + H]⁺ | ¹H-NMR |
|---|---|---|---|---|
| 145 | (method 3) | N-((1R,3r,5S,6r)-3-(6-chloro-1H-indazol-4-yl)-3-hydroxybicyclo[3.1.0]hexan-6-yl)-3-(trifluoromethoxy)benzamide | 452.1 | 1H NMR (400 MHz, DMSO-d6) δ 13.19 (s, 1H), 8.53 (d, J = 4.1 Hz, 1H), 8.07 (s, 1H), 7.88 (d, J = 7.5 Hz, 1H), 7.78 (s, 1H), 7.60 (m, 1H), 7.54 (s, 1H), 7.47 (m, 1H), 7.13 (s, 1H), 5.31 (s, 1H), 3.52 (s, 1H), 2.56 (m, 1H), 2.52 (m, 1H), 2.19 (s, 1H), 2.15 (s, 1H), 1.76 (s, 2H). |
| 146 | (method 3) | 3-bromo-N-((1R,3r,5S,6r)-3-(6-chloro-1H-indazol-4-yl)-3-hydroxybicyclo[3.1.0]hexan-6-yl)benzamide | 446.1 | 1H NMR (400 MHz, DMSO-d6) δ 13.19 (s, 1H), 8.47 (d, J = 4.3 Hz, 1H), 8.07 (s, 1H), 8.00 (s, 1H), 7.83 (d, J = 7.8 Hz, 1H), 7.71 (s, 1H), 7.48-7.40 (m, 2H), 7.12 (s, 1H), 5.30 (s, 1H), 3.51 (s, 1H), 2.54 (m, 2H), 2.18 (d, J = 14.3 Hz, 2H), 1.75 (s, 2H). |
| 147 | (method 3) | 1-((1R,3r,5S,6r)-3-(6-chloro-1H-indazol-4-yl)-3-hydroxybicyclo[3.1.0]hexan-6-yl)-3-(4-fluorophenyl)urea | 401.1 | 1H NMR (400 MHz, CD₃OD) δ 8.11 (s, 1H), 7.43 (s, 1H), 7.37 (m, 2H), 7.20 (d, J = 1.4 Hz, 1H), 6.99 (t, J = 8.8 Hz, 2H), 3.22 (s, 1H), 2.67 (m, 2H), 2.26 (m, 2H), 1.72 (s, 2H). |

TABLE 1-continued

| Example | Structure (Synthetic Method) | Chemical Name | LC/MS [M + H]⁺ | ¹H-NMR |
|---------|------------------------------|---------------|----------------|--------|
| 148 | (method 3) | N-((1R,3r,5S,6r)-3-(6-chloro-1H-indazol-4-yl)-3-hydroxybicyclo[3.1.0]hexan-6-yl)nicotinamide | 369.2 | 1H NMR (400 MHz, DMSO-d6) δ 13.19 (s, 1H), 8.97 (d, J = 1.7 Hz, 1H), 8.69 (dd, J = 4.8, 1.6 Hz, 1H), 8.54 (d, J = 4.4 Hz, 1H), 8.16 (dt, J = 8.0, 1.9 Hz, 1H), 8.07 (s, 1H), 7.49 (m, 2H), 7.13 (d, J = 1.4 Hz, 1H), 5.31 (s, 1H), 3.57-3.46 (m, 1H), 2.55 (m, 2H), 2.17 (d, J = 14.0 Hz, 2H), 1.76 (s, 2H). |
| 149 | (method 3) | N-((1R,3r,5S,6r)-3-(6-chloro-1H-indazol-4-yl)-3-hydroxybicyclo[3.1.0]hexan-6-yl)-2-(4-chlorophenyl)acetamide | 416.2 | 1H NMR (400 MHz, CD₃OD) δ 8.09 (s, 1H), 7.42 (m, 1H), 7.29 (m, 4H), 7.17 (m, 1H), 3.45 (s, 2H), 3.32 (m, 1H), 2.63 (m, 2H), 2.25 (d, J = 14.4 Hz, 1H), 1.68 (s, 2H). |
| 150 | (method 3) | 3-chloro-N-((1R,3r,5S,6r)-3-(6-chloro-1H-indazol-4-yl)-3-hydroxybicyclo[3.1.0]hexan-6-yl)-4-fluorobenzamide | 420.0 | 1H NMR (400 MHz, DMSO-d6) δ 13.19 (s, 1H), 8.48 (d, J = 4.3 Hz, 1H), 8.09-8.03 (m, 2H), 7.90-7.84 (m, 1H), 7.52 (m, 1H), 7.47 (s, 1H), 7.12 (d, J = 1.4 Hz, 1H), 5.30 (s, 1H), 3.53-3.49 (m, 1H), 2.55 (s, 1H), 2.52 (s, 1H), 2.16 (m, 2H), 1.75 (s, 2H). |

TABLE 1-continued

| Example | Structure (Synthetic Method) | Chemical Name | LC/MS [M + H]+ | 1H-NMR |
|---|---|---|---|---|
| 151 | 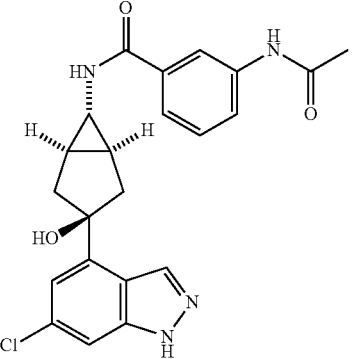 (method 3) | 3-acetamido-N-((1R,3r,5S,6r)-3-(6-chloro-1H-indazol-4-yl)-3-hydroxybicyclo[3.1.0]hexan-6-yl)benzamide | 425.2 | 1H NMR (400 MHz, DMSO-d6) δ 13.35 (s, 1H), 10.15 (s, 1H), 8.33 (d, J = 3.9 Hz, 1H), 8.06 (s, 1H), 7.97 (s, 1H), 7.78 (d, J = 7.7 Hz, 1H), 7.47 (m, 2H), 7.35 (t, J = 7.8 Hz, 1H), 7.13 (s, 1H), 5.32 (s, 1H), 3.50 (m, 1H), 2.55 (m, 2H), 2.17 (m, 2H), 2.06 (s, 3H), 1.75 (s, 2H). |
| 152 | 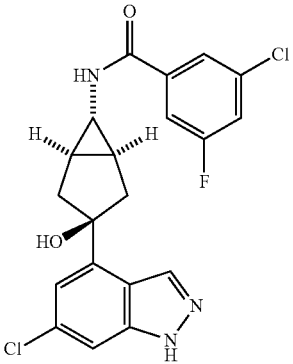 (method 3) | 3-chloro-N-((1R,3r,5S,6r)-3-(6-chloro-1H-indazol-4-yl)-3-hydroxybicyclo[3.1.0]hexan-6-yl)-5-fluorobenzamide | 420.0 | 1H NMR (400 MHz, DMSO-d6) δ 13.34 (s, 1H), 8.65 (s, 1H), 8.06 (s, 1H), 7.78 (s, 1H), 7.71-7.58 (m, 2H), 7.48 (s, 1H), 7.12 (d, J = 1.4 Hz, 1H), 5.32 (s, 1H), 3.58-3.45 (m, 1H), 2.55 (m, 2H), 2.17 (d, J = 14.0 Hz, 2H), 1.78 (s, 2H). |
| 153 | 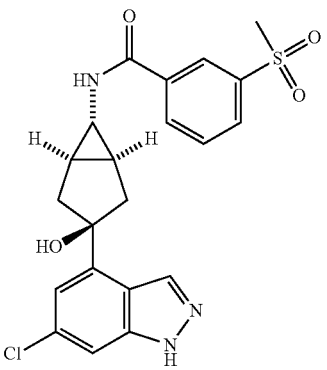 (method 3) | N-((1R,3r,5S,6r)-3-(6-chloro-1H-indazol-4-yl)-3-hydroxybicyclo[3.1.0]hexan-6-yl)-3-(methylsulfonyl)benzamide | 468.2 [M + 23]+ | 1H NMR (400 MHz, DMSO-d6) δ 13.31 (s, 1H), 8.77 (s, 1H), 8.39 (s, 1H), 8.19 (d, J = 7.7 Hz, 1H), 8.06 (d, J = 6.3 Hz, 2H), 7.75 (t, J = 7.8 Hz, 1H), 7.48 (s, 1H), 7.13 (s, 1H), 5.34 (s, 1H), 3.55 (m, 1H), 3.27 (s, 3H), 2.55 (m, 2H), 2.20 (m, 2H), 1.80 (s, 2H). |

TABLE 1-continued

| Example | Structure (Synthetic Method) | Chemical Name | LC/MS [M + H]+ | ¹H-NMR |
|---|---|---|---|---|
| 154 | (method 3) | N-((1R,3r,5S,6r)-3-(6-chloro-1H-indazol-4-yl)-3-hydroxybicyclo[3.1.0]hexan-6-yl)-5-methylisoxazole-3-carboxamide | 395.1 [M + 23]+ | 1H NMR (400 MHz, DMSO-d6) δ 13.19 (s, 1H), 8.66 (d, J = 4.6 Hz, 1H), 8.05 (s, 1H), 7.47 (s, 1H), 7.11 (d, J = 1.3 Hz, 1H), 6.51 (s, 1H), 5.30 (s, 1H), 3.54-3.45 (m, 1H), 2.53 (m, 2H), 2.45 (s, 3H), 2.15 (m, 2H), 1.77 (s, 2H). |
| 155 | (method 3) | N-((1R,3r,5S,6r)-3-(6-chloro-1H-indazol-4-yl)-3-hydroxybicyclo[3.1.0]hexan-6-yl)-1-methyl-1H-pyrazole-4-carboxamide | 394.1 [M + 23]+ | 1H NMR (400 MHz, DMSO-d6) δ 13.28 (s, 1H), 8.11 (s, 1H), 8.05 (s, 1H), 7.98 (s, 1H), 7.82 (s, 1H), 7.47 (s, 1H), 7.11 (s, 1H), 5.28 (s, 1H), 3.83 (s, 3H), 3.39 (m, 1H), 2.54 (m, 2H), 2.14 (m, 2H), 1.68 (s, 2H). |
| 156 | (method 3) | N-((1R,3r,5S,6r)-3-(6-chloro-1H-indazol-4-yl)-3-hydroxybicyclo[3.1.0]hexan-6-yl)-2-(trifluoromethyl)isonicotinamide | 437.1 | 1H NMR (400 MHz, DMSO-d6) δ 13.31 (s, 1H), 8.99 (d, J = 4.4 Hz, 1H), 8.92 (d, J = 4.9 Hz, 1H), 8.26 (s, 1H), 8.12 (d, J = 4.8 Hz, 1H), 8.07 (s, 1H), 7.48 (s, 1H), 7.13 (d, J = 1.2 Hz, 1H), 5.35 (s, 1H), 3.60-3.55 (m, 1H), 2.55 (m, 2H), 2.18 (d, J = 14.0 Hz, 2H), 1.82 (s, 2H). |

TABLE 1-continued

| Example | Structure (Synthetic Method) | Chemical Name | LC/MS [M + H]+ | 1H-NMR |
|---|---|---|---|---|
| 157 | (method 3) | N1-((1R,3r,5S,6r)-3-(6-chloro-1H-indazol-4-yl)-3-hydroxybicyclo[3.1.0]hexan-6-yl)isophthalamide | 411.1 | NA |
| 158 | (method 3) | N-((1R,3r,5S,6r)-3-(6-chloro-1H-indazol-4-yl)-3-hydroxybicyclo[3.1.0]hexan-6-yl)isoxazole-4-carboxamide | 359.2 | 1H NMR (400 MHz, CD$_3$OD) δ 8.63 (s, 1H), 8.11 (s, 1H), 7.42 (s, 1H), 7.19 (s, 1H), 3.34 (s, 1H), 2.66 (s, 1H), 2.63 (s, 1H), 2.27 (s, 1H), 2.23 (s, 1H), 1.67 (s, 2H). |
| 159 | (method 3) | N-((1R,3r,5S,6r)-3-(6-chloro-1H-indazol-4-yl)-3-hydroxybicyclo[3.1.0]hexan-6-yl)-1,2,5-oxadiazole-3-carboxamide | 360.1 | 1H NMR (400 MHz, CD$_3$OD) δ 8.11 (s, 1H), 7.43 (s, 1H), 7.19 (d, J = 1.5 Hz, 1H), 3.41 (s, 1H), 2.68 (d, J = 3.6 Hz, 1H), 2.65 (d, J = 3.5 Hz, 1H), 2.29 (s, 1H), 2.26 (s, 1H), 1.79 (s, 2H). |

TABLE 1-continued

| Example | Structure (Synthetic Method) | Chemical Name | LC/MS [M + H]+ | 1H-NMR |
|---|---|---|---|---|
| 160 | (method 9) | N'-cyclopropyl-N-((1R,3r,5S,6r)-3-(6-chloro-1H-indazol-4-yl)-3-hydroxybicyclo[3.1.0]hexan-6-yl)sulfuric diamide | 383.0 | 1H NMR (400 MHz, CD$_3$OD) δ 8.09 (s, 1H), 7.43 (s, 1H), 7.18 (d, J = 1.5 Hz, 1H), 3.10 (s, 1H), 2.64 (m, 2H), 2.23-2.15 (m, 2H), 1.86 (m, 2H), 0.90 (m, 1H), 0.73-0.60 (m, 4H). |
| 161 | (method 3) | N-((1R,3r,5S,6r)-3-(6-chloro-1H-indazol-4-yl)-3-hydroxybicyclo[3.1.0]hexan-6-yl)-2-(trifluoromethoxy)isonicotinamide | 453.0 | 1H NMR (400 MHz, CD$_3$OD) δ 8.43 (d, J = 5.1 Hz, 1H), 8.12 (s, 1H), 7.71 (dd, J = 5.1, 1.2 Hz, 1H), 7.49 (s, 1H), 7.44 (s, 1H), 7.21 (d, J = 1.4 Hz, 1H), 3.56 (s, 1H), 2.70 (m, 2H), 2.31 (m, 2H), 1.87 (s, 2H). |
| 162 | (method 3 and method 10) | N'-methyl-N-((1R,3r,5S,6r)-3-hydroxy-3-(6-(trifluoromethyl)-1H-indazol-4-yl)bicyclo[3.1.0]hexan-6-yl)sulfuric diamide | 391.1 | 1H NMR (400 MHz, DMSO-d6) δ 13.53 (s, 1H), 8.15 (s, 1H), 7.77 (s, 1H), 7.36 (s, 1H), 7.09 (d, J = 2.1 Hz, 1H), 6.72 (q, J = 5.0 Hz, 1H), 5.29 (s, 1H), 2.97 (d, J = 1.6 Hz, 1H), 2.53 (d, J = 3.3 Hz, 2H), 2.43 (s, 3H), 2.10 (d, J = 14.1 Hz, 2H), 1.70 (s, 2H). |

| Example | Structure (Synthetic Method) | Chemical Name | LC/MS [M + H]+ | 1H-NMR |
|---|---|---|---|---|
| 163 | 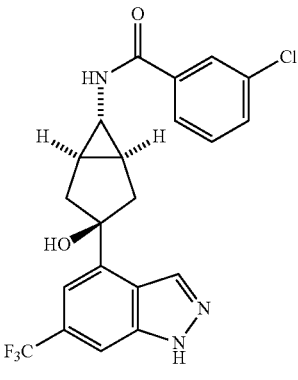<br>(method 10) | 3-chloro-N-((1R,3r,5S,6r)-3-hydroxy-3-(6-(trifluoromethyl)-1H-indazol-4-yl)bicyclo[3.1.0]hexan-6-yl)benzamide | 458.2 [M + 23]+ | 1H NMR (400 MHz, DMSO-d6) δ 13.53 (s, 1H), 8.48 (d, J = 4.4 Hz, 1H), 8.20 (s, 1H), 7.87 (d, J = 1.7 Hz, 1H), 7.80 (d, J = 7.8 Hz, 2H), 7.59 (d, J = 8.9 Hz, 1H), 7.50 (t, J = 7.9 Hz, 1H), 7.39 (s, 1H), 5.38 (s, 1H), 3.62-3.45 (m, 1H), 2.58 (m, 2H), 2.20 (d, J = 14.0 Hz, 2H), 1.78 (s, 2H). |
| 164 | 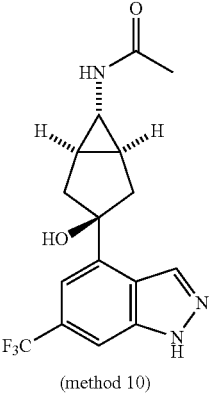 [SMILES: CC(=O)N[C@H]1[C@@H]2C[C@@](O)(c3cc(C(F)(F)F)cc4[nH]ncc34)C[C@@H]21]<br>(method 10) | N-((1R,3r,5S,6r)-3-hydroxy-3-(6-(trifluoromethyl)-1H-indazol-4-yl)bicyclo[3.1.0]hexan-6-yl)acetamide | 340.1 | 1H NMR (400 MHz, DMSO-d6) δ 13.52 (s, 1H), 8.17 (s, 1H), 7.80 (d, J = 4.4 Hz, 1H), 7.77 (s, 1H), 7.36 (s, 1H), 5.30 (s, 1H), 3.27 (d, J = 2.0 Hz, 1H), 2.54 (d, J = 3.5 Hz, 2H), 2.12 (d, J = 14.0 Hz, 2H), 1.77 (s, 3H), 1.56 (s, 2H). |
| 165 | 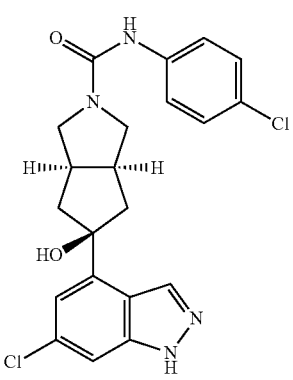<br>(method 3) | (3aR,5r,6aS)-5-(6-chloro-1H-indazol-4-yl)-N-(4-chlorophenyl)-5-hydroxyhexahydrocyclopenta[c]pyrrole-2(1H)-carboxamide | 430.096 [M + 23]+ | 1H NMR (400 MHz, CD3OD) δ 8.27 (s, 1H), 7.46 (s, 1H), 7.43 (d, J = 8.9 Hz, 2H), 7.27-7.22 (m, 2H), 7.16 (s, 1H), 3.82-3.75 (m, 2H), 3.69 (m, 2H), 3.08 (m, 2H), 2.62 (m, 2H), 2.13 (m, 2H). |

TABLE 1-continued

| Example | Structure (Synthetic Method) | Chemical Name | LC/MS [M + H]+ | 1H-NMR |
|---|---|---|---|---|
| 166 | 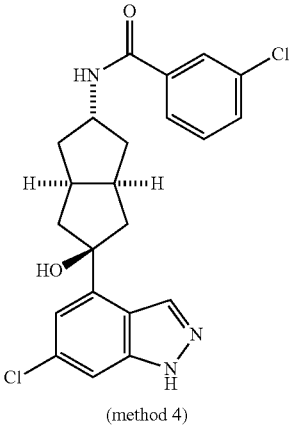 [SMILES: O=C(N[C@H]1C[C@@H]2C[C@@](O)(c3cc(Cl)cc4[nH]ncc34)C[C@@H]2C1)c1cccc(Cl)c1]<br>(method 4) | 3-chloro-N-((2r,3aR,5r,6aS)-5-(6-chloro-1H-indazol-4-yl)-5-hydroxyoctahydro-pentalen-2-yl)benzamide | 430.2 | 1H NMR (400 MHz, DMSO-d6) δ 13.11 (s, 1H), 8.34 (d, J = 7.1 Hz, 1H), 8.19 (s, 1H), 7.89 (s, 1H), 7.80 (d, J = 7.7 Hz, 1H), 7.58 (d, J = 8.1 Hz, 1H), 7.52-7.44 (m, 2H), 7.02 (s, 1H), 5.36 (s, 1H), 4.71-4.56 (m, 1H), 2.69 (s, 2H), 2.45 (m, 2H), 1.84 (m, 6H). |
| 167 | 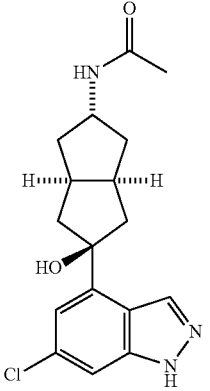<br>(method 4) | N-((2r,3aR,5r,6aS)-5-(6-chloro-1H-indazol-4-yl)-5-hydroxyoctahydro-pentalen-2-yl)acetamide | 356.1 [M + 23]+ | 1H NMR (400 MHz, DMSO-d6) δ 13.10 (s, 1H), 8.16 (s, 1H), 7.71 (d, J = 7.3 Hz, 1H), 7.46 (s, 1H), 6.99 (d, J = 1.3 Hz, 1H), 5.31 (s, 1H), 4.41-4.28 (m, 1H), 2.61 (s, 2H), 2.42 (dd, J = 13.2, 8.4 Hz, 2H), 1.87-1.73 (m, 7H), 1.68-1.52 (m, 2H). |
| 168 | 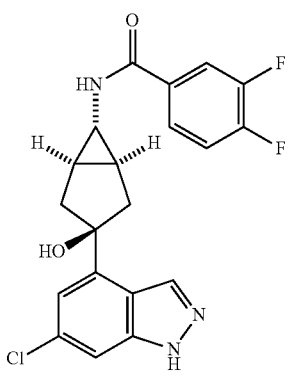<br>(method 3) | N-((1R,3r,5S,6r)-3-(6-chloro-1H-indazol-4-yl)-3-hydroxybicyclo[3.1.0]hexan-6-yl)-3,4-difluorobenzamide | 404.1 | 1H NMR (400 MHz, DMSO-d6) δ 13.19 (s, 1H), 8.45 (d, J = 4.2 Hz, 1H), 8.07 (s, 1H), 7.87 (dd, J = 10.8, 8.6 Hz, 1H), 7.72 (s, 1H), 7.54 (dd, J = 18.8, 8.4 Hz, 1H), 7.47 (s, 1H), 7.12 (s, 1H), 5.30 (s, 1H), 3.50 (s, 1H), 2.54 (m, 2H), 2.16 (d, J = 14.2 Hz, 2H), 1.75 (s, 2H). |

| Example | Structure (Synthetic Method) | Chemical Name | LC/MS [M + H]+ | 1H-NMR |
|---|---|---|---|---|
| 169 | 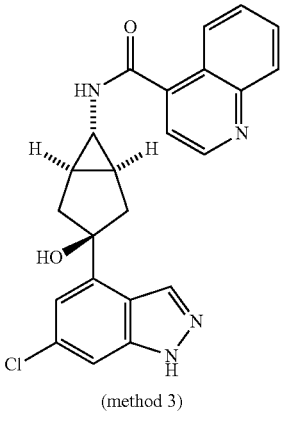 [SMILES: O=C(N[C@H]1[C@@H]2C[C@@](O)(c3cc(Cl)cc4[nH]ncc34)C[C@@H]21)c1ccnc2ccccc12] (method 3) | N-((1R,3r,5S,6r)-3-(6-chloro-1H-indazol-4-yl)-3-hydroxybicyclo[3.1.0]hexan-6-yl)quinoline-4-carboxamide | 419.1 | 1H NMR (400 MHz, DMSO-d6) δ 13.24 (s, 1H), 8.96 (d, J = 4.3 Hz, 1H), 8.75 (d, J = 4.2 Hz, 1H), 8.14 (d, J = 8.0 Hz, 1H), 8.08 (d, J = 7.4 Hz, 2H), 7.81 (t, J = 7.1 Hz, 1H), 7.68 (t, J = 7.1 Hz, 1H), 7.53 (d, J = 4.3 Hz, 1H), 7.48 (s, 1H), 7.15 (d, J = 1.3 Hz, 1H), 5.35 (s, 1H), 3.67-3.60 (m, 1H), 2.58 (m, 2H), 2.21 (d, J = 14.0 Hz, 2H), 1.78 (s, 2H). |
| 170 | 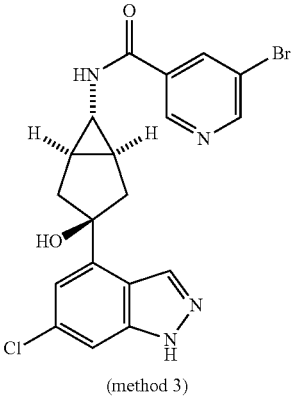 [SMILES: O=C(N[C@H]1[C@@H]2C[C@@](O)(c3cc(Cl)cc4[nH]ncc34)C[C@@H]21)c1cncc(Br)c1] (method 3) | 5-bromo-N-((1R,3r,5S,6r)-3-(6-chloro-1H-indazol-4-yl)-3-hydroxybicyclo[3.1.0]hexan-6-yl)nicotinamide | 449.0 | 1H NMR (400 MHz, DMSO-d6) δ 13.32 (s, 1H), 8.97 (s, 1H), 8.84 (d, J = 2.1 Hz, 1H), 8.73 (s, 1H), 8.43 (s, 1H), 8.06 (s, 1H), 7.48 (s, 1H), 7.12 (d, J = 1.5 Hz, 1H), 5.33 (s, 1H), 3.55 (d, J = 2.1 Hz, 1H), 2.54 (m, 2H), 2.17 (d, J = 14.4 Hz, 2H), 1.78 (s, 2H). |
| 171 | 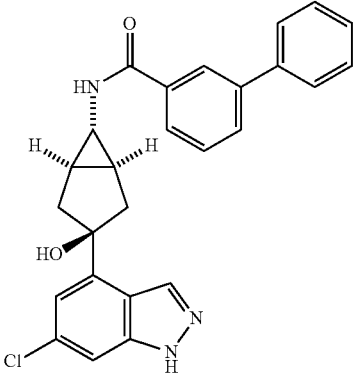 (method 3) | N-((1R,3r,5S,6r)-3-(6-chloro-1H-indazol-4-yl)-3-hydroxybicyclo[3.1.0]hexan-6-yl)-[1,1'-biphenyl]-3-carboxamide | 466.2 [M + 23]+ | 1H NMR (400 MHz, DMSO-d6) δ 13.28 (s, 1H), 8.51 (d, J = 3.7 Hz, 1H), 8.09 (d, J = 14.4 Hz, 2H), 7.85-7.78 (m, 2H), 7.74 (d, J = 7.5 Hz, 2H), 7.58-7.47 (m, 4H), 7.40 (t, J = 7.3 Hz, 1H), 7.14 (s, 1H), 5.32 (s, 1H), 3.54 (s, 1H), 2.56 (m, 2H), 2.19 (d, J = 13.9 Hz, 2H), 1.79 (s, 2H). |

TABLE 1-continued

| Example | Structure (Synthetic Method) | Chemical Name | LC/MS [M + H]+ | 1H-NMR |
|---|---|---|---|---|
| 172 | 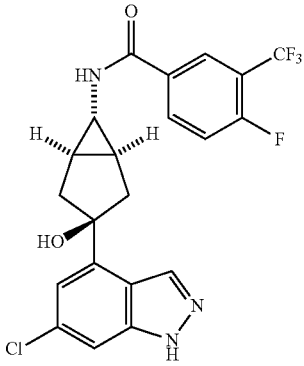 (method 3) | N-((1R,3r,5S,6r)-3-(6-chloro-1H-indazol-4-yl)-3-hydroxybicyclo[3.1.0]hexan-6-yl)-4-fluoro-3-(trifluoromethyl)benzamide | 454.0 | 1H NMR (400 MHz, DMSO-d6) δ 13.19 (s, 1H), 8.63 (d, J = 4.3 Hz, 1H), 8.22 (t, J = 6.3 Hz, 2H), 8.07 (s, 1H), 7.63 (t, J = 9.6 Hz, 1H), 7.47 (s, 1H), 7.13 (s, 1H), 5.31 (s, 1H), 3.53 (d, J = 2.0 Hz, 1H), 2.55 (m, 2H), 2.18 (d, J = 14.0 Hz, 2H), 1.77 (s, 2H). |
| 173 | 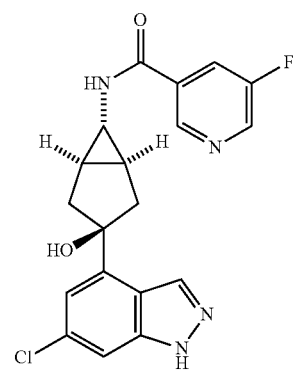 (method 3) | N-((1R,3r,5S,6r)-3-(6-chloro-1H-indazol-4-yl)-3-hydroxybicyclo[3.1.0]hexan-6-yl)-5-fluoronicotinamide | 387.1 | 1H NMR (400 MHz, DMSO-d6) δ 13.19 (s, 1H), 8.86 (s, 1H), 8.73 (d, J = 2.7 Hz, 1H), 8.63 (d, J = 4.3 Hz, 1H), 8.10-8.01 (m, 2H), 7.47 (s, 1H), 7.13 (d, J = 1.4 Hz, 1H), 5.32 (s, 1H), 3.60-3.48 (m, 1H), 2.60-2.51 (m, 2H), 2.17 (d, J = 14.0 Hz, 2H), 1.77 (s, 2H). |
| 174 | 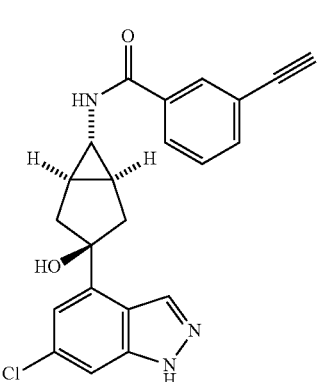 (method 3) | N-((1R,3r,5S,6r)-3-(6-chloro-1H-indazol-4-yl)-3-hydroxybicyclo[3.1.0]hexan-6-yl)-3-ethynylbenzamide | 392.1 | 1H NMR (400 MHz, DMSO-d6) δ 13.19 (s, 1H), 8.45 (d, 1H), 8.07 (s, 1H), 7.93 (s, 1H), 7.86 (d, J = 7.9 Hz, 1H), 7.61 (d, J = 7.7 Hz, 1H), 7.48 (m, 2H), 7.13 (d, J = 1.3 Hz, 1H), 5.30 (s, 1H), 4.27 (s, 1H), 3.55-3.49 (m, 1H), 2.54 (m, 1H), 2.17 (d, J = 14.0 Hz, 2H), 1.75 (s, 2H). |

TABLE 1-continued

| Example | Structure (Synthetic Method) | Chemical Name | LC/MS [M + H]+ | 1H-NMR |
|---|---|---|---|---|
| 175 | (method 3) | 1-((3aR,5r,6aS)-5-(6-chloro-1H-indazol-4-yl)-5-hydroxyhexahydrocyclopenta[c]pyrrol-2(1H)-yl)-2-(4-chlorophenyl)ethanone | 430.1 | 1H NMR (400 MHz, DMSO-d6) δ 13.15 (s, 1H), 8.21 (s, 1H), 7.47 (s, 1H), 7.36 (d, J = 8.3 Hz, 2H), 7.27 (d, J = 8.4 Hz, 2H), 7.09 (s, 1H), 5.36 (s, 1H), 3.82 (t, J = 9.7 Hz, 1H), 3.74-3.56 (m, 4H), 3.50 (dd, J = 11.9, 5.3 Hz, 1H), 3.10-2.85 (m, 2H), 2.47-2.37 (m, 2H), 2.05-1.90 (m, 2H). |
| 176 | (method 3) | 3-bromo-N-((1R,3r,5S,6r)-3-(6-chloro-1H-indazol-4-yl)-3-hydroxybicyclo[3.1.0]hexan-6-yl)-4-fluorobenzamide | 466.0 | 1H NMR (400 MHz, DMSO-d6) δ 13.19 (s, 1H), 8.48 (d, J = 4.1 Hz, 1H), 8.17 (d, J = 5.0 Hz, 1H), 8.07 (s, 1H), 7.95-7.86 (m, 1H), 7.47 m, 2H), 7.13 (s, 1H), 5.30 (s, 1H), 3.51 (s, 1H), 2.54 (m, 2H), 2.17 (d, J = 14.0 Hz, 1H), 1.75 (s, 2H). |
| 177 | (method 3) | N-((1R,3r,5S,6r)-3-(6-chloro-1H-indazol-4-yl)-3-hydroxybicyclo[3.1.0]hexan-6-yl)-6-fluoroquinoline-4-carboxamide | 437.1 | 1H NMR (400 MHz, DMSO-d6) δ 13.21 (s, 1H), 8.97 (d, J = 4.3 Hz, 1H), 8.79 (d, J = 4.5 Hz, 1H), 8.16 (dd, J = 9.2, 5.7 Hz, 1H), 8.09 (s, 1H), 7.90 (dd, J = 10.3, 2.7 Hz, 1H), 7.79-7.72 (m, 1H), 7.62 (d, J = 4.3 Hz, 1H), 7.48 (s, 1H), 7.15 (s, 1H), 5.35 (s, 1H), 3.64 (s, 1H), 2.57 (m, 2H), 2.22 (d, J = 14.0 Hz, 1H), 1.80 (s, 2H). |

TABLE 1-continued

| Example | Structure (Synthetic Method) | Chemical Name | LC/MS [M + H]+ | 1H-NMR |
|---|---|---|---|---|
| 178 | (method 3) | N-((1R,3r,5S,6r)-3-(6-chloro-1H-indazol-4-yl)-3-hydroxybicyclo[3.1.0]hexan-6-yl)-3-cyclopropylbenzamide | 430.2 [M + 23]+ | 1H NMR (400 MHz, DMSO-d6) δ 13.19 (s, 1H), 8.29 (d, J = 4.2 Hz, 1H), 8.06 (s, 1H), 7.58 (d, J = 7.6 Hz, 1H), 7.48 (d, J = 8.9 Hz, 2H), 7.31 (t, J = 7.6 Hz, 1H), 7.22 (d, J = 7.6 Hz, 1H), 7.13 (s, 1H), 5.29 (s, 1H), 3.48 (dd, J = 2.6, 0.8 Hz, 1H), 2.61-2.51 (m, 2H), 2.16 (d, J = 14.0 Hz, 2H), 2.03-1.90 (m, 1H), 1.74 (s, 2H), 1.01-0.93 (m, 2H), 0.75-0.68 (m, 2H). |
| 179 | (method 3) | 5-chloro-N-((1R,3r,5S,6r)-3-(6-chloro-1H-indazol-4-yl)-3-hydroxybicyclo[3.1.0]hexan-6-yl)nicotinamide | 403.1 | 1H NMR (400 MHz, DMSO-d6) δ 13.19 (s, 1H), 8.92 (d, J = 1.7 Hz, 1H), 8.77 (d, J = 2.3 Hz, 1H), 8.64 (d, J = 4.5 Hz, 1H), 8.27 (t, J = 2.1 Hz, 1H), 8.07 (s, 1H), 7.47 (s, 1H), 7.13 (d, J = 1.2 Hz, 1H), 5.32 (s, 1H), 3.57-3.53 (m, 1H), 2.56 (m, 2H), 2.18 (d, J = 14.0 Hz, 2H), 1.77 (s, 2H). |
| 180 | (method 3) | N-((1R,3r,5S,6r)-3-(6-chloro-1H-indazol-4-yl)-3-hydroxybicyclo[3.1.0]hexan-6-yl)-4-fluoro-3-(trifluoromethoxy)benzamide | 470.2 | 1H NMR (400 MHz, DMSO-d6) δ 13.20 (s, 1H), 8.56 (d, J = 4.1 Hz, 1H), 8.07 (s, 1H), 8.02-7.94 (m, 2H), 7.67-7.59 (m, 1H), 7.47 (s, 1H), 7.13 (s, 1H), 5.31 (s, 1H), 3.51 (s, 1H), 2.54 (m, 2H), 2.17 (d, J = 14.0 Hz, 2H), 1.76 (s, 2H). |

TABLE 1-continued

| Example | Structure (Synthetic Method) | Chemical Name | LC/MS [M + H]+ | 1H-NMR |
|---|---|---|---|---|
| 181 | (method 3) | N-((1R,3r,5S,6r)-3-(6-chloro-1H-indazol-4-yl)-3-hydroxybicyclo[3.1.0]hexan-6-yl)-5-cyanonicotinamide | 394.1 | 1H NMR (400 MHz, DMSO-d6) δ 13.19 (s, 1H), 9.20 (d, J = 2.0 Hz, 1H), 9.15 (d, J = 1.9 Hz, 1H), 8.70 (d, J = 4.5 Hz, 1H), 8.63 (t, J = 2.0 Hz, 1H), 8.08 (s, 1H), 7.47 (s, 1H), 7.13 (d, J = 1.2 Hz, 1H), 5.33 (s, 1H), 3.61-3.53 (m, 1H), 2.55 (m, 2H), 2.18 (d, J = 14.0 Hz, 2H), 1.77 (s, 2H). |
| 182 | (method 3) | N-((1R,3r,5S,6r)-3-(6-chloro-1H-indazol-4-yl)-3-hydroxybicyclo[3.1.0]hexan-6-yl)-5-(trifluoromethyl)nicotinamide | 437.1 | 1H NMR (400 MHz, DMSO-d6) δ 13.20 (s, 1H), 9.26 (d, J = 1.4 Hz, 1H), 9.11 (s, 1H), 8.79 (d, J = 4.4 Hz, 1H), 8.54 (s, 1H), 8.10 (d, J = 20.4 Hz, 1H), 7.47 (s, 1H), 7.15 (t, J = 10.6 Hz, 1H), 5.34 (s, 1H), 3.60-3.54 (m, 1H), 2.54 (m, 2H), 2.19 (d, J = 14.0 Hz, 1H), 1.79 (s, 2H). |
| 183 | (method 6) | Racemic-N-((1S,5R,6S)-3-(6-chloro-1H-indazol-4-yl)bicyclo[3.1.0]hex-2-en-6-yl)cyclopropanecarboxamide | 314.2 | 1H NMR (400 MHz, DMSo-d6) δ 13.24 (s, 1H), 8.31 (s, 2H), 7.46 (s, 1H), 6.97 (s, 1H), 6.77 (s, 1H), 2.23 (s, 1H), 2.10 (s, 1H), 1.90 (m, 1H), 1.46 (m, 2H), 0.83 (m, 1H), 0.69-0.57 (m, 4H). |

Example 184

Preparation of N-(((1R,3r,5S,6s)-3-(6-chloro-1H-indazol-4-yl)-3-azabicyclo[3.1.0]hexan-6-ol

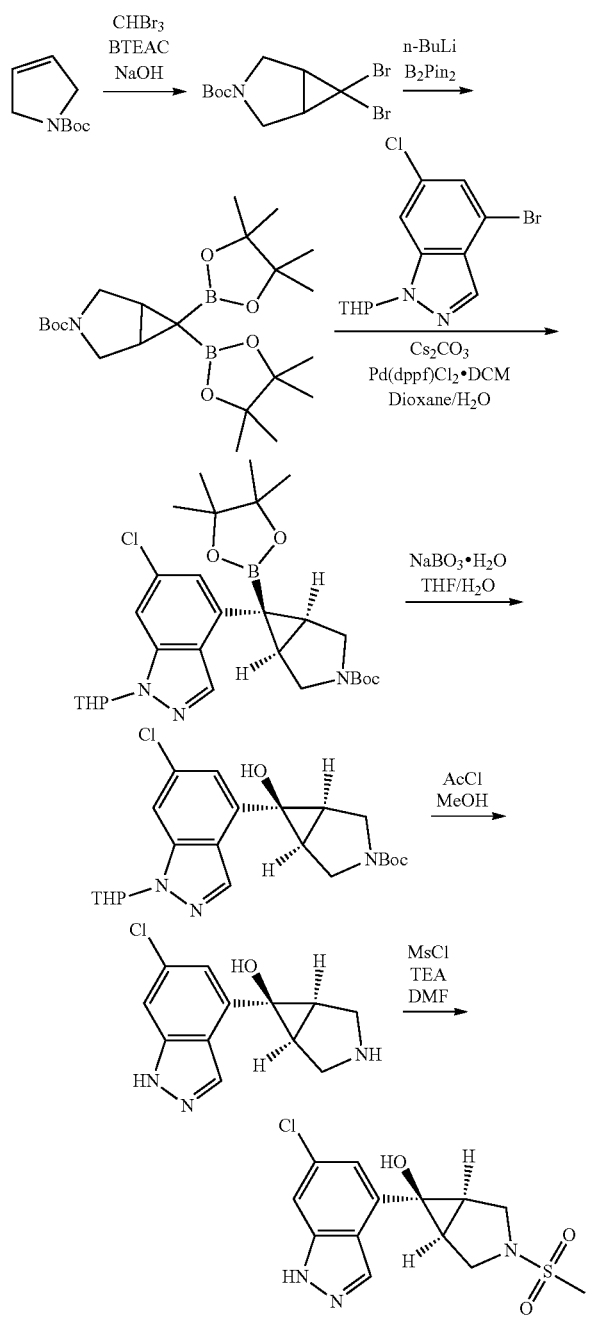

Step 1. tert-Butyl 6,6-dibromo-3-azabicyclo[3.1.0]hexane-3-carboxylate

To a solution of tert-butyl 2,5-dihydro-1H-pyrrole-1-carboxylate (10.0 g, 59.1 mmol), BTEAC (471 mg, 2.07 mmol) in DCM (50 mL) and EtOH (1.0 mL) was added 50% aqueous NaOH (50 mL) slowly, maintaining temperature at 40-50° C. After the addition was complete, the mixture was stirred at 45° C. for 18 h. After cooled to rt, it was diluted with water (100 mL) and DCM (100 mL), and the mixture was filtered through Celite. The filtrate was separated, and the organic layer was dried over anhydrous $Na_2SO_4$, filtered off, and concentrated in vacuo. The residue was purified by silica gel flash column chromatography (PE:EtOAc=10:1) to give the title compound (7.09 g, yield: 35%).

Step 2. tert-Butyl 6,6-bis(4,4,5,5-tetramethyl-1,3,2-dioxaborolan-2-yl)-3-azabicyclo[3.1.0]hexane-3-carboxylate To a solution of product from Step 1 above (3.41 g, 10.0 mmol) and $B_2Pin_2$ (2.54 g, 10.0 mmol) in THF (100 mL) pre-cooled to −78° C. was added n-BuLi (2.5 N in hexane, 4.8 mL, 12 mmol) slowly maintaining internal temperature below −78° C. After the addition was complete, the mixture was stirred at −78° C. for 1 h and allowed to warm to rt and stirred for 2 h. The reaction was quenched with water (100 mL) and extracted with EtOAc (100 mL×2). The combined organic layers were dried over anhydrous $Na_2SO_4$, filtered off, and concentrated in vacuo. The residue was purified by silica gel flash column chromatography (PE:EtOAc=4:1) to give the title compound (2.47 g, yield: 56%).

Step 3. (1R,5S,6r)-tert-butyl 6-(6-chloro-1-(tetrahydro-2H-pyran-2-yl)-1H-indazol-4-yl)-6-(4,4,5,5-tetramethyl-1,3,2-dioxaborolan-2-yl)-3-azabicyclo[3.1.0]hexane-3-carboxylate To a 20 mL of capped vial was added sequentially the product of Step 2 above (1.0 g, 2.3 mmol), 4-bromo-6-chloro-1-(tetrahydro-2H-pyran-2-yl)-1H-indazole (798 mg, 2.53 mmol), $Cs_2CO_3$ (2.25 g, 2.025 mmol), Pd(dppf)Cl$_2$CH$_2$Cl$_2$ (94 mg, 0.115 mmol), dioxane (10 mL), and $H_2O$ (1 mL) The vial was flushed with nitrogen, stirred at 100° C. for 12 h. After cooling to rt, the reaction was diluted with EtOAc (60 mL). The mixture was transferred to a separatory funnel, washed with $H_2O$ (50 mL×2) and brine (50 mL), dried over anhydrous $Na_2SO_4$, filtered off, and concentrated in vacuo. The residue obtained was purified by silica gel flash column chromatography (PE:EtOAc=20:1 to 3:1) to give the title compound (680 mg, yield: 54%).

Step 4. (1R,5S,6r)-tert-butyl 6-(6-chloro-1-(tetrahydro-2H-pyran-2-yl)-1H-indazol-4-yl)-6-hydroxy-3-azabicyclo[3.1.0]hexane-3-carboxylate To a solution of the product of Step 3 above (630 mg, 1.158 mmol) in THF/$H_2O$ (5 mL/5 mL) was added NaBO$_3$.H$_2$O (347 mg, 3.47 mmol) at rt. The reaction mixture was stirred at rt for 18 h before diluting with DCM/MeOH (10:1, 50 mL) The mixture was transferred to a separatory funnel, washed with $H_2O$ (30 mL×2), brine (30 mL), dried over anhydrous $Na_2SO_4$, filtered off, and concentrated in vacuo. The residue was purified by silica gel flash column chromatography (DCM/MeOH=10:1 to 50:1) to give the title compound (260 mg, yield: 48%).

Step 5. (1R,5S,6r)-6-(6-chloro-1H-indazol-4-yl)-3-azabicyclo[3.1.0]hexan-6-ol hydrochloride To a solution of the product of Step 4 above (260 mg, 0.599 mmol) in MeOH (5 mL) in an ice-water bath was added acetyl chloride (393 mg, 5 mmol) dropwise. The reaction mixture was stirred at rt for 2 h and concentrated in vacuo to give the crude title compound (125 mg, 83% yield).

Step 6. (1R,5S,6r)-6-(6-chloro-1H-indazol-4-yl)-3-(methylsulfonyl)-3-azabicyclo[3.1.0]hexan-6-ol To a solution of the product of Step 5 above (75 mg, 0.3 mmol) and TEA (1 mL) in DMF (1 mL) cooled in an ice-water bath was added MsCl (24 mg, 0.3 mmol). After the addition was complete, the mixture was allowed to warm to rt and stirred for 4 h. The mixture was concentrated and the residue was taken up in DCM/i-PrOH (3:1, 40 mL), washed with water (20 mL), dried over anhydrous Na$_2$SO$_4$, filtered off, and concentrated in vacuo. The residue was purified by prep-TLC (silica gel, DCM/MeOH=15:1) to give the title compound (23 mg, yield: 24%). MS (ESI) m/z: 331.8 [M+1]$^+$; $^1$H NMR (400 MHz, DMSO-d$_6$) δ 13.19 (s, 1H), 8.17 (s, 1H), 7.46 (s, 1H), 6.98 (d, J=1.5 Hz, 1H), 6.52 (s, 1H), 3.73-3.62 (m, 2H), 3.48 (d, J=9.9 Hz, 2H), 2.84 (s, 3H), 2.42-2.36 (m, 2H).

Example 185

Preparation of N-(((1R,3r,5S,6s)-3-(6-chloro-1H-indazol-4-yl)-3-hydroxybicyclo[3.1.0]hexan-6-yl)methyl)acetamide

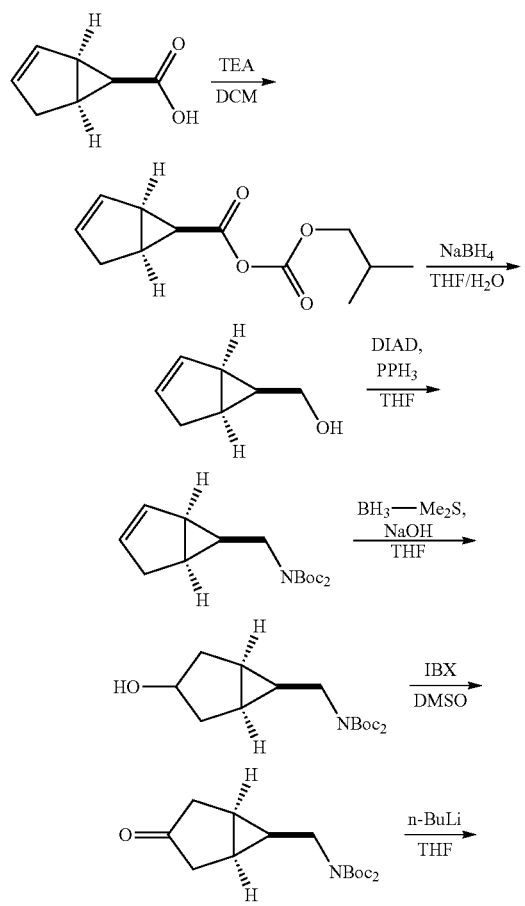

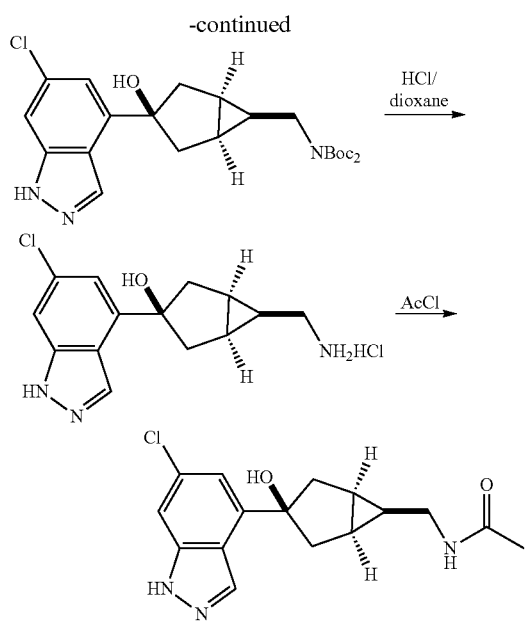

Step 1. (1R,5S,6S)-bicyclo[3.1.0]hex-2-ene-6-carboxylic (isobutyl carbonic) anhydride To a solution of (1R,5S,6S)-bicyclo[3.1.0]hex-2-ene-6-carboxylic acid (5.0 g, 40.3 mmol) and TEA (8.14 g, 80.6 mmol) in DCM (60 mL) was added isobutyl chloroformate (6.03 g, 44.3 mmol) at 0° C. The reaction was stirred for 2 h while temperature was gradually warmed to rt. The reaction was diluted with DCM (200 mL) and the organic layer was separated, washed with H$_2$O (200 mL) and brine (200 mL), dried over anhydrous Na$_2$SO$_4$, filtered off, and concentrated in vacuo to give the title compound (8.9 g, yield: 99%).

Step 2. (1R,5S,6S)-bicyclo[3.1.0]hex-2-en-6-yl-methanol

To a solution of the product of Step 1 above (8.9 g, 39.9 mmol) in THF (90 mL) and H$_2$O (9 mL) was added NaBH$_4$ (15 g, 394 mmol) in several portions at 0° C. The reaction was stirred at rt overnight. The reaction mixture was diluted with EtOAc (400 mL), which was washed with H$_2$O (100 mL) and brine (100 mL), dried over anhydrous Na$_2$SO$_4$, filtered off, and concentrated in vacuo. The residue was purified by silica gel flash column chromatography (PE:EtOAc=8:1 to 4:1) to give the title compound (3.06 g, yield: 70%).

Step 3. N,N-bis-Boc-(1R,5S,6S)-bicyclo[3.1.0]hex-2-en-6-ylmethanamine

To a solution of the product of Step 2 above (5.76 g, 26.5 mmol) and PPh$_3$ (6.94 g, 26.5 mmol) in THF (50 mL) cooled in an ice-water bath under N$_2$ was added DIAD (5.35 g, 26.5 mmol). The mixture was stirred at rt overnight before diluting with EtOAc (200 mL) The mixture was transferred to a separatory funnel, washed with water (50 mL) and brine (50 mL), dried over anhydrous Na$_2$SO$_4$, filtered off, and concentrated in vacuo. The residue was purified by silica gel flash column chromatography (PE:EtOAc=60:1 to 30:1) to give the title compound (3.2 g, yield: 43%).

Step 4. (1R,5S,6s)-6-((bis-Boc-amino)methyl)bicyclo[3.1.0]hexan-3-ol

To a solution of the product of Step 3 above (3.3 g, 10.7 mmol) in THF (30 mL) was added slowly BH$_3$—Me$_2$S (2.0 M, 6 mL) at 0° C. After stirring at rt for 1.5 h, H$_2$O (15 mL) NaOH (12 mL, 2.5M) and H$_2$O$_2$ (3.5 mL, 30%) were added to the reaction mixture slowly at 0° C. The mixture was stirred at rt for 3 h before diluting with EtOAc (250 mL). The mixture was transferred to a separatory funnel, washed by brine (30 mL), dried over anhydrous Na$_2$SO$_4$, and concentrated in vacuo. The residue was purified by silica gel flash column chromatography (PE:EtOAc=10:1) to give the title compound (3.79 g, yield: 100%).

Step 5. (1R,5S,6s)-6-(bis-Boc-aminomethyl)bicyclo[3.1.0]hexan-3-one

To a solution of the product of Step 4 above (3.5 g, 10.7 mmol) in DMSO (35 mL) was added 2-iodoxybenzoic acid (4.5 g, 16.1 mmol) at rt. The reaction was stirred at 50° C. overnight. EtOA (300 mL) and water (100 mL) were added to the reaction mixture, the insoluble materials were filtered off. The filtrate was washed with water (3×50 mL) and brine (30 mL), dried over anhydrous Na$_2$SO$_4$ and concentrated in vacuo. The residue was purified by silica gel flash column chromatography (PE:EtOAc=20:1) to give the title compound (2.3 g, yield: 66%).

Step 6. (1R,3r,5S,6s)-6-(bis-Boc-aminomethyl)-3-(6-chloro-1H-indazol-4-yl) bicyclo[3.1.0]hexan-3-ol To a solution of 4-bromo-6-chloro-1H-indazole (855 mg, 3.69 mmol) in THF (18 mL) was added slowly n-BuLi (2.5 N in hexane, 4.87 mL, 12.2 mmol) at −78° C. under N$_2$. After stirring at −78° C. for 0.5 h, the product of Step 5 above (1.2 g, 3.69 mmol) in THF (8 mL) was added slowly at −78° C. The resulting mixture was stirred at −78° C. for 1 h, quenched with saturated NH$_4$Cl (10 mL), extracted by EtOAc (120 mL), washed by water (20 mL) and brine (20 mL), dried over anhydrous Na$_2$SO$_4$, and concentrated in vacuo. The residue was purified by silica gel flash column chromatography (PE:EtOAc=6:1 to 2:1) to give the title compound (350 mg, yield: 20%).

Step 7. (1R,3r,5S,6s)-6-(aminomethyl)-3-(6-chloro-1H-indazol-4-yl)bicyclo[3.1.0]hexan-3-ol hydrochloride The product of Step 6 above (340 mg, 0.71 mmol) was added to HCl in MeOH (6 mL, 4 M) at 0° C. The reaction was stirred at rt for 3 h and concentrated in vacuo to give the crude title compound (224 mg, yield: 100%).

Step 8. N-(((1R,3r,5S,6s)-3-(6-chloro-1H-indazol-4-yl)-3-hydroxybicyclo[3.1.0]hexan-6-yl) methyl)acetamide To a solution of the product of Step 7 above (50 mg, 0.159 mmol) and TEA (96 mg, 0.954 mmol) in DMF (1 mL) was added AcCl (38 mg, 0.28 mmol) at 0° C. The mixture was stirred at rt overnight before concentrated in vacuo. The residue was purified by prep-TLC (silica gel, DCM:MeOH=10:1) to give the title compound (24 mg, yield: 47%). MS (ESI) m/z: 320.3 [M+1]$^+$; $^1$H NMR (400 MHz, CD$_3$OD) δ 8.27 (d, J=0.7 Hz, 1H), 7.44 (s, 1H), 7.19 (d, J=1.6 Hz, 1H), 3.60 (d, J=7.7 Hz, 2H), 2.59-2.49 (m, 2H), 1.98 (s, 3H), 1.96 (s, 1H), 1.93 (s, 1H), 1.72-1.64 (m, 2H), 1.27 (t, J=7.8 Hz, 1H).

Example 186

Preparation of N-(((1R,3r,5S,6s)-3-(6-chloro-1H-indazol-4-yl)-3-hydroxybicyclo[3.1.0]hexan-6-yl) methyl)methanesulfonamide

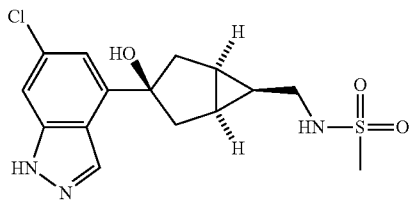 [SMILES: CS(=O)(=O)NC[C@H]1[C@H]2C[C@](O)(c3cc(Cl)cc4[nH]ncc34)C[C@@H]12]

The compound was prepared according to the same method of Example 185, replacing acetyl chloride by methanesulfonyl chloride in Step 8. MS (ESI) m/z: 356.2 [M+1]$^+$; $^1$H NMR (400 MHz, CD$_3$OD) δ 8.27 (d, J=0.6 Hz, 1H), 7.44 (s, 1H), 7.19 (d, J=1.6 Hz, 1H), 3.54 (d, J=7.5 Hz, 2H), 3.02 (s, 3H), 2.62-2.52 (m, 2H), 1.98 (d, J=15.2 Hz, 2H), 1.75 (dd, J=9.1, 4.4 Hz, 2H), 1.33-1.28 (m, 1H).

TDO2 Enzymatic Assay

The TDO2 biochemical inhibitory activity is determined by measuring the decrease in N'-formylkynurenine from tryptophan catalyzed by TDO2 enzyme. Recombinant human TDO2 (200 nM), L-tryptophan (300 μM), L-ascorbic acid (20 mM), methylene Blue (20 μM), catalase (0.2 mg/mL), and serial dilutions of the test compounds in a total volume of 2 μL containing DMSO (with final DMSO concentration of 0.5%) and a pH 7.5 buffer containing potassium phosphate (50 mM) were added into each well in a 96-well plate. After incubation at room temperature for 40 min, the absorbance of the reaction mixture was read at 321 nm to measure the formation of N'-formylkynurenine by SpectraMax microplate reader. Percent inhibition of the test compounds was determined by measuring the decrease in N'-formylkynurenine as compared to the control of DMSO vehicle, which was calculated by formula of (WC-WT)/WC, where WC is the mean absorbance of the control well minus blank well; WT is the mean absorbance of the test well minus the blank well. Data was analyzed by GraphPad Prism 5 and the IC$_{50}$ values were obtained by non-linear regression.

The IC$_{50}$ values of TDO2 biochemical activity for the examples disclosed herein are listed in Table 2, A: ≤0.1 μM; B: >0.10 μM and ≤0.5 μM; C: >0.5 μM and ≤1.0 μM; and D: >1.0 μM.

IDO1 Enzymatic Assay

The IDO1 biochemical inhibitory activity is determined by measuring the decrease in N'-formylkynurenine from tryptophan catalyzed by IDO1 enzyme. Recombinant human IDO1 (40 nM), L-tryptophan (100 μM), L-ascorbic acid (20 mM), methylene Blue (20 μM), catalase (0.2 mg/mL), and serial dilutions of the test compounds in a total volume of 2 μL containing DMSO (with final DMSO concentration of 0.5%) and a pH 7.5 buffer containing potassium phosphate (50 mM) were added into each well in a 96-well plate. After incubation at room temperature for 40 min, the absorbance of the reaction mixture was read at 321 nm to measure the formation of N'-formylkynurenine by SpectraMax microplate reader. Percent inhibition of the test compounds was determined by measuring the decrease in N'-formylkynurenine as compared to the control of DMSO vehicle, which was calculated by formula of (WC−WT)/WC, where WC is the mean absorbance of the control well minus blank well; WT is the mean absorbance of the test well minus the blank well. Data was analyzed by GraphPad Prism 5 and the $IC_{50}$ values were obtained by non-linear regression.

The $IC_{50}$ values of IDO1 biochemical activity for the examples disclosed herein are listed in Table 2, A: ≤0.1 µM; B: >0.10 µM and ≤0.5 µM; C: >0.5 µM and ≤1.0 µM; and D: >1.0 µM.

TDO2 Cellular Assay

A172 cancer cells ($3\times10^4$ per well) in 85 µL DMEM medium containing 10% FBS were seeded in a 96-well plate and incubated at 95% humidity and 5% $CO_2$ at 37° C. for overnight. On the next day, L-Trp solution (10 µL, 1 mM final concentration) and serial dilutions of the test compounds and DMEM medium resulting in a total final volume of 100 µL each well. The test compounds were dissolved in DMSO and successively diluted with pH7.5 butter (with final DMSO concentration of 0.25%) resulting in final concentrations of the test compounds ranging from 0 to 25 µM (0, 2.5, 7.5, 25, 75, 250, 750, 2500, 7500, & 25000 nM). After 24 hours of incubation, 70 uL of the supernatant per well was transferred to a new 96 well plate. 8 µL of trichloroacetic acid (6.1 N) was mixed into each well and incubated at 50° C. for 30 min to hydrolyze N-formylkynurenine to kynurenine. The reaction mixture was then centrifuged for 10 min at 2500 RPM to remove sediments. 50 µL of the supernatant per well was transferred to another 96 well plate and mixed with 50 µL of 2% (w/v) p-dimethylaminobenzaldehyde in acetic acid. The yellow color derived from kynurenine was measured at 490 nm using a microplate reader. Percent inhibition of the test compounds was determined by measuring the decrease in kynurenine as compared to the control of DMSO vehicle, which was calculated by formula of (WC−WT)/WC, where WC is the mean absorbance of the control well minus blank well; WT is the mean absorbance of the test well minus the blank well. Data was analyzed by GraphPad Prism 5 and the $IC_{50}$ values were obtained by non-linear regression.

The $IC_{50}$ values of for Compounds disclosed are listed in Table 2, A': ≤0.5 µM; B': >0.5 µM and ≤1 µM; C': >1.0 µM and ≤5 uM; and D': >5 µM.

IDO1 Cellular Assay

Hela cancer cells ($5\times10^3$ per well) with 85 µL DMEM medium containing 10% FBS were seeded in a 96-well plate and incubated at 95% humidity and 5% $CO_2$ at 37° C. for 24 hours. human IFN-γ (10 µL, 50 ng/mL final concentration) and 5 µL serial dilutions of the test compounds were added into each well. The test compounds were dissolved in DMSO, and successively diluted with pH7.5 buffer (with final DMSO concentration of 0.25%) resulting in final concentrations of the test compounds ranging from 0 to 25 µM (0, 2.5, 7.5, 25, 75, 250, 750, 2500, 7500, & 25000 nM). After 48 hours of incubation, 70 uL of the supernatant per well was transferred to a new 96 well plate. Trichloroacetic acid (6.1 N, 8 µL) was mixed into each well and incubated at 50° C. for 30 min to hydrolyze N-formylkynurenine produced by IDO to kynurenine. The reaction mixture was then centrifuged for 10 min at 2500 RPM to remove sediments. 50 µL of the supernatant per well was transferred to another 96 well plate and mixed with 50 uL of 2% (w/v) p-dimethylaminobenzaldehyde in acetic acid. The yellow color derived from kynurenine was measured at 490 nm using a microplate reader. Percent inhibition of the test compounds was determined by measuring the decrease in kynurenine as compared to the control of DMSO vehicle, which was calculated by formula of (WC-WT)/WC, where WC is the mean absorbance of the control well minus blank well; WT is the mean absorbance of the test well minus the blank well. Data was analyzed by GraphPad Prism 5 and the $IC_{50}$ values were obtained by non-linear regression.

The $IC_{50}$ values of for Compounds disclosed are listed in Table 2, A': ≤0.5 µM; B': >0.5 µM and ≤1 µM; C': >1.0 µM and ≤5 uM; and D': >5 µM.

TABLE 2

| Example | TDO2 bichemical activity* | IDO1 biochemical activity* | TDO2 A172 cellular activity** | IDO1 Hela cellular activity** |
|---|---|---|---|---|
| 1 | | | A' | |
| 1a | A | D | B' | |
| 1b | A | B | A' | D' |
| 2 | A | B | A' | B' |
| 3 | | | A' | D' |
| 4 | | | D' | |
| 5 | | | A' | |
| 6 | | | B' | D' |
| 7 | | | D' | D' |
| 8 | | | D' | D' |
| 9 | | | A' | A' |
| 10 | | | A' | C' |
| 11 | | | A' | D' |
| 12 | | D | A' | |
| 13 | | D | B' | |
| 14 | | D | B' | |
| 15 | | D | A' | |
| 16 | | D | C' | |
| 17 | | D | C' | |
| 18 | A | C | A' | |
| 19 | | D | B' | |
| 20 | | D | D' | |
| 21 | | D | C' | |
| 22 | A | D | A' | D' |
| 23 | | | B' | |
| 24 | | D | C' | |
| 25 | A | C | A' | C' |
| 26 | | | C' | |
| 27 | | D | B' | |
| 28 | | D | A' | |
| 29 | | | B' | |
| 30 | | | A' | |
| 31 | | | A' | |
| 32 | | | A' | C' |
| 33 | | | D' | |
| 34 | | | D' | |
| 35 | | | A' | D' |
| 36 | | | A' | D' |
| 37 | | | A' | |
| 38 | | | A' | D' |
| 39 | | | A' | D' |
| 40 | | | A' | D' |
| 41 | | | C' | D' |
| 42 | | | A' | C' |
| 43 | | | D' | D' |

TABLE 2-continued

| Example | TDO2 bichemical activity* | IDO1 biochemical activity* | TDO2 A172 cellular activity** | IDO1 Hela cellular activity** |
|---|---|---|---|---|
| 44 | | | D' | D' |
| 45 | | | C' | D' |
| 46 | | | C' | D' |
| 47 | | | D' | D' |
| 48 | | | D' | D' |
| 49 | | | C' | |
| 50 | | | D' | D' |
| 51 | | | D' | D' |
| 52 | | | A' | C' |
| 53 | | | C' | D' |
| 54 | | | A' | |
| 55 | | | D' | D' |
| 56 | | | D' | D' |
| 57 | | | D' | |
| 58 | | | D' | |
| 59 | | | A' | |
| 60 | | | A' | |
| 61 | | | A' | |
| 62 | | | A' | |
| 63 | | | A' | B' |
| 64 | | | A' | D' |
| 65 | | | A' | |
| 66 | | | A' | |
| 67 | | | A' | |
| 68 | | | A' | |
| 69 | | | A' | |
| 70 | | | A' | |
| 71 | | | A' | |
| 72 | | | A' | |
| 73 | | | A' | |
| 74 | | | A' | |
| 75 | | | A' | |
| 76 | | | A' | |
| 77 | | | A' | |
| 78 | | | A' | |
| 79 | | | A' | |
| 80 | | | A' | |
| 81 | | | A' | |
| 82 | | | A' | |
| 83 | | | A' | B' |
| 84 | | | A' | |
| 85 | | | A' | |
| 86 | | | A' | |
| 87 | | | A' | C' |
| 88 | | | A' | |
| 89 | | | D' | D' |
| 90 | | | A' | |
| 91 | | | A' | |
| 92 | | | A' | |
| 93 | | | A' | B' |
| 94 | | | A' | |
| 95 | | | A' | D' |
| 96 | | | C' | C' |
| 97 | | | D' | D' |
| 98 | | | D' | D' |
| 99 | | | C' | D' |
| 100 | | | C' | D' |
| 101 | | | C' | D' |
| 102 | | | D' | D' |
| 103 | | | C' | |
| 104 | | | B' | D' |
| 105 | | | A' | D' |
| 106 | | | B' | D' |
| 107 | | | A' | D' |
| 108 | | | A' | D' |
| 109 | | | B' | C' |
| 110 | | | C' | C' |
| 111 | | | A' | C' |
| 112 | | | D' | B' |
| 113 | | | C' | C' |
| 114 | | | A' | D' |
| 115 | | | A' | C' |
| 116 | | | A' | D' |
| 117 | | | D' | D' |
| 118 | | | C' | D' |
| 119 | | | A' | A' |
| 120 | | | A' | D' |
| 121 | | | A' | A' |
| 122 | | | C' | C' |
| 123 | | | A' | C' |
| 124 | | | A' | A' |
| 125 | | | A' | D' |
| 126 | | | A' | D' |
| 127 | | | A' | D' |
| 128 | | | A' | B' |
| 129 | | | C' | C' |
| 130 | | | C' | B' |
| 131 | | | C' | D' |
| 132 | | | B' | C' |
| 133 | | | C' | D' |
| 134 | | | A' | C' |
| 135 | | | A' | D' |
| 136 | | | A' | C' |
| 137 | | | A' | C' |
| 138 | | | A' | D' |
| 139 | | | A' | B' |
| 140 | | | A' | A' |
| 141 | | | B' | D' |
| 142 | | | A' | A' |
| 143 | | | A' | A' |
| 144 | | | A' | A' |
| 145 | | | A' | A' |
| 146 | | | A' | A' |
| 147 | | | A' | C' |
| 148 | | | A' | A' |
| 149 | | | A' | A' |
| 150 | | | A' | A' |
| 151 | | | A' | C' |
| 152 | | | A' | B' |
| 153 | | | A' | C' |
| 154 | | | A' | B' |
| 155 | | | A' | C' |
| 156 | | | A' | A' |
| 157 | | | A' | D' |
| 158 | | | C' | D' |
| 159 | | | A' | D' |
| 160 | | | A' | C' |
| 161 | | | A' | A' |
| 162 | | | A' | A' |
| 163 | | | A' | A' |
| 164 | | | A' | D' |
| 165 | | | A' | C' |
| 166 | | | A' | B' |
| 167 | | | A' | D' |
| 168 | | | A' | A' |
| 169 | | | A' | C' |
| 170 | | | A' | A' |
| 171 | | | A' | B' |
| 172 | | | A' | A' |
| 173 | | | A' | B' |
| 174 | | | A' | A' |
| 175 | | | A' | C' |
| 176 | | | A' | A' |
| 177 | | | A' | B' |
| 178 | | | A' | A' |
| 179 | | | A' | A' |
| 180 | | | A' | A' |
| 181 | | | A' | A' |
| 182 | | | A' | A' |
| 183 | | | C' | D' |

*A: ≤0.1 µM; B: >0.10 µM and ≤0.5 µM; C: >0.5 µM and ≤1.0 µM; and D: >1.0 µM

**A': ≤0.5 µM; B': >0.5 µM and ≤1 µM; C': >1.0 µM and ≤5 uM; and D': >5 µM

INDUSTRIAL APPLICABILITY

The compound of the present invention can be applied to the field of medicine.

What is claimed is:

1. A compound of formula I:

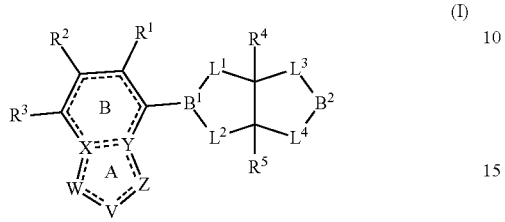

(I)

and/or a stereoisomer, a stable isotope, or a pharmaceutically acceptable salt thereof, wherein $R^1$, $R^2$, $R^3$, $R^4$, $R^5$, $B^1$, $B^2$, $L^1$, $L^2$, $L^3$, $L^4$, X, Y, Z, V, and W are defined as follows:

$R^1$, $R^2$ and $R^3$ are independently selected from H, D, CN, halo, $NH_2$, and an optionally substituted group selected from C1-C6 alkyl, C1-C6 alkenyl, C1-C6 alkynyl, C3-C8 cycloalkyl, C4-C8 cycloalkenyl, saturated or unsaturated 4-8 membered heterocyclyl containing 1-2 heteroatoms independently selected from N, O, and S as ring members, aryl, heteroaryl containing 1-3 heteroatoms independently selected from N, O, and S as ring members, C1-C6-alkyloxyl, C3-C8 cycloalkyloxyl, C1-C6-alkylamino, and C3-C8 cycloalkylamino, wherein the optional substituents are 1-3 substituents independently selected from $R^6$, wherein $R^6$ is independently selected from H, D, halo, —OH, Oxo, CN, $N_3$, ethynyl, and an optionally substituted group selected from C1-C4 alkyl, C1-C4 alkoxy, C1-C4 haloalkyl, C1-C4 hydroxyalkyl, C1-C4 haloalkoxy, C3-C6 cycloalkyl, C3-C6 cycloalkoxy, 4-6 membered heterocyclyl containing 1-2 heteroatoms independently selected from N, O, and S as ring members, aryl, heteroaryl containing 1-3 heteroatoms independently selected from N, O, and S as ring members, $—CO_2R^A$, $—C(O)N(R^B\ R^C)$, $—C(=NR^D)N(R^BR^C)$, $—C(O)R^A$, $—SO_{0-2}R^E$, $—SO(=NR^D)R^E$, $—SO_{1-2}N(R^B\ R^C)$, $—N(R^B\ R^C)$, $—N(R^A)C(O)R^E$, $—N(R^A)C(=NR^D)R^E$, $—N(R^A)SO_{1-2}R^E$, $—N(R^A)C(O)N(R^BR^C)$, $—N(R^A)C(=NR^D)N(R^BR^C)$, $—N(R^A)SO_{1-2}N(R^BR^C)$, and $—N(R^A)CO_2R^E$, wherein the optional substituents are 1-3 groups independently selected from H, halo, —OH, Oxo, $NH_2$, CN, $N_3$, C1-C4 alkyl, C1-C4 alkoxy, C1-C5 alkylamino, C3-C6 cycloalkyl, C3-C6 cycloalkoxy, 4-6 membered heterocyclyl containing 1-2 heteroatoms independently selected from N, O, and S as ring members, aryl, and heteroaryl containing 1-3 heteroatoms independently selected from N, O, and S as ring members; wherein $R^A$, $R^B$, $R^C$ and $R^E$ are independently selected from H and an optionally substituted group selected from C1-C4 alkyl, C3-C6 cycloalkyl, 4-6 membered heterocyclyl containing 1-2 heteroatoms independently selected from N, O, and S as ring members, aryl, and heteroaryl containing 1-3 heteroatoms independently selected from N, O, and S as ring members; $R^D$ is independently selected from H, CN, OH, and an optionally substituted group selected from C1-C4 alkyl and C1-C4 alkoxy, wherein the optional substituents for $R^A$, $R^B$, $R^C$, $R^D$ and $R^E$ are 1-3 substituents independently selected from $R^6$;

$R^4$ and $R^5$ are independently selected from H, D, halo, —OH, CN, $N_3$, and an optionally substituted group selected from C1-C4 alkyl, C1-C4 alkoxy, C1-C4 haloalkyl, C1-C4 hydroxyalkyl, C1-C4 haloalkoxy, C3-C6 cycloalkyl, C3-C6 cycloalkoxy, 4-6 membered heterocyclyl containing 1-2 heteroatoms independently selected from N, O, and S as ring members, aryl, heteroaryl containing 1-3 heteroatoms independently selected from N, O, and S as ring members, $—CO_2R^A$, $—C(O)N(R^B\ R^C)$, $—C(=NR^D)N(R^BR^C)$, $—C(O)R^A$, $—SO_{0-2}R^E$, $—SO(=NR^D)R^E$, $—SO_{1-2}N(R^B\ R^C)$, $—N(R^B\ R^C)$, $—N(R^A)C(O)R^E$, $—N(R^A)C(=NR^D)R^E$, $—N(R^A)SO_{1-2}R^E$, $—N(R^A)C(O)N(R^BR^C)$, $—N(R^A)C(=NR^D)N(R^BR^C)$, $—N(R^A)SO_{1-2}N(R^BR^C)$, and $—N(R^A)CO_2R^E$, wherein $R^A$, $R^B$, $R^C$, $R^D$ and $R^E$ are defined above;

wherein the optional substituents for $R^4$ and $R^5$ are 1-3 groups independently selected from H, halo, —OH, Oxo, $NH_2$, CN, $N_3$, C1-C4 alkyl, C1-C4 alkoxy, C1-C5 alkylamino, C3-C6 cycloalkyl, C3-C6 cycloalkoxy, 4-6 membered heterocyclyl containing 1-2 heteroatoms independently selected from N, O, and S as ring members, aryl, and heteroaryl containing 1-3 heteroatoms independently selected from N, O, and S as ring members;

alternatively, $R^4$ and $R^5$ can optionally be taken together to form a C3-C7 cycloalkyl ring, or a 4-7 membered heterocyclic ring containing 1-2 heteroatoms independently selected from N, O, and S, wherein the ring formed can be optionally substituted with 1-2 groups independently selected from $R^6$, wherein $R^6$ is defined above;

A ring and B ring together form a bicyclic aromatic ring selected from:

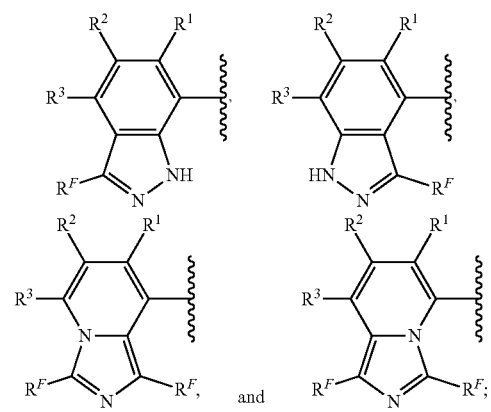

wherein $R^F$ is independently selected from H, D, OH, CN, halo, and an optionally substituted group selected from C1-C4 alkyl, and C1-C4 alkylamino, and wherein the optional substituents are 1-3 groups independently selected from $R^6$, wherein $R^6$ is defined above;

$B^1$ is N,

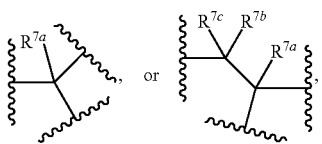

wherein $R^{7a}$, $R^{7b}$ and $R^{7c}$ are independently selected from H, D, OH, CN, halo, and an optionally substituted group selected from C1-C6 alkyl, and C1-C6 alkoxyl, and wherein the optional substituents are 1-3 groups independently selected from $R^6$, wherein $R^6$ is defined above;

$B^2$ is

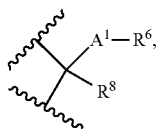

or —N($R^9$)—, wherein $A^1$ is a bond or C1-C4 alkylene; $R^8$ is selected from H, D, halo, and an optionally substituted group selected from C1-C4 alkyl; $R^9$ is selected from H and an optionally substituted group selected from C1-C4 alkyl, C1-C4 haloalkyl, C1-C4 hydroxyalkyl, C1-C4 haloalkoxy, C3-C6 cycloalkyl, 4-6 membered heterocyclyl containing 1-2 heteroatoms independently selected from N, O, and S as ring members, aryl, heteroaryl containing 1-3 heteroatoms independently selected from N, O, and S as ring members, —$CO_2R^A$, —C(O)N($R^B$ $R^C$), —C(=$NR^D$)N($R^B R^C$), —C(O)$R^A$, —$SO_{0-2}R^E$, —SO(=$NR^D$)$R^E$, and —$SO_{1-2}$N($R^B$ $R^C$), wherein $R^A$, $R^B$, $R^C$, $R^D$ and $R^E$ are defined above, wherein the optional substituents are 1-3 groups independently selected from $R^6$, wherein $R^6$ is defined above;

$L^1$ and $L^2$ are independently selected from a bond, —O—, —$NR^B$—, —CO—, —$SO_{1-2}$—, —C($R^{10}R^{11})_n$—, —C($R^{10}R^{11})_nSO_{1-2}$—, and —C($R^{10}R^{11})_n$CO—, wherein n is 1, 2, or 3; $R^{10}$ and $R^{11}$ are each independently selected from H, D, OH, CN, halo, and an optionally substituted group selected from C1-C4 alkyl, and C1-C4 alkoxyl, and wherein the optional substituents are 1-3 groups independently selected from $R^6$, wherein $R^6$ is defined above;

$L^3$ and $L^4$ are independently selected from a bond, —O—, —$NR^B$—, —CO—, —$SO_{1-2}$—, —C($R^{10}R^{11})_n$—, —C($R^{10}R^{11})_nSO_{1-2}$—, —C($R^{10}R^{11})_n$CO—, and —C($R^{10}R^{11})_nNR^B$—, wherein n is 1, 2, or 3; $R^{10}$ and $R^{11}$ are each independently selected from H, D, OH, CN, halo, and an optionally substituted group selected from C1-C4 alkyl, and C1-C4 alkoxyl, and wherein the optional substituents are 1-3 groups independently selected from $R^6$, wherein $R^6$ is defined above; or $R^{10}$ and $R^{11}$ can optionally together form a C3-C7 cycloalkyl ring or a 4-7 membered heterocyclic ring containing 1-2 heteroatoms independently selected from N, O, and S, wherein the ring can be optionally substituted with 1-2 groups independently selected from $R^6$, wherein $R^6$ is defined above.

2. The compound according to claim 1 and/or a stereoisomer, a stable isotope, or a pharmaceutically acceptable salt thereof, wherein W is NH, V is N, X and Y are C, and Z is $CR^F$.

3. The compound according to claim 1 and/or a stereoisomer, a stable isotope, or a pharmaceutically acceptable salt thereof, wherein Z is NH, V is N, X and Y are C, and W is $CR^F$.

4. The compound according to claim 1 and/or a stereoisomer, a stable isotope, or a pharmaceutically acceptable salt thereof, wherein V and Y are N, X is C, and W and Z are $CR^F$.

5. The compound according to claim 1 and/or a stereoisomer, a stable isotope, or a pharmaceutically acceptable salt thereof, wherein V and X are N, Y is C, and W and Z are $CR^F$.

6. The compound according to claim 1 and/or a stereoisomer, a stable isotope, or a pharmaceutically acceptable salt thereof, wherein $B^1$ is N.

7. The compound according to claim 1 and/or a stereoisomer, a stable isotope, or a pharmaceutically acceptable salt thereof, wherein $B^1$ is

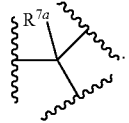

8. The compound according to claim 1 and/or a stereoisomer, a stable isotope, or a pharmaceutically acceptable salt thereof, wherein $L^1$, $L^2$, $L^3$, $L^4$, $B^1$, $B^2$, $R^4$, and $R^5$ together form an optionally substituted structure

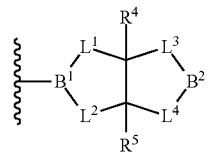

selected from:

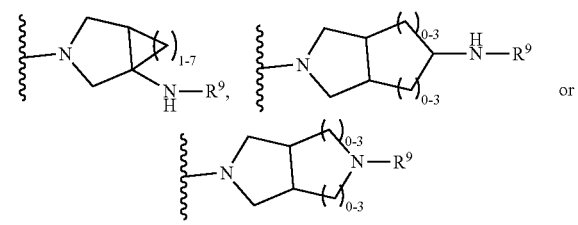

wherein the optional substituents on the rings of above structural motifs are 1-4 groups independently selected from OH, CN, halo, and an optionally substituted group selected from C1-C4 alkyl and C1-C4 alkoxyl, wherein the optional substituents are 1-3 groups independently selected from $R^6$; or wherein two optional substituents on

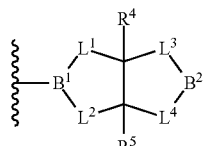

can be taken together to form a C3-C7 cycloalkyl ring or a 4-7 membered heterocyclic ring containing 1-2 heteroatoms independently selected from N, O, and S, wherein the ring formed can be optionally substituted with 1-2 groups independently selected from $R^6$.

9. The compound according to claim 1 and/or a stereoisomer, a stable isotope, or a pharmaceutically acceptable salt thereof, wherein $L^1$, $L^2$, $L^3$, $L^4$, $B^1$, $B^2$, $R^4$, and $R^5$ together form an optionally substituted structure

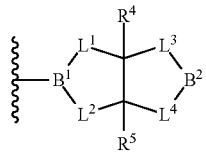

selected from:

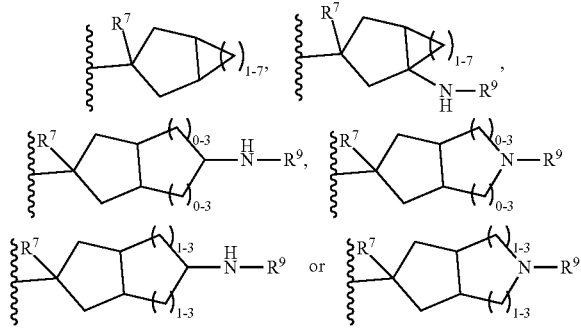

wherein the optional substituents on the rings of above structural motifs are 1-4 groups independently selected from OH, CN, halo, and an optionally substituted group selected from C1-C4 alkyl and C1-C4 alkoxyl, wherein the optional substituents are 1-3 groups independently selected from $R^6$; or wherein two optional substituents on

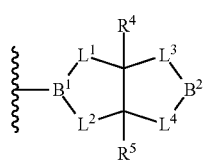

can be taken together to form a C3-C7 cycloalkyl ring or a 4-7 membered heterocyclic ring containing 1-2 heteroatoms independently selected from N, O, and S, wherein the ring formed can be optionally substituted with 1-2 groups independently selected from $R^6$.

10. The compound according to claim 1 and/or a stereoisomer, a stable isotope, or a pharmaceutically acceptable salt thereof, wherein $L^1$, $L^2$, $L^3$, $L^4$, $B^1$, $B^2$, $R^4$, and $R^5$ together form an optionally substituted structure

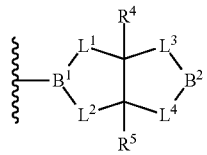

selected from:

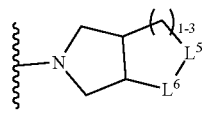

wherein the optional substituents on the rings of above structural motif are 1-4 groups independently selected from OH, CN, halo, and an optionally substituted group selected from C1-C4 alkyl and C1-C4 alkoxyl, wherein the optional substituents are 1-3 groups independently selected from $R^6$; or wherein two optional substituents on

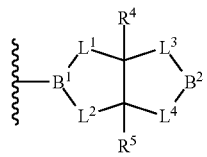

can be taken together to form a C3-C7 cycloalkyl ring or a 4-7 membered heterocyclic ring containing 1-2 heteroatoms independently selected from N, O, and S, wherein the ring formed can be optionally substituted with 1-2 groups independently selected from $R^6$;

$L^5$ is selected from —$NR^{12}CO$—, —$NR^{12}SO_2$—, —$CONR^{12}$—, and —$SO_2NR^{12}$—; and $L^6$ is a bond, or —$(CH_2)_{1-3}$—, wherein $R^{12}$ is an optionally substituted group selected from C1-C6 alkyl, C3-C8 cycloalkyl, C4-C8 cycloalkenyl, saturated or unsaturated 4-8 membered heterocyclyl containing 1-2 heteroatoms independently selected from N, O, and S as ring members, aryl, and heteroaryl containing 1-3 heteroatoms independently selected from N, O, and S as ring members, wherein the optional substituents are 1-3 substituents independently selected from $R^6$.

11. The compound according to claim 1 and/or a stereoisomer, a stable isotope, or a pharmaceutically acceptable salt thereof, wherein $L^1$, $L^2$, $L^3$, $L^4$, $B^1$, $B^2$, $R^4$, and $R^5$ together form an optionally substituted structure

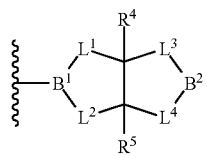

selected from:

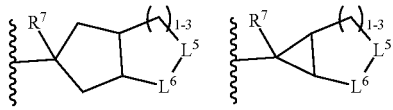

wherein the optional substituents on the rings of above structural motifs are 1-4 groups independently selected from OH, CN, halo, C1-C6 alkyl, and C1-C6 alkoxyl, wherein the optional substituents are 1-3 groups independently selected from $R^6$; or wherein two optional substituents on the rings of above structural motifs can be taken together to form a C3-C7 cycloalkyl ring or a 4-7 membered heterocyclic ring containing 1-2 heteroatoms independently selected from N, O, and S, wherein the ring formed can be optionally substituted with 1-2 groups independently selected from $R^6$;

$L^5$ is selected from —$NR^{12}CO$—, —$NR^{12}SO_2$—, —$CONR^{12}$—, and —$SO_2NR^{12}$—; and $L^6$ is a bond, or —$(CH_2)_{1-3}$—, wherein $R^{12}$ is an optionally substituted group selected from C1-C6 alkyl, C3-C8 cycloalkyl, C4-C8 cycloalkenyl, saturated or unsaturated 4-8 membered heterocyclyl containing 1-2 heteroatoms independently selected from N, O, and S as ring members, aryl, and heteroaryl containing 1-3 heteroatoms independently selected from N, O, and S as ring members, wherein the optional substituents are 1-3 groups independently selected from $R^6$.

12. The compound of claim 1 having structure of formula I-A, I-B, I-C, or I-D:

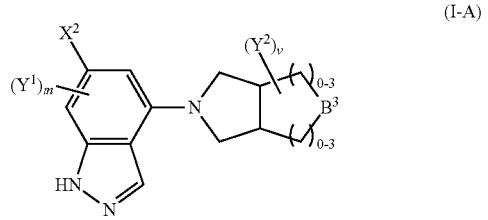
(I-A)

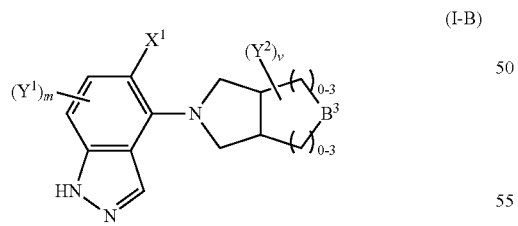
(I-B)

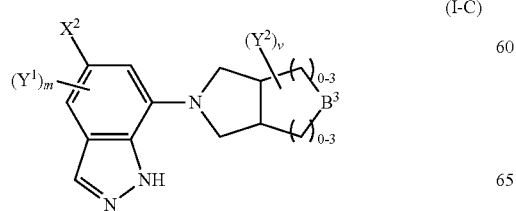
(I-C)

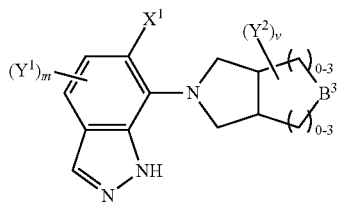
(I-D)

and/or a stereoisomer, a stable isotope, or a pharmaceutically acceptable salt thereof, wherein $X^1$ and $X^2$ are independently selected from CN, halo, $CF_3$, and an optionally substituted group selected from C1-C6 alkyl, C3-C6 cycloalkyl, and C1-C6 alkoxy, wherein the optional substituents are 1-3 groups independently selected from $R^6$;

$Y^1$ is independently selected from H, D, CN, halo, $NH_2$, and an optionally substituted group selected from C1-C6 alkyl, C1-C6 alkoxy, and C1-C6 alkylamino, wherein the optional substituents are 1-3 groups independently selected from $R^6$;

$Y^2$ is independently selected from H, OH, CN, halo, and an optionally substituted group selected from C1-C4 alkyl and C1-C4 alkoxyl, wherein the optional substituents are 1-3 substituents independently selected from $R^6$; or the two adjacent $Y^2$ substituents can optionally be taken together to form a C3-C7 cycloalkyl ring or a 4-7 membered heterocyclic ring containing 1-2 heteroatoms independently selected from N, O, and S, wherein the ring formed can be optionally substituted with 1-2 groups independently selected from $R^6$;

$B^3$ is

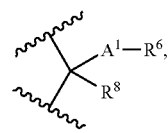

$C(R^8)(NHR^{13})$—, or —$N(R^{13})$—, wherein $R^{13}$ is selected from —$COR^{14}$, —$SO_2R^{14}$, —$CONR^{15}R^{16}$, and —$SO_2NR^{15}R^{16}$, wherein $R^{14}$ is an optionally substituted group selected from C1-C6 alkyl, C3-C8 cycloalkyl, saturated or unsaturated 4-8 membered heterocyclyl containing 1-2 heteroatoms independently selected from N, O, and S as ring members, aryl, and heteroaryl containing 1-3 heteroatoms independently selected from N, O, and S as ring members, wherein the optional substituents are 1-3 groups independently selected from $R^6$; wherein $R^{15}$ and $R^{16}$ are independently H or $R^{14}$;

m is 1-2; and v is 1-4.

13. The compound of claim 1 having structure of formula I-E, I-F, I-G or I-H:

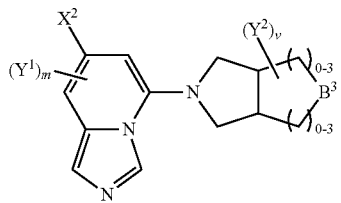
(I-E)

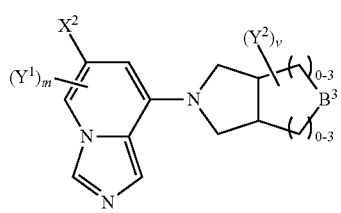
(I-F)

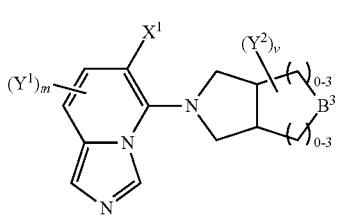
(I-G)

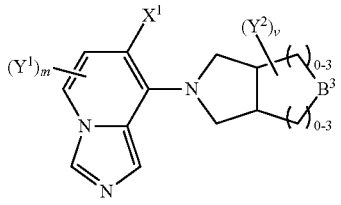
(I-H)

and/or a stereoisomer, a stable isotope, or a pharmaceutically acceptable salt thereof, wherein $X^1$ and $X^2$ are independently selected from CN, halo, and an optionally substituted group selected from C1-C6 alkyl, C1-C6 haloalkyl, C3-C6 cycloalkyl, and C1-C6 alkoxy, wherein the optional substituents are 1-3 groups independently selected from $R^6$;

$Y^1$ is independently selected from H, D, CN, halo, NH$_2$, and an optionally substituted group selected from C1-C6 alkyl, C1-C6 alkoxy, and C1-C6 alkylamino, wherein the optional substituents are 1-3 groups independently selected from $R^6$;

$Y^2$ is independently selected from H, OH, CN, halo, and an optionally substituted group selected from C1-C4 alkyl and C1-C4 alkoxyl, wherein the optional substituents are 1-3 groups independently selected from $R^6$; or two adjacent $Y^2$ substituents can be taken together to form a C3-C7 cycloalkyl ring or a 4-7 membered heterocyclic ring containing 1-2 heteroatoms independently selected from N, O, and S, wherein the ring formed can be optionally substituted with 1-2 groups independently selected from $R^6$;

$B^3$ is

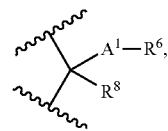

—C($R^8$)(NH$R^{13}$)—, or —N($R^{13}$)—, wherein $R^{13}$ is selected from —CO$R^{14}$, —SO$_2$$R^{14}$, —CONR$^{15}$$R^{16}$, and —SO$_2$NR$^{15}$$R^{16}$, wherein $R^{14}$ is an optionally substituted group selected from C1-C6 alkyl, C3-C8 cycloalkyl, saturated or unsaturated 4-8 membered heterocyclyl containing 1-2 heteroatoms independently selected from N, O, and S as ring members, aryl, and heteroaryl containing 1-3 heteroatoms independently selected from N, O, and S as ring members, wherein the optional substituents are 1-3 groups independently selected from $R^6$; wherein $R^{15}$ and $R^{16}$ are independently H or $R^1$;

m is 1-2; and v is 1-4.

14. The compound of claim 1 having structure of formula I-I, I-J, I-K, I-L, I-M, I-N, I-O, or I-P:

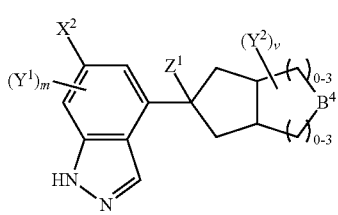
(I-I)

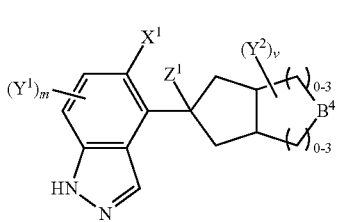
(I-J)

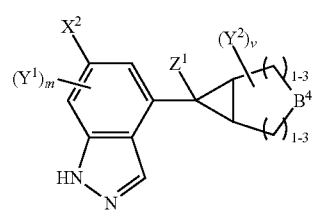
(I-k)

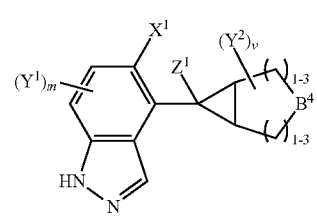
(I-l)

(I-M)

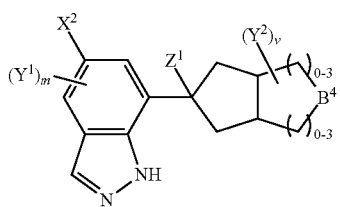

(I-N)

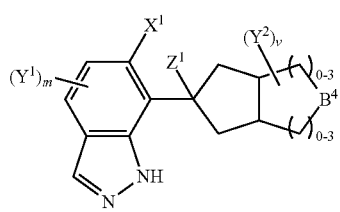

(I-O)

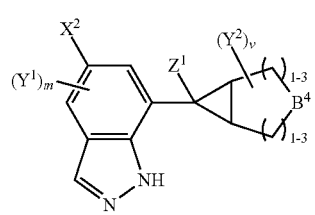

(I-P)

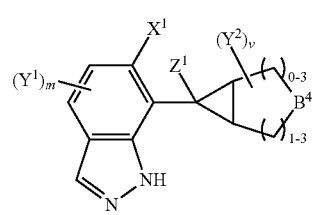

and/or a stereoisomer, a stable isotope, or a pharmaceutically acceptable salt thereof, wherein $Z^1$ is selected from H, OH, CN, halo, and an optionally substituted group selected from C1-C6 alkyl and C1-C6 alkoxy, wherein the optional substituents are 1-3 groups independently selected from $R^6$;

$X^1$ and $X^2$ are independently selected from CN, halo, and an optionally substituted group selected from C1-C6 alkyl, C1-C6 haloalkyl, C3-C6 cycloalkyl, and C1-C6 alkoxy, wherein the optional substituents are 1-3 groups independently selected from $R^6$;

$Y^1$ is independently selected from H, D, CN, halo, $NH_2$, and an optionally substituted group selected from C1-C6 alkyl, C1-C6 alkoxy, and C1-C6 alkylamino, wherein the optional substituents are 1-3 groups independently selected from $R^6$;

$Y^2$ is independently selected from H, OH, CN, halo, and an optionally substituted group selected from C1-C4 alkyl and C1-C4 alkoxyl, wherein the optional substituents are 1-3 groups independently selected from $R^6$; or two adjacent $Y^2$ substituents can be taken together to form a C3-C7 cycloalkyl ring or a 4-7 membered heterocyclic ring containing 1-2 heteroatoms independently selected from N, O, and S, wherein the ring formed can be optionally substituted with 1-2 groups independently selected from $R^6$;

$B^4$ is

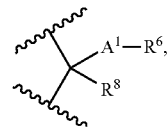

—C($R^8$)(NH$R^{13}$)—, or —N($R^{13}$)—, wherein $R^{13}$ is selected from —CO$R^{14}$, —SO$_2R^{14}$, —CONR$^{15}R^{16}$, and —SO$_2$NR$^{15}R^{16}$, wherein $R^{14}$ is an optionally substituted group selected from C1-C6 alkyl, C3-C8 cycloalkyl, saturated or unsaturated 4-8 membered heterocyclyl containing 1-2 heteroatoms independently selected from N, O, and S as ring members, aryl, and heteroaryl containing 1-3 heteroatoms independently selected from N, O, and S as ring members, wherein the optional substituents are 1-3 groups independently selected from $R^6$; wherein $R^{15}$ and $R^{16}$ are independently H or $R^{14}$;

m is 1-2; and v is 1-4.

15. The compound of claim 1 having structure of formula I-Q, I-R, I-S, I-T, I-U, I-V, I-W, or I-X:

(I-Q)

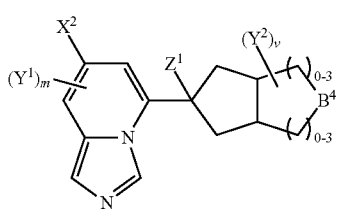

(I-R)

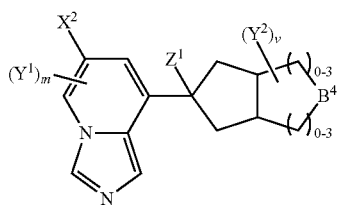

(I-S)

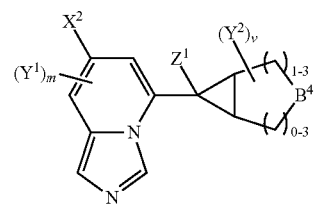

(I-T)

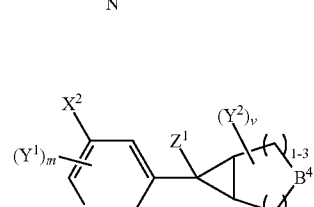

-continued (I-U)
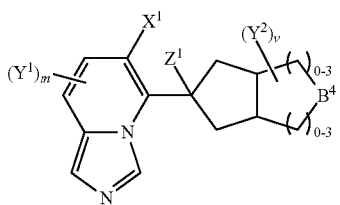

(I-V)
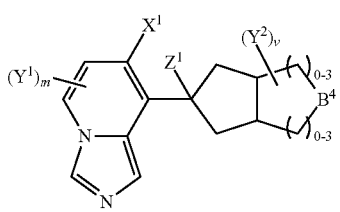

(I-W)
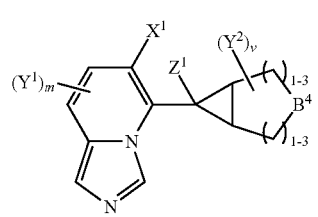

(I-X)
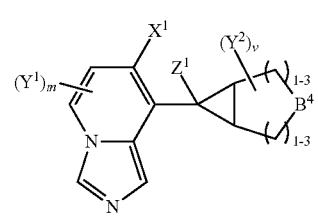

and/or a stereoisomer, a stable isotope, or a pharmaceutically acceptable salt thereof, wherein $Z^1$ is selected from H, OH, CN, halo, and an optionally substituted group selected from C1-C6 alkyl and C1-C6 alkoxy, wherein the optional substituents are 1-3 groups independently selected from $R^6$, $X^1$ and $X^2$ are independently selected from CN, halo, and an optionally substituted group selected from C1-C6 alkyl, C1-C6 haloalkyl, C3-C6 cycloalkyl, and C1-C6 alkoxy, wherein the optional substituents are 1-3 groups independently selected from $R^6$;

$Y^1$ is independently selected from H, D, CN, halo, $NH_2$, and an optionally substituted group selected from C1-C6 alkyl, C1-C6 alkoxy, and C1-C6 alkylamino, wherein the optional substituents are 1-3 groups independently selected from $R^6$;

$Y^2$ is independently selected from H, OH, CN, halo, and an optionally substituted group selected from C1-C4 alkyl and C1-C4 alkoxyl, wherein the optional substituents are 1-3 groups independently selected from $R^6$; or two adjacent $Y^2$ substituents can be taken together to form a C3-C7 cycloalkyl ring or a 4-7 membered heterocyclic ring containing 1-2 heteroatoms independently selected from N, O, and S, wherein the ring formed can be optionally substituted with 1-2 groups independently selected from $R^6$;

$B^4$ is

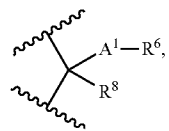

$-C(R^8)(NHR^{13})-$, or $-N(R^{13})-$, wherein $R^{13}$ is selected from $-COR^{14}$, $-SO_2R^{14}$, $-CONR^{15}R^{16}$, and $-SO_2NR^{15}R^{16}$, wherein $R^{14}$ is an optionally substituted group selected from C1-C6 alkyl, C3-C8 cycloalkyl, saturated or unsaturated 4-8 membered heterocyclyl containing 1-2 heteroatoms independently selected from N, O, and S as ring members, aryl, and heteroaryl containing 1-3 heteroatoms independently selected from N, O, and S as ring members, wherein the optional substituents are 1-3 groups independently selected from $R^6$; wherein $R^{15}$ and $R^{16}$ are independently H or $R^{14}$;

m is 1-2; and v is 1-4.

16. The compound of claim 1 having structure of formula I-Y, I-Z, I-AA, I-BB, I-CC, I-DD, I-EE, I-FF, or I-GG:

(I-Y)
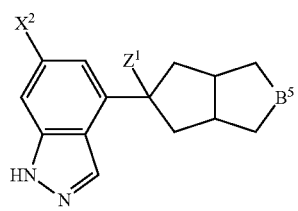

(I-Z)
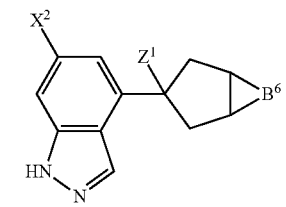

(I-AA)
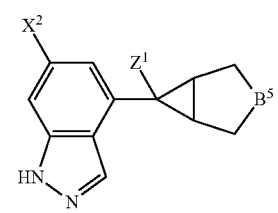

(I-BB)
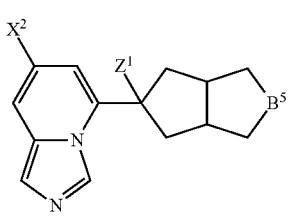

(I-CC)

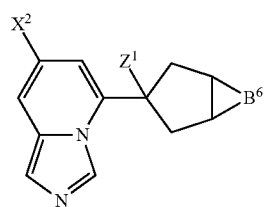

(I-DD)

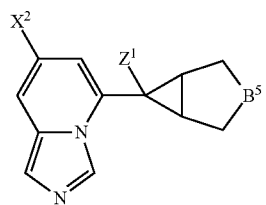

(I-EE)

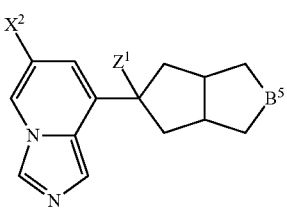

(I-FF)

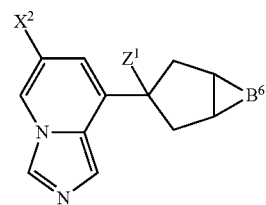

(I-GG)

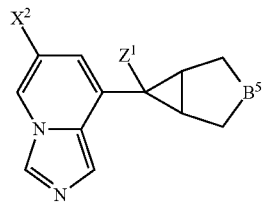

and/or a stereoisomer, a stable isotope, or a pharmaceutically acceptable salt thereof, wherein $Z^1$ is selected from H, OH, CN, halo, and an optionally substituted group selected from C1-C6 alkyl and C1-C6 alkoxy, wherein the optional substituents are 1-3 groups independently selected from $R^6$, X2 are independently selected from CN, halo, and an optionally substituted group selected from C1-C6 alkyl, C1-C6 haloalkyl, C3-C6 cycloalkyl, and C1-C6 alkoxy, wherein the optional substituents are 1-3 groups independently selected from $R^6$;

$B^5$ is

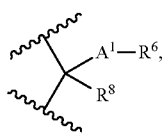

—C($R^8$)(NH$R^{13}$)—, or —N($R^{13}$)—, wherein $R^{13}$ is selected from —COR$^{14}$, —SO$_2$R$^{14}$, —CONR$^{15}$R$^{16}$, and —SO$_2$NR$^{15}$R$^{16}$, wherein $R^{14}$ is an optionally substituted group selected from C1-C6 alkyl, C3-C8 cycloalkyl, saturated or unsaturated 4-8 membered heterocyclyl containing 1-2 heteroatoms independently selected from N, O, and S as ring members, aryl, and heteroaryl containing 1-3 heteroatoms independently selected from N, O, and S as ring members, wherein the optional substituents are 1-3 groups independently selected from $R^6$; wherein $R^{15}$ and $R^{16}$ are independently H or $R^{14}$;

$B^6$ is

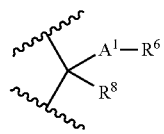

or —C($R^8$)(NH$R^{13}$)—, wherein $R^{13}$ is selected from —COR$^{14}$, —SO$_2$R$^{14}$, —CONR$^{15}$R$^{16}$, and —SO$_2$NR$^{15}$R$^{16}$, wherein $R^{14}$ is an optionally substituted group selected from C1-C6 alkyl, C3-C8 cycloalkyl, saturated or unsaturated 4-8 membered heterocyclyl containing 1-2 heteroatoms independently selected from N, O, and S as ring members, aryl, and heteroaryl containing 1-3 heteroatoms independently selected from N, O, and S as ring members, wherein the optional substituents are 1-3 groups independently selected from $R^6$; wherein $R^{15}$ and $R^{16}$ are independently H or $R^{14}$.

17. The compound of claim 12 and/or a stereoisomer, a stable isotope, or a pharmaceutically acceptable salt thereof, wherein $X^1$ and $X^2$ are independently selected from halogen, C1-C6 alkyl, C1-C6 haloalkyl, and C3-C6 cyclcoalkyl.

18. The compound of claim 17 and/or a stereoisomer, a stable isotope, or a pharmaceutically acceptable salt thereof, wherein $X^1$ and $X^2$ are independently selected from Cl, CF$_3$ and cyclopropyl.

19. The compound of claim 1, selected from the following compounds:
  6-chloro-4-(4,4-dimethyl-5-(methylsulfonyl)hexahydropyrrolo[3,4-c]pyrrol-2(1H)-yl)-1H-indazole;
  6-chloro-4-((3aS,6aR)-4,4-dimethyl-5-(methylsulfonyl)hexahydropyrrolo[3,4-c]pyrrol-2(1H)-yl)-1H-indazole;
  6-chloro-4-((3aR,6aS)-4,4-dimethyl-5-(methylsulfonyl)hexahydropyrrolo[3,4-c]pyrrol-2(1H)-yl)-1H-indazole;
  (3aR,5r,6aS)-5-(6-chloro-1H-indazol-4-yl)-2-(methylsulfonyl)octahydrocyclopenta[c]pyrrol-5-ol;
  N-((2r,3aR,5r,6aS)-5-(6-chloro-1H-indazol-4-yl)-5-hydroxyoctahydropentalen-2-yl)methanesulfonamide;
  1-((3aR,5r,6aS)-5-(6-(trifluoromethyl)imidazo[1,5-a]pyridin-8-yl)hexahydrocyclopenta[c]pyrrol-2(1H)-yl)ethanone;
  Racemic-6-chloro-4-((3aR,6aS)-2-(methylsulfonyl)-1,2,3,3a,4,6a-hexahydrocyclopenta[c]pyrrol-5-yl)-1H-indazole;
  1-((3aR,5r,6aS)-5-(6-chloroimidazo[1,5-a]pyridin-8-yl)-5-hydroxyhexahydrocyclopenta[c]pyrrol-2(1H)-yl)ethanone;
  1-((3aR,5r,6aS)-5-(6-chloroimidazo[1,5-a]pyridin-5-yl)-5-hydroxyhexahydrocyclopenta[c]pyrrol-2(1H)-yl)ethanone;

1-((3aR,5r,6aS)-5-(5-chloro-1H-indazol-7-yl)-5-hydroxyhexahydrocyclopenta[c]pyrrol-2(1H)-yl)ethanone;
N'-methyl-N-((1R,3r,5S,6r)-3-(6-chloro-1H-indazol-4-yl)-3-hydroxybicyclo[3.1.0]hexan-6-yl)sulfuric diamide;
N-((1R,3r,5S,6r)-3-hydroxy-3-(6-(trifluoromethyl)-1H-indazol-4-yl)bicyclo[3.1.0]hexan-6-yl)methanesulfonamide;
1-(6-chloro-1H-indazol-4-yl)cyclopropanol;
6-chloro-4-((3aR,6aS)-5-(methylsulfonyl)hexahydropyrrolo[3,4-c]pyrrol-2(1H)-yl)-1H-indazole;
6-chloro-4-(1-(methylsulfonyl)hexahydro-1H-pyrrolo[3,4-b]pyridin-6(2H)-yl)-1H-indazole;
1-((3aR,6aS)-5-(6-chloro-1H-indazol-4-yl)hexahydropyrrolo[3,4-c]pyrrol-2(1H)-yl)ethanone;
1-(6-(6-chloro-1H-indazol-4-yl)octahydro-1H-pyrrolo[3,4-b]pyridin-1-yl)ethanone;
N-((1R,5S)-3-(6-chloro-1H-indazol-4-yl)-3-azabicyclo[3.1.0]hexan-6-yl)methanesulfonamide;
N-((1R,5S)-3-(6-chloro-1H-indazol-4-yl)-3-azabicyclo[3.1.0]hexan-6-yl)acetamide;
1-(5-(6-chloro-1H-indazol-4-yl)-1,1-dimethylhexahydropyrrolo[3,4-c]pyrrol-2(1H)-yl)ethanone;
1-(5-(6-chloro-1H-indazol-4-yl)hexahydropyrrolo[3,4-b]pyrrol-1(2H)-yl)ethanone;
6-chloro-1-methyl-4-(1-(methylsulfonyl)hexahydropyrrolo[3,4-b]pyrrol-5(1H)-yl)-1H-indazole;
N-((1R,5S,6r)-3-(6-chloro-1H-indazol-4-yl)-3-azabicyclo[3.1.0]hexan-6-yl)acetamide;
1-((3aR,5r,6aS)-5-(6-chloro-1H-indazol-4-yl)-5-hydroxyhexahydrocyclopenta[c]pyrrol-2(1H)-yl)ethanone;
6-chloro-4-(1-(methylsulfonyl)hexahydropyrrolo[3,4-b]pyrrol-5(1H)-yl)-1H-indazole;
N-((1R,5S,6r)-3-(6-chloro-1H-indazol-4-yl)-3-azabicyclo[3.1.0]hexan-6-yl)methanesulfonamide;
(1R,3r,5S)-3-(6-chloro-1H-indazol-4-yl)bicyclo[3.1.0]hexan-3-ol;
4-(5-(6-chloro-1H-indazol-4-yl)-1,1-dimethylhexahydropyrrolo[3,4-c]pyrrol-2(1H)-ylsulfonyl)benzonitrile;
4-(5-(6-chloro-1H-indazol-4-yl)-1,1-dimethyloctahydropyrrolo[3,4-c]pyrrole-2-carbonyl)benzonitrile;
6-chloro-4-(5-(cyclopropylsulfonyl)-4,4-dimethylhexahydropyrrolo[3,4-c]pyrrol-2(1H)-yl)-1H-indazole;
(5-(6-chloro-1H-indazol-4-yl)-1,1-dimethylhexahydropyrrolo[3,4-c]pyrrol-2(1H)-yl)(cyclopropyl)methanone;
(2r,3aR,6aS)-2-(6-chloro-1H-indazol-4-yl)octahydropentalen-2-ol;
Racemic-(3aS,6aR)-5-(6-chloro-1H-indazol-4-yl)-1,1-dimethylhexahydropyrrolo[3,4-c]pyrrole-2(1H)-carboxamide;
(2r,3aR,5s,6aS)-2-(6-chloro-1H-indazol-4-yl)octahydropentalene-2,5-diol;
4-(((3aR,6aS)-5-(6-chloro-1H-indazol-4-yl)hexahydropyrrolo[3,4-c]pyrrol-2(1H)-yl)sulfonyl)benzonitrile;
4-((3aR,6aS)-5-(6-chloro-1H-indazol-4-yl)octahydropyrrolo[3,4-c]pyrrole-2-carbonyl)benzonitrile;
(3aR,5r,6aS)-5-(6-chloro-1H-indazol-4-yl)-2-(phenylsulfonyl)octahydrocyclopenta[c]pyrrol-5-ol;
((3aR,5r,6aS)-5-(6-chloro-1H-indazol-4-yl)-5-hydroxyhexahydrocyclopenta[c]pyrrol-2(1H)-yl)(phenyl)methanone;
(3aR,5r,6aS)-5-(6-chloro-1H-indazol-4-yl)-2-(cyclopropylsulfonyl)octahydrocyclopenta[c]pyrrol-5-ol;
((3aR,5r,6aS)-5-(6-chloro-1H-indazol-4-yl)-5-hydroxyhexahydrocyclopenta[c]pyrrol-2(1H)-yl)(cyclopropyl)methanone;
4-(((3aR,5r,6aS)-5-(6-chloro-1H-indazol-4-yl)-5-hydroxyhexahydrocyclopenta[c]pyrrol-2(1H)-yl)sulfonyl)benzonitrile;
((3aR,5r,6aS)-5-(6-chloro-1H-indazol-4-yl)-5-hydroxyhexahydrocyclopenta[c]pyrrol-2(1H)-yl)(pyridin-4-yl)methanone;
Racemic-1-((3aS,6aR)-5-(6-chloroimidazo[1,5-a]pyridin-8-yl)-1,1-dimethylhexahydropyrrolo[3,4-c]pyrrol-2(1H)-yl)ethanone;
4-((3aR,5r,6aS)-5-(6-chloro-1H-indazol-4-yl)-5-hydroxyoctahydrocyclopenta[c]pyrrole-2-carbonyl)benzonitrile;
Racemic-1-((3aS,6aR)-5-(7-chloroimidazo[1,5-a]pyridin-5-yl)-1,1-dimethylhexahydropyrrolo[3,4-c]pyrrol-2(1H)-yl)ethanone;
Racemic-7-chloro-5-((3aR,6aS)-4,4-dimethyl-5-(methylsulfonyl)hexahydropyrrolo[3,4-c]pyrrol-2(1H)-yl)imidazo[1,5-a]pyridine;
Racemic-1-((3aS,6aR)-1,1-dimethyl-5-(6-(trifluoromethyl)imidazo[1,5-a]pyridin-8-yl)hexahydropyrrolo[3,4-c]pyrrol-2(1H)-yl)ethanone;
Racemic-8-((3aR,6aS)-4,4-dimethyl-5-(methylsulfonyl)hexahydropyrrolo[3,4-c]pyrrol-2(1H)-yl)-6-(trifluoromethyl)imidazo[1,5-a]pyridine;
Racemic-1-((3aS,6aR)-1,1-dimethyl-5-(6-(trifluoromethyl)imidazo[1,5-a]pyridin-5-yl)hexahydropyrrolo[3,4-c]pyrrol-2(1H)-yl)ethanone;
Racemic-5-((3aR,6aS)-4,4-dimethyl-5-(methylsulfonyl)hexahydropyrrolo[3,4-c]pyrrol-2(1H)-yl)-6-(trifluoromethyl)imidazo[1,5-a]pyridine;
Racemic-6-chloro-8-((3aR,6aS)-4,4-dimethyl-5-(methylsulfonyl)hexahydropyrrolo[3,4-c]pyrrol-2(1H)-yl)imidazo[1,5-a]pyridine;
Racemic-5-((3aR,6aS)-4,4-dimethyl-5-(methylsulfonyl)hexahydropyrrolo[3,4-c]pyrrol-2(1H)-yl)-7-(trifluoromethyl)imidazo[1,5-a]pyridine;
Racemic-1-((3aS,6aR)-1,1-dimethyl-5-(7-(trifluoromethyl)imidazo[1,5-a]pyridin-5-yl)hexahydropyrrolo[3,4-c]pyrrol-2(1H)-yl)ethanone;
(3aR,5r,6aS)-5-(6-chloroimidazo[1,5-a]pyridin-8-yl)-2-(methylsulfonyl)octahydrocyclopenta[c]pyrrol-5-ol;
(3aR,5r,6aS)-5-(6-chloroimidazo[1,5-a]pyridin-5-yl)-2-(methylsulfonyl)octahydrocyclopenta[c]pyrrol-5-ol;
(3aR,5r,6aS)-tert-butyl 5-(6-chloro-1H-indazol-4-yl)-5-hydroxyhexahydrocyclopenta[c]pyrrole-2(1H)-carboxylate;
Racemic-6-cyclopropyl-5-((3aR,6aS)-4,4-dimethyl-5-(methylsulfonyl)hexahydropyrrolo[3,4-c]pyrrol-2(1H)-yl)imidazo[1,5-a]pyridine;
Racemic-1-((3aS,6aR)-5-(6-cyclopropylimidazo[1,5-a]pyridin-5-yl)-1,1-dimethylhexahydropyrrolo[3,4-c]pyrrol-2(1H)-yl)ethanone;
Racemic-8-((3aR,6aS)-4,4-dimethyl-5-(methylsulfonyl)hexahydropyrrolo[3,4-c]pyrrol-2(1H)-yl)-7-(trifluoromethyl)imidazo[1,5-a]pyridine;
Racemic-1-((3aS,6aR)-1,1-dimethyl-5-(7-(trifluoromethyl)imidazo[1,5-a]pyridin-8-yl)hexahydropyrrolo[3,4-c]pyrrol-2(1H)-yl)ethanone;
((3aR,5r,6aS)-5-(6-chloro-1H-indazol-4-yl)-5-hydroxyhexahydrocyclopenta[c]pyrrol-2(1H)-yl)(cyclopentyl)methanone;
((3aR,5r,6aS)-5-(6-chloro-1H-indazol-4-yl)-5-hydroxyhexahydrocyclopenta[c]pyrrol-2(1H)-yl)(cyclobutyl)methanone;

(3aR,5r,6aS)-isopropyl 5-(6-chloro-1H-indazol-4-yl)-5-hydroxyhexahydrocyclopenta[c]pyrrole-2(1H)-carboxylate;

((3aR,5r,6aS)-5-(6-chloro-1H-indazol-4-yl)-5-hydroxyhexahydrocyclopenta[c]pyrrol-2(1H)-yl)(cyclohexyl)methanone;

N-((1R,3r,5S,6r)-3-(6-chloro-1H-indazol-4-yl)-3-hydroxybicyclo[3.1.0]hexan-6-yl)methanesulfonamide;

N-((1R,3r,5S,6r)-3-(6-chloro-1H-indazol-4-yl)-3-hydroxybicyclo[3.1.0]hexan-6-yl)acetamide;

1-((3aR,5r,6aS)-5-(6-chloro-1H-indazol-4-yl)-5-hydroxyhexahydrocyclopenta[c]pyrrol-2(1H)-yl)-2-methylpropan-1-one;

((3aR,5R,6aS)-5-(6-chloro-1H-indazol-4-yl)-5-hydroxyhexahydrocyclopenta[c]pyrrol-2(1H)-yl)((1r,4R)-4-hydroxycyclohexyl)methanone;

(3aR,5r,6aS)-methyl 5-(6-chloro-1H-indazol-4-yl)-5-hydroxyhexahydrocyclopenta[c]pyrrole-2(1H)-carboxylate;

((3aR,5r,6aS)-5-(6-chloro-1H-indazol-4-yl)-5-hydroxyhexahydrocyclopenta[c]pyrrol-2(1H)-yl)(tetrahydrofuran-3-yl)methanone;

1-((3aR,5r,6aS)-5-(6-chloro-1H-indazol-4-yl)-5-hydroxyhexahydrocyclopenta[c]pyrrol-2(1H)-yl)-2-cyclopropylethanone;

1-((3aR,5r,6aS)-5-(6-chloro-1H-indazol-4-yl)-5-hydroxyhexahydrocyclopenta[c]pyrrol-2(1H)-yl)propan-1-one;

N-((1R,3r,5S,6r)-3-(6-chloro-1H-indazol-4-yl)-3-hydroxybicyclo[3.1.0]hexan-6-yl)ethanesulfonamide;

N-((1R,3r,5S,6r)-3-(6-chloro-1H-indazol-4-yl)-3-hydroxybicyclo[3.1.0]hexan-6-yl)tetrahydrofuran-3-carboxamide;

N-((1R,3r,5S,6r)-3-(6-chloro-1H-indazol-4-yl)-3-hydroxybicyclo[3.1.0]hexan-6-yl)cyclopropanesulfonamide;

N-((1R,3r,5S,6r)-3-(6-chloro-1H-indazol-4-yl)-3-hydroxybicyclo[3.1.0]hexan-6-yl)cyclopentanesulfonamide;

N-((1R,3r,5S,6r)-3-(6-chloro-1H-indazol-4-yl)-3-hydroxybicyclo[3.1.0]hexan-6-yl)tetrahydrofuran-2-carboxamide;

N-((1R,3r,5S,6r)-3-(6-chloro-1H-indazol-4-yl)-3-hydroxybicyclo[3.1.0]hexan-6-yl)cyclopropanecarboxamide;

N-((1R,3r,5S,6r)-3-(6-chloro-1H-indazol-4-yl)-3-hydroxybicyclo[3.1.0]hexan-6-yl)propane-2-sulfonamide;

N-((1R,3r,5S,6r)-3-(6-chloro-1H-indazol-4-yl)-3-hydroxybicyclo[3.1.0]hexan-6-yl)cyclohexanesulfonamide;

N-((1R,3r,5S,6r)-3-(6-chloro-1H-indazol-4-yl)-3-hydroxybicyclo[3.1.0]hexan-6-yl)cyclopentanecarboxamide;

Methyl ((1R,3r,5S,6r)-3-(6-chloro-1H-indazol-4-yl)-3-hydroxybicyclo[3.1.0]hexan-6-yl)carbamate;

Ethyl ((1R,3r,5S,6r)-3-(6-chloro-1H-indazol-4-yl)-3-hydroxybicyclo[3.1.0]hexan-6-yl)carbamate;

N-((1R,3r,5S,6r)-3-(6-chloro-1H-indazol-4-yl)-3-hydroxybicyclo[3.1.0]hexan-6-yl)propionamide;

N-((1R,3r,5S,6r)-3-(6-chloro-1H-indazol-4-yl)-3-hydroxybicyclo[3.1.0]hexan-6-yl)isonicotinamide;

N-((1R,3r,5S,6r)-3-(6-chloro-1H-indazol-4-yl)-3-hydroxybicyclo[3.1.0]hexan-6-yl)cyclobutanecarboxamide;

N-((1R,3r,5S,6r)-3-(6-chloro-1H-indazol-4-yl)-3-hydroxybicyclo[3.1.0]hexan-6-yl)cyclohexanecarboxamide;

Isopropyl ((1R,3r,5S,6r)-3-(6-chloro-1H-indazol-4-yl)-3-hydroxybicyclo[3.1.0]hexan-6-yl)carbamate;

(3aR,5r,6aS)-5-(6-chloro-1H-indazol-4-yl)-5-hydroxy-N-methylhexahydrocyclopenta[c]pyrrole-2(1H)-sulfonamide;

((3aR,5r,6aS)-5-(6-chloro-1H-indazol-4-yl)-5-hydroxyhexahydrocyclopenta[c]pyrrol-2(1H)-yl)(tetrahydro-2H-pyran-4-yl)methanone;

1-((3aR,5r,6aS)-5-(5-chloro-1H-indazol-7-yl)-5-hydroxyhexahydrocyclopenta[c]pyrrol-2(1H)-yl)ethanone;

N-((1R,3r,5S,6r)-3-(6-chloro-1H-indazol-4-yl)-3-hydroxybicyclo[3.1.0]hexan-6-yl)pivalamide;

N-((1R,3r,5S,6r)-3-(6-chloro-1H-indazol-4-yl)-3-hydroxybicyclo[3.1.0]hexan-6-yl)tetrahydro-2H-pyran-4-carboxamide;

N-((1R,3r,5S,6r)-3-(6-chloro-1H-indazol-4-yl)-3-hydroxybicyclo[3.1.0]hexan-6-yl)isobutyramide;

N-((1R,3r,5S,6r)-3-(6-chloro-1H-indazol-4-yl)-3-hydroxybicyclo[3.1.0]hexan-6-yl)benzamide;

N-((1R,3r,5S,6r)-3-(6-chloro-1H-indazol-4-yl)-3-hydroxybicyclo[3.1.0]hexan-6-yl)tetrahydro-2H-pyran-4-sulfonamide;

N-((1R,3r,5S,6r)-3-(6-chloro-1H-indazol-4-yl)-3-hydroxybicyclo[3.1.0]hexan-6-yl)benzenesulfonamide;

(3aR,5r,6aS)-5-(5-chloro-1H-indazol-7-yl)-2-(methylsulfonyl)octahydrocyclopenta[c]pyrrol-5-ol;

((3aR,5r,6aS)-5-(5-chloro-1H-indazol-7-yl)-5-hydroxyhexahydrocyclopenta[c]pyrrol-2(1H)-yl)(tetrahydro-2H-pyran-4-yl)methanone;

((3aR,5r,6aS)-5-(5-chloro-1H-indazol-7-yl)-5-hydroxyhexahydrocyclopenta[c]pyrrol-2(1H)-yl)(phenyl)methanone;

((3aR,5r,6aS)-5-(5-chloro-1H-indazol-7-yl)-5-hydroxyhexahydrocyclopenta[c]pyrrol-2(1H)-yl)(cyclopropyl)methanone;

(3aR,5r,6aS)-5-(5-chloro-1H-indazol-7-yl)-2-(cyclopropylsulfonyl)octahydrocyclopenta[c]pyrrol-5-ol;

(3aR,5r,6aS)-5-(5-chloro-1H-indazol-7-yl)-2-((tetrahydro-2H-pyran-4-yl)sulfonyl)octahydrocyclopenta[c]pyrrol-5-ol;

(3aR,5r,6aS)-5-(5-chloro-1H-indazol-7-yl)-2-(phenylsulfonyl)octahydrocyclopenta[c]pyrrol-5-ol;

2-amino-N-((1R,3r,5S,6r)-3-(6-chloro-1H-indazol-4-yl)-3-hydroxybicyclo[3.1.0]hexan-6-yl)acetamide hydrochloride;

1-((3aR,6aS)-5-((6-chloro-1H-indazol-4-yl)(hydroxy)methyl)hexahydrocyclopenta[c]pyrrol-2(1H)-yl)ethanone;

(6-chloro-1H-indazol-4-yl)((3aR,6aS)-2-(methylsulfonyl)octahydrocyclopenta[c]pyrrol-5-yl)methanol;

(2r,3aR,5s,6aS)-2-(5-chloro-1H-indazol-7-yl)octahydropentalene-2,5-diol;

N-((1R,3r,5S,6r)-3-(5-chloro-1H-indazol-7-yl)-3-hydroxybicyclo[3.1.0]hexan-6-yl)cyclopropanecarboxamide;

N-((1R,3r,5S,6r)-3-(5-chloro-1H-indazol-7-yl)-3-hydroxybicyclo[3.1.0]hexan-6-yl)acetamide;

N-((1R,3r,5S,6r)-3-(5-chloro-1H-indazol-7-yl)-3-hydroxybicyclo[3.1.0]hexan-6-yl)methanesulfonamide;

N-((1R,3r,5S,6r)-3-(5-chloro-1H-indazol-7-yl)-3-hydroxybicyclo[3.1.0]hexan-6-yl)cyclopropanesulfonamide;

1R,3r,5S)-3-(6-chloro-1H-indazol-4-yl)-6-(hydroxymethyl)bicyclo[3.1.0]hexan-3-ol;
1-((3aR,6aS)-5-((5-chloro-1H-indazol-7-yl)(hydroxy)methyl)hexahydrocyclopenta[c]pyrrol-2(1H)-yl)ethanone;
(5-chloro-1H-indazol-7-yl)((3aR,6aS)-2-(methylsulfonyl)octahydrocyclopenta[c]pyrrol-5-yl)methanol;
1-((1R,3r,5S,6r)-3-(6-chloro-1H-indazol-4-yl)-3-hydroxybicyclo[3.1.0]hexan-6-yl)-3-methylurea;
1-((1R,3r,5S,6r)-3-(6-chloro-1H-indazol-4-yl)-3-hydroxybicyclo[3.1.0]hexan-6-yl)-3-phenylurea;
(3aR,5r,6aS)-5-(6-chloro-1H-indazol-4-yl)-2-(pyridin-4-yl)octahydrocyclopenta[c]pyrrol-5-ol;
(3aR,5r,6aS)-5-(5-chloro-1H-indazol-7-yl)-2-(pyridin-4-yl)octahydrocyclopenta[c]pyrrol-5-ol;
(1R,3r,5S)-3-(5-chloro-1H-indazol-7-yl)bicyclo[3.1.0]hexan-3-ol;
4-chloro-N-((1R,3r,5S,6r)-3-(6-chloro-1H-indazol-4-yl)-3-hydroxybicyclo[3.1.0]hexan-6-yl)benzamide;
1-((1R,3r,5S,6r)-3-(6-chloro-1H-indazol-4-yl)-3-hydroxybicyclo[3.1.0]hexan-6-yl)-3-cyclopropylurea;
1-((1R,3r,5S,6r)-3-(6-chloro-1H-indazol-4-yl)-3-hydroxybicyclo[3.1.0]hexan-6-yl)-3-(4-chlorophenyl)urea;
1-((1R,3r,5S,6r)-3-(6-chloro-1H-indazol-4-yl)-3-hydroxybicyclo[3.1.0]hexan-6-yl)-3-(3-chlorophenyl)urea;
N'-cyclohexyl-N-((1R,3r,5S,6r)-3-(6-chloro-1H-indazol-4-yl)-3-hydroxybicyclo[3.1.0]hexan-6-yl)sulfuric diamide;
3-chloro-N-((1R,3r,5S,6r)-3-(6-chloro-1H-indazol-4-yl)-3-hydroxybicyclo[3.1.0]hexan-6-yl)benzamide;
1-((1R,3r,5S,6r)-3-(6-chloro-1H-indazol-4-yl)-3-hydroxybicyclo[3.1.0]hexan-6-yl)-3-ethylurea;
1-((1R,3r,5S,6r)-3-(6-chloro-1H-indazol-4-yl)-3-hydroxybicyclo[3.1.0]hexan-6-yl)-3-cyclohexylurea;
N-((1R,3r,5S,6r)-3-(6-chloro-1H-indazol-4-yl)-3-hydroxybicyclo[3.1.0]hexan-6-yl)-4-(2-methoxyphenyl)-1H-pyrrole-3-carboxamide;
N'-ethyl-N-((1R,3r,5S,6r)-3-(6-chloro-1H-indazol-4-yl)-3-hydroxybicyclo[3.1.0]hexan-6-yl)sulfuric diamide;
N-((1R,3r,5S,6r)-3-(5-chloro-1H-indazol-7-yl)-3-hydroxybicyclo[3.1.0]hexan-6-yl)benzamide;
N-((1R,3r,5S,6r)-3-(5-chloro-1H-indazol-7-yl)-3-hydroxybicyclo[3.1.0]hexan-6-yl)isonicotinamide;
N-((1R,3r,5S,6r)-3-(5-chloro-1H-indazol-7-yl)-3-hydroxybicyclo[3.1.0]hexan-6-yl)benzenesulfonamide;
1-((1R,3r,5S,6r)-3-(5-chloro-1H-indazol-7-yl)-3-hydroxybicyclo[3.1.0]hexan-6-yl)-3-phenylurea;
1-((1R,3r,5S,6r)-3-(5-chloro-1H-indazol-7-yl)-3-hydroxybicyclo[3.1.0]hexan-6-yl)-3-methylurea;
(5-chloro-1H-benzo[d]imidazol-2-yl)((3aR,5r,6aS)-5-(6-chloro-1H-indazol-4-yl)-5-hydroxyhexahydrocyclopenta[c]pyrrol-2(1H)-yl)methanone;
1-((1R,3r,5S,6r)-3-(6-chloro-1H-indazol-4-yl)-3-hydroxybicyclo[3.1.0]hexan-6-yl)urea;
5-chloro-N-((1R,3r,5S,6r)-3-(6-chloro-1H-indazol-4-yl)-3-hydroxybicyclo[3.1.0]hexan-6-yl)-1H-benzo[d]imidazole-2-carboxamide;
N-((1R,3r,5S,6r)-3-(6-chloro-1H-indazol-4-yl)-3-hydroxybicyclo[3.1.0]hexan-6-yl)-2-cyanoacetamide;
N-((1R,3r,5S,6r)-3-(6-chloro-1H-indazol-4-yl)-3-hydroxybicyclo[3.1.0]hexan-6-yl)-3,3,3-trifluoropropanamide;
N-((1R,3r,5S,6r)-3-(6-chloro-1H-indazol-4-yl)-3-hydroxybicyclo[3.1.0]hexan-6-yl)-2,2,2-trifluoroethanesulfonamide;
N-((1R,3r,5S,6r)-3-(6-chloro-1H-indazol-4-yl)-3-hydroxybicyclo[3.1.0]hexan-6-yl)sulfuric diamide;
N-((1R,3r,5S,6r)-3-(6-chloro-1H-indazol-4-yl)-3-hydroxybicyclo[3.1.0]hexan-6-yl)-3-(methylsulfonamido)benzamide;
N-((1R,3r,5S,6r)-3-(6-chloro-1H-indazol-4-yl)-3-hydroxybicyclo[3.1.0]hexan-6-yl)-3-(trifluoromethyl)benzamide;
N-((1R,3r,5S,6r)-3-(6-chloro-1H-indazol-4-yl)-3-hydroxybicyclo[3.1.0]hexan-6-yl)-3-fluorobenzamide;
N-((1R,3r,5S,6r)-3-(6-chloro-1H-indazol-4-yl)-3-hydroxybicyclo[3.1.0]hexan-6-yl)-3-cyanobenzamide;
N-((1R,3r,5S,6r)-3-(6-chloro-1H-indazol-4-yl)-3-hydroxybicyclo[3.1.0]hexan-6-yl)-3-(trifluoromethoxy)benzamide;
3-bromo-N-((1R,3r,5S,6r)-3-(6-chloro-1H-indazol-4-yl)-3-hydroxybicyclo[3.1.0]hexan-6-yl)benzamide;
1-((1R,3r,5S,6r)-3-(6-chloro-1H-indazol-4-yl)-3-hydroxybicyclo[3.1.0]hexan-6-yl)-3-(4-fluorophenyl)urea;
N-((1R,3r,5S,6r)-3-(6-chloro-1H-indazol-4-yl)-3-hydroxybicyclo[3.1.0]hexan-6-yl)nicotinamide;
N-((1R,3r,5S,6r)-3-(6-chloro-1H-indazol-4-yl)-3-hydroxybicyclo[3.1.0]hexan-6-yl)-2-(4-chlorophenyl)acetamide;
3-chloro-N-((1R,3r,5S,6r)-3-(6-chloro-1H-indazol-4-yl)-3-hydroxybicyclo[3.1.0]hexan-6-yl)-4-fluorobenzamide;
3-acetamido-N-((1R,3r,5S,6r)-3-(6-chloro-1H-indazol-4-yl)-3-hydroxybicyclo[3.1.0]hexan-6-yl)benzamide;
3-chloro-N-((1R,3r,5S,6r)-3-(6-chloro-1H-indazol-4-yl)-3-hydroxybicyclo[3.1.0]hexan-6-yl)-5-fluorobenzamide;
N-((1R,3r,5S,6r)-3-(6-chloro-1H-indazol-4-yl)-3-hydroxybicyclo[3.1.0]hexan-6-yl)-3-(methylsulfonyl)benzamide;
N-((1R,3r,5S,6r)-3-(6-chloro-1H-indazol-4-yl)-3-hydroxybicyclo[3.1.0]hexan-6-yl)-5-methylisoxazole-3-carboxamide;
N-((1R,3r,5S,6r)-3-(6-chloro-1H-indazol-4-yl)-3-hydroxybicyclo[3.1.0]hexan-6-yl)-1-methyl-1H-pyrazole-4-carboxamide;
N-((1R,3r,5S,6r)-3-(6-chloro-1H-indazol-4-yl)-3-hydroxybicyclo[3.1.0]hexan-6-yl)-2-(trifluoromethyl)isonicotinamide;
N1-((1R,3r,5S,6r)-3-(6-chloro-1H-indazol-4-yl)-3-hydroxybicyclo[3.1.0]hexan-6-yl)isophthalamide;
N-((1R,3r,5S,6r)-3-(6-chloro-1H-indazol-4-yl)-3-hydroxybicyclo[3.1.0]hexan-6-yl)isoxazole-4-carboxamide;
N-((1R,3r,5S,6r)-3-(6-chloro-1H-indazol-4-yl)-3-hydroxybicyclo[3.1.0]hexan-6-yl)-1,2,5-oxadiazole-3-carboxamide;
N'-propyl-N-((1R,3r,5S,6r)-3-(6-chloro-1H-indazol-4-yl)-3-hydroxybicyclo[3.1.0]hexan-6-yl)sulfuric diamide;
N-((1R,3r,5S,6r)-3-(6-chloro-1H-indazol-4-yl)-3-hydroxybicyclo[3.1.0]hexan-6-yl)-2-(trifluoromethoxy)isonicotinamide;
N'-methyl-N-((1R,3r,5S,6r)-3-hydroxy-3-(6-(trifluoromethyl)-1H-indazol-4-yl)bicyclo[3.1.0]hexan-6-yl)sulfuric diamide;
3-chloro-N-((1R,3r,5S,6r)-3-hydroxy-3-(6-(trifluoromethyl)-1H-indazol-4-yl)bicyclo[3.1.0]hexan-6-yl)benzamide;
N-((1R,3r,5S,6r)-3-hydroxy-3-(6-(trifluoromethyl)-1H-indazol-4-yl)bicyclo[3.1.0]hexan-6-yl)acetamide;

(3aR,5r,6aS)-5-(6-chloro-1H-indazol-4-yl)-N-(4-chlorophenyl)-5-hydroxyhexahydrocyclopenta[c]pyrrole-2(1H)-carboxamide;
3-chloro-N-((2r,3aR,5r,6aS)-5-(6-chloro-1H-indazol-4-yl)-5-hydroxyoctahydropentalen-2-yl)benzamide;
N-((2r,3aR,5r,6aS)-5-(6-chloro-1H-indazol-4-yl)-5-hydroxyoctahydropentalen-2-yl)acetamide;
N-((1R,3r,5S,6r)-3-(6-chloro-1H-indazol-4-yl)-3-hydroxybicyclo[3.1.0]hexan-6-yl)-3,4-difluorobenzamide;
N-((1R,3r,5S,6r)-3-(6-chloro-1H-indazol-4-yl)-3-hydroxybicyclo[3.1.0]hexan-6-yl)quinoline-4-carboxamide;
5-Bromo-N-((1R,3r,5S,6r)-3-(6-chloro-1H-indazol-4-yl)-3-hydroxybicyclo[3.1.0]hexan-6-yl)nicotinamide;
N-((1R,3r,5S,6r)-3-(6-chloro-1H-indazol-4-yl)-3-hydroxybicyclo[3.1.0]hexan-6-yl)-[1,1'-biphenyl]-3-carboxamide;
N-((1R,3r,5S,6r)-3-(6-chloro-1H-indazol-4-yl)-3-hydroxybicyclo[3.1.0]hexan-6-yl)-4-fluoro-3-(trifluoromethyl)benzamide;
N-((1R,3r,5S,6r)-3-(6-chloro-1H-indazol-4-yl)-3-hydroxybicyclo[3.1.0]hexan-6-yl)-5-fluoronicotinamide;
N-((1R,3r,5S,6r)-3-(6-chloro-1H-indazol-4-yl)-3-hydroxybicyclo[3.1.0]hexan-6-yl)-3-ethynylbenzamide;
1-((3aR,5r,6aS)-5-(6-chloro-1H-indazol-4-yl)-5-hydroxyhexahydrocyclopenta[c]pyrrol-2(1H)-yl)-2-(4-chlorophenyl)ethanone;
3-bromo-N-((1R,3r,5S,6r)-3-(6-chloro-1H-indazol-4-yl)-3-hydroxybicyclo[3.1.0]hexan-6-yl)-4-fluorobenzamide;
N-((1R,3r,5S,6r)-3-(6-chloro-1H-indazol-4-yl)-3-hydroxybicyclo[3.1.0]hexan-6-yl)-6-fluoroquinoline-4-carboxamide;
N-((1R,3r,5S,6r)-3-(6-chloro-1H-indazol-4-yl)-3-hydroxybicyclo[3.1.0]hexan-6-yl)-3-cyclopropylbenzamide;
5-chloro-N-((1R,3r,5S,6r)-3-(6-chloro-1H-indazol-4-yl)-3-hydroxybicyclo[3.1.0]hexan-6-yl)nicotinamide;
N-((1R,3r,5S,6r)-3-(6-chloro-1H-indazol-4-yl)-3-hydroxybicyclo[3.1.0]hexan-6-yl)-4-fluoro-3-(trifluoromethoxy)benzamide;
N-((1R,3r,5S,6r)-3-(6-chloro-1H-indazol-4-yl)-3-hydroxybicyclo[3.1.0]hexan-6-yl)-5-cyanonicotinamide;
N-((1R,3r,5S,6r)-3-(6-chloro-1H-indazol-4-yl)-3-hydroxybicyclo[3.1.0]hexan-6-yl)-5-(trifluoromethyl)nicotinamide;
Racemic-N-((1S,5R,6S)-3-(6-chloro-1H-indazol-4-yl)bicyclo[3.1.0]hex-2-en-6-yl)cyclopropanecarboxamide;
(1R,5S,6r)-6-(6-chloro-1H-indazol-4-yl)-3-(methylsulfonyl)-3-azabicyclo[3.1.0]hexan-6-ol;
N-(((1R,3r,5S,6s)-3-(6-chloro-1H-indazol-4-yl)-3-hydroxybicyclo[3.1.0]hexan-6-yl)methyl)acetamide;
N-(((1R,3r,5S,6s)-3-(6-chloro-1H-indazol-4-yl)-3-hydroxybicyclo[3.1.0]hexan-6-yl)methyl)methanesulfonamide;
N-((1R,3r,5S,6r)-3-(6-chloro-1H-indazol-4-yl)-3-hydroxybicyclo[3.1.0]hexan-6-yl)-5-(trifluoromethoxy)nicotinamide;
N-((1R,3r,5S,6r)-3-(6-chloro-1H-indazol-4-yl)-3-hydroxybicyclo[3.1.0]hexan-6-yl)-5-(trifluoromethyl)isoxazole-3-carboxamide;
N-((1R,3r,5S,6r)-3-(6-chloro-1H-indazol-4-yl)-3-hydroxybicyclo[3.1.0]hexan-6-yl)-3-(trifluoromethyl)isoxazole-5-carboxamide;
1-((1R,5S,6r)-6-(6-chloro-1H-indazol-4-yl)-6-hydroxy-3-azabicyclo[3.1.0]hexan-3-yl)ethanone;
((1R,5S,6r)-6-(6-chloro-1H-indazol-4-yl)-6-hydroxy-3-azabicyclo[3.1.0]hexan-3-yl)(cyclopropyl)methanone;
(1R,5S,6r)-6-(6-chloro-1H-indazol-4-yl)-3-(cyclopropylsulfonyl)-3-azabicyclo[3.1.0]hexan-6-ol;
(1R,5S,6r)-6-(6-chloro-1H-indazol-4-yl)-6-hydroxy-N-methyl-3-azabicyclo[3.1.0]hexane-3-sulfonamide;
((1R,5S,6r)-6-(6-chloro-1H-indazol-4-yl)-6-hydroxy-3-azabicyclo[3.1.0]hexan-3-yl)(5-chloropyridin-3-yl)methanone;
N-((1R,3s,5S,6s)-6-(6-chloro-1H-indazol-4-yl)-6-hydroxybicyclo[3.1.0]hexan-3-yl)acetamide;
N-((1R,3s,5S,6s)-6-(6-chloro-1H-indazol-4-yl)-6-hydroxybicyclo[3.1.0]hexan-3-yl)methanesulfonamide;
N'-methyl-N-((1R,3s,5S,6s)-6-(6-chloro-1H-indazol-4-yl)-6-hydroxybicyclo[3.1.0]hexan-3-yl)sulfuric diamide;
N'-methyl-N-((2r,3aR,5r,6aS)-5-(6-chloro-1H-indazol-4-yl)-5-hydroxyoctahydropentalen-2-yl)sulfuric diamide;
N'-phenyl-N-((1R,3r,5S,6r)-3-(6-chloro-1H-indazol-4-yl)-3-hydroxybicyclo[3.1.0]hexan-6-yl)sulfuric diamide;
N'-(4-chlorophenyl)-N-((1R,3r,5S,6r)-3-(6-chloro-1H-indazol-4-yl)-3-hydroxybicyclo[3.1.0]hexan-6-yl)sulfuric diamide;
N'-(3-chlorophenyl)-N-((1R,3r,5S,6r)-3-(6-chloro-1H-indazol-4-yl)-3-hydroxybicyclo[3.1.0]hexan-6-yl)sulfuric diamide;
N-((1R,3r,5S,6r)-3-(6-chloro-1H-indazol-4-yl)-3-hydroxybicyclo[3.1.0]hexan-6-yl)-1-phenylmethanesulfonamide;
N-(((1R,3r,5S,6r)-3-(6-chloro-1H-indazol-4-yl)-3-hydroxybicyclo[3.1.0]hexan-6-yl)methyl)methanesulfonamide;
N-(((1R,3r,5S,6r)-3-(6-chloro-1H-indazol-4-yl)-3-hydroxybicyclo[3.1.0]hexan-6-yl)methyl)acetamide;
(1R,3r,5S,6r)-3-(6-chloro-1H-indazol-4-yl)-3-hydroxybicyclo[3.1.0]hexane-6-carboxamide;
(1R,3r,5S,6r)-3-(6-chloro-1H-indazol-4-yl)-3-hydroxy-N-methylbicyclo[3.1.0]hexane-6-carboxamide;
N-((1R,3r,5S,6r)-3-(6-chloroimidazo[1,5-a]pyridin-8-yl)-3-hydroxybicyclo[3.1.0]hexan-6-yl)methanesulfonamide;
N'-methyl-N-((1R,3r,5S,6r)-3-(6-chloroimidazo[1,5-a]pyridin-8-yl)-3-hydroxybicyclo[3.1.0]hexan-6-yl)sulfuric diamide;
N-((1R,3r,5S,6r)-3-(6-chloroimidazo[1,5-a]pyridin-8-yl)-3-hydroxybicyclo[3.1.0]hexan-6-yl)acetamide;
3-chloro-N-((1R,3r,5S,6r)-3-(6-chloroimidazo[1,5-a]pyridin-8-yl)-3-hydroxybicyclo[3.1.0]hexan-6-yl)benzamide;
N-((1R,3r,5S,6r)-3-(6-chloroimidazo[1,5-a]pyridin-8-yl)-3-hydroxybicyclo[3.1.0]hexan-6-yl)-3-fluorobenzamide;
3-bromo-N-((1R,3r,5S,6r)-3-(6-chloroimidazo[1,5-a]pyridin-8-yl)-3-hydroxybicyclo[3.1.0]hexan-6-yl)benzamide;
N-((1R,3r,5S,6r)-3-(6-chloroimidazo[1,5-a]pyridin-8-yl)-3-hydroxybicyclo[3.1.0]hexan-6-yl)-3-cyanobenzamide;
N-((1R,3r,5S,6r)-3-(6-chloroimidazo[1,5-a]pyridin-8-yl)-3-hydroxybicyclo[3.1.0]hexan-6-yl)-3-(trifluoromethyl)benzamide;
N-((1R,3r,5S,6r)-3-(6-chloroimidazo[1,5-a]pyridin-8-yl)-3-hydroxybicyclo[3.1.0]hexan-6-yl)-3-(trifluoromethoxy)benzamide;

N-((1R,3r,5S,6r)-3-(6-chloroimidazo[1,5-a]pyridin-8-yl)-3-hydroxybicyclo[3.1.0]hexan-6-yl)nicotinamide;
5-chloro-N-((1R,3r,5S,6r)-3-(6-chloroimidazo[1,5-a]pyridin-8-yl)-3-hydroxybicyclo[3.1.0]hexan-6-yl)nicotinamide;
N-((1R,3r,5S,6r)-3-(6-chloroimidazo[1,5-a]pyridin-8-yl)-3-hydroxybicyclo[3.1.0]hexan-6-yl)-5-fluoronicotinamide;
5-chloro-N-((1R,3r,5S,6r)-3-(6-chloroimidazo[1,5-a]pyridin-8-yl)-3-hydroxybicyclo[3.1.0]hexan-6-yl)nicotinamide;
N-((1R,3r,5S,6r)-3-(6-chloroimidazo[1,5-a]pyridin-8-yl)-3-hydroxybicyclo[3.1.0]hexan-6-yl)-5-cyanonicotinamide;
N-((1R,3r,5S,6r)-3-(6-chloroimidazo[1,5-a]pyridin-8-yl)-3-hydroxybicyclo[3.1.0]hexan-6-yl)-5-(trifluoromethyl)nicotinamide;
N-((1R,3r,5S,6r)-3-(6-chloroimidazo[1,5-a]pyridin-8-yl)-3-hydroxybicyclo[3.1.0]hexan-6-yl)-5-(trifluoromethoxy)nicotinamide;
3-chloro-N-((1R,3r,5S,6r)-3-(6-chloroimidazo[1,5-a]pyridin-8-yl)-3-hydroxybicyclo[3.1.0]hexan-6-yl)-4-fluorobenzamide;
3-chloro-N-((1R,3r,5S,6r)-3-(6-chloroimidazo[1,5-a]pyridin-8-yl)-3-hydroxybicyclo[3.1.0]hexan-6-yl)-5-fluorobenzamide;
N-((1R,3r,5S,6r)-3-(6-chloroimidazo[1,5-a]pyridin-8-yl)-3-hydroxybicyclo[3.1.0]hexan-6-yl)-5-methylisoxazole-3-carboxamide;
N-((1R,3r,5S,6r)-3-(6-chloro-1H-indazol-4-yl)-3-hydroxybicyclo[3.1.0]hexan-6-yl)-2-hydroxyacetamide;
N-((1R,3r,5S,6r)-3-(6-chloro-1H-indazol-4-yl)-3-hydroxybicyclo[3.1.0]hexan-6-yl)-2-hydroxy-2-phenylacetamide;
N-((1R,3r,5S,6r)-3-(6-chloro-1H-indazol-4-yl)-3-hydroxybicyclo[3.1.0]hexan-6-yl)-6-methoxynicotinamide;
(1R,3r,5S)-3-(6-chloro-1H-indazol-4-yl)bicyclo[3.1.0]hexane-3,6-diol;
(1R,5S,6s)-6-(6-chloro-1H-indazol-4-yl)bicyclo[3.1.0]hexane-3,6-diol;
(3aR,5r,6aS)-5-(6-chloro-1H-indazol-4-yl)hexahydro-1H-cyclopenta[c]furan-5-ol;
and pharmaceutically acceptable salt thereof.

20. A pharmaceutical composition comprising a compound according to claim 1 admixed with at least one pharmaceutically acceptable excipient.

21. The pharmaceutical composition of claim 20, further comprising at least one therapeutic co-agent or co-treatment selected from anti-viral agents, chemotherapeutics or other anti-cancer agents, immune enhancers, immunosuppressants, radiation, anti-tumor and anti-viral vaccines, agents for cytokine therapy, another indoleamine 2,3-dioxygenase 1 (IDO1) inhibitor, and kinase inhibitors.

22. The pharmaceutical composition of claim 21, wherein the at least one therapeutic co-agent or co-treatment is combined with the compound in a single dosage form, or the at least one therapeutic co-agent is administered simultaneously or sequentially as separate dosage forms.

23. The pharmaceutical composition of claim 21, wherein the therapeutic co-agent is anticancer compound selected from chemotherapeutic or other anti-cancer agent, immune enhancer, immune checkpoint inhibitor, radiation, anti-tumor vaccine, agent for cytokine therapy, and kinase inhibitor.

24. A method to treat cancer, comprising administering to a subject in need of such treatment a therapeutically effective amount of a compound according to claim 1.

25. The method of claim 24, wherein the cancer is selected from adenoma, bladder cancer, brain cancer, breast cancer, cervical cancer, colorectal cancer, colon cancer, epidermal carcinoma, follicular carcinoma, genitourinary cancers, glioblastoma, head and neck cancers, Hodgkin's disease, non-Hodgkin's lymphoma, hepatoma, head and neck cancers, kidney cancer, lung cancers, leukemias, multiple myeloma, lymphoid disorders, skin cancers, neuroblastoma, ovarian cancer, pancreatic cancer, prostate cancer, rectal cancer, sarcoma, testicular cancer, and thyroid cancer.

26. A method for treating a disease associated with TDO2 and/or IDO1 mediated immunosuppression in a subject in need thereof, comprising administering an effective TDO2 and/or IDO1 inhibiting amount of a compound according to claim 1.

27. A method of claim 26, wherein the treatment comprises co-administering a therapeutic co-agent or co-treatment selected from an anti-viral agent, chemotherapeutic or other anti-cancer agent, immune enhancer, immunosuppressant, radiation, anti-tumor or anti-viral vaccine, agent for cytokine therapy, and kinase inhibitor.

28. The method of claim 27, wherein the administering the compound is conducted simultaneously or serially with the administering the therapeutic co-agent.

29. The method of claim 27, wherein administering the therapeutic co-agent comprises an IDOI inhibitor.

30. The method of claim 27, wherein administering the therapeutic co-agent comprises inhibitors of PD-1 or PD-L1.

31. The method of claim 30, wherein the therapeutic co-agent is pembrolizumab, nivolumab, pidilizumab, BMS 936559, atezolizumab, or avelumab.

32. A kit comprising a compound according to claim 1 or a pharmaceutically acceptable salt thereof, and a therapeutic co-agent.

33. The kit of claim 32, wherein the therapeutic co-agent is pembrolizumab, nivolumab, pidilizumab, BMS 936559, atezolizumab, or avelumab.

34. A method for treating a disease associated with TDO2 and/or IDO1 in kynurenine pathway in a patient comprising administering to a subject in need of such treatment a therapeutically effective amount of a compound according to claim 1 or a pharmaceutically acceptable salt thereof, and a pharmaceutically acceptable carrier, wherein the disease is selected from cancer, viral infection, depression, neurodegenerative disorder, trauma, age-related cataracts, organ transplantation, and autoimmune.

35. The method according to claim 34, wherein the viral infection is HIV infection.

36. The method according to claim 34, wherein the neurodegenerative disorder is Alzheimer's disease or Huntington's disease.

37. The method according to claim 34, wherein the autoimmune disease is asthma, rheumatoid arthritis, multiple sclerosis, inflammatory bowel disease, psoriasis or systemic lupus erythematosus.

38. The method of claim 25, wherein the lung cancer is selected from small cell lung cancer and non-small cell lung cancer.

39. The method of claim 25, wherein the leukemia is selected from AML and CML.

40. The method of claim 25, wherein the skin cancer is melanoma.

* * * * *